United States Patent
Burger et al.

(10) Patent No.: US 9,079,889 B2
(45) Date of Patent: Jul. 14, 2015

(54) KINASE INHIBITORS AND METHODS OF THEIR USE

(71) Applicants: Matthew T. Burger, Albany, CA (US); Wooseok Han, San Ramon, CA (US); Jiong Lan, Moraga, CA (US); Gisele Nishiguchi, Albany, CA (US)

(72) Inventors: Matthew T. Burger, Albany, CA (US); Wooseok Han, San Ramon, CA (US); Jiong Lan, Moraga, CA (US); Gisele Nishiguchi, Albany, CA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/081,132

(22) Filed: Nov. 15, 2013

(65) Prior Publication Data

US 2014/0079693 A1 Mar. 20, 2014

Related U.S. Application Data

(62) Division of application No. 13/327,358, filed on Dec. 15, 2011, now Pat. No. 8,592,455, which is a division of application No. 12/584,158, filed on Aug. 31, 2009, now Pat. No. 8,329,732.

(60) Provisional application No. 61/093,666, filed on Sep. 2, 2008, provisional application No. 61/225,660, filed on Jul. 15, 2009.

(51) Int. Cl.
| | |
|---|---|
| *A61K 31/4418* | (2006.01) |
| *C07D 401/14* | (2006.01) |
| *C07D 401/12* | (2006.01) |
| *A61K 31/444* | (2006.01) |
| *A61K 31/4545* | (2006.01) |
| *A61K 45/06* | (2006.01) |
| *C07D 213/81* | (2006.01) |

(52) U.S. Cl.
CPC ............ *C07D 401/14* (2013.01); *A61K 31/444* (2013.01); *A61K 31/4418* (2013.01); *A61K 31/4545* (2013.01); *A61K 45/06* (2013.01); *C07D 213/81* (2013.01); *C07D 401/12* (2013.01)

(58) Field of Classification Search
CPC .................................................. A61K 31/4418
USPC ......................................................... 514/332
See application file for complete search history.

(56) References Cited

U.S. PATENT DOCUMENTS

| | | |
|---|---|---|
| 2005/0245530 A1 | 11/2005 | Borzilleri |
| 2006/0004197 A1 | 1/2006 | Thrash |
| 2010/0311980 A1 | 12/2010 | Rao |
| 2012/0208815 A1 | 8/2012 | Burger et al. |

FOREIGN PATENT DOCUMENTS

| | | |
|---|---|---|
| WO | WO 01/55155 | 8/2001 |
| WO | WO 02/076986 | 10/2002 |
| WO | WO 2005/033097 | 4/2005 |
| WO | WO 2005/042488 | 5/2005 |
| WO | WO 2005/056547 | 6/2005 |
| WO | WO 2006/105081 | 10/2006 |
| WO | WO 2007/019344 | 2/2007 |
| WO | WO 2007/044724 | 4/2007 |
| WO | WO 2008/054702 | 5/2008 |
| WO | WO 2008/054749 | 5/2008 |
| WO | WO 2008/106692 | 9/2008 |
| WO | WO 2009/014637 | 1/2009 |
| WO | WO 2010/026124 | 3/2010 |
| WO | WO 2011/016234 | 2/2011 |
| WO | WO 2012/100135 | 7/2012 |

OTHER PUBLICATIONS

LeRoith et al., The insulin-like growth factor system and cancer, Cancer Letters, 195, pp. 127-137 (2003).*
Simone, Oncology:Introduction, Cecil Textbook of Medicine, ed Bennett et al. W.B.Saunders Co. 20th ed, vol. 1, 1996, pp. 1004-1010.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Lodish et al., "Endocrine side, etc.," Endocrine-Related Cancer (2010) 17, R233-R244.*
Golub et al, Science, vol. 286, Oct. 15, 1999, pp. 531-537.*
Ouaissi et al., "Rationale for Possible, etc.," Journal of Biomedicine and Biotechnology, 2011, Article: ID 315939, 1-8.*
Dorwald, Side Reactions in Organic Synthesis, 2005 Wiley; VCH Weinheim Preface, pp. 1-15 & Chapter 8, pp. 279-308.
Graham Atwell et al. "Potential Antitumor Agents. 55. 6-Phenylphenanthridine-4-Carboxamides: A New Class of DNA-Intercalating Antitumor" *J. Med. Chem.* 31:774-779, 1988.

* cited by examiner

*Primary Examiner* — Patricia L Morris
(74) *Attorney, Agent, or Firm* — Rona Nardone

(57) ABSTRACT

New compounds, compositions and methods of inhibition of Provirus Integration of Maloney Kinase (PIM kinase) activity associated with tumorigenesis in a human or animal subject are provided. In certain embodiments, the compounds and compositions are effective to inhibit the activity of at least one PIM kinase. The new compounds and compositions may be used either alone or in combination with at least one additional agent for the treatment of a serine/threonine kinase- or receptor tyrosine kinase-mediated disorder, such as cancer.

2 Claims, 3 Drawing Sheets

Example 70 (P.O.)

Example 96 (P.O.)

KINASE INHIBITORS AND METHODS OF THEIR USE

CROSS-REFERENCE TO RELATED APPLICATIONS

This application is a divisional of, and claims the benefit under 35 U.S.C. §120 and §121 of U.S. patent application Ser. No. 13/327,358, filed Dec. 15, 2011, now issued as U.S. Pat. No. 8,592,455, which is a divisional application of U.S. Ser. No. 12/584,158, filed Aug. 31, 2009, which issued as U.S. Pat. No. 8,329,732 and which in turn claims the benefit under 35 U.S.C. §119(e) to U.S. provisional application serial No. 61/093,666, filed on Sep. 2, 2008, and to U.S. provisional application serial No. 61/225,660, filed Jul. 15, 2009. The entire contents of each of these prior applications are incorporated herein by reference in their entirety.

FIELD OF THE INVENTION

The present invention relates to new compounds and their tautomers and stereoisomers, and pharmaceutically acceptable salts, esters, metabolites or prodrugs thereof, compositions of the new compounds together with pharmaceutically acceptable carriers, and uses of the new compounds, either alone or in combination with at least one additional therapeutic agent, in the prophylaxis or treatment of cancer.

BACKGROUND

Infection with the Maloney retrovirus and genome integration in the host cell genome results in development of lymphomas in mice. Provirus Integration of Maloney Kinase (PIM-Kinase) was identified as one of the frequent proto-oncogenes capable of being transcriptionally activated by this retrovirus integration event (Cuypers H T et al., "Murine leukemia virus-induced T-cell lymphomagenesis: integration of proviruses in a distinct chromosomal region," Cell 37(1): 141-50 (1984); Selten G, et al., "Proviral activation of the putative oncogene Pim-1 in MuLV induced T-cell lymphomas" EMBO J 4(7):1793-8 (1985)), thus establishing a correlation between over-expression of this kinase and its oncogenic potential. Sequence homology analysis demonstrated that there are 3 highly homologous Pim-Kinases (Pim1, 2 & 3), Pim1 being the protooncogene originally identified by retrovirus integration. Furthermore, transgenic mice over-expressing Pim1 or Pim2 show increased incidence of T-cell lymphomas (Breuer M et al., "Very high frequency of lymphoma induction by a chemical carcinogen in pim-1 transgenic mice" Nature 340(6228):61-3 (1989)), while over-expression in conjunction with c-myc is associated with incidence of B-cell lymphomas (Verbeek S et al., "Mice bearing the E mu-myc and E mu-pim-1 transgenes develop pre-B-cell leukemia prenatally" Mol Cell Biol 11(2):1176-9 (1991)). Thus, these animal models establish a strong correlation between Pim over-expression and oncogenesis in hematopoietic malignancies. In addition to these animal models, Pim over-expression has been reported in many other human malignancies. Pim1, 2 & 3 over-expression is frequently observed in many hematopoietic malignancies (Amson R et al., "The human protooncogene product p33pim is expressed during fetal hematopoiesis and in diverse leukemias," PNAS USA 86(22):8857-61 (1989); Cohen A M et al., "Increased expression of the hPim-2 gene in human chronic lymphocytic leukemia and non-Hodgkin lymphoma," Leuk Lymph 45(5):951-5 (2004), Huttmann A et al., "Gene expression signatures separate B-cell chronic lymphocytic leukaemia prognostic subgroups defined by ZAP-70 and CD38 expression status," Leukemia 20:1774-1782 (2006)) and in prostate cancer (Dhanasekaran S M, et al., "Delineation of prognostic biomarkers in prostate cancer," Nature 412(6849): 822-6 (2001); Cibull T L, et al., "Overexpression of Pim-1 during progression of prostatic adenocarcinoma," J Clin Pathol 59(3):285-8 (2006)), while overexpression of Pim3 is frequently observed in hepatocellular carcinoma (Fujii C, et al., "Aberrant expression of serine/threonine kinase Pim-3 in hepatocellular carcinoma development and its role in the proliferation of human hepatoma cell lines," Int J Cancer 114:209-218 (2005)) and pancreatic cancer (Li Y Y et al., "Pim-3, a proto-oncogene with serine/threonine kinase activity, is aberrantly expressed in human pancreatic cancer and phosphorylates bad to block bad-mediated apoptosis in human pancreatic cancer cell lines," Cancer Res 66(13):6741-7 (2006)).

Pim1, 2 & 3 are Serine/Threonine kinases that normally function in survival and proliferation of hematopoietic cells in response to growth factors and cytokines. Cytokines signaling through the Jak/Stat pathway leads to activation of transcription of the Pim genes and synthesis of the proteins. No further post-translational modifications are required for the Kinase Pim activity. Thus, signaling down stream is primarily controlled at the transcriptional/translational and protein turnover level. Substrates for Pim kinases include regulators of apoptosis such as the Bcl-2 family member BAD (Aho T et al., "Pim-1 kinase promotes inactivation of the pro-apoptotic Bad protein by phosphorylating it on the Serl 12 gatekeeper site: FEBS Letters 571: 43-49 (2004)), cell cycle regulators such as p21$^{WFA1/CIP1}$ (Wang Z, et al., "Phosphorylation of the cell cycle inhibitor p21Cip1/WAF1 by Pim-1 kinase," Biochem Biophys Acta 1593:45-55 (2002)), CDC25A (1999), C-TAK (Bachmann M et al., "The Oncogenic Serine/Threonine Kinase Pim-1 Phosphorylates and Inhibits the Activity of Cdc25C-associated Kinase 1 (C-TAK1). A novel role for Pim-1 at the G2/M cell cycle checkpoint," J Biol Chem 179:48319-48328 (2004)) and NuMA (Bhattacharya N, et al., "Pim-1 associates with protein complexes necessary for mitosis," Chromosoma 111(2): 80-95 (2002)) and the protein synthesis regulator 4EBP1 (Hammerman P S et al., "Pim and Akt oncogenes are independent regulators of hematopoietic cell growth and survival," Blood 105(11):4477-83 (2005)). The effects of Pim(s) in these regulators are consistent with a role in protection from apoptosis and promotion of cell proliferation and growth. Thus, over-expression of Pim(s) in cancer is thought to play a role in promoting survival and proliferation of cancer cells and, therefore, their inhibitions should be an effective way of treating cancers on which they are over-expressed. In fact several reports indicate that knocking down expression of Pim(s) with siRNA results in inhibition of proliferation and cell death (Dai J M, et al., "Antisense oligodeoxynucleotides targeting the serine/threonine kinase Pim-2 inhibited proliferation of DU-145 cells," Acta Pharmacol Sin 26(3):364-8 (2005); Fujii et al. 2005; Li et al. 2006). Furthermore, mutational activation of several well know oncogenes in hematopoietic malignancies are thought exert its effects at least in part through Pim(s). For example, targeted down regulation of pim expression impairs survival of hematopoietic cells transformed by Flt3 and BCR/ABL (Adam et al. 2006). Thus, inhibitors to Pim1, 2 &3 would be useful in the treatment of these malignancies. In addition to a potential role in cancer treatment and myeloproliferative diseases, such inhibitor could be useful to control expansion of immune cells in other pathologic condition such as autoimmune diseases, allergic reactions and in organ transplantation rejection syndromes.

This notion is supported by the findings that differentiation of Th1 Helper T-cells by IL-12 and IFN-α results in induction of expression of both Pim1&2 (Aho T et al., "Expression of human Pim family genes is selectively up-regulated by cytokines promoting T helper type 1, but not T helper type 2, cell differentiation," *Immunology* 116: 82-88 (2005)). Moreover, Pim(s) expression is inhibited in both cell types by the immunosuppressive TGF-β (Aho et al. 2005). These results suggest that Pim kinases are involved in the early differentiation process of Helper T-cells, which coordinate the immunological responses in autoimmune diseases, allergic reaction and tissue transplant rejection.

A continuing need exists for compounds that inhibit the proliferation of capillaries, inhibit the growth of tumors, treat cancer, modulate cell cycle arrest, and/or inhibit molecules such as Pim1, Pim2 and Pim3, and pharmaceutical formulations and medicaments that contain such compounds. A need also exists for methods of administering such compounds, pharmaceutical formulations, and medicaments to patients or subjects in need thereof.

SUMMARY OF INVENTION

New compounds, and their stereoisomers, tautomers and pharmaceutically acceptable salts, are provided of the Formula I

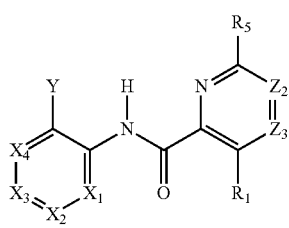

wherein, $X_1$, $X_2$, $X_3$ and $X_4$ are independently selected from $CR_2$ and N; provided that at least one but not more than two of $X_1$, $X_2$, $X_3$ and $X_4$ are N;

Y is selected from a group consisting of cycloalkyl, partially unsaturated cycloalkyl, and heterocycloalkyl, wherein each member of said group may be substituted with up to four substituents;

$Z_2$ and $Z_3$ are independently selected from $CR_{12}$ and N; provided that not more than one of $Z_2$ and $Z_3$ can be N;

$R_1$ is selected from the group consisting of hydrogen, —$NHR_3$ halo, hydroxyl, alkyl, cyano, and nitro;

$R_2$ and $R_{12}$ independently at each occurrence are selected from the group consisting of hydrogen, halo, hydroxyl, nitro, cyano, $SO_3H$ and substituted or unsubstituted alkyl, alkenyl, alkynyl, alkoxy, amino, cycloalkyl, hetero cycloalkyl, and partially saturated cycloalkyl;

$R_3$ is selected from the group consisting of hydrogen, —CO—$R_4$ and substituted or unsubstituted alkyl, cycloalkyl, heterocyclyl, aryl and heteroaryl;

$R_4$ is selected from the group consisting of alkyl, substituted alkyl, alkoxy, substituted alkoxy, amino, substituted amino, and alkylamino; and $R_5$ represents a group selected from substituted or unsubstituted aryl, $C_3$-$C_7$ cycloalkyl, heteroaryl, partially unsaturated cycloalkyl and alkyl, wherein each said substituted $R_5$ group may be substituted with up to four substituents selected from halo, cyano, amino, $C_{1-4}$ alkyl, $C_{3-6}$ cycloalkyl, alkoxy, nitro, carboxy, carbonyl, carboalkoxy, aminocarboxy, substituted aminocarbonyl, aminosulfonyl, substituted aminosulfonyl and alkoxyalkyl.

In some embodiments, new compounds of Formula I, or a stereoisomer, tautomer, or pharmaceutically acceptable salt thereof are provided wherein $X_2$ is N and $X_1$, $X_3$ and $X_4$ are $CR_2$.

In some embodiments, new compounds of Formula I, or a stereoisomer, tautomer, or pharmaceutically acceptable salt thereof are provided wherein $R_2$ is selected from hydrogen, methyl, ethyl, halo, cyano.

In some embodiments, compounds of Formula I, or a stereoisomer, tautomer, or pharmaceutically acceptable salt thereof are provided wherein $Z_2$ and $Z_3$ are $CR_{12}$.

In some embodiments, compounds of Formula I, or a stereoisomer, tautomer, or pharmaceutically acceptable salt thereof are provided wherein $R_{12}$ is selected from hydrogen, halo, methyl, ethyl and cyano.

In other embodiments, new compounds, and their stereoisomers, tautomers and pharmaceutically acceptable salts, are provided of the Formula II

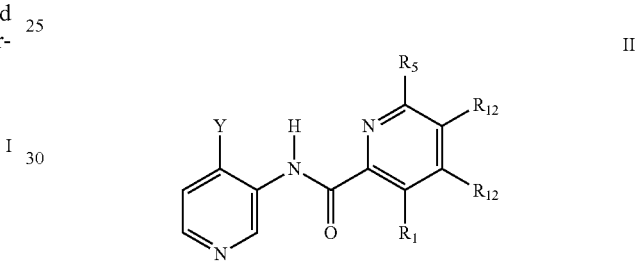

wherein,

Y is selected from a group consisting of cyclohexyl, partially unsaturated cyclohexyl, and heterocyclo-$C_5$-alkyl, wherein each member of said group may be substituted with up to four substituents;

$R_1$ is selected from the group consisting of hydrogen, —$NHR_3$ halo, hydroxyl, alkyl, $C_{3-4}$ cycloalkyl, cyano, and nitro;

$R_{12}$ independently at each occurrence is selected from the group consisting of hydrogen, halo, hydroxyl, amino, nitro, cyano, $SO_3H$ and substituted or unsubstituted alkyl, alkenyl, alkynyl, alkoxy, amino, cycloalkyl, hetero cycloalkyl, and partially saturated cycloalkyl;

$R_3$ is selected from the group consisting of hydrogen, —CO—$R_4$ and substituted or unsubstituted alkyl, cycloalkyl, heterocyclyl, aryl and heteroaryl;

$R_4$ is selected from the group consisting of alkyl, substituted alkyl, alkoxy, substituted alkoxy, amino, substituted amino, and alkylamino; and $R_5$ represents a group selected from hydrogen and substituted or unsubstituted alkyl, $C_6$-cycloalkyl, aryl and heteroaryl, wherein each said substituted $R_5$ group may be substituted with up to four substituents selected from halo, cyano, amino, $C_{1-4}$ alkyl, $C_{3-6}$ cycloalkyl, alkoxy, nitro, carboxy, carbonyl, carboalkoxy, aminocarboxy, substituted aminocarbonyl, aminosulfonyl, substituted aminosulfonyl and alkoxyalkyl.

In some embodiments, compounds of Formulas I or II, or a stereoisomer, tautomer, or pharmaceutically acceptable salt thereof are provided wherein Y is selected from a group consisting of substituted or unsubstituted cycloalkyl, cycloalkenyl, piperidinyl and piperazinyl, wherein each member of said group is substituted with up to four substituents. In some embodiments, Y is substituted with up to four substituents selected from, cyano, nitro, halo, hydroxyl, amino, alkoxy, substituted amino, $C_{1-4}$ alkyl, $C_{1-4}$ halo alkyl and $C_{3-4}$ cycloalkyl. In yet other embodiments, Y is substituted with up to four substituents selected from methyl, propyl, i-propyl, ethyl, hydroxyl, amino, halo, monohalo $C_{1-3}$ alkyl, trihalo $C_{1-3}$ alkyl and dihalo $C_{1-3}$ alkyl.

In some embodiments, new compounds of Formula II, or a stereoisomer, tautomer, or pharmaceutically acceptable salt thereof are provided wherein Y is selected from a group consisting of substituted or unsubstituted cyclohexyl, cyclohexynyl, and piperidinyl, wherein each member of said group is substituted with up to four substituents.

In some embodiments, new compounds of Formula II, or a stereoisomer, tautomer, or pharmaceutically acceptable salt thereof are provided wherein Y is substituted with up to four substituents independently selected from hydrogen, cyano, nitro, halo, hydroxyl, amino, alkoxy, substituted amino, $C_{1-4}$ alkyl, $C_{1-4}$ halo alkyl and $C_{3-4}$ cycloalkyl. In some embodiments, the substituents are independently selected from methyl, propyl, i-propyl, ethyl, hydroxyl, amino, halo, monohalo $C_{1-3}$ alkyl, trihalo $C_{1-3}$ alkyl and dihalo $C_{1-3}$ alkyl.

In some embodiments, compounds of Formula II, or a stereoisomer, tautomer, or pharmaceutically acceptable salt thereof are provided wherein $R_{12}$ is selected from hydrogen, halo, methyl, ethyl and cyano.

In some embodiments, compounds of Formulas I or II, or a stereoisomer, tautomer, or pharmaceutically acceptable salt thereof are provided wherein Y is selected from the group consisting of substituted or unsubstituted cyclohexyl, cyclohexenyl, piperidinyl, piperazinyl, wherein said the Y group may be substituted with up to three substituents selected from methyl, ethyl, hydroxyl, amino, and methoxy; $R_1$ is selected from the group consisting of hydrogen, and amino; and $R_{12}$ independently are each occurrence represents hydrogen, halo, or methyl.

In some embodiments, compounds of Formula II, or a stereoisomer, tautomer, or pharmaceutically acceptable salt thereof are provided, wherein Y is selected from a group consisting of substituted cyclohexyl, cyclohexenyl, piperidinyl, and piperazinyl; $R_1$ is selected from the group consisting of hydrogen, —$NH_2$ halo, $C_{1-4}$ alkyl, $C_{3-4}$ cycloalkyl, and —CN; $R_{12}$ independently at each occurrence is selected from the group consisting of hydrogen, halo, $C_{1-4}$ alkyl, and amino; and $R_5$ is selected from the group consisting of substituted or unsubstituted phenyl, cyclohexyl, cyclopentyl, thiazole, pyridyl, pyrimidyl and pyrazinyl, wherein the $R_5$ group may be substituted with up to three substituents selected from halo, hydrogen, methyl, substituted aminocarbonyl and alkoxy.

In a representative embodiment, compounds of Formulas I or II, or a stereoisomer, tautomer, or pharmaceutically acceptable salt thereof are provided, selected from the group consisting of N-(4-((1R,3R,4R,5S)-3-amino-4-hydroxy-5-methylcyclohexyl)pyridin-3-yl)-6-(2,6-difluorophenyl)-5-fluoropicolinamide, N-(4-((1R,3S,5S)-3-amino-5-methylcyclohexyl)pyridin-3-yl)-6-(2,6-difluorophenyl)-5-fluoropicolinamide. N-(4-((3R,4R,5S)-3-amino-4-hydroxy-5-methylpiperidin-1-yl)pyridin-3-yl)-6-(2,6-difluorophenyl)-5-fluoropicolinamide, 3-amino-N-(4-((3R,4R,5S)-3-amino-4-hydroxy-5-methylpiperidin-1-yl)pyridin-3-yl)-6-(2,6-difluorophenyl)-5-fluoropicolinamide, and N-(4-((1R,3S)-3-aminocyclohexyl)pyridin-3-yl)-6-(2,6-difluorophenyl)-5-fluoropicolinamide, and 3-amino-N-(4-((1R,3S)-3-aminocyclohexyl)pyridin-3-yl)-6-(2,6-difluorophenyl)-5-fluoropicolinamide.

In other aspects, the present invention provides methods for treating Provirus Integration of Maloney Kinase (PIM Kinase) related disorders in a human or animal subject in need of such treatment comprising administering to said subject an amount of a compound of Formula I or II effective to inhibit PIM activity in the subject.

In other aspects, the present invention provides methods for treating PIM related disorders in a human or animal subject in need of such treatment comprising administering to said subject an amount of a compound of Formula I or II effective to reduce or prevent tumor growth in the subject.

In yet other aspects, the present invention provides methods for treating PIM related disorders in a human or animal subject in need of such treatment comprising administering to said subject an amount of a compound of Formula I or II effective to reduce or prevent tumor growth in the subject in combination with at least one additional agent for the treatment of cancer.

In yet other aspects, the present invention provides therapeutic compositions comprising at least one compound of Formula I or II in combination with one or more additional agents for the treatment of cancer, as are commonly employed in cancer therapy.

The compounds of the invention are useful in the treatment of cancers, including hematopoietic malignancies, carcinomas (e.g., of the lungs, liver, pancreas, ovaries, thyroid, bladder or colon), melanoma, myeloid disorders (e.g., myeloid leukemia, multiple myeloma and erythroleukemia), adenomas (e.g., villous colon adenoma), sarcomas (e.g., osteosarcoma), autoimmune diseases, allergic reactions and in organ transplantation rejection syndromes.

The invention further provides compositions, methods of use, and methods of manufacture as described in the detailed description of the invention.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
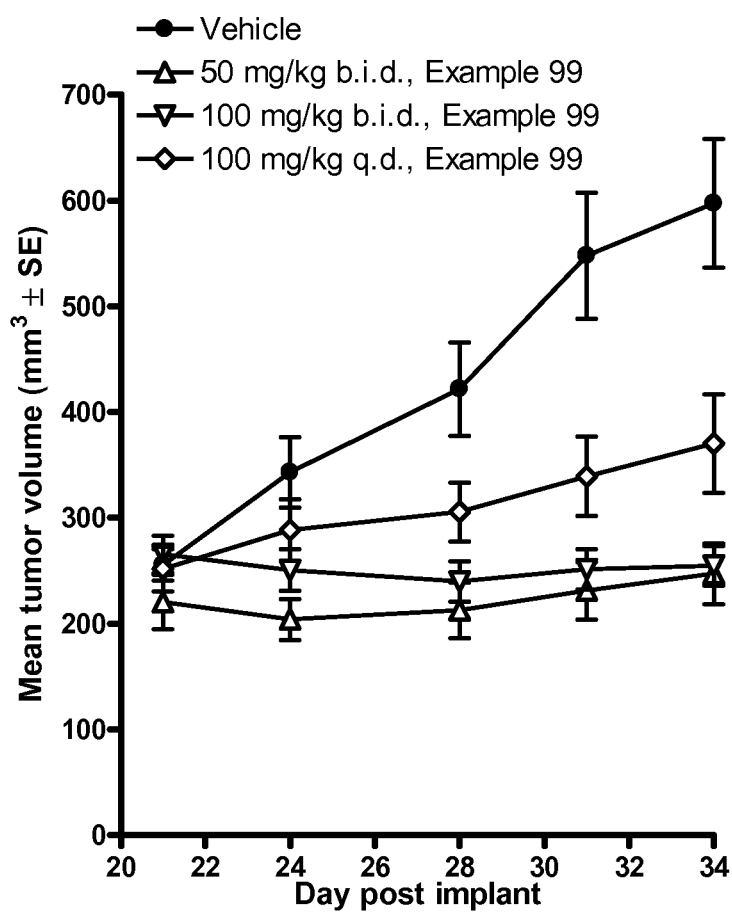
FIG. 1 is a graph showing the efficacy of the compound of Example 99 from an evaluation in the KMS11-luc xenograft model, as described in Example 144.

In accordance with one aspect of the present invention, new compounds, and their stereoisomers, tautomers and pharmaceutically acceptable salts, are provided of the Formula I:

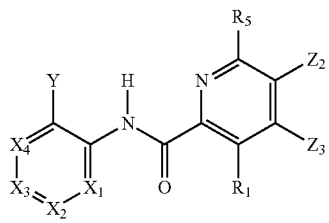

I

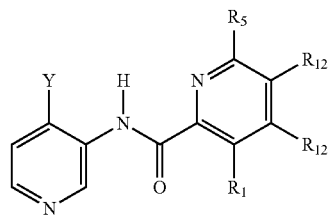

II wherein, $X_1, X_2, X_3$ and $X_4$ are independently selected from $CR_2$ and N; provided that at least one but not more than two of $X_1$, $X_2$, $X_3$ and $X_4$ are N;

Y is selected from a group consisting of cycloalkyl, partially unsaturated cycloalkyl, and heterocycloalkyl, wherein each member of said group may be substituted with up to four substituents;

$Z_2$ and $Z_3$ are independently selected from $CR_{12}$ and N; provided that not more than one of $Z_2$ and $Z_3$ can be N;

$R_1$ is selected from the group consisting of hydrogen, —$NHR_3$ halo, hydroxyl, alkyl, cyano, and nitro;

$R_2$ and $R_{12}$ independently at each occurrence are selected from the group consisting of hydrogen, halo, hydroxyl, nitro, cyano, $SO_3H$ and substituted or unsubstituted alkyl, alkenyl, alkynyl, alkoxy, amino, cycloalkyl, hetero cycloalkyl, and partially saturated cycloalkyl;

$R_3$ is selected from the group consisting of hydrogen, —CO—$R_4$ and substituted or unsubstituted alkyl, cycloalkyl, heterocyclyl, aryl and heteroaryl;

$R_4$ is selected from the group consisting of alkyl, substituted alkyl, alkoxy, substituted alkoxy, amino, substituted amino, and alkylamino; and $R_5$ represents a group selected from substituted or unsubstituted aryl, $C_3$-$C_7$ cycloalkyl, heteroaryl, partially unsaturated cycloalkyl and alkyl, wherein each said substituted $R_5$ group may be substituted with up to four substituents selected from halo, cyano, amino, $C_{1-4}$ alkyl, $C_{3-6}$ cycloalkyl, alkoxy, nitro, carboxy, carbonyl, carboalkoxy, aminocarboxy, substituted aminocarbonyl, aminosulfonyl, substituted aminosulfonyl and alkoxyalkyl.

In some embodiments, new compounds of Formula I, or a stereoisomer, tautomer, or pharmaceutically acceptable salt thereof are provided wherein $X_2$ is N and $X_1$, $X_3$ and $X_4$ are $CR_2$.

In some embodiments, new compounds of Formula I, or a stereoisomer, tautomer, or pharmaceutically acceptable salt thereof are provided wherein $R_2$ is selected from hydrogen, methyl, ethyl, halo, cyano.

In some embodiments, compounds of formula I, or a stereoisomer, tautomer, or pharmaceutically acceptable salt thereof are provided wherein $Z_2$ and $Z_3$ are $CR_{12}$.

In some embodiments, compounds of formula I, or a stereoisomer, tautomer, or pharmaceutically acceptable salt thereof are provided wherein $R_{12}$ is selected from hydrogen, halo, methyl, ethyl and cyano.

In other embodiments, new compounds, and their stereoisomers, tautomers and pharmaceutically acceptable salts, are provided of the Formula II wherein, Y is selected from a group consisting of cyclohexyl, partially unsaturated cyclohexyl, and heterocyclo-$C_5$-alkyl, wherein each member of said group may be substituted with up to four substituents;

$R_1$ is selected from the group consisting of hydrogen, —$NHR_3$ halo, hydroxyl, alkyl, $C_{3-4}$ cycloalkyl, cyano, and nitro;

$R_{12}$ independently at each occurrence is selected from the group consisting of hydrogen, halo, hydroxyl, amino, nitro, cyano, $SO_3H$ and substituted or unsubstituted alkyl, alkenyl, alkynyl, alkoxy, amino, cycloalkyl, hetero cycloalkyl, and partially saturated cycloalkyl;

$R_3$ is selected from the group consisting of hydrogen, —CO—$R_4$ and substituted or unsubstituted alkyl, cycloalkyl, heterocyclyl, aryl and heteroaryl;

$R_4$ is selected from the group consisting of alkyl, substituted alkyl, alkoxy, substituted alkoxy, amino, substituted amino, and alkylamino; and $R_5$ is represents a group selected from hydrogen and substituted or unsubstituted alkyl, $C_6$-cycloalkyl, aryl and heteroaryl.

In some embodiments, compounds of Formulas I or II, or a stereoisomer, tautomer, or pharmaceutically acceptable salt thereof are provided wherein Y is selected from a group consisting of substituted or unsubstituted cycloalkyl, cycloalkenyl, piperidinyl and piperazinyl, wherein each member of said group is substituted with up to four substituents. In some embodiments, compounds of Formulas I or II, or a stereoisomer, tautomer, or pharmaceutically acceptable salt thereof are provided wherein Y is selected from a group consisting of substituted or unsubstituted cyclohexyl, cyclohexynyl, and piperidinyl, wherein each member of said group is substituted with up to four substituents. In some embodiments, Y is substituted with up to four substituents selected from hydrogen, cyano, nitro, halo, hydroxyl, amino, alkoxy, substituted amino, $C_{1-4}$ alkyl, $C_{1-4}$ halo alkyl and $C_{3-4}$ cycloalkyl. In yet other embodiments, Y is substituted with up to four substituents selected from methyl, propyl, i-propyl, ethyl, hydroxyl, amino, halo, monohalo $C_{1-3}$ alkyl, trihalo $C_{1-3}$ alkyl and dihalo $C_{1-3}$ alkyl.

In some embodiments, compounds of Formulas I or II, or a stereoisomer, tautomer, or pharmaceutically acceptable salt thereof are provided wherein $R_1$ is hydrogen, amino or fluoro. In one embodiment are provided compounds of Formula II selected from Table I or Table II.

In some embodiments, compounds of Formulas I or II, or a stereoisomer, tautomer, or pharmaceutically acceptable salt thereof are provided wherein $R_5$ is selected from substituted or unsubstituted aryl, $C_5$-$C_6$ cycloalkyl, heteroaryl, partially unsaturated $C_5$-$C_6$ cycloalkyl and $C_1$-$C_4$ alkyl, wherein each said group can be substituted with up to four substituents selected from halo, cyano, amino, $C_{1-4}$ alkyl, $C_{3-5}$ cycloalkyl, alkoxy, nitro, carboxy, carbonyl, carboalkoxy, aminocarboxy, substituted aminocarbonyl, aminosulfonyl, substituted aminosulfonyl and alkoxyalkyl. In some embodiments, compounds of Formulas I or II, or a stereoisomer, tautomer, or pharmaceutically acceptable salt thereof are provided wherein $R_5$ is substituted or unsubstituted phenyl, wherein the phenyl group can be substituted with up to four substituents selected from hydrogen, cyano, nitro, halo, hydroxyl, amino, alkoxy, substituted amino, $C_{1-4}$ alkyl, $C_{1-4}$ halo alkyl and $C_{3-4}$ cycloalkyl. In some embodiments, compounds of Formulas I or II, or a stereoisomer, tautomer, or pharmaceutically acceptable salt thereof are provided wherein $R_5$ is 2,6-difluororphenyl.

In some embodiments, compounds of Formulas I or II, or a stereoisomer, tautomer, or pharmaceutically acceptable salt thereof are provided wherein $R_{12}$ is selected from hydrogen, halo, methyl, ethyl and cyano. In some embodiments, compounds of Formulas I or II, or a stereoisomer, tautomer, or pharmaceutically acceptable salt thereof are provided wherein Y is selected from the group consisting of substituted or unsubstituted cyclohexyl, cyclohexenyl, piperidinyl, piperazinyl, wherein said the Y group may be substituted with up to three substituents selected from methyl, ethyl, hydroxyl, amino, and methoxy; $R_1$ is selected from the group consisting of hydrogen, and amino; and $R_{12}$ independently are each occurrence represents hydrogen, halo, or methyl.

In some embodiments, compounds of Formula II, or a stereoisomer, tautomer, or pharmaceutically acceptable salt thereof are provided, wherein Y is selected from a group consisting of substituted cyclohexyl, cyclohexenyl, piperidinyl, and piperazinyl; $R_1$ is selected from the group consisting of hydrogen, —$NH_2$ halo, $C_{1-4}$ alkyl, $C_{3-4}$ cycloalkyl, and —CN; $R_{12}$ independently at each occurrence is selected from the group consisting of hydrogen, halo, $C_{1-4}$ alkyl, and amino; and $R_5$ is selected from the group consisting of substituted or unsubstituted phenyl, cyclohexyl, cyclopentyl, thiazole, pyridyl, pyrimidyl and pyrazinyl, wherein the $R_5$ group may be substituted with up to three substituents selected from halo, hydrogen, methyl, substituted aminocarbonyl and alkoxy.

A preferred embodiment of the present invention is a compound of Formula (II), wherein Y is cyclohexyl, substituted with one to three substitutents, said substituents preferably selected from hydroxyl, amino, $C_{1-4}$ alkyl or $C_{1-4}$ halo alkyl, and more preferably, selected from methyl, hydroxyl, amino, and $CF_3$, and most preferably from methyl, amino, and hydroxy; $R_1$ is hydrogen, $NH_2$, or halo (preferably, $R_1$ is hydrogen, amino or fluoro, more preferably, $R_1$ is hydrogen); $R_{12}$ are each independently hydrogen or halo (preferably, each $R_{12}$ is hydrogen, chloro or fluoro); $R_5$ is cyclohexyl, phenyl, or pyridyl, wherein said cyclohexyl, said phenyl and said pyridyl are each independently substituted with up to three substituents selected form halo, hydroxyl, $C_{1-4}$ alkyl, and $C_{1-4}$ alkoxy (preferably, $R_5$ is pyridyl or phenyl each independently substituted with up to three substitutents selected form halo, hydroxyl, $C_{1-4}$ alkyl or $C_{1-4}$ alkoxy, more preferably, $R_5$ is phenyl substituted with up to three substituents selected form halo, hydroxyl, $C_{1-4}$ alkoxy and $C_{1-4}$ alkyl, most preferably, phenyl substituted with up to three substitutents selected from fluoro, hydroxyl, methyl, ethyl, methoxy, or propoxy, most preferably, $R_5$ is 2,6-difluorophenyl.

Yet another preferred embodiment of the present invention provides a compound of Formula II, wherein Y is piperidinyl substituted with methyl, hydroxyl, and amino; $R_1$ is hydrogen, $NH_2$, or fluoro; $R_{12}$ independently at each occurrence is selected from the group consisting of hydrogen, and halo; and $R_5$ is pyridyl, fluoro pyridyl, cyclohexyl, or phenyl, wherein said phenyl is substituted with up to three substituents selected from fluoro, hydroxyl, and methyl, preferably $R_5$ being difluoro phenyl. In a further preferred embodiment preferably Y is 3-amino-4-hydroxy-5-methylpiperidin-1-yl; $R_1$ is hydrogen; and $R_5$ is 2,6-difluoro phenyl.

In a representative embodiment, preferred compounds of Formulas I or II, or a stereoisomer, tautomer, or pharmaceutically acceptable salt thereof are selected from the group consisting of N-(4-((3S,5S)-3-amino-5-methylcyclohexyl)pyridin-3-yl)-6-(2,6-difluorophenyl)-5-fluoropicolinamide; 3-amino-N-(4-((1R,3R,4S,5S)-3-amino-4-hydroxy-5-methylcyclohexyl)pyridin-3-yl)-6-(2,6-difluorophenyl)picolinamide; N-(4-((3R,4R,5S)-3-amino-4-hydroxy-5-methylpiperidin-1-yl)pyridin-3-yl)-6-(2,6-difluorophenyl)-5-fluoropicolinamide; N-(4-((3R,4R,5S)-3-amino-4-hydroxy-5-methylpiperidin-1-yl)pyridin-3-yl)-6-(2,6-difluorophenyl)-5-fluoropicolinamide; 3-amino-N-(4-((3R,4R,5S)-3-amino-4-hydroxy-5-methylpiperidin-1-yl)pyridin-3-yl)-6-(2,6-difluorophenyl)-5-fluoropicolinamide; N-(4-((3R,4R,5S)-3-amino-4-hydroxy-5-methylpiperidin-1-yl)pyridin-3-yl)-6-(2,6-difluoro-3-methylphenyl)-5-fluoropicolinamide; 3-amino-N-(4-((1R,3S)-3-aminocyclohexyl)pyridin-3-yl)-6-(2,6-difluorophenyl)-5-fluoropicolinamide; N-(4-((3S)-3-aminocyclohexyl)pyridin-3-yl)-6-(2,6-difluorophenyl)-5-fluoropicolinamide; N-(4-((1R,3R,4R,5S)-3-amino-4-hydroxy-5-methylcyclohexyl)pyridin-3-yl)-6-(2,6-difluorophenyl)-5-fluoropicolinamide; N-(4-((1R,3S,5S)-3-amino-5-methylcyclohexyl)pyridin-3-yl)-6-(2,6-difluorophenyl)-5-fluoropicolinamide); N-(4-((3R,4R,5S)-3-amino-4-hydroxy-5-methylpiperidin-1-yl)pyridin-3-yl)-6-(2,6-difluorophenyl)-5-fluoropicolinamide; N-(4-((1R,3S)-3-aminocyclohexyl)-pyridin-3-yl)-6-(2,6-difluorophenyl)-5-fluoropicolinamide; 3-amino-N-(4-((3R,4R,5S)-3-amino-4-hydroxy-5-methylpiperidin-1-yl)pyridin-3-yl)-6-(2,6-difluorophenyl)-5-fluoropicolinamide; and 3-amino-N-(4-((1R,3S)-3-aminocyclohexyl)pyridin-3-yl)-6-(2,6-difluorophenyl)-5-fluoropicolinamide.

In other aspects, the present invention provides methods for treating Provirus Integration of Maloney Kinase (PIM Kinase) related disorders in a human or animal subject in need of such treatment comprising administering to said subject an amount of a compound of Formula I or II effective to inhibit PIM activity in the subject. A preferred embodiment of the present invention provides a method for treating a condition by modulation of Provirus Integration of Maloney Kinase (PIM Kinase) activity comprising administering to a patient in need of such treatment an effective amount of a compound of Formula I.

In other aspects, the present invention provides methods for treating PIM related disorders in a human or animal subject in need of such treatment comprising administering to said subject an amount of a compound of Formula I or II effective to reduce or prevent tumor growth in the subject. In yet other aspects, the present invention provides methods for treating PIM related disorders in a human or animal subject in need of such treatment comprising administering to said subject an amount of a compound of Formula I or II effective to reduce or prevent tumor growth in the subject in combination with at least one additional agent for the treatment of cancer.

In yet other aspect, the present invention provides therapeutic compositions comprising at least one compound of Formula I or II in combination with one or more additional agents for the treatment of cancer, as are commonly employed in cancer therapy. The present invention thus provides a pharmaceutical composition comprising a compound of Formula I or Formula II. A preferred embodiment of this aspect provides a pharmaceutical composition comprising a compound selected from N-(4-((3S,5S)-3-amino-5-methylcyclohexyl)pyridin-3-yl)-6-(2,6-difluorophenyl)-5-fluoropicolinamide;

3-amino-N-(4-((1R,3R,4S,5S)-3-amino-4-hydroxy-5-methylcyclohexyl)pyridin-3-yl)-6-(2,6-difluorophenyl)picolinamide; N-(4-((3R,4R,5S)-3-amino-4-hydroxy-5-methylpiperidin-1-yl)pyridin-3-yl)-6-(2,6-difluorophenyl)-5-fluoropicolinamide; 3-amino-N-(4-((1R,3S)-3-aminocyclohexyl)pyridin-3-yl)-6-(2,6-difluorophenyl)-5-fluoropicolinamide; N-(4-((3S)-3-aminocyclohexyl)pyridin-3-yl)-6-(2,6-difluorophenyl)-5-fluoropicolinamide; N-(4-((1R,3R,4R,5S)-3-amino-4-hydroxy-5-methylcyclohexyl)pyridin-3-yl)-6-(2,6-difluorophenyl)-5-fluoropicolinamide; N-(4-((1R,3S,5S)-3-amino-5-methylcyclohexyl)pyridin-3-yl)-6-(2,6-difluorophenyl)-5-fluoropicolinamide); N-(4-((3R,4R,5S)-3-amino-4-hydroxy-5-methylpiperidin-1-yl)pyridin-3-yl)-6-(2,6-difluorophenyl)-5-fluoropicolinamide; N-(4-((1R,3S)-3-aminocyclohexyl)-pyridin-3-yl)-6-(2,6-difluorophenyl)-5-fluoropicolinamide; 3-amino-N-(4-((3R,4R,5S)-3-amino-4-hydroxy-5-methylpiperidin-1-yl)pyridin-3-yl)-6-(2,6-difluorophenyl)-5-fluoropicolinamide; 3-amino-N-(4-((1R,3S)-3-aminocyclohexyl)pyridin-3-yl)-6-(2,6-difluorophenyl)-5-fluoropicolinamide; N-(4-((3R,4R,5S)-3-amino-4-hydroxy-5-methylpiperidin-1-yl)pyridin-3-yl)-6-(2,6-difluorophenyl)-5-fluoropicolinamide; 3-amino-N-(4-((3R,4R,5S)-3-amino-4-hydroxy-5-methylpiperidin-1-yl)pyridin-3-yl)-6-(2,6-difluorophenyl)-5-fluoropicolinamide; and N-(4-((3R,4R,5S)-3-amino-4-hydroxy-5-methylpiperidin-1-yl)pyridin-3-yl)-6-(2,6-difluoro-3-methylphenyl)-5-fluoropicolinamide. Another preferred embodiment provides a pharmaceutical composition further comprising an additional agent for the treatment of cancer, wherein preferably the additional agent is selected from irinotecan, topotecan, gemcitabine, 5-fluorouracil, leucovorin carboplatin, cisplatin, taxanes, tezacitabine, cyclophosphamide, vinca alkaloids, imatinib (Gleevec), anthracyclines, rituximab, and trastuzumab.

The compounds of the invention are useful in the treatment of cancers, including hematopoietic malignancies, carcinomas (e.g., of the lungs, liver, pancreas, ovaries, thyroid, bladder or colon), melanoma, myeloid disorders (e.g., myeloid leukemia, multiple myeloma and erythroleukemia), adenomas (e.g., villous colon adenoma), sarcomas (e.g., osteosarcoma), autoimmune diseases, allergic reactions and in organ transplantation rejection syndromes.

In yet another aspect of the present invention is provided a use of a compound of Formula I or Formula II for preparing a medicament for treating a condition by modulation of Provirus Integration of Maloney Kinase (PIM Kinase) activity. In a preferred embodiment of this aspect of the invention the condition is a cancer selected from carcinoma of the lungs, pancreas, thyroid, ovarian, bladder, breast, prostate, or colon, melanoma, myeloid leukemia, multiple myeloma and erythro leukemia, villous colon adenoma, and osteosarcoma.

In another aspect, the present invention relates to methods of inhibiting the activity of at least one kinase selected from the group consisting of Pim1, Pim2 and Pim3, in a subject, or treating a biological condition mediated by at least one of Pim1, Pim2 and Pim3, in a human or animal subject in need of such treatment, comprising administering to the subject at least one compound of Formula I or II in an amount effective to inhibit the kinase in the subject. The therapeutic compounds are useful for treating patients with a need for such inhibitors (e.g., those suffering from cancer mediated by abnormal serine/threonine kinase receptor signaling).

Definitions

"PIM inhibitor" is used herein to refer to a compound that exhibits an $IC_{50}$ with respect to PIM Kinase activity of no more than about 100 µM and more typically not more than about 50 µM, as measured in the PIM depletion assays described hereinbelow.

The phrase "alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$—CH(CH$_3$)$_2$, —CH(CH$_3$)CH(CH$_3$)CH(CH$_3$)$_2$, —CH(CH$_2$CH$_3$)CH(CH$_3$)CH(CH$_3$)(CH$_2$CH$_3$), and others. Thus the phrase alkyl groups includes primary alkyl groups, secondary alkyl groups, and tertiary alkyl groups. Preferred alkyl groups include straight and branched chain alkyl groups having 1 to 12 carbon atoms. A preferred "alkyl" definition refers to $C_{1-4}$ straight chain alkyl groups such as methyl, ethyl, n-propyl, and n-butyl. The preferred alkyl definition also includes $C_{3-5}$ branched alkyl groups, including CH(CH$_3$)$_2$, CH$_2$CH(CH$_3$)$_2$, CH(CH$_3$)CH$_2$CH$_3$, C(CH$_3$)$_3$, CH(CH$_3$)CH$_2$CH$_2$CH$_3$, CH(CH$_3$)CH(CH$_3$)$_2$, CH$_2$CH(CH$_3$)CH$_2$CH$_3$, CH$_2$CH$_2$CH(CH$_3$)$_2$, and CH(CH$_2$CH$_3$)$_2$, etc.

The term "alkenyl" refers to alkyl groups as defined above, wherein there is at least one point of unsaturation, i.e., wherein two adjacent carbon atoms are attached by a double bond. The term "alkynyl" refers to alkyl groups wherein two adjacent carbon atoms are attached by a triple bond. The term "alkoxy" refers to —OR, wherein R is alkyl.

As used herein, the term "halogen" or "halo" refers to chloro, bromo, fluoro and iodo groups. "Haloalkyl" refers to an alkyl radical substituted with one or more halogen atoms. The term "haloalkyl" thus includes monohalo alkyl, dihalo alkyl, trihalo alkyl and the like. Representative monohalo alkyl groups include —CH$_2$F, —CH$_2$Cl, —CH$_2$CH$_2$F, —CH$_2$CH$_2$Cl, —CH(F)CH$_3$, —CH(Cl)CH$_3$; representative dihalo alkyl groups include CHCl$_2$, —CHF$_2$, —CCl$_2$CH$_3$, —CH(Cl)CH$_2$Cl, —CH$_2$CHCl$_2$, —CH$_2$CHF$_2$; representative trihalo alkyl groups include —CCl$_3$, —CF$_3$, —CCl$_2$CH$_2$Cl, —CF$_2$CH$_2$F, —CH(Cl)CHCl$_2$, —CH(F)CHF$_2$; and representative perhalo alkyl groups include —CCl$_3$, —CF$_3$, —CCl$_2$CCl$_3$, —CF$_2$CF$_3$.

"Amino" refers herein to the group —NH$_2$. The term "alkylamino" refers herein to the group —NRR' where R and R' are each independently selected from hydrogen or a lower alkyl. The term "arylamino" refers herein to the group —NRR' where R is aryl and R' is hydrogen, a lower alkyl, or an aryl. The term "aralkylamino" refers herein to the group —NRR' where R is a lower aralkyl and R' is hydrogen, a loweralkyl, an aryl, or a loweraralkyl. The term cyano refers to the group —CN. The term nitro refers to the group —NO$_2$.

The term "alkoxyalkyl" refers to the group -alk$_1$-O-alk$_2$ where alk$_1$ is alkyl or alkenyl, and alk$_2$ is alkyl or alkenyl. The term "loweralkoxyalkyl" refers to an alkoxyalkyl where alk$_1$ is loweralkyl or loweralkenyl, and alk$_2$ is loweralkyl or loweralkenyl. The term "aryloxyalkyl" refers to the group -alkyl-O-aryl. The term "aralkoxyalkyl" refers to the group -alkylenyl-O-aralkyl, where aralkyl is a loweraralkyl.

The term "aminocarbonyl" refers herein to the group —C(O)—NH$_2$. "Substituted aminocarbonyl" refers herein to the group —C(O)—NRR' where R is loweralkyl and R' is hydrogen or a loweralkyl. In some embodiments, R and R', together with the N atom attached to them may be taken together to form a "heterocycloalkylcarbonyl" group. The term "arylaminocarbonyl" refers herein to the group —C(O)—NRR' where R is an aryl and R' is hydrogen, loweralkyl or aryl. "aralkylaminocarbonyl" refers herein to the group —C(O)—NRR' where R is loweraralkyl and R' is hydrogen, loweralkyl, aryl, or loweraralkyl.

"Aminosulfonyl" refers herein to the group —S(O)$_2$—NH$_2$. "Substituted aminosulfonyl" refers herein to the group —S(O)$_2$—NRR' where R is loweralkyl and R' is hydrogen or a loweralkyl. The term "aralkylaminosulfonlyaryl" refers herein to the group -aryl-S(O)$_2$—NH-aralkyl, where the aralkyl is loweraralkyl.

"Carbonyl" refers to the divalent group —C(O)—. "Carboxy" refers to —C(=O)—OH. "Alkoxycarbonyl" refers to ester —C(=O)—OR wherein R is alkyl. "Loweralkoxycarbonyl" refers to ester —C(=O)—OR wherein R is loweralkyl. "Cycloalkyloxycarbonyl" refers to —C(=O)—OR wherein R is cycloalkyl.

"Cycloalkyl" refers to a mono- or polycyclic, carbocyclic alkyl substituent. Carbocycloalkyl groups are cycloalkyl groups in which all ring atoms are carbon. Typical cycloalkyl substituents have from 3 to 8 backbone (i.e., ring) atoms in which each backbone atom is either carbon or a heteroatom. The term "heterocycloalkyl" refers herein to cycloalkyl substituents that have from 1 to 5, and more typically from 1 to 4 heteroatoms in the ring structure. Suitable heteroatoms employed in compounds of the present invention are nitrogen, oxygen, and sulfur. Representative heterocycloalkyl moieties include, for example, morpholino, piperazinyl, piperidinyl and the like. Carbocycloalkyl groups are cycloalkyl groups in which all ring atoms are carbon. When used in connection with cycloalkyl substituents, the term "polycyclic" refers herein to fused and non-fused alkyl cyclic structures. The term "partially unsaturated cycloalkyl", "partially saturated cycloalkyl", and "cycloalkenyl" all refer to a cycloalkyl group wherein there is at least one point of unsaturation, i.e., wherein to adjacent ring atoms are connected by a double bond or a triple bond. Illustrative examples include cyclohexynyl, cyclohexynyl, cyclopropenyl, cyclobutynyl, and the like.

The terms "substituted heterocycle", "heterocyclic group" or "heterocycle" as used herein refers to any 3- or 4-membered ring containing a heteroatom selected from nitrogen, oxygen, and sulfur or a 5- or 6-membered ring containing from one to three heteroatoms selected from the group consisting of nitrogen, oxygen, or sulfur; wherein the 5-membered ring has 0-2 double bonds and the 6-membered ring has 0-3 double bonds; wherein the nitrogen and sulfur atom maybe optionally oxidized; wherein the nitrogen and sulfur heteroatoms may be optionally quarternized; and including any bicyclic group in which any of the above heterocyclic rings is fused to a benzene ring or another 5- or 6-membered heterocyclic ring independently defined above. The term or "heterocycloalkyl" as used herein refers to a 5- or 6-membered ring containing from one to three heteroatoms selected from the group consisting of nitrogen, oxygen, or sulfur, wherein the ring has no double bonds. For example, the term heterocyclo-C$_5$-alkyl refers to a 6-membered ring containing 5 carbon atoms and a heteroatom, such as N. The term "heterocycle" thus includes rings in which nitrogen is the heteroatom as well as partially and fully-saturated rings. Preferred heterocycles include, for example: diazapinyl, pyrryl, pyrrolinyl, pyrrolidinyl, pyrazolyl, pyrazolinyl, pyrazolidinyl, imidazoyl, imidazolinyl, imidazolidinyl, pyridyl, piperidinyl, pyrazinyl, piperazinyl, N-methyl piperazinyl, azetidinyl, N-methylazetidinyl, pyrimidinyl, pyridazinyl, oxazolyl, oxazolidinyl, isoxazolyl, isoazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, triazolyl and benzothienyl.

Heterocyclic moieties can be unsubstituted or monosubstituted or disubstituted or trisubstituted with various substituents independently selected from hydroxy, halo, oxo (C=O), alkylimino (RN=, wherein R is a loweralkyl or loweralkoxy group), amino, alkylamino, dialkylamino, acylaminoalkyl, alkoxy, thioalkoxy, polyalkoxy, loweralkyl, cycloalkyl or haloalkyl.

The heterocyclic groups may be attached at various positions as will be apparent to those having skill in the organic and medicinal chemistry arts in conjunction with the disclosure herein.

Representative heterocyclics include, for example, imidazolyl, pyridyl, piperazinyl, piperidinyl, azetidinyl, thiazolyl, furanyl, triazolyl benzimidazolyl, benzothiazolyl, benzoxazolyl, quinolinyl, isoquinolinyl, quinazolinyl, quinoxalinyl, phthalazinyl, indolyl, naphthpyridinyl, indazolyl, and quinolizinyl.

"Aryl" refers to optionally substituted monocyclic and polycyclic aromatic groups having from 3 to 14 backbone carbon or hetero atoms, and includes both carbocyclic aryl groups and heterocyclic aryl groups. Carbocyclic aryl groups are aryl groups in which all ring atoms in the aromatic ring are carbon. The term "heteroaryl" refers herein to aryl groups having from 1 to 4 heteroatoms as ring atoms in an aromatic ring with the remainder of the ring atoms being carbon atoms. When used in connection with aryl substituents, the term "polycyclic aryl" refers herein to fused and non-fused cyclic structures in which at least one cyclic structure is aromatic, such as, for example, benzodioxozolo (which has a heterocyclic structure fused to a phenyl group, i.e., and the like. Exemplary aryl moieties employed as substituents in compounds of the present invention include phenyl, pyridyl, pyrimidinyl, thiazolyl, indolyl, imidazolyl, oxadiazolyl, tetrazolyl, pyrazinyl, triazolyl, thiophenyl, furanyl, quinolinyl, purinyl, naphthyl, benzothiazolyl, benzopyridyl, and benzimidazolyl, and the like.

"Optionally substituted" or "substituted" refers to the replacement of one or more hydrogen atoms with a monovalent or divalent radical. Suitable substitution groups include, for example, hydroxy, nitro, amino, imino, cyano, halo, thio, sulfonyl, thioamido, amidino, imidino, oxo, oxamidino, methoxamidino, imidino, guanidino, sulfonamido, carboxyl, formyl, loweralkyl, haloloweralkyl, loweralkylamino, haloloweralkylamino, loweralkoxy, haloloweralkoxy, loweralkoxyalkyl, alkylcarbonyl, aminocarbonyl, arylcarbonyl, aralkylcarbonyl, heteroarylcarbonyl, heteroaralkylcarbonyl, alkylthio, aminoalkyl, cyanoalkyl, aryl and the like.

The substitution group can itself be substituted. The group substituted onto the substitution group can be carboxyl, halo; nitro, amino, cyano, hydroxy, loweralkyl, loweralkoxy, aminocarbonyl, —SR, thioamido, —SO₃H, —SO₂R or cycloalkyl, where R is typically hydrogen, hydroxyl or loweralkyl.

When the substituted substituent includes a straight chain group, the substitution can occur either within the chain (e.g., 2-hydroxypropyl, 2-aminobutyl, and the like) or at the chain terminus (e.g., 2-hydroxyethyl, 3-cyanopropyl, and the like). Substituted substituents can be straight chain, branched or cyclic arrangements of covalently bonded carbon or heteroatoms. It is understood that the above definitions are not intended to include impermissible substitution patterns (e.g., methyl substituted with five fluoro groups or a halogen atom substituted with another halogen atom). Such impermissible substitution patterns are well known to the skilled artisan.

It will also be apparent to those skilled in the art that the compounds of the invention, or their stereoisomers, as well as the pharmaceutically acceptable salts, esters, metabolites and prodrugs of any of them, may be subject to tautomerization and may therefore exist in various tautomeric forms wherein a proton of one atom of a molecule shifts to another atom and the chemical bonds between the atoms of the molecules are consequently rearranged. See, e.g., March, *Advanced Organic Chemistry: Reactions, Mechanisms and Structures*, Fourth Edition, John Wiley & Sons, pages 69-74 (1992). As used herein, the term "tautomer" refers to the compounds produced by the proton shift, and it should be understood that the all tautomeric forms, insofar as they may exist, are included within the invention.

The compounds of the invention, or their tautomers, as well as the pharmaceutically acceptable salts, esters, metabolites and prodrugs of any of them, may comprise asymmetrically substituted carbon atoms. Such asymmetrically substituted carbon atoms can result in the compounds of the invention existing in enantiomers, diastereomers, and other stereoisomeric forms that may be defined, in terms of absolute stereochemistry, such as in (R)- or (S)-forms. As a result, all such possible isomers, individual stereoisomers in their optically pure forms, mixtures thereof, racemic mixtures (or "racemates"), mixtures of diastereomers, as well as single diastereomers of the compounds of the invention are included in the present invention. The terms "S" and "R" configuration, as used herein, are as defined by the IUPAC 1974 RECOMMENDATIONS FOR SECTION E, FUNDAMENTAL STEREOCHEMISTRY, *Pure Appl. Chem.* 45:13-30 (1976). The terms α and β are employed for ring positions of cyclic compounds. The α-side of the reference plane is that side on which the preferred substituent lies at the lower numbered position. Those substituents lying on the opposite side of the reference plane are assigned β descriptor. It should be noted that this usage differs from that for cyclic stereoparents, in which "α" means "below the plane" and denotes absolute configuration. The terms α and β configuration, as used herein, are as defined by the CHEMICAL ABSTRACTS INDEX GUIDE-APPENDIX IV (1987) paragraph 203.

As used herein, the term "pharmaceutically acceptable salts" refers to the nontoxic acid or alkaline earth metal salts of the compounds of Formula I or II. These salts can be prepared in situ during the final isolation and purification of the compounds of Formula I or II, or by separately reacting the base or acid functions with a suitable organic or inorganic acid or base, respectively. Representative salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, pamoate, pectinate, persulfate, 3-phenylproionate, picrate, pivalate, propionate, succinate, sulfate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulfuric acid and phosphoric acid and such organic acids as oxalic acid, maleic acid, methanesulfonic acid, succinic acid and citric acid. Basic addition salts can be prepared in situ during the final isolation and purification of the compounds of formula (I), or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

As used herein, the term "pharmaceutically acceptable ester" refers to esters, which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}F$, $^{32}F$, $^{35}S$, $^{36}Cl$, $^{125}I$ respectively. The invention includes various isotopically labeled compounds as defined herein, for example those into which radioactive isotopes, such as $^3H$, $^{13}C$, and $^{14}C$, are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

It will be apparent to those skilled in the art that the compounds of the invention, or their tautomers, prodrugs and stereoisomers, as well as the pharmaceutically acceptable salts, esters and prodrugs of any of them, may be processed in vivo through metabolism in a human or animal body or cell to produce metabolites. The term "metabolite" as used herein refers to the formula of any derivative produced in a subject after administration of a parent compound. The derivatives may be produced from the parent compound by various biochemical transformations in the subject such as, for example, oxidation, reduction, hydrolysis, or conjugation and include, for example, oxides and demethylated derivatives. The metabolites of a compound of the invention may be identified using routine techniques known in the art. See, e.g., Bertolini, G. et al., *J. Med. Chem.* 40:2011-2016 (1997); Shan, D. et al., *J. Pharm. Sci.* 86(7):765-767; Bagshawe K., *Drug Dev. Res.* 34:220-230 (1995); Bodor, N., *Advances in Drug Res.* 13:224-331 (1984); Bundgaard, H., *Design of Prodrugs* (Elsevier Press 1985); and Larsen, I. K., *Design and application of Prodrugs, Drug Design and Development* (Krogsgaard-Larsen et al., eds., Harwood Academic Publishers, 1991). It should be understood that individual chemical compounds that are metabolites of the compounds of formula I, formula II, or their tautomers, prodrugs and stereoisomers, as well as the pharmaceutically acceptable salts, esters and prodrugs of any of them, are included within the invention.

The term "cancer" refers to cancer diseases that can be beneficially treated by the inhibition of Pim kinase, including, for example, solid cancers, such as carcinomas (e.g., of the lungs, pancreas, thyroid, ovarian, bladder, breast, prostate, or colon), melanomas, myeloid disorders (e.g., myeloid leukemia, multiple myeloma and erythroleukemia), adenomas (e.g., villous colon adenoma) and sarcomas (e.g., osteosarcoma).

Synthetic Methods

The compounds of the invention can be obtained through procedures known to the skilled in the art. For example, as shown in Scheme 1, cyclohexanediones can be converted via monotriflates to the corresponding cyclohexenoneboronate esters which can undergo palladium mediated carbon bond formation with 4-chloro, 3-nitro pyridine to yield nitropyridine substituted cyclohexenones I. Reduction of the enone functionality can yield a cyclohexenol II which upon alcohol protection, nitro and alkene reduction, amide coupling and deprotection can yield cyclohexanol amides III. Cyclohexenol II can also undergo Mitsunobu reaction with phthalimide to yield a protected aminocyclohexene IV. Following nitro and alkene reduction, phthalimide protected aminocyclohexyl pyridyl aniline Va can undergo amide coupling and deprotection, to yield aminocyclohexane amides VI. The corresponding Boc protected aminocyclohexane pyridyl aniline Vb can also be prepared from cyclohexenol II in the following manner: alcohol protection, alkene and nitro reduction, pyridyl amine Cbz protection, silyl ether deprotection, Dess-Martin oxidation to the cyclohexanone, reductive amination with benzylamine, Cbz and Bn deprotection and primary aliphatic amine Boc protection. In the amide products III and VI, if $R_2$ is halo or triflate, the amides III and VI can be further modified by standard modifications to introduce substituted aryls, alkyls and heteroaryls at $R_2$. For example, if $R_2$ is Br, by reaction with boronic acids or organometallic reagents, or conversion to the corresponding boronate ester and reaction with aryl/heteroaryl halides or triflates, a variety of $R_2$ modifications are possible.

Scheme 1.

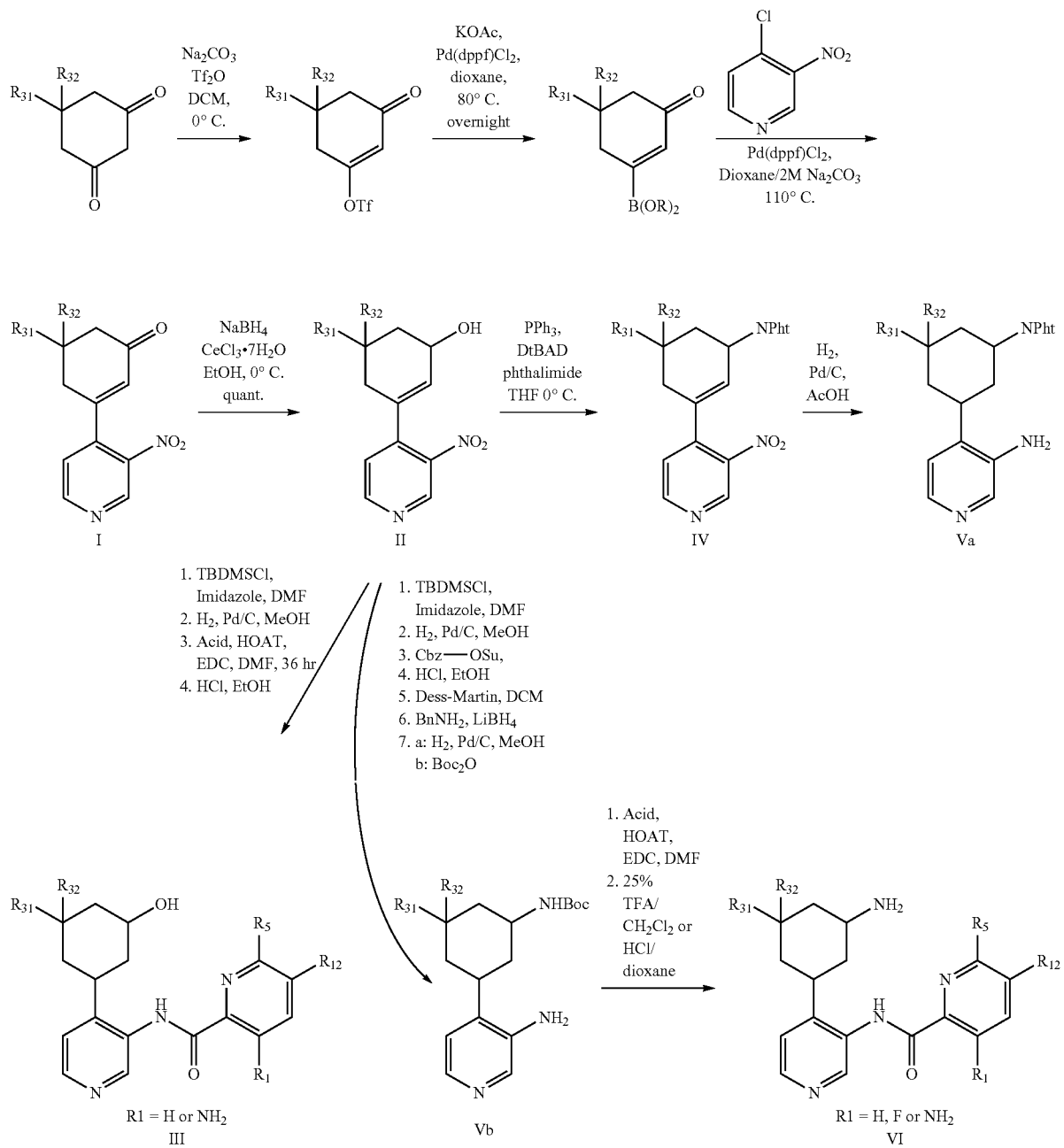

Alternatively, as shown in Scheme 2, cyclohexenol II can be dehydrated yielding a cyclohexadiene which upon epoxidation (via bromohydrin formation and HBr elimination or from mCPBA directly) and azide epoxide opening yields cyclohexenyl azido alcohol VI. Cyclohexenyl azido alcohol VI can be converted to the trans protected amino hydroxy aniline VIIa by azide reduction, alcohol protection and alkene and nitro reduction. Alternatively, the cyclohexenyl azido alcohol VI can be converted to the protected cis amino hydroxy aniline VIIb by azide reduction and Boc protection, alcohol mesylation and intramolecular cyclization to the cis cyclic carbamate, followed by Boc protection and alkene and nitro reduction. The resulting cyclohexylpyridyl anilines VIIa and VIIb can be converted to the corresponding pyridine amides VIIIa and VIIIb by amide coupling, acetate or cyclic carbamate cleavage and Boc deprotection. If $R_2$ is halo or triflate, the amides VIIIa and VIIIb can be further modified by standard modifications to introduce substituted aryls, alkyls and heteroaryls at $R_2$ after amide bond formation and prior to full deprotection. For example, if $R_2$ is Br, by reaction with boronic acids or organometallic reagents, or conversion to the corresponding boronate ester and reaction with aryl/heteroaryl halides or triflates, a variety of $R_2$ modifications are possible.

Scheme 2.
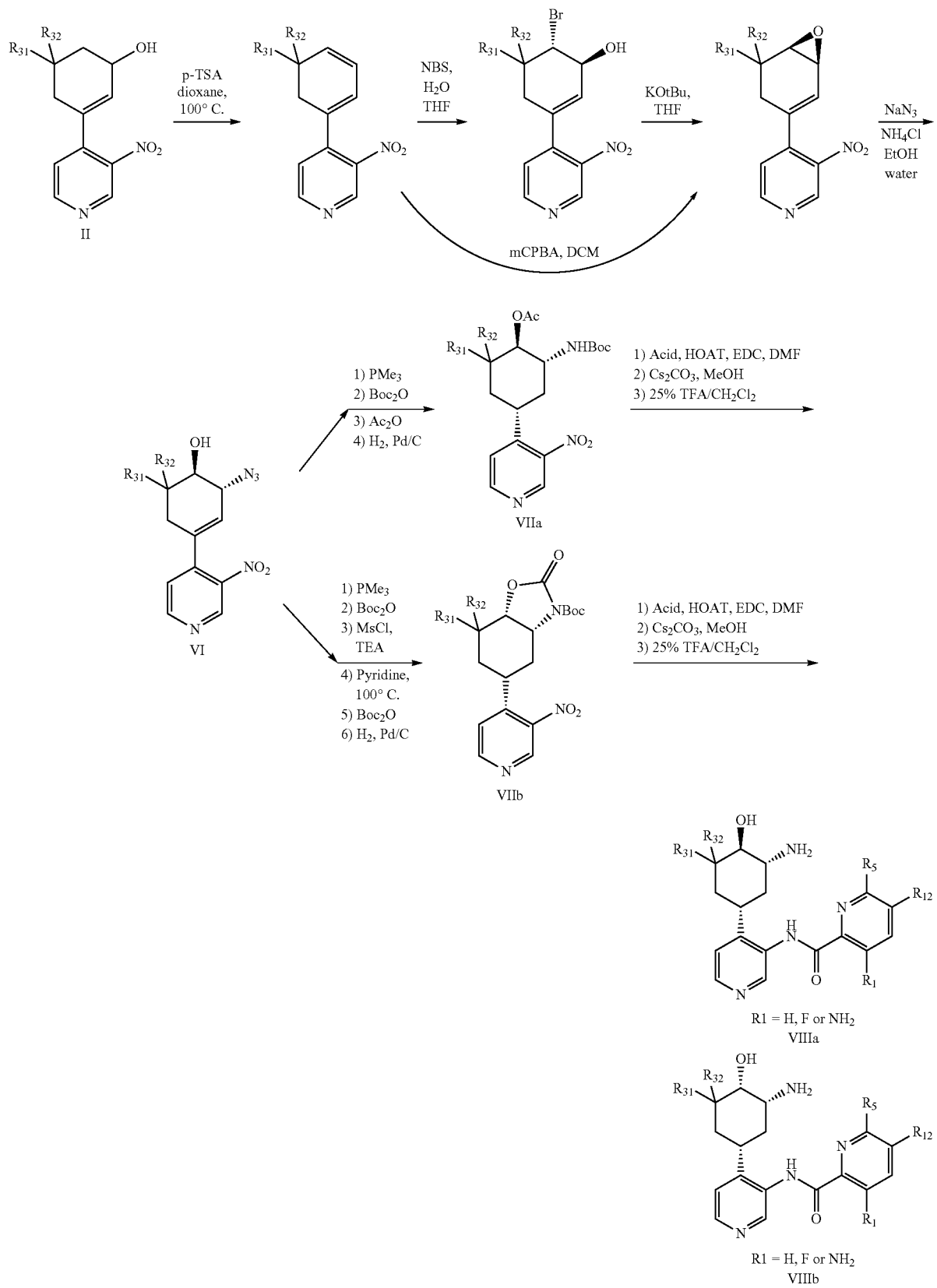

Alternatively, as shown in Scheme 3, trisubstituted 5-alkyl, 4-hydroxy, 3-aminopiperidines can be prepared and modified to yield trisubstituted 5-alkyl, 4-hydroxy, 3-aminopiperidinyl pyridine amides IX as follows. Reaction of Garner's aldehyde with (R)-4-benzyl-3-propionyloxazolidin-2-one followed by TBS protection of the resulting alcohol affords compound X. Reduction of the oxazolidinone followed by introduction of the azide group yields intermediate XI. Deprotection under acidic conditions reveals the corresponding amino alcohol, which upon protection with the Boc group followed by mesylation of the primary alcohol yields intermediate XII. Reduction of the azide affords formation of the piperidine which is subsequently reacted with 4-chloro-3-nitropyridine, reduced to the amine, coupled with the corresponding carboxylic acid and deprotected to provide trisubstituted 5-methyl,4-hydroxy-3-aminopiperidinyl pyridine amides IX. If $R_1$ is halo or triflate, the amide IX can be further modified by standard modifications to introduce substituted aryls, alkyls and heteroaryls at $R_1$ after amide bond formation and prior to full deprotection. For example, if $R_1$ is Br, by reaction with boronic acids or organometallic reagents, or conversion to the corresponding boronate ester and reaction with aryl/heteroaryl halides or triflates, a variety of $R_1$ modifications are possible.

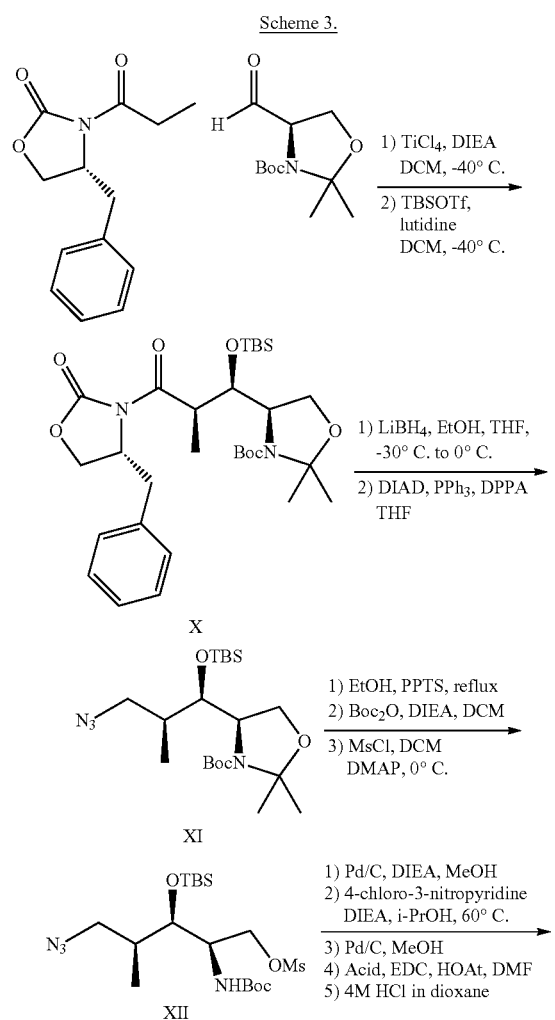

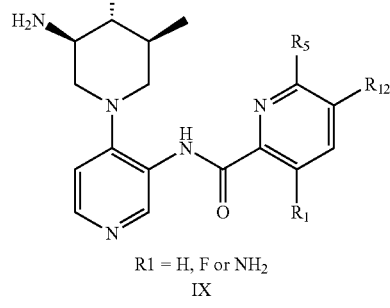

R1 = H, F or NH$_2$

IX

Alternatively, as shown in Scheme 4, trisubstituted 5-methyl, 4-hydroxy, 3-aminopiperidines can also be prepared and modified to yield trisubstituted 5-methyl, 4-hydroxy, 3-aminopiperidinyl amides XIII as follows. Reaction of crotyl boronate esters with SerOBn aldehyde followed by cyclic carbamate formation, alkene oxidative cleavage and reduction yields hydroxyl compound XIV. Benzyl deprotection followed by bistosylation and reaction with p-methoxybenzylamine, and amine deprotection yields piperidine XV. Reaction of substituted piperidine XV with halo nitro substituted arenes or heteroarenes followed by carbamate protection, nitro reduction, amide coupling, cyclic carbamate opening and deprotection yields trisubstituted 5-methyl, 4-hydroxy, 3-aminopiperidinyl amides XIII. If $R_3$ is halo or triflate, the amide XV can be further modified by standard modifications to introduce substituted aryls, alkyls and heteroaryls at $R_3$. For example, if $R_3$ is Br, by reaction with boronic acids or organometallic reagents, or conversion to the corresponding boronate ester and reaction with aryl/heteroaryl halides or triflates, a variety of $R_3$ modifications are possible.

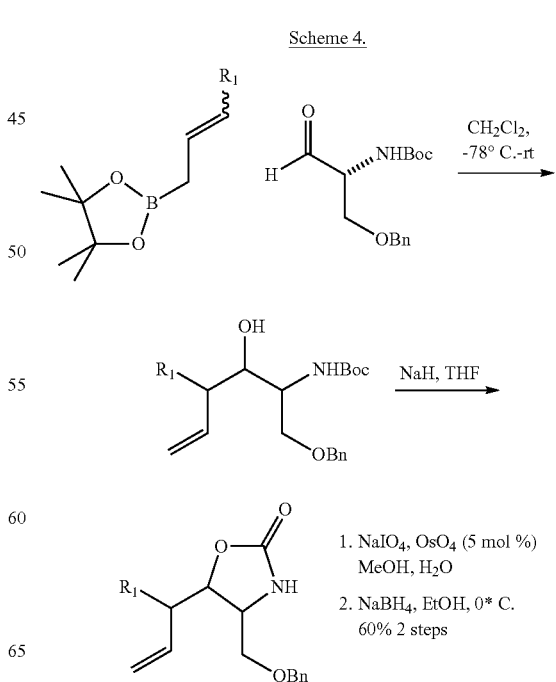

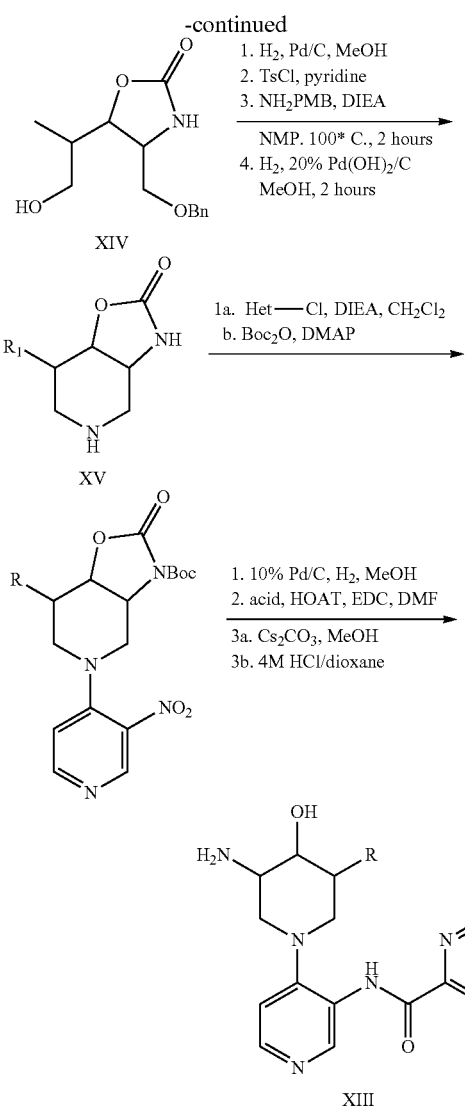

The compounds of the invention are useful in vitro and/or in vivo in inhibiting the growth of cancer cells. The compounds may be used alone or in compositions together with a pharmaceutically acceptable carrier or excipient. Suitable pharmaceutically acceptable carriers or excipients include, for example, processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), incorporated herein by reference.

Effective amounts of the compounds of the invention generally include any amount sufficient to detectably inhibit Pim activity by any of the assays described herein, by other Pim kinase activity assays known to those having ordinary skill in the art or by detecting an inhibition or alleviation of symptoms of cancer. The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

For purposes of the present invention, a therapeutically effective dose will generally be a total daily dose administered to a host in single or divided doses may be in amounts, for example, of from 0.001 to 1000 mg/kg body weight daily and more preferred from 1.0 to 30 mg/kg body weight daily. Dosage unit compositions may contain such amounts of submultiples thereof to make up the daily dose.

The compounds of the present invention may be administered orally, parenterally, sublingually, by aerosolization or inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols, which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings. Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any nontoxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.W., p. 33 et seq. (1976).

While the compounds of the invention can be administered as the sole active pharmaceutical agent, they can also be used in combination with one or more other agents used in the treatment of cancer. The compounds of the present invention are also useful in combination with known therapeutic agents and anti-cancer agents, and combinations of the presently disclosed compounds with other anti-cancer or chemotherapeutic agents are within the scope of the invention. Examples of such agents can be found in *Cancer Principles and Practice of Oncology*, V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents and agents that interfere with cell cycle checkpoints. The compounds of the invention are also useful when co-administered with radiation therapy.

Therefore, in one embodiment of the invention, the compounds of the invention are also used in combination with known anticancer agents including, for example, estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

In certain presently preferred embodiments of the invention, representative agents useful in combination with the compounds of the invention for the treatment of cancer include, for example, irinotecan, topotecan, gemcitabine, 5-fluorouracil, leucovorin carboplatin, cisplatin, taxanes, tezacitabine, cyclophosphamide, vinca alkaloids, imatinib (Gleevec), anthracyclines, rituximab, trastuzumab, as well as other cancer chemotherapeutic agents.

The above compounds to be employed in combination with the compounds of the invention will be used in therapeutic amounts as indicated in the *Physicians' Desk Reference* (*PDR*) 47th Edition (1993), which is incorporated herein by reference, or such therapeutically useful amounts as would be known to one of ordinary skill in the art.

The compounds of the invention and the other anticancer agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions, which are given at the same time or different times, or the therapeutic agents, can be given as a single composition.

In one embodiment, the invention provides a method of inhibiting Pim1, Pim2 or Pim3 in a human or animal subject. The method includes administering an effective amount of a compound, or a pharmaceutically acceptable salt thereof, of any of the embodiments of compounds of Formula I or II to a subject in need thereof.

The present invention will be understood more readily by reference to the following examples, which are provided by way of illustration and are not intended to be limiting of the present invention.

EXAMPLES

Referring to the examples that follow, compounds of the preferred embodiments were synthesized using the methods described herein, or other methods, which are known in the art.

The compounds and/or intermediates were characterized by high performance liquid chromatography (HPLC) using a Waters Millenium chromatography system with a 2695 Separation Module (Milford, Mass.). The analytical columns were reversed phase Phenomenex Luna C18-5µ, 4.6×50 mm, from Alltech (Deerfield, Ill.). A gradient elution was used (flow 2.5 mL/min), typically starting with 5% acetonitrile/95% water and progressing to 100% acetonitrile over a period of 10 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburgh, Pa.).

In some instances, purity was assessed by thin layer chromatography (TLC) using glass or plastic backed silica gel plates, such as, for example, Baker-Flex Silica Gel 1B2-F flexible sheets. TLC results were readily detected visually under ultraviolet light, or by employing well-known iodine vapor and other various staining techniques.

Mass spectrometric analysis was performed on one of three LCMS instruments: a Waters System (Alliance HT HPLC and a Micromass ZQ mass spectrometer; Column. Eclipse XDB-C18, 2.1×50 mm; gradient: 5-95% (or 35-95%, or 65-95% or 95-95%) acetonitrile in water with 0.05% TFA over a 4 min period; flow rate 0.8 mL/min; molecular weight range 200-1500; cone Voltage 20 V; column temperature 40° C.), another Waters System (ACQUITY UPLC system and a ZQ 2000 system; Column. ACQUITY UPLC HSS-C18, 1.8 um, 2.1×50 mm; gradient: 5-95% (or 35-95%, or 65-95% or 95-95%) acetonitrile in water with 0.05% TFA over a 1.3 min period; flow rate 1.2 mL/min; molecular weight range 150-850; cone Voltage 20 V; column temperature 50° C.) or a Hewlett Packard System (Series 1100 HPLC; Column: Eclipse XDB-C18, 2.1×50 mm; gradient: 5-95% acetonitrile in water with 0.05% TFA over a 4 min period; flow rate 0.8 mL/min; molecular weight range 150-850; cone Voltage 50V; column temperature 30° C.). All masses were reported as those of the protonated parent ions.

Nuclear magnetic resonance (NMR) analysis was performed on some of the compounds with a Varian 400 MHz NMR (Palo Alto, Calif.). The spectral reference was either TMS or the known chemical shift of the solvent.

Preparative separations are carried out using a Flash 40 chromatography system and KP-Sil, 60A (Biotage, Charlottesville, Va.), or by flash column chromatography using silica gel (230-400 mesh) packing material, or by HPLC using a Waters 2767 Sample Manager, C-18 reversed phase column, 30×50 mm, flow 75 mL/min. Typical solvents employed for the Flash 40 Biotage system and flash column chromatography are dichloromethane, methanol, ethyl acetate, hexane, acetone, aqueous ammonia (or ammonium hydroxide), and triethyl amine. Typical solvents employed for the reverse phase HPLC are varying concentrations of acetonitrile and water with 0.1% trifluoroacetic acid.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

It is understood that the invention is not limited to the embodiments set forth herein for illustration, but embraces all such forms thereof as come within the scope of the above disclosure.

The examples below as well as throughout the application, the following abbreviations have the following meanings. If not defined, the terms have their generally accepted meanings.

| ABBREVIATIONS | |
|---|---|
| DAST | (diethylamino)sulfurtrifluoride |
| DCM | Dichloromethane |
| DIEA | diisopropylethylamine |
| DMA | Dimethylacetamide |
| DMAP | 4-dimethylaminopyridine |
| DME | 1,2-dimethoxyethane |
| DMF | N,N-dimethylformamide |
| DPPF | 1,1'-bis(diphenylphosphino)ferrocene |
| EDC | 1-(3-Dimethylaminopropyl)-3-ethylcarbodiimide hydrochloride |
| EtOAc | ethyl acetate |
| EtOH | Ethanol |
| HOAT | Hydroxyazabenzotriazole |
| $K_2CO_3$ | Potassium carbonate |
| MeCN | Acetonitrile |
| $MgSO_4$ | Magnesium sulfate |
| MeOH | Methanol |
| $Na_2CO_3$ | sodium carbonate |
| NaCl | Sodium chloride |
| $NaHCO_3$ | sodium bicarbonate |
| NBS | N-bromosuccinimide |
| NMP | N-methyl-2-pyrrolidone |
| $Pd_2(dba)_3$ | Tris(dibenzylideneacetone)dipalladium(0) |
| $Pd(PPh_3)_4$ | Tetrakis(triphenylphospine)palladium(0) |
| $Pd(dppf)Cl_2$-DCM | Dichloro-(1,2-bis(diphenylphosphino)ethan)-Palladium(II)-dichloromothethane adduct |
| RT or rt | room temperature |
| TBDMSCl | tert-butyldimethylsilylchloride |
| TEA | Triethylamine |
| THF | tetrahydrofuran |

Synthesis of 3-oxocyclohex-1-enyl trifluoromethanesulfonate

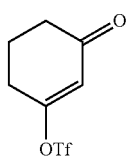

To a solution of cyclohexane-1,3-dione (1 equiv) in DCM (0.4 M) was added $Na_2CO_3$ (1.0 equiv.) and cooled to 0° C. Added $Tf_2O$ (1.0 equiv.) in DCM (5 M) dropwise over 1 hr at room temperature under a nitrogen atmosphere. Upon addition, the reaction was stirred for 2 hr (dark red solution). The solution was filtered and to the filtrate was added saturated $NaHCO_3$ (carefully), then extracted the organics, dried with brine, then $Na_2SO_4$, and concentrated. The crude was used for the next step without further purification. 3-oxocyclohex-1-enyl trifluoromethanesulfonate was obtained in 67% yield. The triflate decomposes upon storage and should be used immediately for the next reaction. LC/MS=244.9/286.0 (M+H and M+$CH_3CN$); Rt=0.88 min.

Synthesis of 3-(4,4,5,5-tetramethyl-1,3,2-dioxaborolan-2-yl)cyclohex-2-enone

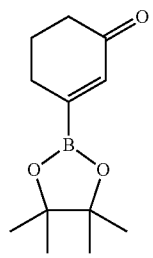 [SMILES: CC1(C)OB(C2=CC(=O)CCC2)OC1(C)C]

To a solution of 3-oxocyclohex-1-enyl trifluoromethanesulfonate (1.0 equiv.) in degassed dioxane (0.3 M) was added bis(pinacolato)diboron (2.0 equiv.), KOAc (3.0 equiv.), and $Pd(dppf)Cl_2$-DCM (0.05 equiv.). The reaction was heated to 80° C. for 2 h, then filtered. The dioxane solution was used for the next step without further purification. LC/MS=140.9 (M+H of boronic acid).

Synthesis of 3-(3-nitropyridin-4-yl)cyclohex-2-enone

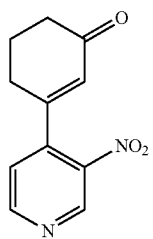

To a solution of 3-(4,4,5,5-tetramethyl-1,3,2-dioxaborolan-2-yl)cyclohex-2-enone (1.0 equiv.) in degassed dioxane and 2M $Na_2CO_3$ was added 4-chloro-3-nitropyridine (1.2 equiv.) and $Pd(dppf)Cl_2$-DCM (0.05 equiv.). The reaction was heated in an oil bath to 110° C. for 2 hours. Cooled to room temperature, then diluted with EtOAc, added $H_2O$—dark solution, lots of emulsions. Filtered to get rid of the solids, then extracted the organic phase, dried with $Na_2SO_4$, and concentrated. The crude was purified via silica gel chromatography eluting with ethyl acetate and hexanes (1:1) to yield 3-(3-nitropyridin-4-yl)cyclohex-2-enone (55%, 2 steps). LC/MS=219 (M+H), LC=2.294 min.

Synthesis of 3-(3-nitropyridin-4-yl)cyclohex-2-enol

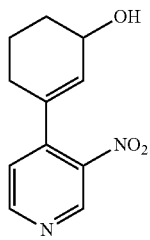 [SMILES: O=[N+]([O-])c1cnccc1C1=CC(O)CCC1]

To a solution of 3-(3-nitropyridin-4-yl)cyclohex-2-enone (1.0 equiv.) was added EtOH (0.2 M) and CeCl$_3$·7H$_2$O (1.3 equiv.). The reaction was cooled to 0° C., then NaBH$_4$ (1.3 equiv.) was added in portions. Stirred for 2 h at 0° C., then quenched by adding water, concentrated to remove the EtOH, added EtOAc, extracted the organics, dried with brine, then Na$_2$SO$_4$, and concentrated to yield 3-(3-nitropyridin-4-yl)cyclohex-2-enol (99%). LC/MS=221.1 (M+H), LC=2.235 min.

Synthesis of 2-(3-(3-nitropyridin-4-yl)cyclohex-2-enyl)isoindoline-1,3-dione

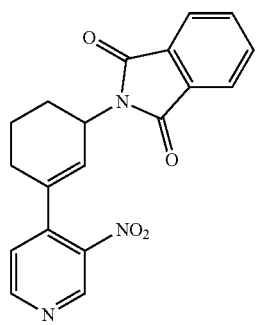 [SMILES: O=C1c2ccccc2C(=O)N1C1C=C(c2ccncc2[N+](=O)[O-])CCC1]

To a solution of 3-(3-nitropyridin-4-yl)cyclohex-2-enol (1.0 equiv.), triphenylphosphine (1.5 equiv.) and phthalimide (1.5 equiv.) in THF (0.3 M) at 0° C. was added (E)-di-tert-butyl diazene-1,2-dicarboxylate (1.5 equiv.) dropwise. The reaction was stirred at 0° C. for 2 hours. Concentrated to dryness under vacuo, then purified the crude via silica gel column chromatography eluting with EtOAc and hexanes (1:1 with 5% methanol) to afford the 2-(3-(3-nitropyridin-4-yl)cyclohex-2-enyl)isoindoline-1,3-dione (63% yield). LC/MS=350.3 (M+H), LC=3.936 min.

Synthesis of 2-(3-(3-aminopyridin-4-yl)cyclohex-2-enyl)isoindoline-1,3-dione

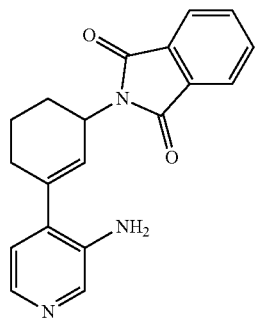 [SMILES: Nc1cnccc1C1=CC(N2C(=O)c3ccccc3C2=O)CCC1]

To a solution of 2-(3-(3-nitropyridin-4-yl)cyclohex-2-enyl)isoindoline-1,3-dione (1.0 equiv.) in AcOH (0.38 M) was added Fe (6.0 equiv.) and the reaction was stirred at room temperature for 2 h. Filtered, then washed with methanol and concentrated the filtrate. To the crude was added ethyl acetate and saturated NaHCO$_3$, the organics were dried with Na$_2$SO$_4$, and concentrated to give 2-(3-(3-aminopyridin-4-yl)cyclohex-2-enyl)isoindoline-1,3-dione as a yellow thick gum in 96% yield. LC/MS=320.0 (M+H), LC=2.410 min.

Synthesis of 2-(3-(3-aminopyridin-4-yl)cyclohexyl)isoindoline-1,3-dione

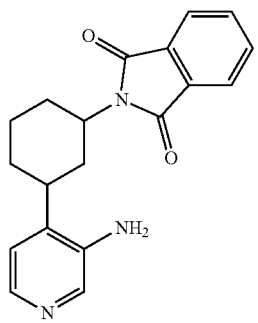 [SMILES: Nc1cnccc1C1CCCC(N2C(=O)c3ccccc3C2=O)C1]

To a solution of 2-(3-(3-nitropyridin-4-yl)cyclohex-2-enyl)isoindoline-1,3-dione (1.0 equiv.) in acetic acid (0.1 M) was added 10% Pd/C (0.2 equiv.) and the reaction was stirred under a H$_2$ balloon. After 3 days, the reaction was filtered through Celite, washed with ethyl acetate and methanol, the filtrate was diluted with ethyl acetate and washed twice with sat. 2M Na$_2$CO$_3$. The organic phase was dried with magnesium sulfate, filtered and concentrated. The crude material was triturated with hexanes and ethyl acetate to afford 2-(3-(3-aminopyridin-4-yl)cyclohexyl)isoindoline-1,3-dione in 73% yield. LC/MS=322.2 (M+H), Rt=0.64 min.

Synthesis of 5,5-dimethyl-3-oxocyclohex-1-enyl trifluoromethanesulfonate

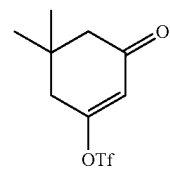

In a 3-neck round-bottom flask, 5,5-dimethylcyclohexane-1,3-dione (1.0 eq) was dissolved in DCM (0.2 M). Sodium carbonate (1.1 eq) was added and the mixture was cooled with magnetic stirring on an ice/salt water bath to ~−5° C. under N$_2$. Triflic anhydride (1.05 equiv.) diluted in DCM was added dropwise via addition funnel over 90 minutes. Upon completion of addition, the reaction was stirred at ~0° C. for 1 h. From LCMS and $^1$H NMR, there was still starting material left. Additional sodium carbonate (0.51 eq) and triflic anhydride (0.50 eq) were added. After 2 hours, the mixture was filtered through a coarse frit glass funnel (the cake was washed with DCM), transferred to an Erlenmeyer flask, quenched by careful addition of saturated aqueous sodium bicarbonate with vigorous stirring until pH=7, transferred to a separatory funnel and the layers separated. The organic layer was washed with brine, dried over MgSO$_4$, filtered and concentrated to give 5,5-dimethyl-3-oxocyclohex-1-enyl trifluoromethanesulfonate, which was used to the next step without further purification. LC/MS (m/z): MH$^+$=273.1, Rt=1.03.

Synthesis of 5,5-dimethyl-3-(4,4,5,5-tetramethyl-1,3,2-dioxaborolan-2-yl)cyclohex-2-enone

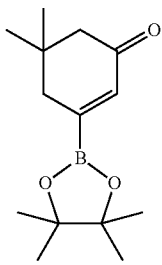 [SMILES: CC1(C)CC(=O)C=C(B2OC(C)(C)C(C)(C)O2)C1]

All of reagents 5,5-dimethyl-3-oxocyclohex-1-enyl trifluoromethanesulfonate (1.0 eq), potassium acetate (3.0 eq), and bis(pinacolato)diboron (2.0 eq) were added to 1,4-dioxane (0.2 M) in a round bottomed flask and degassed by bubbling N$_2$ through the mixture for 10 min. PdCl$_2$(dppf)-DCM adduct (0.03 eq) was added and the reaction heated to 80° C. fitted with a reflux condenser on an oil bath under N$_2$ overnight. The mixture was cooled to room temperature, filtered through a coarse frit glass funnel, the cake rinsed with 1,4-dioxane to give the 5,5-dimethyl-3-(4,4,5,5-tetramethyl-1,3,2-dioxaborolan-2-yl)cyclohex-2-enone in 1,4-dioxane which was used to next step without further purification. LC/MS (m/z): MH$^+$(boronic acid)=169.1, Rt=0.50.

Synthesis of 5,5-dimethyl-3-(3-nitropyridin-4-yl)cyclohex-2-enone

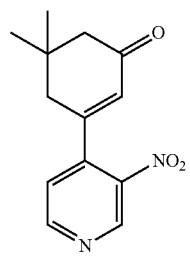 [SMILES: CC1(C)CC(=O)C=C(c2ccncc2[N+](=O)[O-])C1]

The boronate ester 5,5-dimethyl-3-(4,4,5,5-tetramethyl-1,3,2-dioxaborolan-2-yl)cyclohex-2-enone (1.0 eq) was dissolved in 1,4-dioxane in a round bottomed flask and degassed by bubbling N$_2$ through the solution for 30 minutes. 4-chloro-3-nitro-pyridine (1.3 eq) and 2M(aq) sodium carbonate (2.0 eq) were added and N$_2$ was bubbled through for 10 minutes and then PdCl$_2$(dppf)-DCM (0.05 eq) was added. The reaction mixture was stirred at 110° C. for 2 hr. The mixture was added to EtOAc and water. The resulting mixture was filtered through celite, the cake was washed with EtOAc. The organic layer was separated and the aqueous was extracted with EtOAc. The combined organic layers were washed with brine, dried over MgSO$_4$, filtered and concentrated. The residue was purified by silica gel chromatography (eluted with EtOAc:Hexanes=1:10 to 2:1) to give 5,5-dimethyl-3-(3-nitropyridin-4-yl)cyclohex-2-enone (46.7% for three steps). LC/MS (m/z): MH$^+$=247.2, Rt=0.79.

Synthesis of 5,5-dimethyl-3-(3-nitropyridin-4-yl)cyclohex-2-enol

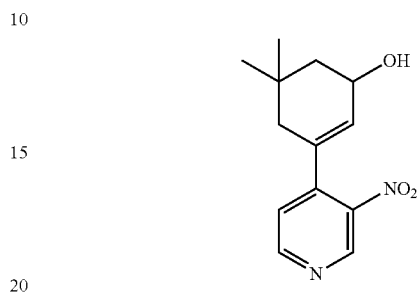

To a solution of 5,5-dimethyl-3-(3-nitropyridin-4-yl)cyclohex-2-enone (1.0 eq), and CeCl$_3$-7H$_2$O (1.2 eq) in MeOH (0.2 M) was added NaBH$_4$ (1.0 eq) at 0° C. The solution was stirred for 1 hour, and then quenched by the addition of 5 mL of water. The volatiles were removed in vacuum and the residue was partitioned between EtOAc and H$_2$O. The organic layer was separated and washed with brine. The combined aqueous was back extracted with EtOAc and the organic was washed with brine. The combined organics were dried over MgSO$_4$, filtered and concentrated. The residue was purified by column (5% methanol in 1:1 ethyl acetate and hexanes) to give 5,5-dimethyl-3-(3-nitropyridin-4-yl)cyclohex-2-enol (74%). LC/MS (m/z): MH$^+$=249.2, Rt=0.76.

Synthesis of 2-(5,5-dimethyl-3-(3-nitropyridin-4-yl)-cyclohex-2-enyl)isoindoline-1,3-dione

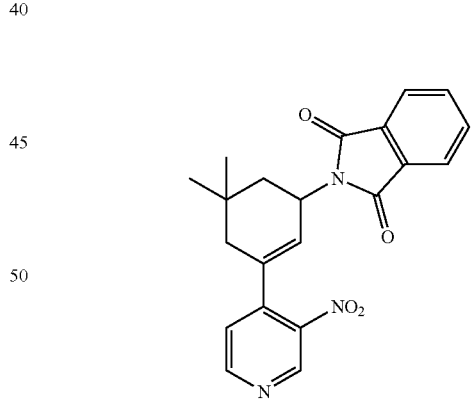

To a homogeneous solution of 5,5-dimethyl-3-(3-nitropyridin-4-yl)cyclohex-2-enol (1.0 eq), triphenyl phosphine (1.5 eq), and phthalimide (1.5 eq) in THF (0.2 M) cooled to 0° C., ditertbutyl azodicarboxylate (1.5 eq) in THF was added to the solution. The mixture was stirred at 0° C. for 2 hours. The reaction was concentrated in vacuo. The residue was purified by column (5% methanol in 1:1 ethyl acetate and hexanes) to give 2-(5,5-dimethyl-3-(3-nitropyridin-4-yl)cyclohex-2-enyl)isoindoline-1,3-dione (99%). LC/MS (m/z): MH$^+$=378.2, Rt=1.10.

Synthesis of 2-(3-(3-aminopyridin-4-yl)-5,5-dimethyl-cyclohex-2-enyl)isoindoline-1,3-dione

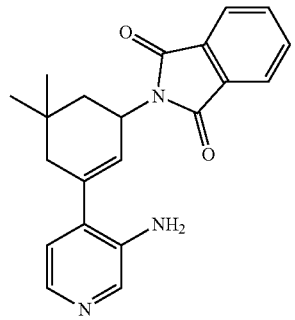 [SMILES: CC1(C)CC(c2ccncc2[N+](=O)[O-])=CC(N2C(=O)c3ccccc3C2=O)C1]

A solution of 2-(5,5-dimethyl-3-(3-nitropyridin-4-yl)cyclohex-2-enyl)isoindoline-1,3-dione (1 eq) in acetic acid (0.1M) was purged with nitrogen for 10 min. Then 10% Pd/C (0.10 eq) was added. The reaction mixture was stirred at room temperature overnight under an atmosphere of hydrogen. Solids were removed by filtration over celite, then rinsed with EtOAc and MeOH. The filtrate was concentrated, diluted with EtOAc and washed 2× with sat. aq. 2M $Na_2CO_3$. The organic layer was dried with $MgSO_4$, filtered, and concentrated. The residue was purified by column (5% methanol in 1:1 ethyl acetate and hexanes) to give 2-(3-(3-aminopyridin-4-yl)-5,5-dimethylcyclohex-2-enyl)isoindoline-1,3-dione (89%). LC/MS (m/z): $MH^+$=348.3, Rt=0.79.

Synthesis of 2-(5-(3-aminopyridin-4-yl)-3,3-dimethylcyclohexyl)isoindoline-1,3-dione

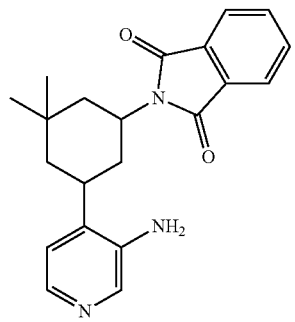 [SMILES: CC1(C)CC(c2ccncc2N)CC(N2C(=O)c3ccccc3C2=O)C1]

A solution of 2-(3-(3-aminopyridin-4-yl)-5,5-dimethylcyclohex-2-enyl)isoindoline-1,3-dione (1.0 eq) in acetic acid (0.1M) was purged with nitrogen for 10 min. Then 10% Pd/C (0.1 eq) was added. The reaction mixture was stirred at 45° C., 300 psi hydrogen atmosphere in a steel bomb overnight and at 65° C., 300 psi for 5 hours. Solids were removed by filtration over celite, then rinsed with EtOAc and MeOH. The filtrate was concentrated, diluted with EtOAc and washed 2× with sat. aq. 2M $Na_2CO_3$. The organic layer was dried with $MgSO_4$, filtered, and concentrated. The residue was purified by column (5% methanol in 1:1 ethyl acetate and hexanes) to give 2-(5-(3-aminopyridin-4-yl)-3,3-dimethylcyclohexyl)isoindoline-1,3-dione (53%). LC/MS (m/z): $MH^+$=350.3, Rt=0.78. The enantiomerically pure 2-((1R,5R)-5-(3-aminopyridin-4-yl)-3,3-dimethylcyclohexyl)isoindoline-1,3-dione and 2-((1S,5S)-5-(3-aminopyridin-4-yl)-3,3-dimethylcyclohexyl)isoindoline-1,3-dione were resolved by chiral HPLC (For analysis $R_t$=7.526 min and 13.105 min respectively; hexanes:ethanol=80:20 (v:v), Chiralcel OJ-H 100×4.6 mm at 1 mL/min. For preparative separation, hexanes:ethanol=80:20 (v:v), Chiralcel OJ-H (250×20 mm at 20 mL/min). $^1$H NMR ($CDCl_3$): δ 8.04 (s, 1H), 8.00 (d, 1H), 7.82 (m, 2H), 7.71 (m, 2H), 7.06 (d, 1H), 4.54 (m, 1H), 3.71 (m, 2H), 2.89 (m, 1H), 2.23-2.44 (m, 2H), 1.90 (m, 1H), 1.20-1.60 (m, 3H), 1.18 (s, 3H), 1.07 (s, 3H).

Synthesis of 4-(cyclohexa-1,3-dienyl)-3-nitropyridine

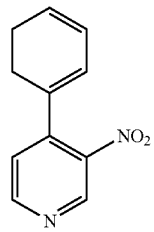

To a solution of 3-(3-nitropyridin-4-yl)cyclohex-2-enol (1.0 equiv.) was added dioxane (0.18 $\underline{M}$) and p-TSA (1.1 equiv.). The solution was heated to 100° C. for 4 h. Cooled to room temperature, worked up with sat. $NaHCO_3$ and ethyl acetate, the organic phase was dried with $Na_2SO_4$ and concentrated. The crude was purified via silica gel column chromatography eluting with 100% DCM to give 4-(cyclohexa-1,3-dienyl)-3-nitropyridine as a yellow oil (27% yield). LCMS (m/z): 203.1 ($MH^+$), LC $R_t$=3.53 min, $^1$H-NMR ($CDCl_3$): 9.02 (s, 1H), 8.70 (d, J=5.3, 1H), 7.30 (d, J=5.3, 1H), 6.15-6.17 (m, 1H), 6.02-6.11 (m, 2H), 2.35-2.38 (m, 4H).

Synthesis of (+/−)-2-azido-4-(3-nitropyridin-4-yl)cyclohex-3-enol

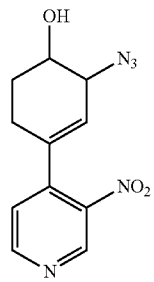

To a solution of 4-(cyclohexa-1,3-dienyl)-3-nitropyridine (1.0 equiv.) in DCM (0.1 $\underline{M}$) was added $NaHCO_3$ (1.2 equiv.) to give a yellow solution. Cooled to 0° C., then added m-CPBA (1.0 equiv.) to the solution at once as a solid. The reaction was stirred at 0° C. for 3.5 hr. Monitored by both TLC and LC/MS. The product ionizes as M+H=237 (diol); Rt=0.41 min on UPLC. Quenched reaction with sat. $NaHCO_3$, then extracted with DCM (3 times). The organic phase was further dried with brine, then $Na_2SO_4$, filtered and concentrated to give the crude epoxide as a yellow oil, which was used without further purification.

To a solution of the above crude material in EtOH and water (3:1) (cloudy yellow solution) was added NaN₃ (2.0 equiv.) and NH₄Cl (2.0 equiv.) to give a clear orange solution. The reaction was stirred for 16 h, then concentrated. EtOAc and water were added, the organic phase was further dried with MgSO₄ and concentrated to give a brown oil. The oil was loaded in silica gel and purified via column chromatography (ISCO, 0-50% EtOAc) to give (+/−)-2-azido-4-(3-nitropyridin-4-yl)cyclohex-3-enol as a yellow oil (44% for 2 steps). LCMS (m/z)=262 (MH⁺), LC $R_f$=2.35 min.

Synthesis of (+/−)-4-(3-azido-4-(tert-butyldimethyl-silyloxy)cyclohex-1-enyl)-3-nitropyridine

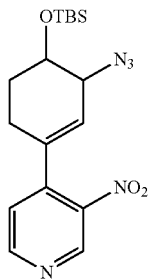 [SMILES: CC(C)(C)[Si](C)(C)OC1CCC(c2ccncc2[N+](=O)[O-])=CC1N=[N+]=[N-]]

To a solution of (+/−)-2-azido-4-(3-nitropyridin-4-yl)cyclohex-3-enol (1.0 equiv.) in DCM (0.15 M) was added TBSCl (2.0 equiv.), imidazole (2.0 equiv.) and DMAP (0.1 equiv.) at room temperature. After 18 h, water was added, the organics were dried with brine, then Na₂SO₄, and concentrated. The crude material was loaded to silica gel and purified via column chromatography (ISCO) eluting with ethyl acetate and hexanes (20%). Obtained (+/−)-4-(3-azido-4-(tert-butyldimethylsilyloxy)cyclohex-1-enyl)-3-nitropyridine as a yellow oil in 60% yield. LCMS (m/z): 376.3 (MH⁺), LC $R_f$=5.848 min.

Synthesis of (+/−)-tert-butyl 6-(tert-butyldimethylsilyloxy)-3-(3-nitropyridin-4-yl)cyclohex-2-enylcarbamate

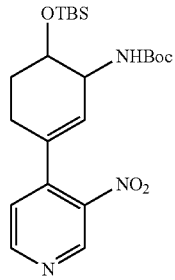 [SMILES: CC(C)(C)OC(=O)NC1C=C(c2ccncc2[N+](=O)[O-])CCC1O[Si](C)(C)C(C)(C)C]

In a round-bottomed flask was added (+/−)-4-(3-azido-4-(tert-butyldimethylsilyloxy)cyclohex-1-enyl)-3-nitropyridine (1.0 equiv.) and pyridine (0.1 M) to give a yellow solution. Ammonium hydroxide (10:1 pyridine: ammonium hydroxide) was added followed by PMe₃ (3.0 equiv.). The reaction turned dark brown after 10 min. Stirred at room temperature for 1.5 h. Quenched by adding EtOH, and concentrated. Repeated 2 more times. To the crude was added sat. NaHCO₃ and dioxane (1:1, 0.1M). Boc₂O (1.0 equiv.) was added. Stirred for one hour at room temperature. Washed with H₂O and EtOAc, the organic phase was dried with MgSO₄, filtered and concentrated. The residue was purified via silica gel column chromatography (ISCO, 5:1 Hex/EtOAc). Collected the pure fractions and concentrated to give (+/−)-tert-butyl 6-(tert-butyldimethylsilyloxy)-3-(3-nitropyridin-4-yl)cyclohex-2-enylcarbamate as a foam. LCMS (m/z): 450.3 (MH⁺), LC $R_f$=5.83 min.

Synthesis of (+/−)-tert-butyl 3-(3-aminopyridin-4-yl)-6-(tert-butyldimethylsilyloxy) cyclohex-2-enyl-carbamate

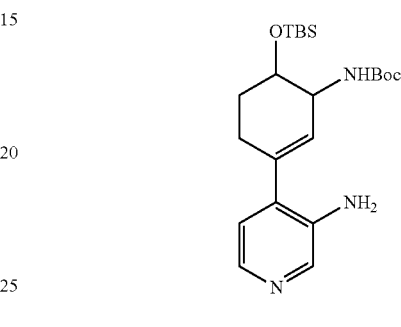

To a solution of (+/−)-tert-butyl 6-(tert-butyldimethylsilyloxy)-3-(3-nitropyridin-4-yl)cyclohex-2-enylcarbamate (1.0 equiv.) in AcOH (0.18 M) was added Fe (6.0 equiv.) and the reaction was stirred for 20 h. Worked up by diluting the reaction with methanol, filtered, and concentrated the filtrate. To the crude was added ethyl acetate and saturated NaHCO₃, the organics were dried with sodium sulfate and concentrated to give (+/−)-tert-butyl 3-(3-aminopyridin-4-yl)-6-(tert-butyldimethylsilyloxy)cyclohex-2-enylcarbamate as a yellow oil in 94% yield. LCMS (m/z): 420.3 (MH⁺), LC $R_f$=3.88 min.

Synthesis of (+/−)-tert-butyl 5-(3-aminopyridin-4-yl)-2-(tert-butyldimethylsilyloxy) cyclohexylcarbamate

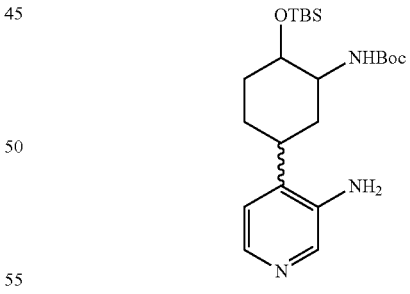

To a solution of (+/−)-tert-butyl 3-(3-aminopyridin-4-yl)-6-(tert-butyldimethylsilyloxy)cyclohex-2-enylcarbamate (1.0 equiv.) in MeOH (0.1 M) was added Pd/C (20% by wt) and the reaction was stirred under a hydrogen balloon for 18 h. LC/MS of the reaction indicated mixture of diastereomers, the reaction was filtered, washed with EtOAc and concentrated the filtrate. The crude material was purified via prep-HPLC (in DMSO), and the pure fractions were combined, neutralized with solid NaHCO₃, extracted with ethyl acetate, washed with brine, dried under Na₂SO₄, and concentrated to give product A (8% yield) and product B (51% yield).

Product A: LCMS (m/z): 422.4 (MH+), LC R$_f$=3.75 min.
Product B: LCMS (m/z): 422.4 (MH+), LC R$_f$=3.94 min.

Synthesis of 1,4-dioxaspiro[4.5]dec-7-en-8-yl trifluoromethanesulfonate

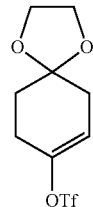

1,4-Dioxaspiro[4.5]decan-8-one (1.0 equiv) was dissolved in Ether (0.1 M) and stirred at −15° C. then 1M NaHMDS (1.05 equiv.) was added and stirred for 70 min then Tf$_2$O (1.05 equiv.) added and reaction allowed to slowly warm to rt. The mixture was stirred for 28 hr, washed with sat. aq. NaHCO$_3$ and then water. Aqueous layers combined and extracted with ether. Organic layers combined, dried over MgSO$_4$, filtered, and concentrated. The residue was purified by column (ethyl ether:hexanes=1:4) to give 1,4-dioxaspiro[4.5]dec-7-en-8-yl trifluoromethanesulfonate (65%). LC/MS (m/z): MH+=289.0, Rt=0.97. HPLC Rt=3.77.

Synthesis of 4,4,5,5-tetramethyl-2-(1,4-dioxaspiro[4.5]dec-7-en-8-yl)-1,3,2-dioxaborolane

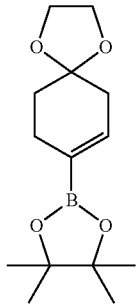

A solution of 1,4-dioxaspiro[4.5]dec-7-en-8-yl trifluoromethanesulfonate (1.0 equiv.) in dioxane (0.5 M) was purged with nitrogen for 30 min. Then 4,4,4',4',5,5,5',5'-octamethyl-2,2'-bi(1,3,2-dioxaborolane) (1.0 equiv.), KOAc (3.0 equiv.), Pd(dppf)Cl$_2$-DCM (0.2 equiv.) were added and the solution was stirred in a sealed bomb at 80° C. The reaction was filtered over a pad of celite, then to the filtrate was added ethyl acetate, and washed with brine, dried over MgSO$_4$, filtered, and concentrated. The residue was purified by column (ethyl acetate:hexanes=1:1) to give 4,4,5,5-tetramethyl-2-(1,4-dioxaspiro[4.5]dec-7-en-8-yl)-1,3,2-dioxaborolane (95%). LC/MS (m/z): MH+=267.1, Rt=0.95.

Synthesis of 3-nitro-4-(1,4-dioxaspiro[4.5]dec-7-en-8-yl)pyridine

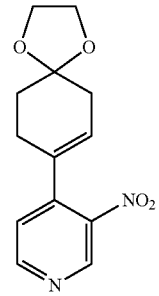 [SMILES: O=[N+]([O-])c1cnccc1C1=CCC2(CC1)OCCO2]

A solution of DME (0.2 M) and 2M aq. sodium carbonate (1.7 equiv.) was purged with nitrogen for 20 min. Then 4-chloro-3-nitropyridine (1.6 equiv.), 4,4,5,5-tetramethyl-2-(1,4-dioxaspiro[4.5]dec-7-en-8-yl)-1,3,2-dioxaborolane (1.0 equiv.), Pd(dppf)Cl$_2$-DCM (0.05 equiv.) were added and stirred in a sealed bomb at 110° C. The reaction was stirred at that temperature for 3.5 hours. The reaction was diluted with ethyl acetate, washed with water, dried over MgSO$_4$, filtered, and concentrated. The residue was purified by column (ethyl acetate:hexanes=1:1 with 10% methanol) to give 3-nitro-4-(1,4-dioxaspiro[4.5]dec-7-en-8-yl)pyridine (83%). LC/MS (m/z): MH+=263.2, Rt=0.71.

Synthesis of 4-(3-nitropyridin-4-yl)cyclohex-3-enone

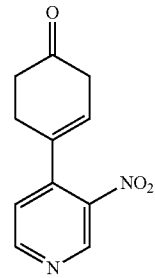

A mixture of 3-nitro-4-(1,4-dioxaspiro[4.5]dec-7-en-8-yl)pyridine (1.0 equiv.) in 20% TFA in CH$_2$Cl$_2$ (0.2 M) was stirred at room temperature overnight. The solvents were removed under reduced pressure. The residue was dissolved with ethyl acetate (200 mL), and washed with sat NaHCO$_3$ (30 mL), and sat NaCl (30 mL). The organic was dried with MgSO$_4$, filtered and concentrated to give 4-(3-nitropyridin-4-yl)cyclohex-3-enone (85%). The crude product was used to next step without further purification. LC/MS (m/z): MH+=218.9, Rt=0.60

Synthesis of 4-(3-nitropyridin-4-yl)cyclohex-3-enol

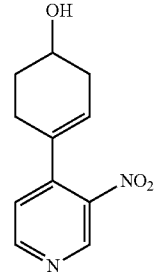

To a solution of 4-(3-nitropyridin-4-yl)cyclohex-3-enone (1.0 eq) in methanol (0.2 M) was added sodium borohydride (1.8 equiv.) at 0° C. The reaction mixture was stirred at 0° C. for 2 hr. Methanol was removed under reduced pressure. The residue was dissolved with ethyl acetate (200 mL), and washed with sat. NaCl (30 mL). The organic was dried with MgSO$_4$, filtered and concentrated to give 4-(3-nitropyridin-4-yl)cyclohex-3-enol (85%). The crude product was used in the next step without further purification. LC/MS (m/z): MH$^+$=221.0, Rt=0.55

Synthesis of 4-(3-nitropyridin-4-yl)cyclohex-3-enyl methanesulfonate

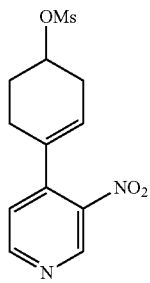 [SMILES: CS(=O)(=O)OC1CC=C(c2ccncc2[N+](=O)[O-])CC1]

To a solution of 4-(3-nitropyridin-4-yl)cyclohex-3-enol (1.0 equiv.) and DIPEA (2.5 equiv.) in CH$_2$Cl$_2$ (0.15 M) was added methanesulfonyl chloride (1.8 equiv.) at 0° C. The reaction mixture was stirred at 0° C. for 1 hr. The reaction mixture was diluted with ethyl acetate (200 mL), and washed with sat NaCl (30 mL). The organic was dried MgSO$_4$, filtered and concentrated to give 4-(3-nitropyridin-4-yl)cyclohex-3-enyl methanesulfonate (93%). The residue was used in the next step without further purification. LC/MS (m/z): MH$^+$=299.0, Rt=0.70

Synthesis of 4-(cyclohexa-1,3-dienyl)-3-nitropyridine

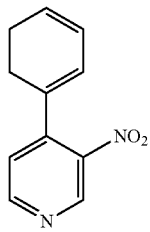 [SMILES: O=[N+]([O-])c1cnccc1C1=CC=CCC1]

To a solution of 4-(3-nitropyridin-4-yl)cyclohex-3-enyl methanesulfonate (1.0 equiv) in tetrahydrofuran (0.1M) was added DBU (1.8 equiv.) at room temperature. The reaction mixture was stirred at rt overnight. The reaction mixture was diluted with ethyl acetate (200 mL), and washed with sat NaCl (30 mL). The organic was dried with MgSO$_4$, filtered and concentrated. The residue was purified by column (5% methanol in 1:1 ethyl acetate and hexanes) to give 4-(cyclohexa-1,3-dienyl)-3-nitropyridine. LC/MS (m/z): MH$^+$=203.2, Rt=0.85.

Synthesis of (+/−)-tert-butyl 6-hydroxy-3-(3-nitropyridin-4-yl)cyclohex-2-enylcarbamate

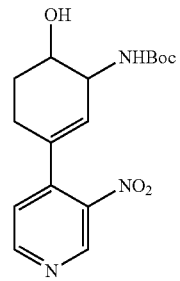 [SMILES: CC(C)(C)OC(=O)NC1C=C(c2ccncc2[N+](=O)[O-])CCC1O]

To a solution of (+/−)-2-azido-4-(3-nitropyridin-4-yl)cyclohex-3-enol (1.0 equiv.) in Pyridine and NH$_4$OH (8:1, 0.23 M) was added trimethylphosphine (3.0 equiv.) at room temperature. The mixture was stirred at room temperature for 3 hours. Solvents were removed. To the residue was added ethanol. Then ethanol was removed in vacuo to ensure removal of the ammonia totally. The residue was dissolved in 1,4-dioxane and sat. aq. sodium bicarbonate, and then Boc$_2$O (1.0 eq) in THF were added to the mixture. The resulting mixture was stirred at room temperature for 2 hours. The reaction mixture was diluted with ethyl acetate, and washed with sat NaCl. The organic was dried with MgSO$_4$, filtered and concentrated. The residue was purified by column (5% methanol in 1:1 ethyl acetate and hexanes) to give (+/−)-tert-butyl 6-hydroxy-3-(3-nitropyridin-4-yl)cyclohex-2-enylcarbamate (82%). LC/MS (m/z): MH$^+$=336.0, Rt=0.71

Synthesis of (+/−)-2-(tert-butoxycarbonylamino)-4-(3-nitropyridin-4-yl)cyclohex-3-enyl methanesulfonate

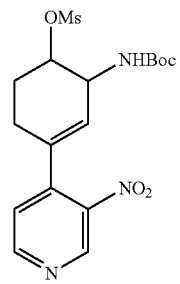 [SMILES: CC(C)(C)OC(=O)NC1C=C(c2ccncc2[N+](=O)[O-])CCC1OS(C)(=O)=O]

To a solution of (+/−)-tert-butyl 6-hydroxy-3-(3-nitropyridin-4-yl)cyclohex-2-enylcarbamate (1.0 equiv.) and triethyl amine (1.5 equiv.) in CH$_2$Cl$_2$ (0.2 M) was added methanesulfonyl chloride (1.2 equiv.) at 0° C. The mixture was stirred for 2 hours at that temperature. The reaction mixture was diluted with ethyl acetate, and washed with sat NaCl. The organic was dried with MgSO$_4$, filtered and concentrated to give (+/−)-2-(tert-butoxycarbonylamino)-4-(3-nitropyridin-4-yl)cyclohex-3-enyl methanesulfonate (85%), which was used in the next step without further purification. LC/MS (m/z): MH$^+$=414.0, Rt=0.82

Synthesis of (+/−)-5-(3-nitropyridin-4-yl)-3,3a,7,7a-tetrahydrobenzo[d]oxazol-2(6H)-one

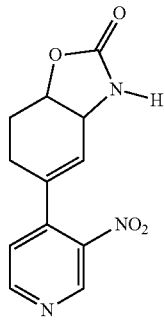 [SMILES: O=C1NC2C=C(c3ccncc3[N+](=O)[O-])CCC2O1]

The mixture of (+/−)-2-(tert-butoxycarbonylamino)-4-(3-nitropyridin-4-yl)cyclohex-3-enyl methanesulfonate (1.0 equiv.) in pyridine (0.21M) was stirred at 110° C. for 10 min in microwave. Pyridine was removed under reduced pressure. The residue was dissolved in ethyl acetate, and washed with sat NaCl. The organic was dried with MgSO$_4$, filtered and concentrated to give (+/−)-5-(3-nitropyridin-4-yl)-3,3a,7,7a-tetrahydrobenzo[d]oxazol-2(6H)-one (85%), which was used in the next step without further purification. LC/MS (m/z): MH$^+$=262.1, Rt=0.49

Synthesis of (+/−)-tert-butyl 5-(3-nitropyridin-4-yl)-2-oxo-3a,6,7,7a-tetrahydrobenzo[d]oxazole-3(2H)-carboxylate

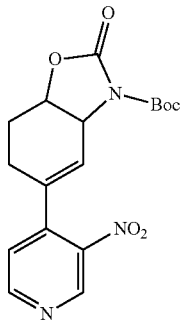 [SMILES: CC(C)(C)OC(=O)N1C(=O)OC2CCC(c3ccncc3[N+](=O)[O-])=CC21]

To a solution of (+/−)-5-(3-nitropyridin-4-yl)-3,3a,7,7a-tetrahydrobenzo[d]oxazol-2(6H)-one (1.0 equiv.), TEA (1.8 equiv.), and catalytic amount DMAP in CH$_2$Cl$_2$ (0.19 M) was added di-tert-butyl dicarbonate (1.2 eqiv) at room temperature. The reaction mixture was stirred for 1 hour. The reaction mixture was diluted with ethyl acetate (100 mL), and washed with sat NaCl (30 mL). The organic was dried with MgSO$_4$, filtered and concentrated. The residue was purified by column (5% methanol in 1:1 ethyl acetate and hexanes) to give (+/−)-tert-butyl 5-(3-nitropyridin-4-yl)-2-oxo-3a,6,7,7a-tetrahydrobenzo[d]oxazole-3(2H)-carboxylate (98%). LC/MS (m/z): MH$^+$=306.0, Rt=0.75

Synthesis of (+/−)-tert-butyl 5-(3-aminopyridin-4-yl)-2-oxohexahydrobenzo[d]Oxazole-3(2H)-carboxylate

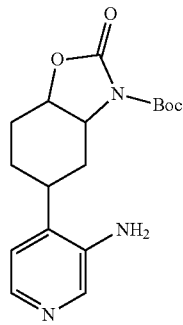 [SMILES: CC(C)(C)OC(=O)N1C(=O)OC2CCC(c3ccncc3N)CC21]

To a solution of (+/−)-tert-butyl 5-(3-nitropyridin-4-yl)-2-oxo-3a,6,7,7a-tetrahydrobenzo[d]oxazole-3(2H)-carboxylate (1.0 equiv.) in methanol and ethyl acetate (1:1, 0.1 M) was added 10% Pd/C (0.1 equiv.). The resulting mixture was stirred under H$_2$ atmosphere for 6 hours. The solid was removed by filtration. The filtrate was concentrated under reduced pressure to give (+/−)-tert-butyl 5-(3-aminopyridin-4-yl)-2-oxohexahydrobenzo[d]oxazole-3(2H)-carboxylate (87%), which was used in the next step without further purification. LC/MS (m/z): MH$^+$=334.1, Rt=0.51.

Synthesis of 5-methyl-3-oxocyclohex-1-enyltrifluoromethanesulfonate

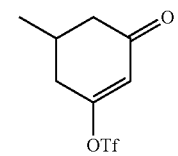

To a solution of 5-methylcyclohexane-1,3-dione (1.0 equiv.) in DCM (0.5M) was added Na$_2$CO$_3$ (1.1 equiv.) and cooled to 0° C. Added Tf$_2$O (1.0 equiv.) in DCM (5.0 M) dropwise over 1 hr at 0° C. under a nitrogen atmosphere. Upon addition, the reaction was stirred for 1 hr at room temperature (dark red solution). The solution was filtered and the filtrate was quenched by careful addition of saturated NaHCO$_3$ with vigorous stirring until pH=7. The solution was transferred to a separatory funnel and the layers were separated. The organic layer was washed with brine, dried with Na$_2$SO$_4$, filtered, concentrated under vacuo and dried under high vacuum for 15 min to yield 5-methyl-3-oxocyclohex-1-enyl trifluoromethanesulfonate as light yellow oil in 78% yield. The triflate decomposes upon storage and should be used immediately for the next reaction. LC/MS=259.1/300.1 (M+H and M+CH$_3$CN); Rt=0.86 min, LC=3.84 min. $^1$H-NMR (400 MHz, CDCl$_3$) δ ppm: 6.05 (s, 1H), 2.70 (dd, J=17.2, 4.3, 1H), 2.53 (dd, J=16.6, 3.7, 1H), 2.48-2.31 (m, 2H), 2.16 (dd, J=16.4, 11.7, 1H), 1.16 (d, J=5.9, 3H).

Synthesis of 5-methyl-3-(4,4,5,5-tetramethyl-1,3,2-dioxaborolan-2-yl)cyclohex-2-enone

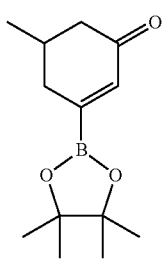 [SMILES: CC1CC(=O)C=C(B2OC(C)(C)C(C)(C)O2)C1]

To a solution of 5-methyl-3-oxocyclohex-1-enyl trifluoromethanesulfonate (1.0 equiv.) in degassed dioxane (0.7 M) was added bis(pinacolato)diboron (2.0 equiv.), KOAc (3.0 equiv.), and Pd(dppf)Cl$_2$-DCM (0.03 equiv.). The reaction was heated to 80° C. for 10 h (initial heating at large scale results in exothermic formation of an orange foam on top of the solution, the heating bath should be removed until the foam retracts, reheating to 80° C. at this point appears to be fine), then cooled to room temperature and filtered through a coarse frit glass funnel. The cake was rinsed with more dioxane and the filtrate solution was used for the next step without further purification. LC/MS=155.1 (M+H of boronic acid); Rt=0.41 min, LC=1.37 min.

Synthesis of 5-methyl-3-(3-nitropyridin-4-yl)cyclohex-2-enone

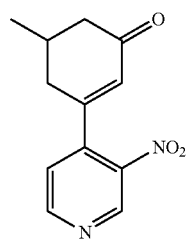 [SMILES: CC1CC(=O)C=C(c2ccncc2[N+](=O)[O-])C1]

To a solution of 5-methyl-3-(4,4,5,5-tetramethyl-1,3,2-dioxaborolan-2-yl)cyclohex-2-enone (1.0 equiv.) in degassed dioxane (0.5 M) and 2M Na$_2$CO$_3$ (2 equiv.) was added 4-chloro-3-nitropyridine (1.3 equiv.) and Pd(dppf)Cl$_2$-DCM (0.05 equiv.). The reaction was placed under a reflux condenser and heated in an oil bath to 110° C. for 1 h. Cooled to room temperature, filtered through a pad of Celite, washed the pad with ethyl acetate and concentrated the filtrate under vacuo. The residue was further pumped at 80° C. on a rotary evaporator for one hour to remove boronate by-products (M+H=101) via sublimation. The residue was partitioned between brine and ethyl acetate, and the layers were separated, the aqueous phase was further extracted with ethyl acetate (4×), the organics were combined, dried over sodium sulfate, filtered, and concentrated. The crude was purified via silica gel chromatography loading in DCM and eluting with 2-50% ethyl acetate and hexanes. The pure fractions were concentrated in vacuo to yield an orange oil. The oil was placed under high vacuum (~500 mtorr) with seed crystals overnight to yield an orange solid. The solid was further purified via trituration in hexanes to yield 5-methyl-3-(3-nitropyridin-4-yl)cyclohex-2-enone (48% 2 steps). LC/MS=233.2 (M+H); Rt=0.69 min, LC=2.70 min. $^1$H-NMR (400 MHz, CdCl$_3$) δ ppm: 9.31 (s, 1H), 8.88 (d, J=5.1, 1H), 7.30 (d, J=5.1, 1H), 6.00 (d, J=2.4, 1H), 2.62 (dd, J=16.4, 3.5, 1H), 2.53-2.34 (m, 3H), 2.23 (dd, J=16.1, 11.7, 1H), 1.16 (d, J=6.3, 3H).

Synthesis of cis-(+/−)-5-methyl-3-(3-nitropyridin-4-yl)cyclohex-2-enol

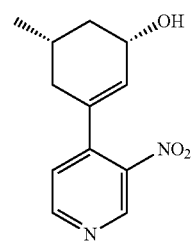 [SMILES: C[C@H]1CC(c2ccncc2[N+](=O)[O-])=C[C@@H](O)C1]

To a solution of 5-methyl-3-(3-nitropyridin-4-yl)cyclohex-2-enone (1.0 equiv.) in EtOH (0.3 M) was added CeCl$_3$·7H$_2$O (1.2 equiv.). The reaction was cooled to 0° C., then NaBH$_4$ (1.2 equiv.) was added in portions. Stirred for 1 h at 0° C., then quenched by adding water, concentrated to remove the EtOH, added EtOAc, extracted the organics, washed with brine, then dried with Na$_2$SO$_4$, filtered and concentrated to yield cis-(+/−)-5-methyl-3-(3-nitropyridin-4-yl)cyclohex-2-enol (94%). LC/MS=235.2 (M+H), LC=2.62 min.

Synthesis of 4-(3-(tert-butyldimethylsilyloxy)-5-methylcyclohex-1-enyl)-3-nitropyridine

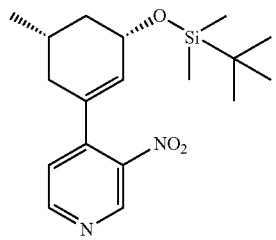 [SMILES: C[C@H]1CC(c2ccncc2[N+](=O)[O-])=C[C@@H](O[Si](C)(C)C(C)(C)C)C1]

To a solution of 5-methyl-3-(3-nitropyridin-4-yl)cyclohex-2-enol (1.0 equiv.) in DMF (0.5 M) was added imidazole (4.0 equiv.) and TBDMSCl (2.5 equiv.). After stirring for 18 hours the solution was portioned between EtOAc and H$_2$O and separated. After washing further with H$_2$O (3×) and NaCl$_{(sat.)}$, drying over MgSO$_4$, filtering and removal of solvents, 4-(3-(tert-butyldimethylsilyloxy)-5-methylcyclohex-1-enyl)-3-nitropyridine was obtained (85%). LC/MS=349.2 (M+H), LC=5.99 min.

Synthesis of 4-(3-(tert-butyldimethylsilyloxy)-5-methylcyclohex-1-enyl)pyridin-3-amine

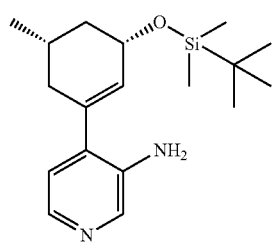

A heterogeneous solution of 4-(3-(tert-butyldimethylsilyloxy)-5-methylcyclohex-1-enyl)-3-nitropyridine (1.0 eq.) and iron (6.0 eq) in acetic acid, at a concentration of 0.4 M, was stirred vigorously for 2 hours. The mixture was then passed through a celite pad, eluting with MeOH. Upon removal of the volatiles in vacuo, the residue was dissolved in EtOAc, washed with Na₂CO₃(sat.), NaCl(sat.), was dried over MgSO₄, was filtered and the volatiles were removed in vacuo yielding 4-(3-(tert-butyldimethylsilyloxy)-5-methylcyclohex-1-enyl)pyridin-3-amine (78%). LCMS (m/z): 319.3 (MH⁺); LC R$_t$=3.77 min.

Synthesis of 4-(3-(tert-butyldimethylsilyloxy)-5-methylcyclohexyl)pyridin-3-amine

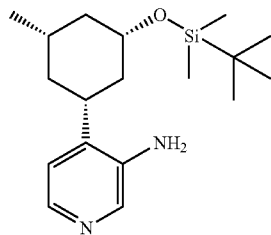 [SMILES: C[C@@H]1C[C@H](O[Si](C)(C)C(C)(C)C)C[C@H](c2ccncc2N)C1]

To a solution of 4-(3-(tert-butyldimethylsilyloxy)-5-methylcyclohex-1-enyl)-3-nitropyridine (1.0 equiv.) in methanol, at a concentration of 0.1M, was added 10% palladium on carbon (0.1 eq.). The resultant heterogeneous solution was put under an atmosphere of hydrogen and was stirred for 15 hours. At this time the mixture was filtered through a pad of celite eluting with methanol. The volatiles were removed in vacuo yielding 4-(3-(tert-butyldimethylsilyloxy)-5-methylcyclohexyl)pyridin-3-amine (90%). LCMS (m/z): 321.3 (MH⁺); LC R$_t$=3.85 min.

Synthesis of cis (+/−) benzyl 4-3-(tert-butyldimethylsilyloxy)-5-methylcyclohexyl) pyridin-3-ylcarbamate

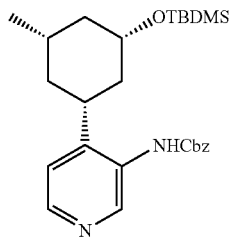 [SMILES: C[C@@H]1C[C@H](O[Si](C)(C)C(C)(C)C)C[C@H](c2ccncc2NC(=O)OCc2ccccc2)C1]

To a solution of cis-(+/−)-4-(3-(tert-butyldimethylsilyloxy)-5-methylcyclohexyl)pyridin-3-amine in dichloromethane at a concentration of 0.5 M was added benzyl 2,5-dioxopyrrolidin-1-yl carbonate (1.1 equiv.) and DMAP (0.05 equiv.). After stirring for 16 hours at rt, additional benzyl 2,5-dioxopyrrolidin-1-yl carbonate (0.55 equiv.) and DMAP (0.03 equiv.) were added. After stirring for an additional 24 hours at rt, additional benzyl 2,5-dioxopyrrolidin-1-yl carbonate (0.1 equiv.) and DMAP (0.03 equiv.) were added. After stirring for 18 more hours the solution was partitioned between EtOAc and Na₂CO₃(sat.) and separated. Upon further washing with Na₂CO₃(sat.) (2×) and NaCl(sat.), drying over MgSO₄, filtering and removal of solvents, cis (+/−) benzyl 4-3-(tert-butyldimethylsilyloxy)-5-methylcyclohexyl)pyridin-3-ylcarbamate was obtained. The crude material was used as is. LC/MS=455.3 (M+H), LC=4.39 min.

Synthesis of cis-(+/−)benzyl 4-(3-hydroxy-5-methylcyclohexyl)pyridin-3-ylcarbamate

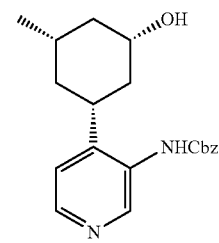 [SMILES: C[C@@H]1C[C@H](O)C[C@H](c2ccncc2NC(=O)OCc2ccccc2)C1]

A solution of cis (+/−) benzyl 4-3-(tert-butyldimethylsilyloxy)-5-methylcyclohexyl)pyridin-3-ylcarbamate in 1:2:1 6N HCl/THF/MeOH at a concentration of 0.1M was stirred at rt for 6 hours. The pH was than adjusted to pH=7 by addition of 6N NaOH and the volatiles were removed in vacuo. The aqueous layer was extracted with EtOAc and the organic was washed with NaCl(sat.), dried over MgSO₄, filtered and upon removal of the volatiles in vacuo, cis-(+/−)benzyl 4-(3-hydroxy-5-methylcyclohexyl)pyridin-3-ylcarbamate was obtained. The crude material was used as is. LC/MS=341.2 (M+H), LC=2.38 min.

Synthesis of cis (+/−)-benzyl 4-(3-methyl-5-oxocyclohexyl)pyridin-3-ylcarbamate

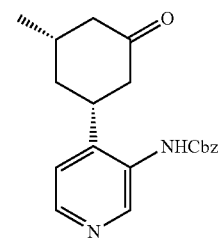 [SMILES: C[C@@H]1CC(=O)C[C@H](c2ccncc2NC(=O)OCc2ccccc2)C1]

To a 0° C. solution of cis-(+/−)-benzyl 4-(3-hydroxy-5-methylcyclohexyl)pyridin-3-ylcarbamate in wet CH₂Cl₂ at a concentration of 0.16 M was added Dess-Martin Periodinane (1.5 equiv.) and the solution was stirred for 18 hours as it warmed to rt. The solution was partitioned between EtOAc and 1:1 10% Na₂S₂O₃/NaHCO₃(sat.) and separated. Upon further washing with 1:1 10% Na₂S₂O₃/NaHCO₃(sat.) (2×) and NaCl(sat.), drying over MgSO₄, filtering, removal of solvents and purification by silica gel chromatography (75-100% EtOAc/hexanes), cis-(+/−)-benzyl-4-(3-methyl-5-oxocyclohexyl)pyridin-3-ylcarbamate was obtained as a white solid (53%, 5 steps). LC/MS=339.2 (M+H).

Synthesis of cis-(+/−)-benzyl 4-(−3-(benzylamino)-5-methylcyclohexyl)pyridin-3-ylcarbamate

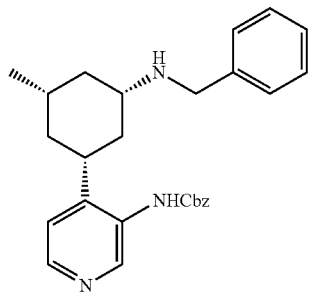 [SMILES: C[C@@H]1C[C@H](NCc2ccccc2)C[C@H](c2ccncc2NC(=O)OCc2ccccc2)C1]

A solution of cis-(+/−)-benzyl-4-(3-methyl-5-oxocyclohexyl)pyridin-3-ylcarbamate (1.0 equiv) and benzylamine (3.0 equiv) in MeOH, at a concentration of 0.25 M, was stirred at rt for 2 hours. Upon cooling in a −78° C. bath, LiBH$_4$ (1.1 equiv, 2.0 M in THF) was added and the solution was allowed to warm to rt with stirring over 16 hours. The solution was partitioned between EtOAc and NaHCO$_{3(sat.)}$, separated, washed further with NaHCO$_{3(sat.)}$ and NaCl$_{(sat.)}$, dried over MgSO$_4$, filtered and after removal of volatiles in vacuo, cis-(+/−)-benzyl 4-(-3-(benzylamino)-5-methylcyclohexyl)pyridin-3-ylcarbamate was obtained as a 4:1 mixture of isomers, with the all cis as predominant LC/MS=430.3 (M+H), LC=0.62 min.

Synthesis of cis (+/−)-tert-butyl(-3-(3-aminopyridin-4-yl)-5-methylcyclohexylcarbamate

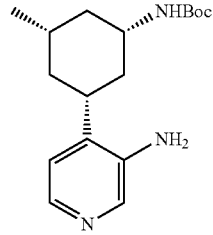 [SMILES: C[C@@H]1C[C@H](NC(=O)OC(C)(C)C)C[C@H](c2ccncc2N)C1]

To a solution of cis-(+/−)-benzyl 4-(-3-(benzylamino)-5-methylcyclohexyl)pyridin-3-ylcarbamate was (1.0 equiv.) in methanol, at a concentration of 0.07 M, was added 20% palladium hydroxide on carbon (0.2 eq.). The resultant heterogeneous solution was put under an atmosphere of hydrogen and was stirred for 14 hours. At this time the reaction was purged with Ar, Boc$_2$O (1.0 equiv.) was added and the solution was stirred for 8 hours. Additional Boc$_2$O (1.0 equiv.) was added and the solution was stirred for 16 more hours. At this time the mixture was filtered through a pad of celite eluting with methanol. Upon removal of volatiles in vacuo, purification by silica gel chromatography (2.5-2.5 MeOH/CH$_2$Cl$_2$ with 0.1% DIEA) and recrystallization from 10% EtOAc/hexanes yielded cis (+/−)-tert-butyl (-3-(3-aminopyridin-4-yl)-5-methylcyclohexylcarbamate (49%). LCMS (m/z): 306.3 (MH$^+$), LC R$_t$=2.59 min. Pure enantiomers could be obtained by chiral chromatography.

Synthesis of (+/−)-4-(5-methylcyclohexa-1,3-dienyl)-3-nitropyridine

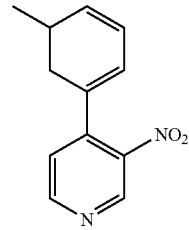 [SMILES: CC1C=CC=C(c2ccncc2[N+](=O)[O-])C1]

To a solution of (+/−)-5-methyl-3-(3-nitropyridin-4-yl)cyclohex-2-enol (1.0 equiv.) in dioxane (0.1M) was added p-TSA (1.0 equiv.), and the reaction was stirred at 100° C. for 3 h. The solution was cooled to room temperature, then passed through a pad of neutral alumina eluting with EtOAc to yield (+/−)-4-(5-methylcyclohexa-1,3-dienyl)-3-nitropyridine as a yellow oil in 68% yield. LC/MS=217.1 (M+H), LC=3.908 min.

Synthesis of (+/−)-2-azido-6-methyl-4-(3-nitropyridin-4-yl)cyclohex-3-enol

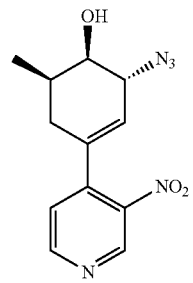 [SMILES: C[C@@H]1CC(c2ccncc2[N+](=O)[O-])=C[C@@H](N=[N+]=[N-])[C@@H]1O]

To a solution of (+/−)-4-(5-methylcyclohexa-1,3-dienyl)-3-nitropyridine (1.0 equiv.) in DCM (0.1M) at 0° C. was added m-CPBA (1.1 equiv.) and the reaction was allowed to warm to room temperature. After 3 hours, the mixture was quenched with saturated NaHCO$_3$, extracted with DCM, and the organic phase was dried with sodium sulfate, filtered, and concentrated to give a yellow oil. The crude was dissolved in ethanol and water (3:1, 0.1 M), and sodium azide (2.0 equiv.) and ammonium chloride (2.0 equiv.) were added. The reaction was stirred for 4 hours, then concentrated in vacuo. To the crude was added ethyl acetate and water, the organic phase was washed with brine, dried with sodium sulfate, filtered, and concentrated. The crude material was purified via silica gel column chromatography eluting with ethyl acetate and hexanes (1:1) to afford (+/−)-2-azido-6-methyl-4-(3-nitropyridin-4-yl)cyclohex-3-enol as an oil in 49% yield. LC/MS=276.1 (M+H), Rt=0.71 min.

Synthesis of tert-butyl (+/−)-6-hydroxy-5-methyl-3-(3-nitropyridin-4-yl)cyclohex-2-enylcarbamate

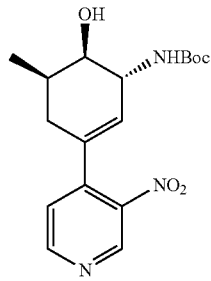 [SMILES: C[C@@H]1CC(c2ccncc2[N+](=O)[O-])=C[C@@H](NC(=O)OC(C)(C)C)[C@@H]1O]

To a solution of (+/−)-2-azido-6-methyl-4-(3-nitropyridin-4-yl)cyclohex-3-enol (1.0 equiv.) in pyridine and ammonium hydroxide (8:1, 0.08 M) was added trimethylphosphine (3.0 equiv.) and the brown solution was stirred at room temperature for 2 hours. Ethanol was added to the mixture and the solution was concentrated under vacuo (2×). The crude mixture was then dissolved in dioxane and sat. NaHCO₃ (1:1, 0.08 M) and Boc₂O (1.0 equiv.) was added. The solution was stirred at room temperature for 2 hours, then partitioned between ethyl acetate and water. The organic phase was dried with magnesium sulfate, filtered, and concentrated in vacuo. The crude product was purified via silica gel column chromatography eluting with ethyl acetate and hexanes (1:1) to afford tert-butyl (+/−)-6-hydroxy-5-methyl-3-(3-nitropyridin-4-yl)cyclohex-2-enylcarbamate in 69% yield. LC/MS=350.1 (M+H), Rt=0.76 min.

Synthesis of (+/−)-2-(tert-butoxycarbonylamino)-6-methyl-4-(3-nitropyridin-4-yl) cyclohex-3-enyl methanesulfonate

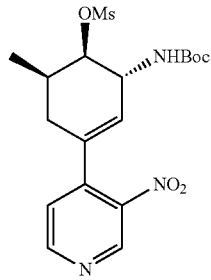 [SMILES: C[C@@H]1CC(c2ccncc2[N+](=O)[O-])=C[C@@H](NC(=O)OC(C)(C)C)[C@@H]1OS(C)(=O)=O]

To a solution of tert-butyl (+/−)-6-hydroxy-5-methyl-3-(3-nitropyridin-4-yl)cyclohex-2-enylcarbamate (1.0 equiv.) in DCM (0.09 M) was added triethyl amine (1.5 equiv.). The reaction mixture was cooled to 0° C. and MsCl (1.2 equiv.) was added to the reaction and stirred for 3 hours. To the solution was added water, the organic phase was dried with sodium sulfate, filtered, and concentrated. The crude material was purified via silica gel column chromatography eluting with ethyl acetate and hexanes (1:1) to give (+/−)-2-(tert-butoxycarbonylamino)-6-methyl-4-(3-nitropyridin-4-yl)cyclohex-3-enyl methanesulfonate as a white foam in 65% yield. LC/MS=428.2 (M+H), Rt=0.88 min.

Synthesis of (+/−)-tert-butyl 7-methyl-5-(3-nitropyridin-4-yl)-2-oxo-3a,6,7,7a-tetrahydrobenzo[d]oxazole-3(2H)-carboxylate

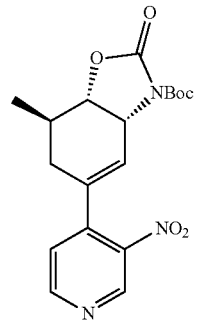 [SMILES: C[C@@H]1CC(c2ccncc2[N+](=O)[O-])=C[C@@H]2[C@H]1OC(=O)N2C(=O)OC(C)(C)C]

A solution of (+/−)-2-(tert-butoxycarbonylamino)-6-methyl-4-(3-nitropyridin-4-yl)cyclohex-3-enyl methanesulfonate (1.0 equiv.) in pyridine (0.2 M) in a microwave vessel was heated to 110° C. for 10 min. The orange solution was then concentrated to dryness and worked up by partitioning between ethyl acetate and water. The organic phase was dried with sodium sulfate, filtered and concentrated. The crude material was dissolved in DCM (0.2 M) and triethyl amine (1.8 equiv.) was added to the reaction, followed by Boc₂O (1.2 eqiv.). After stirring at room temperature for 40 min, the reaction was concentrated in vacuo and purified via silica gel column chromatography eluting with ethyl acetate and hexanes (1:1) to give (+/−)-tert-butyl 7-methyl-5-(3-nitropyridin-4-yl)-2-oxo-3a,6,7,7a-tetrahydrobenzo[d]oxazole-3(2H)-carboxylate as a white foam in 66% yield. LC/MS=376.0 (M+H), Rt=0.87 min.

Synthesis of (+/−)-tert-butyl 5-(3-aminopyridin-4-yl)-7-methyl-2-oxohexahydrobenzo[d]oxazole-3(2H)-carboxylate

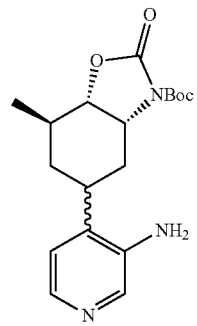 [SMILES: C[C@@H]1CC(c2ccncc2N)C[C@@H]2[C@H]1OC(=O)N2C(=O)OC(C)(C)C]

To a solution of (+/−)-tert-butyl 7-methyl-5-(3-nitropyridin-4-yl)-2-oxo-3a,6,7,7a-tetrahydrobenzo[d]oxazole-3(2H)-carboxylate (1.0 equiv.) in MeOH and ethyl acetate (1:1, 0.07 M) was added 10% Pd/C (0.1 equiv.) and the reaction was stirred at room temperature under an atmosphere of hydrogen. Upon completion of the reaction, the solution was filtered through a pad of Celite, washed with MeOH and ethyl acetate, the filtrate was concentrated to dryness under vacuo to give (+/−)-tert-butyl 5-(3-aminopyridin-4-yl)-7-methyl-2-oxohexahydrobenzo[d]oxazole-3(2H)-carboxylate as a mixture of diastereomers in >99% yield. LC/MS=348.2 (M+H), Rt=0.50 min.

Synthesis of (+/−)-6-bromo-5-methyl-3-(3-nitropyridin-4-yl)cyclohex-2-enol

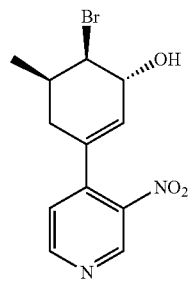 [SMILES: C[C@@H]1CC(c2ccncc2[N+](=O)[O-])=C[C@@H](O)[C@@H]1Br]

To a solution of 4-(5-methylcyclohexa-1,3-dienyl)-3-nitropyridine (1.0 equiv.) in THF and water (1:1, 0.13 M) was added NBS (1.5 equiv.) and the reaction was stirred at room temperature for 30 min. Upon completion, ethyl acetate and water were added to the reaction, the organic phase was dried with brine, then sodium sulfate, filtered, and concentrated. The crude material was purified via silica gel column chromatography eluting with ethyl acetate and hexanes (1:1) to give (+/−)-6-bromo-5-methyl-3-(3-nitropyridin-4-yl)cyclohex-2-enol as a yellow oil in 80% yield. LC/MS=315.0/313.0 (M+H), LC=2.966 min.

Synthesis of (+/−)-2-azido-6-methyl-4-(3-nitropyridin-4-yl)cyclohex-3-enol

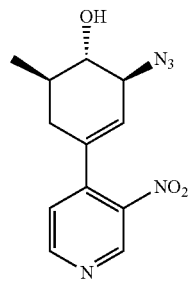 [SMILES: C[C@@H]1CC(c2ccncc2[N+](=O)[O-])=C[C@H](N=[N+]=[N-])[C@H]1O]

To a solution of (+/−)-6-bromo-5-methyl-3-(3-nitropyridin-4-yl)cyclohex-2-enol (1.0 equiv.) in THF (0.1M) was added potassium tert-butoxide (1.5 equiv.). The reaction turned from orange to black almost immediately. By TLC, the formation of product is clean in 30 min. Quenched by adding saturated ammonium chloride and ethyl acetate. The organic phase was dried with brine, then sodium sulfate, filtered, and concentrated. The crude product was dissolved in ethanol and water (3:1, 0.1M), and ammonium chloride (2.0 equiv) and sodium azide (2.0 equiv.) were added. The dark orange reaction was stirred at room temperature overnight. The conversion to product is clean as indicated by LC/MS. The reaction was concentrated to remove the ethanol, ethyl acetate and water were added, and the organic phase was dried with sodium sulfate, filtered, and concentrated. The crude material was purified via silica gel column chromatography eluting with ethyl acetate and hexanes (1:1) to give (+/−)-2-azido-6-methyl-4-(3-nitropyridin-4-yl)cyclohex-3-enol in 55% yield. LC/MS=276.0 (M+H), LC=2.803 min.

Synthesis of (+/−)-tert-butyl 6-hydroxy-5-methyl-3-(3-nitropyridin-4-yl)cyclohex-2-enylcarbamate

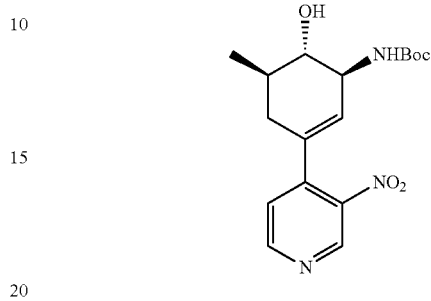

To a solution of (+/−)-2-azido-6-methyl-4-(3-nitropyridin-4-yl)cyclohex-3-enol (1.0 equiv.) in pyridine and ammonium hydroxide (8:1, 0.08 M) was added trimethylphosphine (3.0 equiv.) and the brown solution was stirred at room temperature for 2 h. Upon completion, EtOH was added and the solution was concentrated in vacuo. More ethanol was added and the reaction was concentrated again. Dioxane and sat. NaHCO$_3$ (1:1, 0.08 M) were added to the crude, followed by Boc$_2$O (1.0 equiv.). Stirred the reaction mixture at room temperature for 2 h, then added water and ethyl acetate. The organic phase was dried with MgSO$_4$, and concentrated. The crude product was purified via silica gel column chromatography eluting with ethyl acetate and hexanes (1:1) to afford (+/−)-tert-butyl 6-hydroxy-5-methyl-3-(3-nitropyridin-4-yl)cyclohex-2-enylcarbamate (59%). LC/MS=350.1 (M+H), Rt: 0.76 min.

Synthesis of (+/−)-2-(tert-butoxycarbonylamino)-6-methyl-4-(3-nitropyridin-4-yl)cyclohex-3-enyl acetate

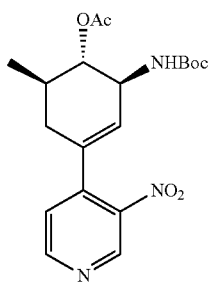 [SMILES: CC(=O)O[C@H]1[C@H](C)CC(c2ccncc2[N+](=O)[O-])=C[C@@H]1NC(=O)OC(C)(C)C]

To a solution of (+/−)-tert-butyl 6-hydroxy-5-methyl-3-(3-nitropyridin-4-yl)cyclohex-2-enylcarbamate (1.0 equiv.) in pyridine (0.1 M) was added Ac$_2$O (2.0 equiv.) and the reaction was stirred at room temperature overnight. Upon completion, the reaction was concentrated to dryness, then worked-up with ethyl acetate and water. The organic phase was dried with brine, then sodium sulfate, filtered, and concentrated to give (+/−)-2-(tert-butoxycarbonylamino)-6-methyl-4-(3-nitropyridin-4-yl)cyclohex-3-enyl acetate in 94% yield. LC/MS=392.2 (M+H), Rt=0.94 min.

Synthesis of (+/−)-4-(3-aminopyridin-4-yl)-2-(tert-butoxycarbonylamino)-6-methylcyclohexyl acetate

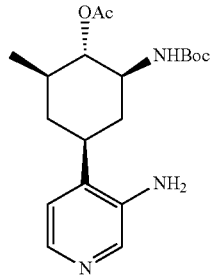 [SMILES: CC(=O)O[C@H]1[C@H](C)C[C@H](c2ccncc2N)C[C@@H]1NC(=O)OC(C)(C)C]

To a degassed solution of (+/−)-2-(tert-butoxycarbonylamino)-6-methyl-4-(3-nitropyridin-4-yl)cyclohex-3-enyl acetate (1.0 equiv.) in MeOH and EtOAc (1:1, 0.1M) was added 10% Pd/C (0.1 equiv.) and the reaction was stirred at room temperature under a hydrogen balloon for 3 days. Upon completion, the solution was filtered through a pad of Celite, the pad was washed with ethyl acetate and the filtrate was concentrated. The crude material contained about 10% of the undesired isomer. The crude was dissolved in ethyl acetate (~20%) and hexanes and heated until all dissolved. The solution was allowed to sit at room temperature for 2 days. The precipitate was then collected to give (+/−)-4-(3-aminopyridin-4-yl)-2-(tert-butoxycarbonylamino)-6-methylcyclohexyl acetate as the pure product in 59% yield. LC/MS=364.3 (M+H), Rt=0.63 min.

Synthesis of 2-(tert-butoxycarbonylamino)-6-methyl-4-(3-nitropyridin-4-yl)cyclohex-3-enyl methanesulfonate

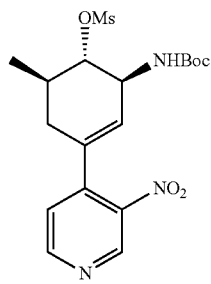 [SMILES: C[C@@H]1CC(c2ccncc2[N+](=O)[O-])=C[C@H](NC(=O)OC(C)(C)C)[C@H]1OS(C)(=O)=O]

To a solution of tert-butyl 6-hydroxy-5-methyl-3-(3-nitropyridin-4-yl)cyclohex-2-enylcarbamate (1.0 equiv.) in DCM (0.09 M) was added triethylamine (1.5 equiv.) and the reaction was cooled to 0° C. MsCl (1.2 equiv.) was added to the reaction and stirred for 3 h. Another 1.0 equiv. of MsCl was added to the reaction and stirred for another 2 h. Worked up the reaction by adding water, the organic phase was dried with brine, sodium sulfate, and concentrated. The crude product was purified via silica gel column chromatography eluting with ethyl acetate and hexanes (1:1) to afford 2-(tert-butoxycarbonylamino)-6-methyl-4-(3-nitropyridin-4-yl)cyclohex-3-enyl methanesulfonate as a white foam in 65% yield. LC/MS=428.2 (M+H), LC: 3.542 min.

Synthesis of (+/−)-tert-butyl 7-methyl-5-(3-nitropyridin-4-yl)-2-oxo-3a,6,7,7a-tetrahydrobenzo[d]oxazole-3(2H)-carboxylate

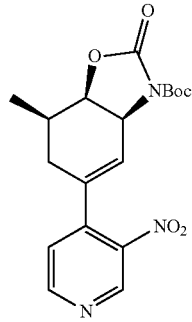 [SMILES: C[C@@H]1CC(c2ccncc2[N+](=O)[O-])=C[C@H]2[C@@H]1OC(=O)N2C(=O)OC(C)(C)C]

A solution of (+/−)-2-(tert-butoxycarbonylamino)-6-methyl-4-(3-nitropyridin-4-yl)cyclohex-3-enyl methanesulfonate (1.0 equiv.) in pyridine (0.2 M) was heated in the microwave at 110° C. for 10 min. The orange reaction was then concentrated under vacuo, the crude was dissolved in ethyl acetate and water, the organic phase was dried with sodium sulfate and concentrated under vacuo. The crude material was dissolved in DCM (0.2 M), triethylamine (1.8 equiv.) was added, followed by Boc₂O (1.2 equiv.). The reaction was stirred for 40 min, then concentrated to dryness. The crude material was purified via silica gel column chromatography eluting with hexane and ethyl acetate (1:1) to afford (+/−)-tert-butyl 7-methyl-5-(3-nitropyridin-4-yl)-2-oxo-3a,6,7,7a-tetrahydrobenzo[d]oxazole-3(2H)-carboxylate as a white foam in 66% yield. LC/MS=376.0 (M+H), LC: 3.424 min.

Synthesis of (+/−)-tert-butyl 5-(3-aminopyridin-4-yl)-7-methyl-2-oxohexahydrobenzo[d]oxazole-3(2H)-carboxylate

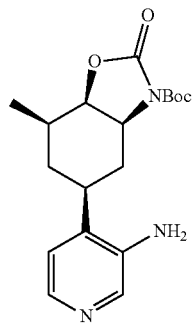 [SMILES: C[C@@H]1C[C@H](c2ccncc2N)C[C@H]2[C@@H]1OC(=O)N2C(=O)OC(C)(C)C]

To a degassed solution of (+/−)-tert-butyl 7-methyl-5-(3-nitropyridin-4-yl)-2-oxo-3a,6,7,7a-tetrahydrobenzo[d]oxazole-3(2H)-carboxylate (1.0 equiv.) in MeOH and EtOAc (1:1, 0.1M) was added 10% Pd/C (0.1 equiv.). The reaction was stirred under a hydrogen balloon overnight. Upon completion, the solution was filtered through a pad of Celite and the pad was washed with ethyl acetate. The filtrate was concentrated under vacuo to give (+/−)-tert-butyl 5-(3-aminopyridin-4-yl)-7-methyl-2-oxohexahydrobenzo[d]oxazole-3(2H)-carboxylate as the desired product as a yellow foam in 93% yield. LC/MS=348.1 (M+H), Rt=055 min.

Synthesis of ((+/−)-(1R,2R,6S)-6-methyl-4-(3-nitro-pyridin-4-yl)cyclohex-3-ene-1,2-diol and (+/−)-(1R,2S,6S)-6-methyl-4-(3-nitropyridin-4-yl)cyclohex-3-ene-1,2-diol)

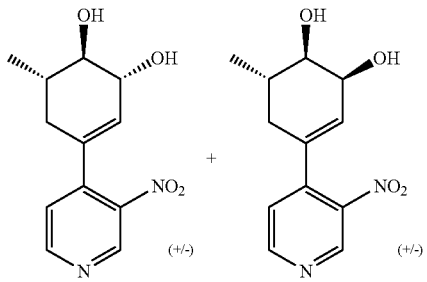 [SMILES: C[C@H]1CC(c2ccncc2[N+](=O)[O-])=C[C@@H](O)[C@@H]1O ; C[C@H]1CC(c2ccncc2[N+](=O)[O-])=C[C@H](O)[C@@H]1O]

To a solution of (+/−)-(1S,5S,6S)-6-bromo-5-methyl-3-(3-nitropyridin-4-yl)cyclohex-2-enol (1.0 equiv.) in THF (0.1 M) was added potassium tert-butoxide (1.5 equiv.) at room temperature. The reaction mixture was stirred for 10 min. The reaction mixture was quenched with $NH_4Cl$ solution and worked up with EtOAc by washing with water and brine. The organic layer was dried over anhydrous sodium sulfate, filtered off, and dried in vacuo. The crude product was used for next step without further purification. $R_f$=0.5 (50% EtOAc/Hexanes). LCMS: MH+251.2 (as a diol), $R_t$=0.49 min. To a solution of crude (+/−)-4-((1S,5S)-5-methyl-7-oxabicyclo[4.1.0]hept-2-en-3-yl)-3-nitropyridine (1.0 equiv.) in 2:1 $CH_3CN/H_2O$ (0.1 M) was added acetic acid (0.3 equiv.) at room temperature. The reaction mixture was stirred for 16 h at room temperature. After quenched with $NaHCO_3$ solution, the reaction mixture was concentrated to remove the majority of $CH_3CN$ and the residue was partitioned between EtOAc and water. The combined organic layer was washed with water and brine, dried over anhydrous sodium sulfate, filtered and concentrated in vacuo. A mixture of diols ((+/−)-(1R,2R,6S)-6-methyl-4-(3-nitropyridin-4-yl)cyclohex-3-ene-1,2-diol and (+/−)-(1R,2S,6S)-6-methyl-4-(3-nitropyridin-4-yl)cyclohex-3-ene-1,2-diol) was obtained in 33.1% yield as a white solid by flash column chromatography. $R_f$=0.3 (100% EtOAc; diols were not separable on TLC). LCMS: MH+251.2, $R_t$=0.49 min.

Synthesis of (+/−)-4-((3S,4R,5S)-3,4-bis(tert-butyldimethylsilyloxy)-5-methylcyclohex-1-enyl)-3-nitropyridine and (+/−)-4-((3R,4R,5S)-3,4-bis(tert-butyldimethylsilyloxy)-5-methylcyclohex-1-enyl)-3-nitropyridine

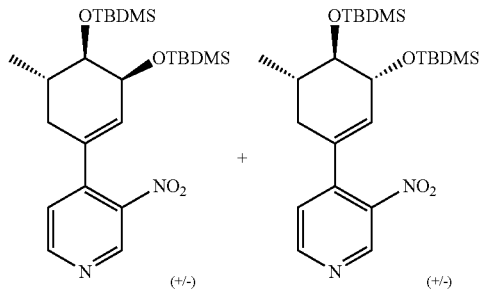 [SMILES: C[C@H]1CC(c2ccncc2[N+](=O)[O-])=C[C@H](O[Si](C)(C)C(C)(C)C)[C@@H]1O[Si](C)(C)C(C)(C)C ; C[C@H]1CC(c2ccncc2[N+](=O)[O-])=C[C@@H](O[Si](C)(C)C(C)(C)C)[C@@H]1O[Si](C)(C)C(C)(C)C]

To a solution of a mixture of diols (1.0 equiv) in DMF (0.3 M) was added TBDMSCl (7.0 equiv.) and imidazole (9 equiv.) at room temperature. The reaction mixture was stirred at room temperature overnight. After quenched with sat $NaHCO_3$, The reaction mixture was extracted with EtOAc. The combined organic layer was washed with water and brine, dried over anhydrous sodium sulfate, filtered and concentrated in vacuo. The mixture was purified by sequential automated silica column chromatography (gradient eluting with EtOAc and Hexanes) and preparative reverse phase HPLC (55%-95% acetonitrile in water, then run 5%-95% acetonitrile in water to yield (+/−)-4-((3S,4R,5S)-3,4-bis(tert-butyldimethylsilyloxy)-5-methylcyclohex-1-enyl)-3-nitropyridine (27.2%) and (+/−)-4-((3R,4R,5S)-3,4-bis(tert-butyldimethylsilyloxy)-5-methylcyclohex-1-enyl)-3-nitropyridine (50.2%). LCMS: MH+479.2, $R_t$=1.60 and 1.63 min.

Synthesis of 4-((1S,3S,4S,5R)-3,4-bis(tert-butyldimethylsilyloxy)-5-methylcyclohexyl)pyridin-3-amine and of 4-((1R,3R,4R,5S)-3,4-bis(tert-butyldimethylsilyloxy)-5-methylcyclohexyl)pyridin-3-amine

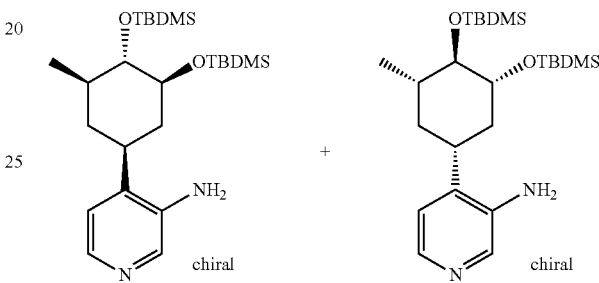

To a solution of (+/−)-4-((3R,4R,5S)-3,4-bis(tert-butyldimethyl-silyloxy)-5-methylcyclohex-1-enyl)-3-nitropyridine (1.0 equiv.) in ethanol/EtOAc, at a concentration of 0.1 M, was added 10% palladium on carbon (0.1 eq.). The resultant heterogeneous solution was put under an atmosphere of hydrogen and was stirred for 14 hours. At this time the mixture was filtered through a pad of celite eluting with EtOAc. The volatiles were removed in vacuo and the crude material was purified by automated silica column chromatography ($R_f$=0.2, 40% EtOAc in Heptane) to yield pure racemic product. LCMS: MH+451.3, Rt=1.35 min. The racemic compound was resolved by chiral chromatography (IC column, 1 mL/min, 5% IPA in Heptane) to yield 4-((1S,3S,4S,5R)-3,4-bis(tert-butyldimethylsilyloxy)-5-methylcyclohexyl)pyridin-3-amine (6.01 min) and 4-((1R,3R,4R,5S)-3,4-bis(tert-butyldimethylsilyloxy)-5-methylcyclohexyl)pyridin-3-amine (8.34 min)

Synthesis of 4-((1R,3R,4S,5R)-3,4-bis(tert-butyldimethylsilyloxy)-5-methylcyclohexyl)pyridin-3-amine and of 4-((1S,3S,4R,5S)-3,4-bis(tert-butyldimethylsilyloxy)-5-methylcyclohexyl)pyridin-3-amine

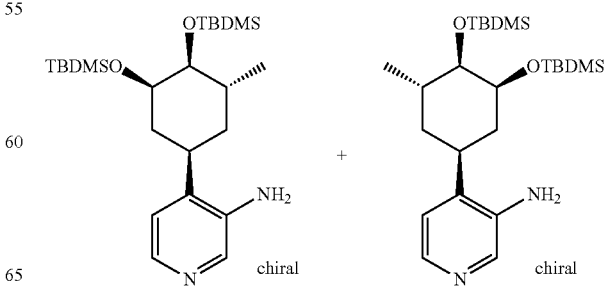

To a solution of (+/−)-4-((3S,4R,5S)-3,4-bis(tert-butyldimethyl-silyloxy)-5-methylcyclohex-1-enyl)-3-nitropyridine (1.0 equiv.) in ethanol, at a concentration of 0.1 M, was added 10% palladium on carbon (0.1 eq.). The resultant heterogeneous solution was put under an atmosphere of hydrogen and was stirred for 14 hours. At this time the mixture was filtered through a pad of celite eluting with ethanol. The volatiles were removed in vacuo and the crude material was purified by automated silica column chromatography ($R_f$=0.2, 40% EtOAc in Heptane) to yield pure racemic product (50.4%). LCMS: MH+451.3, $R_t$=1.35 min. The racemic compound was resolved by chiral chromatography (IC column, 1 mL/min, 5% IPA in Heptane) to yield 4-((1R,3R,4S,5R)-3,4-bis(tert-butyldimethylsilyloxy)-5-methylcyclohexyl)pyridin-3-amine (6.98 min) and 4-((1S,3S,4R,5S)-3,4-bis(tert-butyldimethylsilyloxy)-5-methyl-cyclohexyl)pyridin-3-amine (8.67 min)

Synthesis of sodium 6-(methoxycarbonyl)-3-oxo-5-(trifluoromethyl)cyclohex-1-enolate

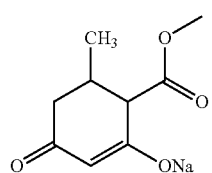

To a freshly prepared solution of sodium (1.0 eq) in t-BuOH (1M) was added ethyl acetoacetate (1.0 eq) by dropwise and the mixture stirred on an ice bath for an additional 15 min. ethyl 4,4,4-trifluorocrotonate (1.0 eq) was added dropwise and the mixture stirred at room temperature for an additional 30 min. After refluxing for 2 h, the mixture was cooled and hexanes was added. The precipitate was filtered without further purification to give sodium 6-(methoxycarbonyl)-3-oxo-5-(trifluoromethyl)cyclohex-1-enolate (46%). LC/MS (m/z): MH+=253.1, Rt=0.70 min.

Synthesis of 5-(trifluoromethyl)cyclohexane-1,3-dione

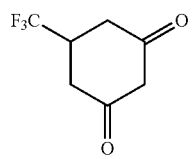

Sodium 6-(Methoxycarbonyl)-3-oxo-5-(trifluoromethyl)cyclohex-1-enolate (1.0 eq) was dissolved in 1M NaOH (1.0 eq), and the mixture refluxed for 1 h. After cooling to room temperature, the mixture was acidified with 5 M sulfuric acid. The mixture was extracted with EtOAc. After washing with water, the organic layer was dried over magnesium sulfate, the solvent was removed under reduced pressure to give 5-(trifluoromethyl)cyclohexane-1,3-dione, which was used to the next step without further purification (98%). LC/MS (m/z): MH+=181.1, Rt=0.55 min.

Synthesis of 3-oxo-5-(trifluoromethyl)cyclohex-1-enyl trifluoromethanesulfonate

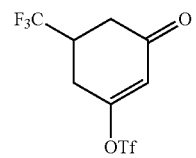

To a suspension of 5-(trifluoromethyl)cyclohexane-1,3-dione (1.0 eq) in DCM (0.23 M) was added TEA (1.2 eq) to give a clear solution. The mixture was cooled to 0° C. And then Tf$_2$O (1.05 eq) in DCM was added dropwise. The reaction mixture was stirred at that temperature for 2 hours. The reaction mixture was diluted with DCM, and washed with water, aq. NaHCO$_3$, brine, and was dried over MgSO$_4$, filtered and concentrated to give 3-oxo-5-(trifluoromethyl)cyclohex-1-enyl trifluoromethanesulfonate, which was used to next step directly. LC/MS (m/z): MH+=313.0, Rt=1.02 min.

Synthesis of 3-(4,4,5,5-tetramethyl-1,3,2-dioxaborolan-2-yl)-5-(trifluoromethyl)cyclohex-2-enone

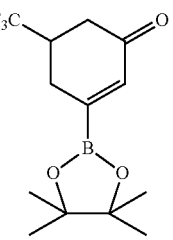

All of reagents 3-oxo-5-(trifluoromethyl)cyclohex-1-enyl trifluoromethanesulfonate (1.0 eq), NaOAc (3.0 eq), and bis(pinacolato)diboron (2.0 eq) were added to 1,4-dioxane (0.23 M) in a round bottom flask and degassed by bubbling N$_2$ through the mixture for 10 min. PdCl$_2$(dppf).CH$_2$Cl$_2$ adduct (0.1 eq) was added and the reaction heated to 80° C. fitted with a reflux condenser on an oil bath under N$_2$ for two hours. The mixture was cooled to room temperature, filtered through a coarse frit glass funnel, the cake rinsed with ~10 mL 1,4-dioxane to give 3-(4,4,5,5-tetramethyl-1,3,2-dioxaborolan-2-yl)-5-(trifluoromethyl)cyclohex-2-enone in 1,4-dioxane, which was used to next step directly. LC/MS (m/z): MH+=209.1 (boronic acid), Rt=0.60 min.

Synthesis of 3-(3-nitropyridin-4-yl)-5-(trifluoromethyl)cyclohex-2-enone

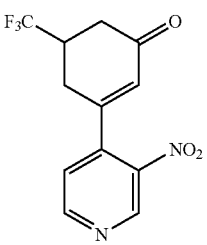 [SMILES: O=C1C=C(c2ccncc2[N+](=O)[O-])CC(C(F)(F)F)C1]

The boronate ester 3-(4,4,5,5-tetramethyl-1,3,2-dioxaborolan-2-yl)-5-(trifluoromethyl)cyclohex-2-enone (1.0 eq) was dissolved in 1,4-dioxane (0.14 M) in a round bottom flask was degassed by bubbling N$_2$ through the solution for 30 minutes. 4-chloro-3-nitropyridine (1.3 eq) and aq. Na$_2$CO$_3$ (2M, 2.0 eq) were added and N$_2$ was bubbled through for 10 minutes and then PdCl$_2$(dppf).CH$_2$Cl$_2$ adduct (0.1 eq) was added. The reaction mixture was stirred at 100° C. for 2 Hours. The mixture was added EtOAc and brine. The resulting mixture was filtered through celite, the cake was washed with EtOAc. The organic layer was separated, and washed with brine, dried over MgSO4, and filtered and concentrated. The crude product was purified by silica gel chromatography (eluted with EtOAc:Hexanes=1:10 to 2:1) to give 3-(3-nitropyridin-4-yl)-5-(trifluoromethyl)cyclohex-2-enone (73% for three steps from diketone). LC/MS (m/z): MH$^+$=287.1, Rt=0.85 min.

Synthesis of cis-3-(3-nitropyridin-4-yl)-5-(trifluoromethyl)cyclohex-2-enol

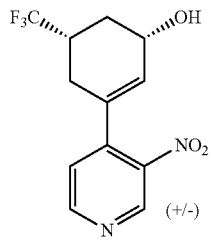

3-(3-Nitropyridin-4-yl)-5-(trifluoromethyl)cyclohex-2-enone (1.0 eq) was mixed with cerium(III) chloride heptahydrate (1.0 eq) and absolute ethanol (0.17) was added. The mixture was stirred at ambient temperature until all solids dissolved. the mixture was cooled on an ice bath and NaBH$_4$ (1.2 eq) was added portion wise. The reaction was stirred on the ice bath for 1 h. The mixture was diluted with EtOAc, washed with water, dried over MgSO$_4$, filtered and concentrated. The residue was purified by column (1:1 ethyl acetate and hexanes) to give cis-3-(3-nitropyridin-4-yl)-5-(trifluoromethyl)cyclohex-2-enol (66%). LC/MS (m/z): MH$^+$=289.2, Rt=0.72 min.

Synthesis of cis-4-(3-azido-5-(trifluoromethyl)cyclohex-1-enyl)-3-nitropyridine

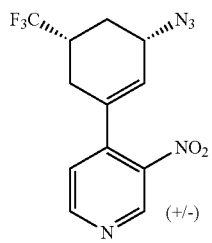 [SMILES: [N-]=[N+]=N[C@@H]1C=C(c2ccncc2[N+](=O)[O-])C[C@H](C(F)(F)F)C1]

To a solution of cis-3-(3-nitropyridin-4-yl)-5-(trifluoromethyl)cyclohex-2-enol (1.0 eq) in DCM (0.14 M) was added TEA (2.5 eq), and followed by MsCl (1.8 eq) at room temperature. The reaction mixture was stirred at room temperature for 2 hours. The solvent was removed. The residue was dissolved in DMF (0.19 M), and then the mixture was added sodium azide (1.2 eq). The resulting mixture was stirred at room temperature for 1 hour. Another 1.2 eq of sodium azide was added. The mixture was stirred at room temperature overnight. The reaction mixture was diluted with ethyl acetate and heptane, and washed with sat NaCl. The organic was dried over MgSO$_4$, filtered and concentrated. The residue was purified by column (1:1 ethyl acetate and hexanes) to give cis-4-(3-azido-5-(trifluoromethyl)cyclohex-1-enyl)-3-nitropyridine (58%). LC/MS (m/z): MH$^+$=314.1, Rt=0.96 min.

Synthesis of tert-butyl (1R,3R,5S)-3-(3-aminopyridin-4-yl)-5-(trifluoromethyl)cyclohexylcarbamate

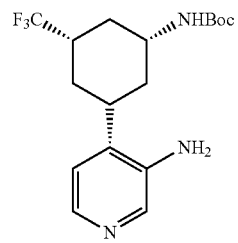

A solution of cis-4-(3-azido-5-(trifluoromethyl)cyclohex-1-enyl)-3-nitropyridine (1.0 eq) in Ethanol (0.13 M) was bubbled with N$_2$ for 20 min. Then the reaction mixture was added Boc-anhydride (1.5 eq) and Pd/C (0.2 eq). The reaction mixture was stirred at room temperature under H$_2$ atmosphere overnight. Solid was removed by filtration over celite and rinsed with EtOH. The residue was purified by column (5% methanol in 1:1 ethyl acetate and hexanes) to give racemic cis-3-(3-aminopyridin-4-yl)-5-(trifluoromethyl)cyclohexylcarbamate (57%). LC/MS (m/z): MH+=360.2, Rt=0.72 min. The enantiomerically pure tert-butyl (1R,3R,5S)-3-(3-aminopyridin-4-yl)-5-(trifluoromethyl)cyclohexylcarbamate and N-(4-((1S,3S,5R)-3-amino-5-(trifluoromethyl)cyclohexyl)pyridin-3-yl)-6-(2,6-difluorophenyl)-5-fluoropicolinamide were resolved by chiral HPLC (For analysis R$_t$=8.14 min and 10.59 min respectively; heptane:isopropanol=90:10 (v:v), Chiralcel IC 100×4 6 mm at 1 mL/min. For preparative separation, heptane:isopropanol=90:10 (v:v), Chiralcel IC 250×20 mm at 15 mL/min)

Synthesis of (R)-4-benzyl-3-((2R,3R)-3-((R)-2,2-dimethyl-1,3-dioxolan-4-yl)-3-hydroxy-2-methylpropanoyl)oxazolidin-2-one

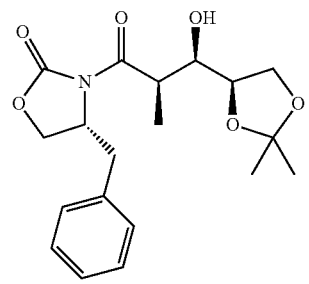 [SMILES: C[C@@H](C(=O)N1C(=O)OC[C@H]1Cc1ccccc1)[C@@H](O)[C@H]1COC(C)(C)O1]

(R)-4-benzyl-3-((2R,3R)-3-((R)-2,2-dimethyl-1,3-dioxolan-4-yl)-3-hydroxy-2-methylpropanoyl)oxazolidin-2-one was prepared in the reported manner (Proc.Nat.Acad. .Sciences, 101, 33, 2004, pages 12042-12047) for the enantiomeric compound by starting with (R)-4-benzyl-3-propionyloxazolidin-2-one and R-glyceraldehyde acetonide.

Synthesis of (R)-4-benzyl-3-((2R,3R)-3-(tert-butyldimethylsilyloxy)-3-((R)-2,2-dimethyl-1,3-dioxolan-4-yl)-2-methylpropanoyl)oxazolidin-2-one

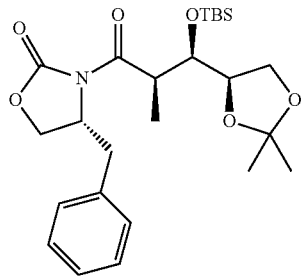 [SMILES: C[C@@H](C(=O)N1C(=O)OC[C@H]1Cc1ccccc1)[C@@H](O[Si](C)(C)C(C)(C)C)[C@H]1COC(C)(C)O1]

(R)-4-benzyl-3-((2R,3R)-3-(tert-butyldimethylsilyloxy)-3-((R)-2,2-dimethyl-1,3-dioxolan-4-yl)-2-methylpropanoyl)oxazolidin-2-one was prepared in the reported manner (Proc.Nat.Acad.Sciences, 101, 33, 2004, pages 12042-12047) for the enantiomeric compound by starting with (R)-4-benzyl-3-((2R,3R)-3-((R)-2,2-dimethyl-1,3-dioxolan-4-yl)-3-hydroxy-2-methylpropanoyl)oxazolidin-2-one.

Synthesis of (2S,3R)-3-(tert-butyldimethylsilyloxy)-3-((R)-2,2-dimethyl-1,3-dioxolan-4-yl)-2-methylpropan-1-ol

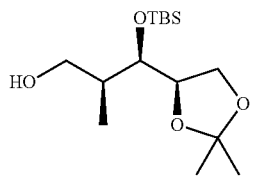 [SMILES: C[C@@H](CO)[C@@H](O[Si](C)(C)C(C)(C)C)[C@H]1COC(C)(C)O1]

To a solution of (R)-4-benzyl-3-((2R,3R)-3-(tert-butyldimethylsilyloxy)-3-((R)-2,2-dimethyl-1,3-dioxolan-4-yl)-2-methylpropanoyl)oxazolidin-2-one (1.0 equiv.) and ethanol (3.0 equiv.) in THF (0.09 M) was added LiBH$_4$ (1.0 equiv.) at −40° C. The reaction mixture was allowed to warm up to rt slowly and stirred at that temperature for 12 hours. The solution was cooled back to −40° C. and additional LiBH$_4$ (0.3 equiv.) was added. After warming back up to rt and stirring for 2 hours the solution was then diluted with diethyl ether and 1N NaOH was added. The resulting mixture was extracted with ethyl acetate, the organic layer was separated, washed with NaCl$_{(sat.)}$, dried over magnesium sulfate, filtered, and concentrated. The residue was purified via silica gel column chromatography (10-30% EtOAc/n-heptanes) yielding (2S,3R)-3-(tert-butyldimethylsilyloxy)-3-((R)-2,2-dimethyl-1,3-dioxolan-4-yl)-2-methylpropan-1-ol in (75%). LC/MS=247.1 (M+H-ketal-H$_2$O), R$_t$=0.64 min.

Synthesis of a ((1R,2S)-3-azido-1-((R)-2,2-dimethyl-1,3-dioxolan-4-yl)-2-methylpropoxy)(tert-butyl)dimethylsilane

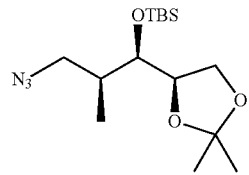 [SMILES: C[C@@H](CN=[N+]=[N-])[C@@H](O[Si](C)(C)C(C)(C)C)[C@H]1COC(C)(C)O1]

To a solution of (2S,3R)-3-(tert-butyldimethylsilyloxy)-3-((R)-2,2-dimethyl-1,3-dioxolan-4-yl)-2-methylpropan-1-ol (1.0 equiv.), DIAD (2.0 equiv.), and PPh$_3$ (2.0 equiv.) in THF (0.18 M) was added DPPA (1.0 equiv., 1M solution in THF). The reaction mixture was stirred at room temperature overnight. Upon removal of the volatiles under vacuo, the residue was purified by silica gel column chromatography (2-3-5% EtOAc/n-heptanes) yielding ((1R,2S)-3-azido-1-((R)-2,2-dimethyl-1,3-dioxolan-4-yl)-2-methylpropoxy)(tert-butyl)dimethylsilane (62%). $^1$H-NMR (400 MHz, CDCl$_3$): δ 4.04-4.10 (m, 1H), 3.94 (dd, J=8.0, 6.4, 1H), 3.72 (d, J=7.2, 1H), 3.53 (t, J=8.0, 1H), 3.36 (dd, J=12, 8.0, 1H), 3.19 (dd, J=12.0, 6.7, 1H), 1.52-1.60 (m, 1H), 1.41 (s, 3H), 1.34 (s, 3H), 0.92 (d, J=7.2, 3H), 0.90 (s, 9H), 0.12 (s, 3H), 0.09 (s, 3H).

Synthesis of (2R,3R,4S)-5-azido-3-(tert-butyldimethylsilyloxy)-4-methylpentane-1,2-diol

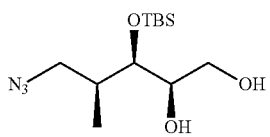 [SMILES: C[C@@H](CN=[N+]=[N-])[C@@H](O[Si](C)(C)C(C)(C)C)[C@H](O)CO]

To a solution of ((1R,2S)-3-azido-1-((R)-2,2-dimethyl-1,3-dioxolan-4-yl)-2-methylpropoxy)(tert-butyl)dimethylsilane (1.0 equiv.) in MeOH (0.1 M) was added PPTS (1.0 equiv.) and the mixture was stirred at rt for 14 hours, 50° C. for 2 hours and 80° C. for 1 hour. The volatiles were removed under vacuo and the residue was purified via silica gel column chromatography (10-25% EtOAc/n-heptanes) yielding (2R,3R,4S)-5-azido-3-(tert-butyldimethylsilyloxy)-4-methylpentane-1,2-diol (40%).

Synthesis of (2R,3R,4S)-5-azido-3-(tert-butyldimethylsilyloxy)-2-hydroxy-4-methylpentyl 4-methylbenzenesulfonate

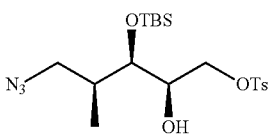 [SMILES: Cc1ccc(S(=O)(=O)OC[C@@H](O)[C@H](O[Si](C)(C)C(C)(C)C)[C@@H](C)CN=[N+]=[N-])cc1]

To a solution of tert-butyl (2R,3R,4S)-5-azido-3-(tert-butyldimethylsilyloxy)-1-hydroxy-4-methylpentan-2-ylcarbamate (1.0 equiv.) in pyridine (0.2 M) was added pTsCl (1.3 equiv.) at 0° C. The mixture held at this temperature for 16 hours. The volatiles were removed in vacuo and the residue was purified by silica gel column chromatography (10-15-20% EtOAc/n-heptanes) yielding (2R,3R,4S)-5-azido-3-(tert-butyldimethylsilyloxy)-2-hydroxy-4-methylpentyl 4-methylbenzenesulfonate.

Synthesis of (2R,3R,4S)-5-azido-2,3-bis(tert-butyldimethylsilyloxy)-4-methylpentyl 4-methylbenzenesulfonate

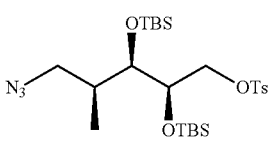 [SMILES: Cc1ccc(S(=O)(=O)OC[C@@H](O[Si](C)(C)C(C)(C)C)[C@H](O[Si](C)(C)C(C)(C)C)[C@@H](C)CN=[N+]=[N-])cc1]

To a solution of (2R,3R,4S)-5-azido-3-(tert-butyldimethylsilyloxy)-2-hydroxy-4-methylpentyl 4-methylbenzenesulfonate (1.0 equiv.) and 2,6-lutidine (3.4 equiv.) was added TBDMSOTf (1.7 equiv.) at 0° C. The solution was stirred for 7 hours as it warmed to rt. The solution was diluted with EtOAc, washed with 10% CuSO$_4$, H$_2$O, Na$_2$CO$_{3(sat.)}$, NaCl$_{(sat.)}$, dried over MgSO$_4$, filtered and concentrated. The residue was purified by silica gel column chromatography (2.5-5-10-20% EtOAc/n-heptanes) yielding (2R,3R,4S)-5-azido-2,3-bis(tert-butyldimethylsilyloxy)-4-methylpentyl 4-methylbenzenesulfonate (75%).

Synthesis of 4-((3R,4R,5S)-3,4-bis(tert-butyldimethylsilyloxy)-5-methylpiperidin-1-yl)-3-nitropyridine

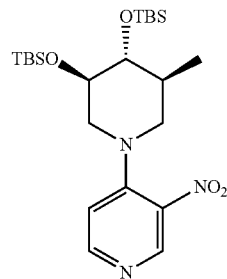 [SMILES: C[C@H]1CN(c2ccncc2[N+](=O)[O-])C[C@@H](O[Si](C)(C)C(C)(C)C)[C@@H]1O[Si](C)(C)C(C)(C)C]

A solution of (2R,3R,4S)-5-azido-2,3-bis(tert-butyldimethylsilyloxy)-4-methylpentyl 4-methylbenzenesulfonate in EtOH (0.05 M) was degassed with argon. DIEA (1.5 equiv.) was added, followed by 10% Pd/C (0.1 equiv.). The reaction mixture was stirred under a hydrogen balloon for 3 hours. The solution was degassed and purged to argon, at which time 4-chloro-3-nitropyridine (1.5 equiv.) and additional DIEA (1.5 equiv.) were added. After stirring at rt for 15 hours the solution was filtered to remove the Pd/C and the volatiles were removed in vacuo. The residue was diluted with ethyl acetate and washed with Na$_2$CO$_{3(sat.)}$, NaCl$_{(sat.)}$, dried over MgSO$_4$, filtered and concentrated. The residue was purified by silica gel column chromatography (10-15% EtOAc/n-heptanes) yielding 4-((3R,4R,5S)-3,4-bis(tert-butyldimethylsilyloxy)-5-methylpiperidin-1-yl)-3-nitropyridine (40%). LC/MS=482.4 (M+H), R$_t$=1.26 min.

Synthesis of 4-((3R,4R,5S)-3,4-bis(tert-butyldimethylsilyloxy)-5-methylpiperidin-1-yl)pyridin-3-amine

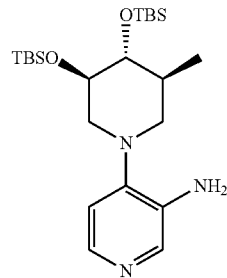 [SMILES: C[C@H]1CN(c2ccncc2N)C[C@@H](O[Si](C)(C)C(C)(C)C)[C@@H]1O[Si](C)(C)C(C)(C)C]

To a solution of 4-((3R,4R,5S)-3,4-bis(tert-butyldimethylsilyloxy)-5-methylpiperidin-1-yl)-3-nitropyridine (1.0 equiv.) in ethanol, at a concentration of 0.05 M, was added 10% palladium on carbon (0.1 eq.). The resultant heterogeneous solution was put under an atmosphere of hydrogen and was stirred for 14 hours. At this time the mixture was filtered through a pad of celite eluting with ethanol. The volatiles were removed in vacuo yielding 4-((3R,4R,5S)-3,4-bis(tert-butyldimethylsilyloxy)-5-methylpiperidin-1-yl)pyridin-3-amine LC/MS=452.4 (M+H), R$_t$=1.31 min.

Synthesis of (R)-tert-butyl 4-((1R,2R)-3-((R)-4-benzyl-2-oxooxazolidin-3-yl)-1-hydroxy-2-methyl-3-oxopropyl)-2,2-dimethyloxazolidine-3-carboxylate

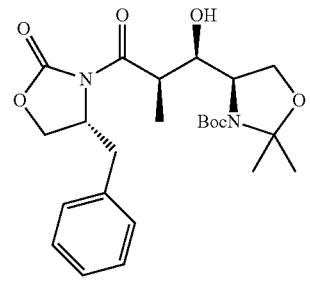 [SMILES: C[C@@H](C(=O)N1C(=O)OC[C@H]1Cc1ccccc1)[C@@H](O)[C@H]1COC(C)(C)N1C(=O)OC(C)(C)C]

To a solution of (R)-4-benzyl-3-propionyloxazolidin-2-one (1.0 equiv.) in DCM (0.13 M) was added TiCl$_4$ (1.0 equiv.) at −40° C. The mixture was stirred at −40° C. for 10 min (yellow suspension), then DIPEA (2.5 equiv.) was added (dark red solution) and stirred at 0° C. for 20 min. (R)-tert-butyl 4-formyl-2,2-dimethyloxazolidine-3-carboxylate (1.0 equiv.) in DCM (0.5 M) was then added dropwise and the resulting mixture was stirred for 1.5 hours. The reaction was quenched by the addition of aqueous ammonium chloride and the mixture was extracted with ethyl acetate. The organic phase was separated, washed with brine, dried with magnesium sulfate, filtered, and concentrated. The residue was purified via column chromatography eluting with ethyl acetate and hexanes (1:4) to give (R)-tert-butyl 4-((1R,2R)-3-((R)-4-benzyl-2-oxooxazolidin-3-yl)-1-hydroxy-2-methyl-3-oxopropyl)-2,2-dimethyloxazolidine-3-carboxylate as the major product (5:2) in 58% yield. LC/MS=363.3 (M+H-Boc), Rt=1.09 min.

Synthesis of (R)-tert-butyl 4-((1R,2R)-3-((R)-4-benzyl-2-oxooxazolidin-3-yl)-1-(tert-butyldimethylsilyloxy)-2-methyl-3-oxopropyl)-2,2-dimethyloxazolidine-3-carboxylate

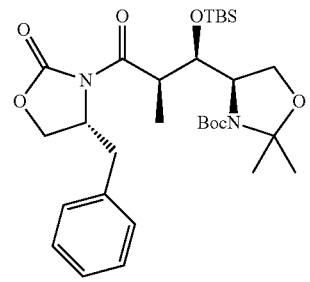 [SMILES: C[C@@H](C(=O)N1C(=O)OC[C@H]1Cc1ccccc1)[C@@H](O[Si](C)(C)C(C)(C)C)[C@H]1COC(C)(C)N1C(=O)OC(C)(C)C]

To a solution of (R)-tert-butyl 4-((1R,2R)-3-((R)-4-benzyl-2-oxooxazolidin-3-yl)-1-hydroxy-2-methyl-3-oxopropyl)-2,2-dimethyloxazolidine-3-carboxylate (1.0 equiv.) and lutidine (1.8 equiv.) in DCM (0.1 M) was added TBSOTf (1.4 equiv.) at −40° C. The reaction mixture was stirred at −40° C. for 2 hours. The solution was diluted with ethyl acetate and washed with sat. NaHCO$_3$, sat. NaCl, dried with magnesium sulfate, filtered, and concentrated. The residue was purified by silica gel column chromatography eluting with ethyl acetate and hexanes (1:4) to give (R)-tert-butyl 4-((1R,2R)-3-((R)-4-benzyl-2-oxooxazolidin-3-yl)-1-(tert-butyldimethylsilyloxy)-2-methyl-3-oxopropyl)-2,2-dimethyloxazolidine-3-carboxylate as the major product (5:2) in 83% yield. LC/MS=577.3 (M+H), Rt=1.33 min (Frac 65%-95% method).

Synthesis of (R)-tert-butyl 4-((1R,2S)-1-(tert-butyldimethylsilyloxy)-3-hydroxy-2-methylpropyl)-2,2-dimethyloxazolidine-3-carboxylate

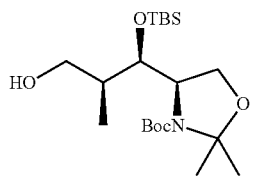 [SMILES: C[C@@H](CO)[C@@H](O[Si](C)(C)C(C)(C)C)[C@H]1COC(C)(C)N1C(=O)OC(C)(C)C]

To a solution of (R)-tert-butyl 4-((1R,2R)-3-((R)-4-benzyl-2-oxooxazolidin-3-yl)-1-(tert-butyldimethylsilyloxy)-2-methyl-3-oxopropyl)-2,2-dimethyloxazolidine-3-carboxylate (1.0 equiv.) and ethanol (3.0 equiv.) in THF (0.09$\underline{M}$) was added LiBH$_4$ (3.0 equiv.) at −30° C. The reaction mixture was allowed to warm up to 0° C. and stirred at that temperature for 3 hours. The solution was then diluted with diethyl ether and 1N NaOH was added. The resulting mixture was extracted with ethyl acetate, the organic layer was separated, washed with sat. NaCl, dried over magnesium sulfate, filtered, and concentrated. The residue was purified via silica gel column chromatography eluting with ethyl acetate and hexanes (1:4) to give (R)-tert-butyl 4-((1R,2S)-1-(tert-butyldimethylsilyloxy)-3-hydroxy-2-methylpropyl)-2,2-dimethyloxazolidine-3-carboxylate as the major product (5:2 ratio) in 71% yield. LC/MS=304.3 (M+H-Boc), Rt=0.95 min (Frac 65%-95% method).

Synthesis of (R)-tert-butyl 4-((1R,2S)-3-azido-1-(tert-butyldimethylsilyloxy)-2-methylpropyl)-2,2-dimethyloxazolidine-3-carboxylate

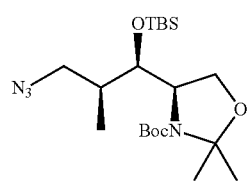 [SMILES: C[C@@H](CN=[N+]=[N-])[C@@H](O[Si](C)(C)C(C)(C)C)[C@H]1COC(C)(C)N1C(=O)OC(C)(C)C]

To a solution of (R)-tert-butyl 4-((1R,2S)-1-(tert-butyldimethyl-silyloxy)-3-hydroxy-2-methylpropyl)-2,2-dimethyloxazolidine-3-carboxylate (1.0 equiv.), DIAD (2.0 equiv.), and PPh$_3$ (2.0 equiv.) in THF (0.18 $\underline{M}$) was added DPPA (2.0 equiv., 1M solution in THF). The reaction mixture was stirred at room temperature overnight. Upon removal of the volatiles under vacuo, the residue was purified by silica gel column chromatography eluting with ethyl acetate and hexanes (1:6) to give (R)-tert-butyl 4-((1R,2S)-3-azido-1-(tert-butyldimethylsilyloxy)-2-methylpropyl)-2,2-dimethyloxazolidine-3-carboxylate as the major product (5:2) in 86% yield. LC/MS=329.3 (M+H-Boc), Rt=1.40 min (Frac 65%-95% method).

Synthesis of tert-butyl (2R,3R,4S)-5-azido-3-(tert-butyldimethylsilyloxy)-1-hydroxy-4-methylpentan-2-ylcarbamate

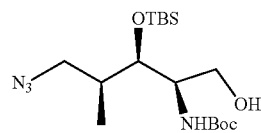 [SMILES: C[C@@H](CN=[N+]=[N-])[C@@H](O[Si](C)(C)C(C)(C)C)[C@@H](CO)NC(=O)OC(C)(C)C]

To a solution of (R)-tert-butyl 4-((1R,2S)-3-azido-1-(tert-butyldimethylsilyloxy)-2-methylpropyl)-2,2-dimethyloxazolidine-3-carboxylate (1.0 equiv.) in EtOH (0.1 $\underline{M}$) was added PPTS (1.3 equiv.) and the mixture was refluxed for 2 days. The volatiles were removed under vacuo, the residue was dissolved in DCM (0.1 $\underline{M}$) and DIEA (1.5 equiv.) and Boc$_2$O (1.0 equiv.) were added to the reaction mixture. The solution was stirred for 3 hours at room temperature. The solvents were removed under reduced pressure and the residue was diluted with ethyl acetate, washed with water, aqueous NaHSO$_4$, aqueous NaHCO$_3$, sat. NaCl, the organic phase was dried with magnesium sulfate, filtered, and concentrated. The residue was purified via silica gel column chromatography eluting with ethyl acetate and hexanes (1:3) to give tert-butyl (2R,3R,4S)-5-azido-3-(tert-butyldimethylsilyloxy)-1-hydroxy-4-methylpentan-2-ylcarbamate as the major isomer (5:2) in 70% yield. LC/MS=289.3 (M+H-Boc), Rt=0.76 min (Frac 65%-95% method).

Synthesis of (2R,3R,4S)-5-azido-2-(tert-butoxycarbonylamino)-3-(tert-butyldimethylsilyloxy)-4-methylpentyl methanesulfonate

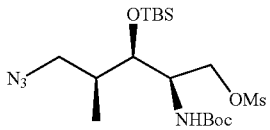 [SMILES: C[C@@H](CN=[N+]=[N-])[C@@H](O[Si](C)(C)C(C)(C)C)[C@@H](COS(C)(=O)=O)NC(=O)OC(C)(C)C]

To a solution of tert-butyl (2R,3R,4S)-5-azido-3-(tert-butyldimethylsilyloxy)-1-hydroxy-4-methylpentan-2-ylcarbamate (1.0 equiv.) in pyridine (0.2 $\underline{M}$) was added MsCl (1.3 equiv.) followed by DMAP (catalytic amount) at 0° C. The mixture was stirred at that temperature for 1 hour. The solution was diluted with ether and ethyl acetate (4:1), washed with aq. NaHSO$_4$, sat. NaHCO$_3$, brine, dried over magnesium sulfate, filtered, and concentrated. The residue was purified by silica gel column chromatography eluting with ethyl acetate and hexanes (1:3) to give (2R,3R,4S)-5-azido-2-(tert-butoxycarbonylamino)-3-(tert-butyldimethylsilyloxy)-4-methylpentyl methanesulfonate as the major isomer (5:2) in 90% yield. LC/MS=367.3 (M+H-Boc), Rt=0.81 min (Frac 65%-95% method).

Synthesis of tert-butyl (3R,4R,5S)-4-(tert-butyldimethylsilyloxy)-5-methylpiperidin-3-ylcarbamate

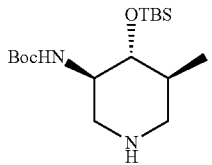 [SMILES: C[C@H]1CNC[C@@H](NC(=O)OC(C)(C)C)[C@@H]1O[Si](C)(C)C(C)(C)C]

A solution of (2R,3R,4S)-5-azido-2-(tert-butoxycarbonylamino)-3-(tert-butyldimethylsilyloxy)-4-methylpentyl methanesulfonate in MeOH (0.09 M) was degassed with nitrogen for 20 min. DIEA (2.5 equiv.) was added, followed by 10% Pd/C (0.1 equiv.). The reaction mixture was stirred under a hydrogen balloon for 2 hours. The solution was filtered and the filtrate was concentrated under vacuo to afford tert-butyl (3R,4R,5S)-4-(tert-butyldimethylsilyloxy)-5-methylpiperidin-3-ylcarbamate as the major isomer (5:2) in >99% yield. LC/MS=345.2 (M+H-Boc), Rt=0.95 and 0.99 min.

Synthesis of tert-butyl (3R,4R,5S)-4-(tert-butyldimethylsilyloxy)-5-methyl-1-(3-nitropyridin-4-yl)piperidin-3-ylcarbamate

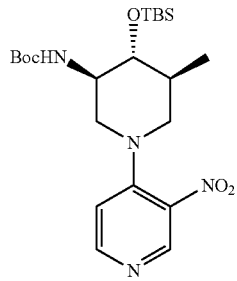 [SMILES: C[C@H]1CN(c2ccncc2[N+](=O)[O-])C[C@@H](NC(=O)OC(C)(C)C)[C@@H]1O[Si](C)(C)C(C)(C)C]

To a solution of tert-butyl (3R,4R,5S)-4-(tert-butyldimethylsilyloxy)-5-methylpiperidin-3-ylcarbamate (1.0 equiv.) in i-PrOH (0.09 M) was added DIEA (2.5 equiv.) and 4-chloro-3-nitropyridine (1.5 equiv.). The reaction mixture was stirred at 60° C. for 2 hours. The volatiles were removed under vacuo, the residue was diluted with ethyl acetate and washed with sat. NaCl. The organic phase was dried with magnesium sulfate, filtered, and concentrated. The crude material was purified by silica gel column chromatography eluting with ethyl acetate and hexanes (1:2) to give tert-butyl (3R,4R,5S)-4-(tert-butyldimethylsilyloxy)-5-methyl-1-(3-nitropyridin-4-yl)piperidin-3-ylcarbamate in 76% yield. LC/MS=467.3 (M+H), Rt=1.09 min.

Synthesis of tert-butyl (3R,4R,5S)-1-(3-aminopyridin-4-yl)-4-(tert-butyldimethylsilyloxy)-5-methylpiperidin-3-ylcarbamate

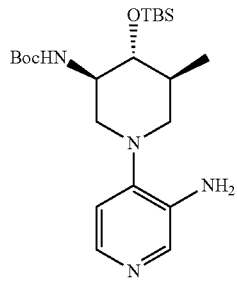 [SMILES: C[C@H]1CN(c2ccncc2N)C[C@@H](NC(=O)OC(C)(C)C)[C@@H]1O[Si](C)(C)C(C)(C)C]

A solution of tert-butyl (3R,4R,5S)-4-(tert-butyldimethylsilyloxy)-5-methyl-1-(3-nitropyridin-4-yl)piperidin-3-ylcarbamate (1.0 equiv.) in MeOH (0.05 M) was degassed with nitrogen for 20 min. 10% Pd/C (0.2 equiv.) was added to the mixture and the solution was stirred under a hydrogen balloon for 3 hours. The reaction was filtered and the filtrate was concentrated under reduced pressure to give tert-butyl (3R,4R,5S)-1-(3-aminopyridin-4-yl)-4-(tert-butyldimethylsilyloxy)-5-methylpiperidin-3-ylcarbamate as the desired product in 94% yield. LC/MS=437.4 (M+H), Rt=1.08 min. $^1$H-NMR (300 MHz, CDCl$_3$): δ 8.01 (s, 1H), 7.95 (d, J=6.0 Hz, 1H), 6.76 (d, J=6.0 Hz, 1H), 4.44 (br s, 1H), 3.74 (br s, 2H), 3.59-3.55 (m, 1H), 3.25-3.13 (m, 2H), 2.47-2.35 (m, 2H), 1.89 (br s, 2H), 1.44 (s, 9H), 1.04 (d, J=6.0, 3H), 0.92 (s, 9H), 0.13 (d, J=9.0, 6H).

Synthesis of tert-butyl (2R)-1-(benzyloxy)-3-hydroxy-4-methylhex-5-en-2-ylcarbamate

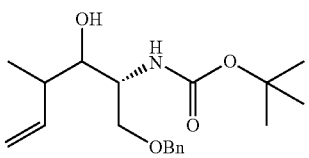 [SMILES: C=CC(C)C(O)[C@@H](COCc1ccccc1)NC(=O)OC(C)(C)C]

To a solution of N-Boc, O-benzyl-D-Serine aldehyde (1.0 equiv) in DCM (0.1 M) at −78° C. under an Ar atmosphere was added (Z)-2-(but-2-enyl)-4,4,5,5-tetramethyl-1,3,2-dioxaborolane (1.1 equiv) and the clear solution stirred for 16 hours as it warmed to rt. The solution was added to EtOAc and was washed with H$_2$O (3×), and NaCl$_{(sat.)}$, dried over MgSO$_4$ and purified by silica gel chromatography (15% EtOAc/hexanes) to yield tert-butyl (2R)-1-(benzyloxy)-3-hydroxy-4-methylhex-5-en-2-ylcarbamate (54%) as a 3:1 mixture of isomers as judged by $^1$H NMR. LCMS (m/z): 236.3 (MH$^+$-Boc); LC R$_t$=4.37 and 4.51 min.

Synthesis of (4R)-4-(benzyloxymethyl)-5-(but-3-en-2-yl)oxazolidin-2-one

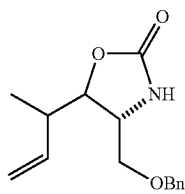

To a solution of (2R)-1-(benzyloxy)-3-hydroxy-4-methylhex-5-en-2-in THF (0.1 M) was added 60% sodium hydride in mineral oil (1.5 equiv.). After stirring for 3 days, the reaction was quenched by addition of NH$_4$Cl$_{(sat.)}$ and solution was diluted with EtOAc and washed with NH$_4$Cl$_{(sat.)}$ and NaCl$_{(sat.)}$, dried over MgSO$_4$ and purified by silica gel chromatography (50% EtOAc/hexanes) to yield (4R)-4-(benzyloxymethyl)-5-(but-3-en-2-yl)oxazolidin-2-one (89%) as a 3:1 mixture. LCMS (m/z): 262.2 (MH$^+$); LC R$_t$=3.47 min.

Synthesis of (4R)-4-(benzyloxymethyl)-5-(1-hydroxypropan-2-yl)oxazolidin-2-one

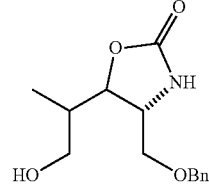

To a solution of (4R)-4-(benzyloxymethyl)-5-(but-3-en-2-yl)oxazolidin-2-one (1.0 equiv.) in 2:1 MeOH/H₂O (0.04 M) was added osmium tetroxide 4% in H₂O (0.07 equiv) and sodium periodate (3.0 equiv.). After stirring for 3 hours, the white precipitate was filtered and rinsed with EtOAc. The combined filtrate was concentrated in vacuo and the residue was dissolved in EtOAc, washed with NaCl$_{(sat.)}$, dried over MgSO₄, filtered and concentrated. The crude aldehyde was dissolved in EtOH (0.08 M) and upon cooling to 0° C., sodium borohydride (2.0 equiv.) was added. After stirring for 15 hours and coming to room temperature the reaction was quenched by addition of H₂O. After stirring for 20 minutes, the EtOH was removed in vacuo, EtOAc was added and the solution was washed with 1N HCl, NaHCO$_{3(sat.)}$ and NaCl$_{(sat.)}$, dried over MgSO₄, filtered and concentrated yielding after purification by silica gel chromatography (4R)-4-(benzyloxymethyl)-5-(1-hydroxypropan-2-yl)oxazolidin-2-one as a 3:1 mixture of isomers (60%). LCMS (m/z): 266.1 (MH⁺); LC R$_t$=2.28 min.

Synthesis of (4R)-4-(hydroxymethyl)-5-(1-hydroxypropan-2-yl)oxazolidin-2-one

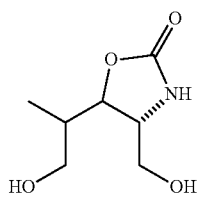

To a solution of (4R)-4-(benzyloxymethyl)-5-(1-hydroxypropan-2-yl)oxazolidin-2-one (1.0 equiv.) in methanol, at a concentration of 0.1 M, was added 10% palladium on carbon (0.1 eq.). The resultant heterogeneous solution was put under an atmosphere of hydrogen and was stirred for 15 hours. At this time the mixture was filtered through a pad of celite eluting with methanol. The volatiles were removed in vacuo yielding (4R)-4-(hydroxymethyl)-5-(1-hydroxypropan-2-yl)oxazolidin-2-one (99%). LCMS (m/z): 176.1 (MH⁺).

Synthesis of 2-((4R)-2-oxo-4-(tosyloxymethyl)oxazolidin-5-yl)-propyl 4-methylbenzenesulfonate

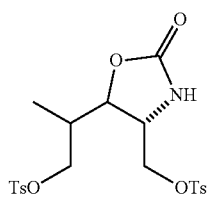

To a solution of (4R)-4-(hydroxymethyl)-5-(1-hydroxypropan-2-yl)oxazolidin-2-one (1.0 equiv.) in pyridine (0.15 M) at 0° C. was added p-toluenesulfonylchloride (2.1 equiv.). The solution was allowed to warm to rt as it stirred for 14 hours, at which time EtOAc was added and the solution was washed with H₂O (3×), CuSO$_{4(sat.)}$ (2×), H₂O, Na₂CO$_{3(sat.)}$ and NaCl$_{(sat.)}$, dried over MgSO₄, filtered, concentrated and purified by silica gel chromatography (75% EtOAc/hexanes eluent) yielding 2-((4R)-2-oxo-4-(tosyloxymethyl)oxazolidin-5-yl)propyl 4-methylbenzenesulfonate (68%). LCMS (m/z): 484.1 (MH⁺); LC R$_t$=4.06 min.

Synthesis of (3 aR,7R,7aS)-5-(4-methoxybenzyl)-7-methylhexahydrooxazolo[4,5-c]pyridin-2(3H)-one and (3aR,7S,7aR)-5-(4-methoxybenzyl)-7-methyl-hexahydrooxazolo[4,5-c]pyridin-2(3H)-one

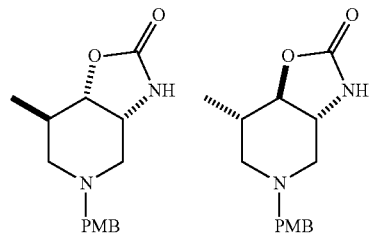

A solution of 2-((4R)-2-oxo-4-(tosyloxymethyl)oxazolidin-5-yl)propyl 4-methylbenzenesulfonate (1.0 equiv.), diisopropylethyl amine (3.0 equiv.) and para-methoxybenzylamine (1.5 equiv.) in NMP (0.05 M) was heated at 100° C. for 14 hours. The solution was purified directly by RP HPLC. The product fractions were desalted by addition to EtOAc and Na₂CO$_{3(s)}$, washed further with NaCl(sat.), dried over MgSO₄ and concentrated yielding two separate isomers of (3aR,7R,7aS)-5-(4-methoxybenzyl)-7-methylhexahydrooxazolo[4,5-c]pyridin-2(3H)-one and (3aR,7S,7aR)-5-(4-methoxybenzyl)-7-methylhexahydrooxazolo[4,5-c]pyridin-2(3H)-one (27% and 8%). LCMS (m/z): 277.2 (MH⁺) at 0.40 and 0.42 min.

Synthesis of (3aR,7R,7aS)-7-methylhexahydrooxazolo[4,5-c]pyridin-2(3H)-one

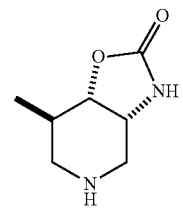

To a solution of (3aR,7R,7aS)-5-(4-methoxybenzyl)-7-methylhexahydrooxazolo[4,5-c]pyridin-2(3H)-one (1.0 equiv.) in methanol, at a concentration of 0.1M, was added 20% palladium hydroxide on carbon (0.3 eq.). The resultant heterogeneous solution was put under an atmosphere of hydrogen and was stirred for 2 hours. At this time the mixture was filtered through a pad of celite eluting with methanol. The volatiles were removed in vacuo yielding (3aR,7R,7aS)-7-methylhexahydrooxazolo[4,5-c]pyridin-2(3H)-one (99%). LCMS (m/z): 157.1 (MH⁺) at 0.16 min.

Synthesis of (3aR,7R,7aS)-tert-butyl 7-methyl-5-(3-nitropyridin-4-yl)-2-oxohexahydrooxazolo[4,5-c]pyridine-3(2H)-carboxylate

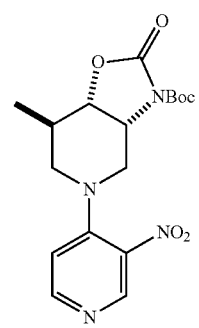

A solution of 4-chloro-3-nitropyridine (1.3 equiv.) and (3aR,7R,7aS)-7-methylhexahydrooxazolo[4,5-c]pyridin-2(3H)-one (1.5 equiv.) in CH$_2$Cl$_2$, at a concentration of 0.1 M, was stirred at rt for 48 hours at which piperidine (0.4 equiv) was added to consume excess 4-chloro-3-nitropyridine. After stirring for an additional 2 hours, di-tert-butyl dicarbonate (2.0 equiv.) and dimethylaminopyridine (0.1 equiv.) were added. After stirring for 4 hours, the solution was partitioned between EtOAc and NaHCO$_{3(sat.)}$, was washed further with NaHCO$_{3(sat.)}$, and NaCl$_{(sat.)}$, was dried over MgSO$_4$, was filtered and purified by silica gel chromatography yielding (3aR,7R,7aS)-tert-butyl 7-methyl-5-(3-nitropyridin-4-yl)-2-oxohexahydrooxazolo[4,5-c]pyridine-3(2H)carboxylate (62%). LCMS (m/z): 379.0 (MH$^+$) at 0.58 min.

Synthesis of (3aR,7R,7aS)-tert-butyl 5-(3-aminopyridin-4-yl)-7-methyl-2-oxohexahydrooxazolo[4,5-c]pyridine-3(2H)-carboxylate

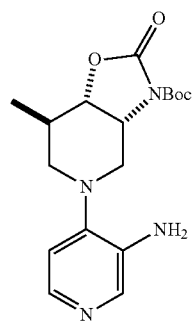

To a solution of (3aR,7R,7aS)-tert-butyl 7-methyl-5-(3-nitropyridin-4-yl)-2-oxohexahydrooxazolo[4,5-c]pyridine-3(2H)-carboxylate (1.0 equiv.) in methanol, at a concentration of 0.1 M, was added 10% palladium on carbon (0.1 eq.). The resultant heterogeneous solution was put under an atmosphere of hydrogen and was stirred for 14 hours. At this time the mixture was filtered through a pad of celite eluting with methanol. The volatiles were removed in vacuo yielding (3aR,7R,7aS)-tert-butyl 5-(3-aminopyridin-4-yl)-7-methyl-2-oxohexahydrooxazolo[4,5-c]pyridine-3 (2H)-carboxylate. LCMS (m/z): 349.1 (MH$^+$); LC R$_t$=2.06 min.

Synthesis of (3aR,7S,7aR)-7-methylhexahydrooxazolo[4,5-c]pyridin-2(3H)-one

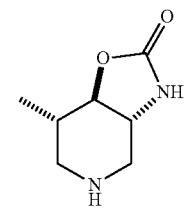

To a solution of (3aR,7S,7aR)-5-(4-methoxybenzyl)-7-methylhexahydrooxazolo[4,5-c]pyridin-2(3H)-one (1.0 equiv.) in methanol, at a concentration of 0.1 M, was added 20% palladium hydroxide on carbon (0.3 eq.). The resultant heterogeneous solution was put under an atmosphere of hydrogen and was stirred for 2 hours. At this time the mixture was filtered through a pad of celite eluting with methanol. The volatiles were removed in vacuo yielding (3aR,7S,7aR)-7-methylhexahydrooxazolo[4,5-c]pyridin-2(3H)-one (99%). LCMS (m/z): 157.1 (MH$^+$) at 0.17 min.

Synthesis of (3aR,7S,7aR)-tert-butyl 7-methyl-5-(3-nitropyridin-4-yl)-2-oxohexahydrooxazolo[4,5-c]pyridine-3(2H)-carboxylate

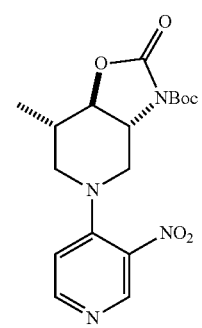

A solution of 4-chloro-3-nitropyridine (1.3 equiv.) and (3aR,7S,7aR)-7-methylhexahydrooxazolo[4,5-c]pyridin-2(3H)-one (1.5 equiv.) in CH$_2$Cl$_2$, at a concentration of 0.1 M, was stirred at rt for 48 hours at which piperidine (0.4 equiv) was added to consume excess 4-chloro-3-nitropyridine. After stirring for an additional 2 hours, di-tert-butyl dicarbonate (2.0 equiv.) and dimethylaminopyridine (0.1 equiv.) were added. After stirring for 4 hours, the solution was partitioned between EtOAc and NaHCO$_{3(sat.)}$, was washed further with NaHCO$_{3(sat.)}$, and NaCl$_{(sat.)}$, was dried over MgSO$_4$, was filtered and purified by silica gel chromatography (75% EtOAc/hexanes eluent) yielding (3aR,7S,7aR)-tert-butyl 7-methyl-5-(3-nitropyridin-4-yl)-2-oxohexahydrooxazolo[4,5-c]pyridine-3(2H)-carboxylate (35%). LCMS (m/z): 379.0 (MH$^+$). LC R$_t$=2.42 min.

Synthesis of (3aR,7S,7aS)-tert-butyl 5-(3-aminopyridin-4-yl)-7-methyl-2-oxohexahydrooxazolo[4,5-c]pyridine-3(2H)-carboxylate

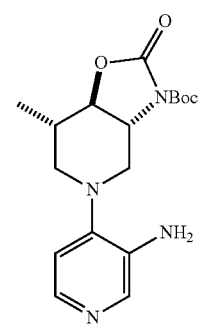

To a solution of (3aR,7S,7aR)-tert-butyl 7-methyl-5-(3-nitropyridin-4-yl)-2-oxohexahydrooxazolo[4,5-c]pyridine-3(2H)-carboxylate (1.0 equiv.) in methanol, at a concentration of 0.1 M, was added 10% palladium on carbon (0.1 eq.). The resultant heterogeneous solution was put under an atmosphere of hydrogen and was stirred for 14 hours. At this time the mixture was filtered through a pad of celite eluting with methanol. The volatiles were removed in vacuo yielding (3aR,7S,7aR)-tert-butyl 5-(3-aminopyridin-4-yl)-7-methyl-2-oxohexahydrooxazolo[4,5-c]pyridine-3(2H)-carboxylate. LCMS (m/z): 349.1 (MH$^+$); LC R$_t$=2.18 min.

Method 1

Synthesis of methyl 3-amino-6-(2,6-difluorophenyl)picolinate

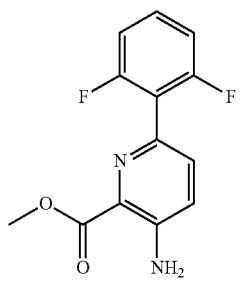 [SMILES: COC(=O)c1nc(-c2c(F)cccc2F)ccc1N]

A solution of methyl 3-amino-6-bromopicolinate (1.0 equiv.), 2,6-difluorophenyl-boronic acid (3.0 equiv), and Pd(dppf)Cl$_2$-DCM (0.1 equiv.) in 3:1 DME/2M Na$_2$CO$_3$ (0.5 M) was subjected to microwave irradiation at 120° C. for 15 min intervals. The reaction was filtered and washed with EtOAc. The organic was partitioned with H$_2$O (25 mL), was further washed with NaCl$_{(sat.)}$ (25 mL), was dried over MgSO$_4$, and the volatiles were removed in vacuo. The residue was diluted in EtOAc and passed through a silica gel plug and the volatiles were removed in vacuo yielding methyl 3-amino-6-(2,6-difluorophenyl)picolinate (47%). LCMS (m/z): 265.1 (MH$^+$); LC R$_t$=2.70 min

Synthesis of 6-(2,3-difluorophenyl)-5-fluoropicolinic acid

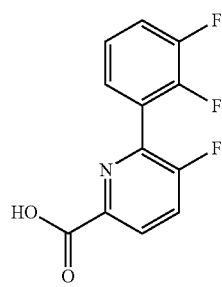 [SMILES: O=C(O)c1ccc(F)c(-c2cccc(F)c2F)n1]

To a solution of 6-bromo-5-fluoropicolinic acid (1.0 equiv.) in DME and 2M Na$_2$CO$_3$ (3:1, 0.25 M) was added 2,3-difluorophenylboronic acid (1.3 equiv.) and Pd(dppf)Cl$_2$-DCM (0.05 equiv.) in a microwave vial. The vial was heated in the microwave at 120° C. for 30 minutes. The mixture was diluted with ethyl acetate and 1N NaOH was added. The organic phase was separated and extracted three more times with 1N NaOH and once with 6N NaOH. The combined aqueous phases were filtered and acidified to pH 1 by the addition of concentrated HCl and extracted with ethyl acetate. The organic layer was dried over magnesium sulfate, filtered, and concentrated to give 6-(2,3-difluorophenyl)-5-fluoropicolinic acid in 78%. LC/MS=254.1 (M+H), Rt=0.75 min.

Method 2

Synthesis of 3-amino-6-(2,6-difluorophenyl)picolinic acid

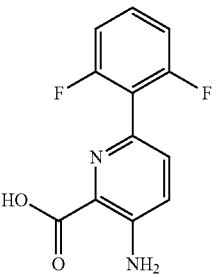 [SMILES: Nc1ccc(-c2c(F)cccc2F)nc1C(=O)O]

To a solution of methyl 3-amino-6-(2,6-difluorophenyl)picolinate (1.0 equiv) in THF (0.5 M), was added 1M LiOH (4.0 equiv). After stirring for 4 hours at 60° C., 1N HCl (4.0 equiv.) was added and the THF was removed in vacuo. The resulting solid was filtered and rinsed with cold H$_2$O (3×20 mL) to yield 3-amino-6-(2,6-difluorophenyl)picolinic acid (90%). LCMS (m/z): 251.1 (MH$^+$); LC R$_t$=2.1 min.

Synthesis of 3-amino-6-(2-fluoro-5-propoxyphenyl)picolinic acid

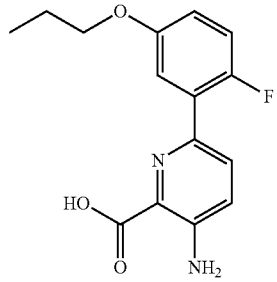 [SMILES: CCCOc1ccc(F)c(-c2ccc(N)c(C(=O)O)n2)c1]

Method 1 was followed using 3-amino-6-bromopicolinic acid (1.0 equiv.) and 2-fluoro-5-propoxyphenylboronic acid (1.5 equiv.) and Pd(dppf)Cl$_2$-DCM (0.05 equiv.) to give 3-amino-6-(2-fluoro-5-propoxyphenyl)picolinic acid in 75% yield. LC/MS=291.0 (M+H), Rt=0.81 min.

Synthesis of 3-amino-5-fluoro-6-(2-fluoro-5-propoxyphenyl)picolinic acid

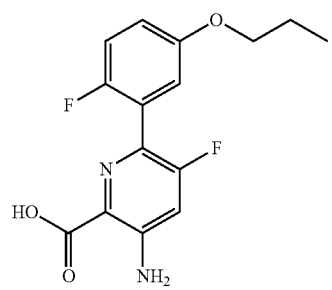 [SMILES: CCCOc1ccc(F)c(-c2nc(C(=O)O)c(N)cc2F)c1]

Method 1 was followed using 3-amino-6-bromo-5-fluoropicolinic acid (1.0 equiv.) and 2-fluoro-5-propoxyphenylboronic acid (1.3 equiv.) and Pd(dppf)Cl$_2$-DCM (0.05 equiv.) to give 3-amino-5-fluoro-6-(2-fluoro-5-propoxyphenyl)picolinic acid in 28% yield. LC/MS=309.1 (M+H), Rt=1.00 min.

Synthesis of methyl
3-amino-5-fluoro-6-(2-fluorophenyl)picolinate

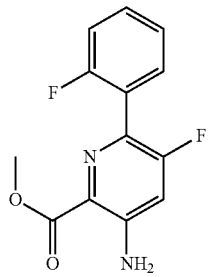 [SMILES: COC(=O)c1nc(-c2ccccc2F)c(F)cc1N]

Method 1 was followed using methyl 3-amino-6-bromo-5-fluoropicolinate (1.0 equiv.) and 2-fluoro-phenylboronic acid (1.5 equiv.) and Pd(dppf)Cl$_2$-DCM (0.05 equiv.) to give methyl 3-amino-5-fluoro-6-(2-fluorophenyl)picolinate in >99% yield. LC/MS=265.0 (M+H), Rt=0.77 min.

Synthesis of
3-amino-5-fluoro-6-(2-fluorophenyl)picolinic acid

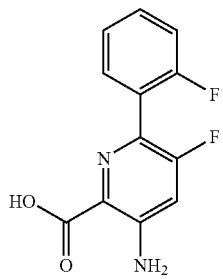

Method 2 was followed using 3-amino-5-fluoro-6-(2-fluorophenyl)picolinate (1.0 equiv.) and LiOH (5.0 equiv.) to give 3-amino-5-fluoro-6-(2-fluorophenyl)picolinic acid in 90% yield. LC/MS=251.1 (M+H), Rt=0.80 min.

Synthesis of methyl
3-amino-6-(2,6-difluorophenyl)-5-fluoropicolinate

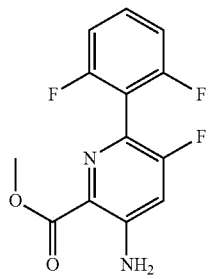 [SMILES: COC(=O)c1nc(-c2c(F)cccc2F)c(F)cc1N]

Method 1 was followed using methyl 3-amino-6-bromo-5-fluoropicolinate (1.0 equiv.) and 2,6-difluorophenylboronic acid (1.3 equiv.) and Pd(dppf)Cl$_2$-DCM (0.05 equiv.) to give 3-amino-6-(2,6-difluorophenyl)-5-fluoropicolinate in 94% yield. LC/MS=283.0 (M+H), Rt=0.76 min.

Synthesis of
3-amino-6-(2,6-difluorophenyl)-5-fluoropicolinic acid

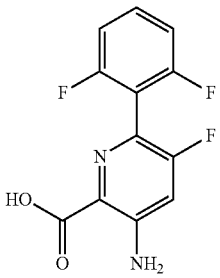 [SMILES: Nc1cc(F)c(-c2c(F)cccc2F)nc1C(=O)O]

Method 2 was followed using 3-amino-6-(2,6-difluorophenyl)-5-fluoropicolinate (1.0 equiv.) and LiOH (1.0 equiv.) to give 3-amino-6-(2,6-difluorophenyl)-5-fluoropicolinic acid in 79% yield. LC/MS=269.0 (M+H), Rt=0.79 min.

Synthesis of 5-fluoro-6-(2-fluorophenyl)picolinic acid

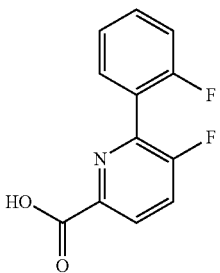 [SMILES: O=C(O)c1ccc(F)c(-c2ccccc2F)n1]

Method 1 was followed using 6-bromo-5-fluoropicolinic acid (1.0 equiv.) and 2-fluorophenylboronic acid (1.3 equiv.) and Pd(dppf)Cl$_2$-DCM (0.05 equiv.) to give 5-fluoro-6-(2-fluorophenyl)picolinic acid in 43% yield. LC/MS=236.1 (M+H), Rt=0.72 min.

Synthesis of 6-(3,4-difluorophenyl)-5-fluoropicolinic acid

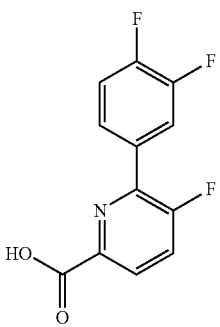 [SMILES: O=C(O)c1ccc(F)c(-c2ccc(F)c(F)c2)n1]

Method 1 was followed using 6-bromo-5-fluoropicolinic acid (1.0 equiv.) and 3,4-difluorophenylboronic acid (1.3 equiv.) and Pd(dppf)Cl$_2$-DCM (0.05 equiv.) to give 6-(3,4-difluorophenyl)-5-fluoropicolinic acid in 70% yield. LC/MS=254.1 (M+H), Rt=0.81 min.

Synthesis of 6-(2,5-difluorophenyl)-5-fluoropicolinic acid

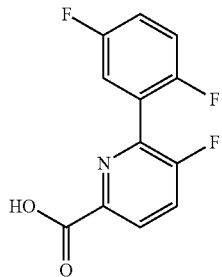 [SMILES: O=C(O)c1ccc(F)c(-c2cc(F)ccc2F)n1]

Method 1 was followed using 6-bromo-5-fluoropicolinic acid (1.0 equiv.) and 2,5-difluorophenylboronic acid (1.3 equiv.) and Pd(dppf)Cl$_2$-DCM (0.05 equiv.) to give 6-(2,5-difluorophenyl)-5-fluoropicolinic acid in 80% yield. LC/MS=254.1 (M+H), Rt=0.74 min.

Synthesis of 6-(2,4-difluorophenyl)-5-fluoropicolinic acid

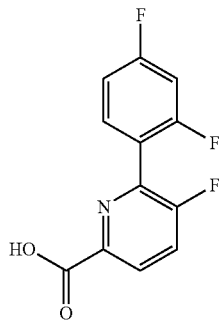 [SMILES: O=C(O)c1ccc(F)c(-c2ccc(F)cc2F)n1]

Method 1 was followed using 6-bromo-5-fluoropicolinic acid (1.0 equiv.) and 2,4-difluorophenylboronic acid (1.3 equiv.) and Pd(dppf)Cl$_2$-DCM (0.05 equiv.) to give 6-(2,4-difluorophenyl)-5-fluoropicolinic acid in 79% yield. LC/MS=254.1 (M+H), Rt=0.75 min.

Synthesis of 5-fluoro-6-(2-fluoro-5-propoxyphenyl)picolinic acid

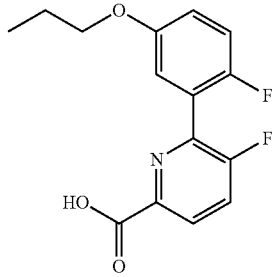 [SMILES: CCCOc1ccc(F)c(-c2nc(C(=O)O)ccc2F)c1]

Method 1 was followed using 6-bromo-5-fluoropicolinic acid (1.0 equiv.) and 2-fluoro-5-propoxyphenylboronic acid (1.5 equiv.) and Pd(dppf)Cl$_2$-DCM (0.05 equiv.) to give 5-fluoro-6-(2-fluoro-5-propoxyphenyl)picolinic acid. LC/MS=294.2 (M+H), Rt=0.95 min.

Synthesis of 6-(2-fluorophenyl)picolinic acid

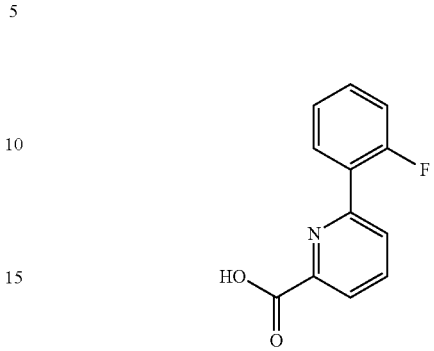

Method 1 was followed using 6-bromopicolinic acid (1.0 equiv.) and 2-fluorophenylboronic acid (1.5 equiv.) and Pd(dppf)Cl$_2$-DCM (0.05 equiv.) to give 6-(2-fluorophenyl)picolinic acid in 93% yield. LC/MS=218.0 (M+H), Rt=0.66 min.

Synthesis of 6-(2,6-difluorophenyl)picolinic acid

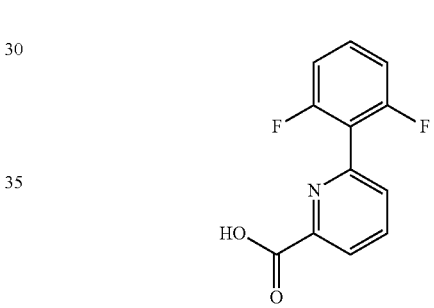

Method 1 was followed using 6-bromopicolinic acid (1.0 equiv.) and 2,6-difluorophenylboronic acid (1.5 equiv.) and Pd(dppf)Cl$_2$-DCM (0.05 equiv.) to give 6-(2,6-difluorophenyl)picolinic acid in 38% yield. LC/MS=236.0 (M+H), Rt=0.87 min.

Synthesis of 6-(2-fluoro-5-methoxyphenyl)picolinic acid

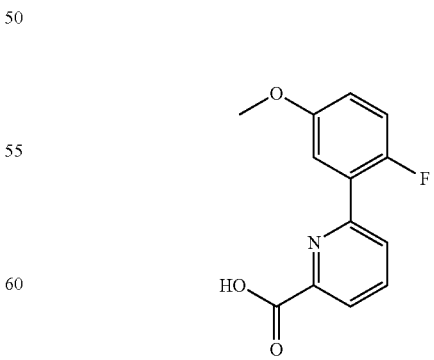

Method 1 was followed using 6-bromopicolinic acid (1.0 equiv.) and 2-fluoro-5-methoxyphenylboronic acid (1.3 equiv.) and Pd(dppf)Cl$_2$-DCM (0.15 equiv.) to give 6-(2- fluoro-5-methoxyphenyl)picolinic acid in 95% yield. LC/MS=248.2 (M+H), Rt=0.78 min.

Synthesis of 6-(2-fluoro-5-propoxyphenyl)picolinic acid

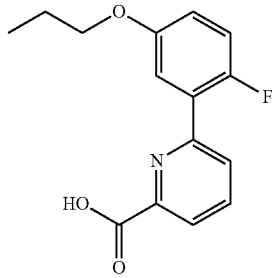 [SMILES: CCCOc1ccc(F)c(-c2cccc(C(=O)O)n2)c1]

Method 1 was followed using 6-bromopicolinic acid (1.0 equiv.) and 2-fluoro-5-propoxyphenylboronic acid (1.5 equiv.) and Pd(dppf)Cl$_2$-DCM (0.15 equiv.) to give 6-(2-fluoro-5-propoxyphenyl)picolinic acid in 20% yield. LC/MS=276.0 (M+H), Rt=0.87 min.

Synthesis of 6-(2,6-difluoro-4-methoxyphenyl)picolinic acid

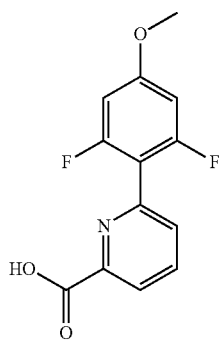 [SMILES: COc1cc(F)c(-c2cccc(C(=O)O)n2)c(F)c1]

Method 1 was followed using 6-bromopicolinic acid (1.0 equiv.) and 2,6-difluoro-4-methoxyphenylboronic acid (1.3 equiv.) and Pd(dppf)Cl$_2$-DCM (0.15 equiv.) to give 6-(2,6-difluoro-4-methoxyphenyl)picolinic acid in 42% yield. LC/MS=266.1 (M+H), Rt=0.75 min.

Synthesis of 3-fluoro-6-(2-fluorophenyl)picolinic acid

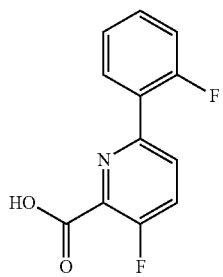 [SMILES: O=C(O)c1nc(-c2ccccc2F)ccc1F]

Method 1 was followed using 6-bromo-3-fluoropicolinic acid (1.0 equiv.) and 2-fluorophenylboronic acid (1.5 equiv.) and Pd(dppf)Cl$_2$-DCM (0.05 equiv.) to give 3-fluoro-6-(2-fluorophenyl)picolinic acid in 81% yield. LC/MS=236.1 (M+H), Rt=0.72 min.

Synthesis of 3-fluoro-6-(2-fluoro-5-methoxyphenyl)picolinic acid

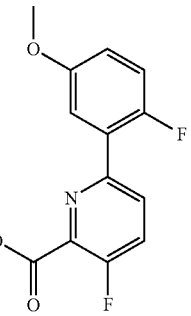

Method 1 was followed using 6-bromo-3-fluoropicolinic acid (1.0 equiv.) and 2-fluoro-5-methoxyphenylboronic acid (1.3 equiv.) and Pd(dppf)Cl$_2$-DCM (0.15 equiv.) to give 3-fluoro-6-(2-fluoro-5-methoxyphenyl)picolinic acid in 89% yield. LC/MS=266.1 (M+H), Rt=0.79 min.

Synthesis of 5-fluoro-6-(2-fluoro-5-methoxyphenyl)picolinic acid

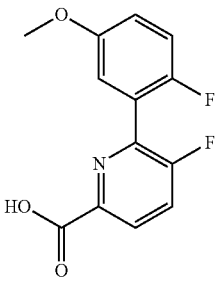 [SMILES: COc1ccc(F)c(-c2nc(C(=O)O)ccc2F)c1]

Method 1 was followed using 6-bromo-5-fluoropicolinic acid (1.0 equiv.) and 2-fluoro-5-methoxyphenylboronic acid (1.3 equiv.) and Pd(dppf)Cl$_2$-DCM (0.15 equiv.) to give 5-fluoro-6-(2-fluoro-5-methoxyphenyl)picolinic acid in 86% yield. LC/MS=266.1 (M+H), Rt=0.79 min.

Synthesis of 6-(4-(benzyloxy)-2-fluorophenyl)-5-fluoropicolinic acid

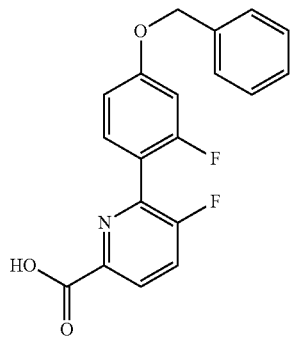 [SMILES: O=C(O)c1ccc(F)c(-c2ccc(OCc3ccccc3)cc2F)n1]

Method 1 was followed using 6-bromo-5-fluoropicolinic acid (1.0 equiv.) and 4-(benzyloxy)-2-fluorophenylboronic acid (1.3 equiv.) and Pd(dppf)Cl$_2$-DCM (0.15 equiv.) to give 6-(4-(benzyloxy)-2-fluorophenyl)-5-fluoropicolinic acid in 28% yield. LC/MS=342.1 (M+H), Rt=1.05 min.

Synthesis of 6-(4-(benzyloxy)-2-fluorophenyl)-3-fluoropicolinic acid

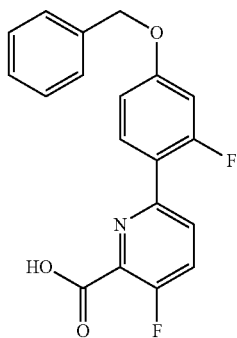 [SMILES: O=C(O)c1nc(-c2ccc(OCc3ccccc3)cc2F)ccc1F]

Method 1 was followed using 6-bromo-3-fluoropicolinic acid (1.0 equiv.) and 4-(benzyloxy)-2-fluorophenylboronic acid (1.3 equiv.) and Pd(dppf)Cl$_2$-DCM (0.15 equiv.) to give 6-(4-(benzyloxy)-2-fluorophenyl)-3-fluoropicolinic acid in 41% yield. LC/MS=342.1 (M+H), Rt=1.06 min.

Synthesis of 6-(2,6-difluoro-4-methoxyphenyl)-3-fluoropicolinic acid

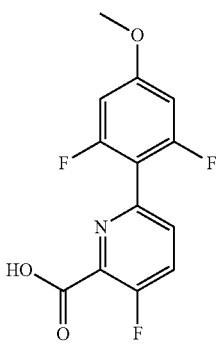

Method 1 was followed using 6-bromo-3-fluoropicolinic acid (1.0 equiv.) and 2,6-difluoro-4-methoxyphenylboronic acid (1.3 equiv.) and Pd(dppf)Cl$_2$-DCM (0.15 equiv.) to give 6-(2,6-difluoro-4-methoxyphenyl)-3-fluoropicolinic acid in 9% yield. LC/MS=284.0 (M+H), Rt=0.74 min.

Synthesis of 6-cyclohexenyl-5-fluoropicolinic acid

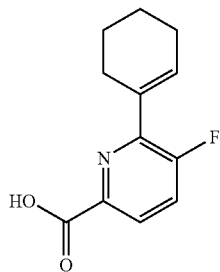

Method 1 was followed using 6-bromo-5-fluoropicolinic acid (1.0 equiv.) and cyclohexenylboronic acid (1.3 equiv.) and Pd(dppf)Cl$_2$-DCM (0.15 equiv.) to give 6-cyclohexenyl-5-fluoropicolinic acid in 61% yield. LC/MS=222.0 (M+H), Rt=0.52 min.

Method 3

Synthesis of 6-cyclohexyl-5-fluoropicolinic acid

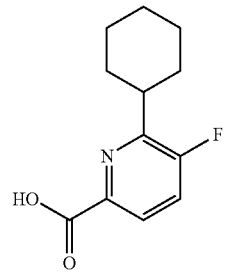 [SMILES: O=C(O)c1ccc(F)c(C2CCCCC2)n1]

To a degassed solution of 6-cyclohexenyl-5-fluoropicolinic acid (1.0 equiv.) in MeOH (0.07M) was added 10% Pd/C (0.1 equiv.) and the reaction was stirred under a hydrogen balloon overnight. The solution was then filtered, rinsed with MeOH, and the filtrate was concentrated to afford 6-cyclohexyl-5-fluoropicolinic acid in 65% yield. LC/MS=224.2 (M+H), Rt=0.95 min.

Synthesis of 5-fluoro-6-(1,4-dioxaspiro[4.5]dec-7-en-8-yl)picolinic acid

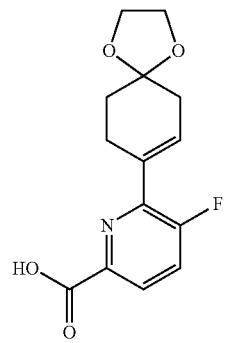 [SMILES: O=C(O)c1ccc(F)c(C2=CCC3(CC2)OCCO3)n1]

Method 1 was followed using 6-bromo-5-fluoropicolinic acid (1.0 equiv.) and 4,4,5,5-tetramethyl-2-(1,4-dioxaspiro[4.5]dec-7-en-8-yl)-1,3,2-dioxaborolane (2.0 equiv.) and Pd(dppf)Cl$_2$-DCM (0.2 equiv.) to give 5-fluoro-6-(1,4-dioxaspiro[4.5]dec-7-en-8-yl)picolinic acid. LC/MS=280.2 (M+H), Rt=0.66 min.

Synthesis of methyl 5-fluoro-6-(1,4-dioxaspiro[4.5]dec-7-en-8-yl)picolinate

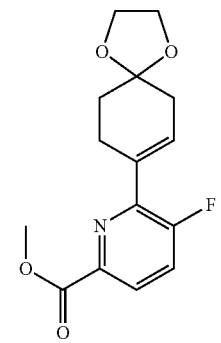 [SMILES: COC(=O)c1ccc(F)c(C2=CCC3(CC2)OCCO3)n1]

To a solution of 5-fluoro-6-(1,4-dioxaspiro[4.5]dec-7-en-8-yl)picolinic acid (1.0 equiv.) in DCM (0.3 M) was added EDC-HCl (1.0 equiv.), DMAP (1.0 equiv.), and MeOH (10 equiv.). The reaction mixture was allowed to stir at room temperature for 5 days, then diluted with ethyl acetate, washed with water, brine, dried over magnesium sulfate, filtered and concentrated. The crude product was purified by silica gel column chromatography eluting with 25-50% ethyl acetate in hexanes to yield methyl 5-fluoro-6-(1,4-dioxaspiro[4.5]dec-7-en-8-yl)picolinate as the desired product in 35% yield. LC/MS=294.2 (M+H), Rt=0.79 min.

Synthesis of methyl 5-fluoro-6-(1,4-dioxaspiro[4.5]decan-8-yl)picolinate

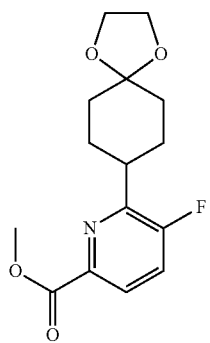 [SMILES: COC(=O)c1ccc(F)c(C2CCC3(CC2)OCCO3)n1]

To a degassed solution of methyl 5-fluoro-6-(1,4-dioxaspiro[4.5]dec-7-en-8-yl)picolinate (1.0 equiv.) in MeOH (0.07M) was added 10% Pd/C (0.1 equiv.) and the reaction was stirred under a hydrogen balloon overnight. The solution was then filtered, rinsed with MeOH, and the filtrate was concentrated to afford methyl 5-fluoro-6-(1,4-dioxaspiro[4.5]decan-8-yl)picolinate in 91% yield. LC/MS=296.2 (M+H), Rt=0.83 min.

Synthesis of methyl 5-fluoro-6-(4-oxocyclohexyl)picolinate

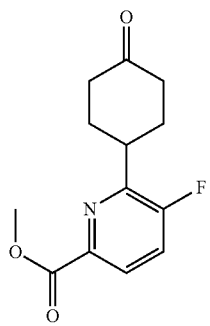 [SMILES: COC(=O)c1ccc(F)c(C2CCC(=O)CC2)n1]

To a solution of methyl 5-fluoro-6-(1,4-dioxaspiro[4.5]decan-8-yl)picolinat (1.0 equiv.) in acetone and water (1:1, 0.04 M) was added oxalic acid dehydrate (2.0 equiv.) and the reaction mixture was stirred for 3 days. The solution was then neutralized by the addition of solid NaHCO$_3$, the mixture was added to ethyl acetate and brine, the organic phase was dried over magnesium sulfate, filtered, and concentrated. Methyl 5-fluoro-6-(4-oxocyclohexyl)picolinate was obtained in 98% yield. LC/MS=252.1 (M+H), Rt=0.68 min.

Synthesis of methyl 5-fluoro-6-(4-hydroxycyclohexyl)picolinate

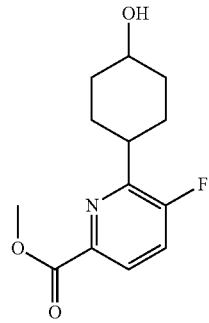 [SMILES: COC(=O)c1ccc(F)c(C2CCC(O)CC2)n1]

To a 0° C. solution of methyl 5-fluoro-6-(4-oxocyclohexyl)picolinate (1.0 equiv.) win MeOH (0.08 M) was added NaBH$_4$. The solution was allowed to warm to room temperature overnight then partitioned between ethyl acetate and brine, the organic phase was dried over magnesium sulfate, filtered, and concentrated to give methyl 5-fluoro-6-(4-hydroxycyclohexyl)picolinate as a mixture of two isomers (5:1). LC/MS=254.2 (M+H), Rt=0.63 min.

Synthesis of methyl 6-(4-(tert-butyldimethylsilyloxy)cyclohexyl)-5-fluoropicolinate

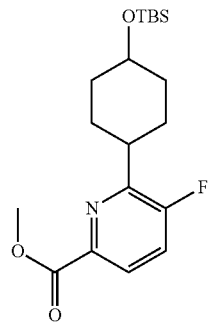 [SMILES: COC(=O)c1ccc(F)c(C2CCC(O[Si](C)(C)C(C)(C)C)CC2)n1]

To a solution of methyl 5-fluoro-6-(4-hydroxycyclohexyl)picolinate (1.0 equiv.) in DMF (0.15 M) was added imidazole (4.0 equiv.) and TBDMSCl (2.5 equiv.). The reaction mixture was stirred at room temperature for 2 days, then added to ethyl acetate, washed with water, brine, dried over magnesium sulfate, filtered and concentrated to give methyl 6-(4-(tert-butyldimethylsilyloxy)cyclohexyl)-5-fluoropicolinate in 97% yield as a mixture of isomers (3:1). LC/MS=368.3 (M+H), Rt=1.4 and 1.42 min.

Synthesis of 6-(4-(tert-butyldimethylsilyloxy)cyclohexyl)-5-fluoropicolinic acid

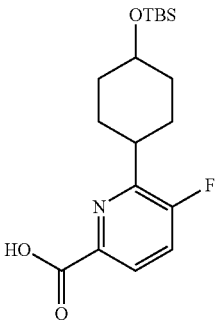 [SMILES: CC(C)(C)[Si](C)(C)OC1CCC(c2nc(C(=O)O)ccc2F)CC1]

To a solution of methyl 6-(4-(tert-butyldimethylsilyloxy) cyclohexyl)-5-fluoropicolinate (1.0 equiv.) in THF/MeOH (2:1, 0.09 M) was added LiOH (1.5 equiv.). The reaction mixture was stirred overnight at room temperature, then 1N HCl and ethyl acetate were added, the organic phase was washed with brine, dried over magnesium sulfate, filtered and concentrated to give 6-(4-(tert-butyldimethylsilyloxy)cyclohexyl)-5-fluoropicolinic acid as a mixture of isomers (3:1) in 82% yield. LC/MS=354.2 (M+H), Rt=1.38 and 1.41 min.

Synthesis of 6-bromo-5-fluoropicolinic acid

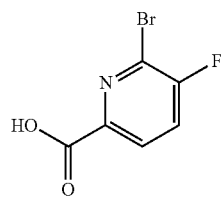

To 2-bromo-3-fluoro-6-methylpyridine (1.0 equiv.) in H$_2$O (30 mL) was added potassium permanganate (1.0 equiv.). The solution was heated at 100° C. for 5 hours at which time more potassium permanganate (1.0 equiv.) was added. After heating for an additional 48 hours the material was filtered through celite (4 cm×2 inches) and rinsed with H$_2$O (150 mL). The combined aqueous was acidified with 1N HCl to pH=4, extracted with ethyl acetate (200 mL), washed with NaCl(sat.), dried over MgSO$_4$, filtered and concentrated to yield 6-bromo-5-fluoropicolinic acid (17%) as a white solid. LCMS (m/z): 221.9 (MH$^+$); LC Rt=2.05 min.
Method 4

Synthesis of 2-(2,6-difluorophenyl)-3-fluoro-6-methylpyridine

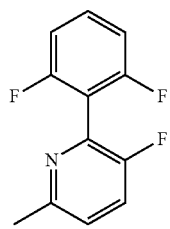 [SMILES: Cc1ccc(F)c(-c2c(F)cccc2F)n1]

To a solution of 2-bromo-3-fluoro-6-methylpyridine (1.0 equiv.) in THF and Water (10:1, 0.2 M) was added 2,6-difluorophenylboronic acid (2.0 equiv.) and potassium fluoride (3.3 equiv.). The reaction was degassed for 10 minutes, then Pd$_2$(dba)$_3$ (0.05 equiv.) was added, followed by tri-t-butylphosphine (0.1 equiv.). The reaction was stirred to 60° C. for 1 hour at which point, all starting material was consumed as indicated by LC/MS. The reaction was allowed to cool to room temperature, partitioned with ethyl acetate and water, the organic phase was dried with sodium sulfate, filtered, and concentrated. The crude material was diluted in EtOH to 0.1 M, and 0.5 equiv. of NaBH$_4$ was added to reduce the dba. The reaction was stirred for one hour at room temperature, then quenched with water and concentrated under vacuo to remove the ethanol. The product was extracted in ether, washed with brine, the organics were dried over sodium sulfate, filtered, and concentrated. The crude material was loaded on silica gel and purified via column chromatography (ISCO) eluting with hexanes and ethyl acetate (0%-10% ethyl acetate). The pure fractions were combined, and concentrated to yield 2-(2,6-difluorophenyl)-3-fluoro-6-methylpyridine as a light yellow oil in 86% yield. LC/MS=224.0 (M+H), Rt=0.84 min.
Method 5

Synthesis of 6-(2,6-difluorophenyl)-5-fluoropicolinic acid

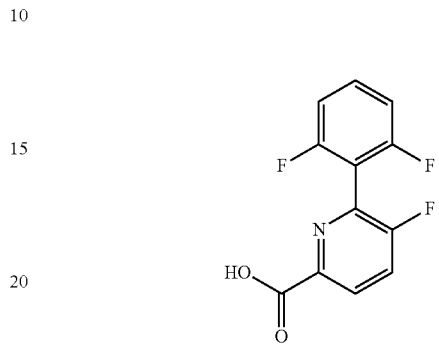

To a solution of 2-(2,6-difluorophenyl)-3-fluoro-6-methylpyridine (1.0 equiv.) in water (0.05 M) was added KMnO$_4$ (2.0 equiv.) and the reaction was heated to reflux overnight. Another 2.0 equiv. of KMnO$_4$ were added and stirred at reflux for another 8 hours. The solution was cooled to room temperature, filtered through Celite and washed with water. The filtrate was acidified with 6N HCl to pH=3, the white precipitate was filtered. The filtrate was further acidified to pH=1 and filtered again. The filtrate was extracted with ethyl acetate until no more product in the aqueous layer. The organic phase was washed with brine and dried over magnesium sulfate, filtered, and concentrated. The residue was dissolved in ethyl acetate, washed with 1N NaOH, the aqueous layer was acidified to pH=1 and the white crystals were filtered. The combined products yielded 6-(2,6-difluorophenyl)-5-fluoropicolinic acid in 32% yield as a white solid. LC/MS=254.0 (M+H), Rt=0.71 min.

Synthesis of 6-(2,6-difluorophenyl)-3-fluoro-2-methylpyridine

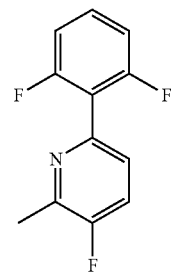 [SMILES: Cc1nc(-c2c(F)cccc2F)ccc1F]

To a solution of 6-bromo-3-fluoro-2-methylpyridine (1.0 equiv.) in ethanol and toluene (1:1, 0.2 M) was added 2,6-difluorophenylboronic acid, DIEA (5 equiv.) and Pd(PPh$_3$)$_4$ (0.2 equiv.). The reaction was heated in the microwave at 120° C. for 30 min. The solution was filtered and rinsed with ethyl acetate. The volatiles were removed in vacuo and the crude was purified via silica gel column chromatography eluting with ethyl acetate and hexanes (2.5-20% ethyl acetate). Upon concentration of the pure fractions, 6-(2,6-difluorophenyl)-

3-fluoro-2-methylpyridine was isolated in 88% yield. LC/MS=224.1 (M+H), Rt=0.87 min.

Synthesis of 6-(2,6-difluorophenyl)-3-fluoropicolinic acid

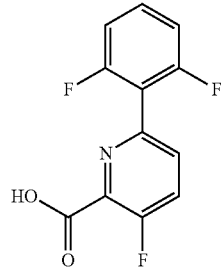

Method 5 was followed using 6-(2,6-difluorophenyl)-3-fluoro-2-methylpyridine (1.0 equiv.) and potassium permanganate (6.0 equiv.) to give 6-(2,6-difluorophenyl)-3-fluoropicolinic acid in 30% yield. LC/MS=254.1 (M+H), Rt=0.70 min.

Synthesis of 2-(2,6-difluoro-3-methoxyphenyl)-3-fluoro-6-methylpyridine

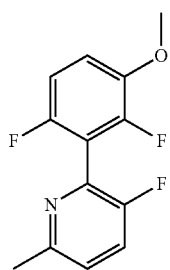 [SMILES: COc1ccc(F)c(-c2nc(C)ccc2F)c1F]

Method 4 was followed using 2-bromo-3-fluoro-6-methylpyridine (1.0 equiv.) and 2,6-difluoro-3-methoxyphenylboronic acid (2.0 equiv.) to give 2-(2,6-difluoro-3-methoxyphenyl)-3-fluoro-6-methylpyridine in 60% yield. LC/MS=254.1 (M+H), Rt=0.85 min.

Synthesis of 6-(2,6-difluoro-3-methoxyphenyl)-5-fluoropicolinic acid

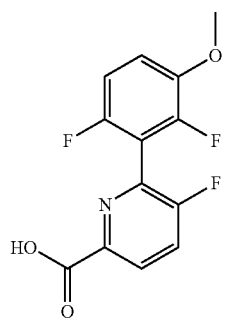 [SMILES: COc1ccc(F)c(-c2nc(C(=O)O)ccc2F)c1F]

Method 5 was followed using 2-(2,6-difluoro-3-methoxyphenyl)-3-fluoro-6-methylpyridine (1.0 equiv.) and potassium permanganate (4.0 equiv.) to give 6-(2,6-difluoro-3-methoxyphenyl)-5-fluoropicolinic acid in 27% yield. LC/MS=284.1 (M+H), Rt=0.75 min.

Synthesis of 3-fluoro-6-methyl-2-(2,3,5-trifluorophenyl)pyridine

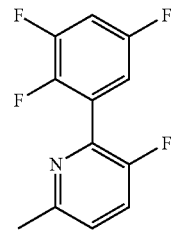 [SMILES: Cc1ccc(F)c(-c2cc(F)cc(F)c2F)n1]

To a solution of 2-bromo-3-fluoro-6-methylpyridine (1.0 equiv.) in dioxane (0.2 M) was added 2,3,5-trifluorophenylboronic acid and Pd(dppf)Cl$_2$-DCM (0.1 equiv.). Aqueous sodium carbonate (2M solution, 2.0 equiv.) was added and the reaction was heated in the microwave at 120° C. for 15 min. The solution was partitioned between ethyl acetate and sat. NaHCO$_3$, the organic phase was washed with brine, dried with magnesium sulfate, filtered, and concentrated. The crude material was purified via silica gel column chromatography eluting with ethyl acetate and hexanes (1:3) to give 3-fluoro-6-methyl-2-(2,3,5-trifluorophenyl)pyridine in 87% yield. LC/MS=242.1 (M+H), Rt=0.98 min.

Synthesis of 5-fluoro-6-(2,3,5-trifluorophenyl)picolinic acid

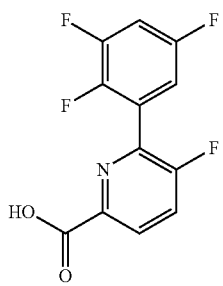 [SMILES: O=C(O)c1ccc(F)c(-c2cc(F)cc(F)c2F)n1]

To a solution of 3-fluoro-6-methyl-2-(2,3,5-trifluorophenyl)pyridine (1.0 equiv.) in water and t-BuOH (2:1, 0.06 M) was added potassium permanganate (10 equiv.) and the solution was heated at 90° C. for 5 hours. Upon cooling to room temperature, the solution was filtered, and the filtrate was concentrated under reduced pressure to yield 5-fluoro-6-(2,3,5-trifluorophenyl)picolinic acid in 89% yield. LC/MS=272.0 (M+H), Rt=0.80 min.

Synthesis of methyl 6-bromo-5-fluoropicolinate

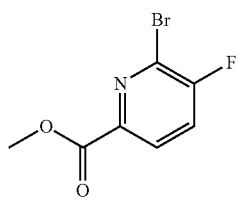

To a solution of 6-bromo-5-fluoropicolinic acid (1.0 equiv.) in methanol (0.2 M) was added H$_2$SO$_4$ (4.2 equiv.) and the reaction was stirred at room temperature for two hours.

Upon completion of the reaction as monitored by LC/MS, the reaction was diluted with ethyl acetate and quenched slowly with saturated aqueous NaHCO$_3$. The reaction was poured into a separatory funnel and extracted with ethyl acetate. The organic phase was dried with magnesium sulfate, filtered, and concentrated in vacuo to provide methyl 6-bromo-5-fluoropicolinate as a white solid (>99%). LC/MS=233.9/235.9 (M+H), Rt=0.69 min.

Method 6

Synthesis of methyl 6-(3-(benzyloxy)-2,6-difluorophenyl)-5-fluoropicolinate

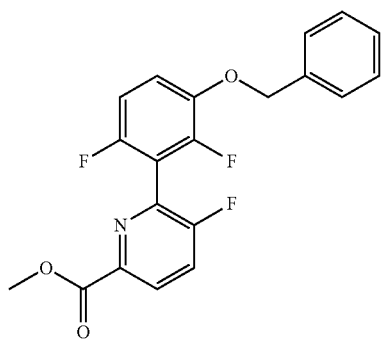 [SMILES: COC(=O)c1ccc(F)c(-c2c(F)ccc(OCc3ccccc3)c2F)n1]

To a solution of methyl 6-bromo-5-fluoropicolinate (1.0 equiv.) in THF and water (10:1, 0.1 M) was added 3-(benzyloxy)-2,6-difluorophenylboronic acid (2.5 equiv.) and potassium fluoride (3.3 equiv.). The reaction was degassed with nitrogen, then Pd$_2$(dba)$_3$ (0.25 equiv.) and tri-tert-butylphosphine (0.5 equiv.) were added and the reaction was heated to 80° C. for one hour. LC/MS analysis indicated complete conversion of the starting material to product. The reaction was cooled to room temperature, then concentrated in vacuo and fused to silica gel. The crude product was purified by ISCO flash chromatography eluting with ethyl acetate and hexanes (0% to 30% ethyl acetate) to provide methyl 6-(3-(benzyloxy)-2,6-difluorophenyl)-5-fluoropicolinate as the desired product as a light yellow oil in 96% yield. LC/MS=374.0 (M+H), Rt=1.07 min.

Synthesis of methyl 6-(3-(benzyloxy)-2,6-difluorophenyl)picolinate

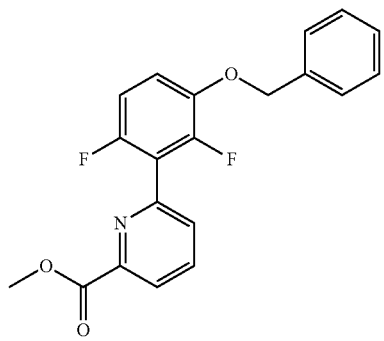 [SMILES: COC(=O)c1cccc(-c2c(F)ccc(OCc3ccccc3)c2F)n1]

Method 6 was followed using methyl 6-bromopicolinate (1.0 equiv.) and 3-(benzyloxy)-2,6-difluorophenylboronic acid (2.5 equiv.) to give methyl 6-(3-(benzyloxy)-2,6-difluorophenyl)picolinate as a light yellow solid in 95% yield. LC/MS=356.2 (M+H), Rt=1.03 min.

Synthesis of methyl 6-(2,6-difluoro-4-methoxyphenyl)-5-fluoropicolinate

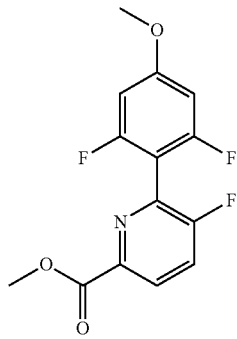 [SMILES: COC(=O)c1ccc(F)c(-c2c(F)cc(OC)cc2F)n1]

Method 6 was followed using methyl 6-bromopicolinate (1.0 equiv.) and 2,6-difluoro-4-methoxyphenylboronic acid (2.5 equiv.) to give methyl 6-(2,6-difluoro-4-methoxyphenyl)-5-fluoropicolinate as a white solid in 85% yield. LC/MS=298.0 (M+H), Rt=0.89 min.

Synthesis of 6-(2,6-difluoro-4-methoxyphenyl)-5-fluoropicolinic acid

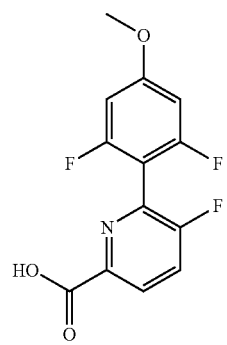 [SMILES: COc1cc(F)c(-c2nc(C(=O)O)ccc2F)c(F)c1]

To a solution of methyl 6-(2,6-difluoro-4-methoxyphenyl)-5-fluoropicolinate (1.0 equiv.) in THF/MeOH (2:1, 0.09 M) was added LiOH (1.5 equiv.) and the reaction was stirred at room temperature for 1 hour. The solution was quenched with 1N HCl, extracted with ethyl acetate, washed with brine, dried with sodium sulfate, filtered and concentrated to give 6-(2,6-difluoro-4-methoxyphenyl)-5-fluoropicolinic acid in 84% yield. LC/MS=284.1 (M+H), Rt=0.76 min.

Method 7

Synthesis of methyl 6-(2,6-difluoro-3-hydroxyphenyl)-5-fluoropicolinate

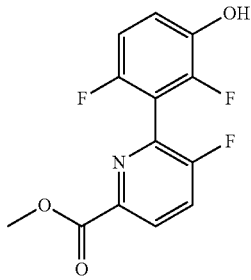 [SMILES: COC(=O)c1ccc(F)c(-c2c(F)ccc(O)c2F)n1]

To a solution of methyl 6-(3-(benzyloxy)-2,6-difluorophenyl)-5-fluoropicolinate (1.0 equiv.) in methanol (0.1 M) was added 10% Pd/C (0.1 equiv.) in ethyl acetate. The reaction was placed under an atmosphere of hydrogen and stirred for 2 hours. Upon completion, the solution was filtered over a pad of Celite, the pad was washed with methanol, the filtrate was concentrated in vacuo to give methyl 6-(2,6-difluoro-3-hydroxyphenyl)-5-fluoropicolinate as a grey oil in 86% yield. LC/MS=284.0 (M+H), Rt=0.90 min.

Synthesis of methyl 6-(2,6-difluoro-3-hydroxyphenyl)picolinate

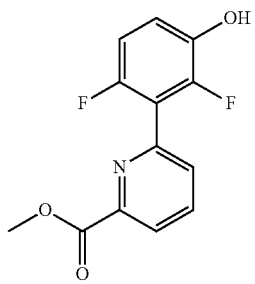 [SMILES: COC(=O)c1cccc(-c2c(F)ccc(O)c2F)n1]

Method 7 was followed using methyl 6-(3-(benzyloxy)-2,6-difluorophenyl)picolinate (1.0 equiv.) to yield methyl 6-(2,6-difluoro-3-hydroxyphenyl)picolinate as a light brown solid in 96% yield. LC/MS=266.0 (M+H), Rt=0.68 min.

Synthesis of methyl 6-(2-fluoro-5-formylphenyl)picolinate

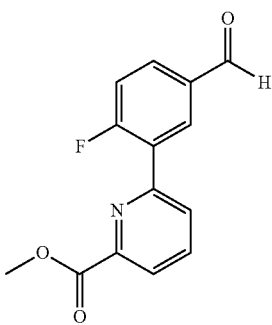 [SMILES: COC(=O)c1cccc(-c2cc(C=O)ccc2F)n1]

To a solution of methyl 6-bromopicolinate (1.0 equiv.) in DME (0.03 M) in a microwave vial was added Pd(dppf)Cl$_2$-DCM (0.05 equiv.), 2-fluoro-5-formylphenylboronic acid (1.5 equiv.) and 2M Na$_2$CO$_3$ (2 equiv.). The reagents were heated to 120° C. for 20 min. A mixture of the desired product and the corresponding carboxylic acid was detected by LC/MS, the reaction was diluted with ethyl acetate, washed with HCl (pH=5), the acidic phase was extracted with ethyl acetate, the combined organic layers were dried with magnesium sulfate, filtered, and concentrated in vacuo to provide a light brown solid. The solid was dissolved in MeOH and treated with 3 equiv. of TMS-diazomethane at room temperature. Upon complete conversion of the carboxylic acid to the corresponding methyl ester, the reaction was concentrated in vacuo and the crude material was purified via silica gel column chromatography (ISCO) eluting with 30% ethyl acetate in hexanes to provide methyl 6-(2-fluoro-5-formylphenyl)picolinate as a yellow solid in 58% yield. LC/MS=260.0 (M+H), Rt=0.70 min.

Synthesis of (E)-methyl 6-(2-fluoro-5-(prop-1-enyl)phenyl)picolinate

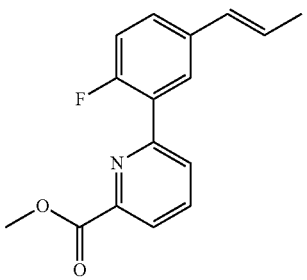 [SMILES: C/C=C/c1ccc(F)c(-c2cccc(C(=O)OC)n2)c1]

To a solution of methyl 6-(2-fluoro-5-formylphenyl)picolinate (1.0 equiv.) in MeOH (0.17 M) was added ethyltriphenylphosphonium bromide (1.0 equiv.) followed by sodium methoxide (1.5 equiv.). The reaction was heated to 65° C. for 5 hours, then cooled to room temperature and concentrated in vacuo. The crude material was purified via silica gel column chromatography (ISCO) eluting with 50% ethyl acetate in hexanes to provide (E)-methyl 6-(2-fluoro-5-(prop-1-enyl)phenyl)picolinate as a white solid in 81% yield. LC/MS=272.0 (M+H), Rt=0.73 min.

Synthesis of methyl 6-(2-fluoro-5-propylphenyl)picolinate

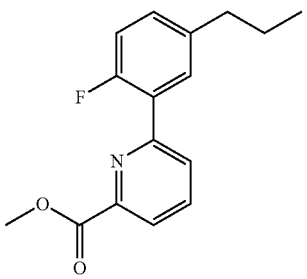 [SMILES: CCCc1ccc(F)c(-c2cccc(C(=O)OC)n2)c1]

To a solution of (E)-methyl 6-(2-fluoro-5-(prop-1-enyl)phenyl)-picolinate (1.0 equiv.) in MeOH (0.04 M) was 10% Pd/C (0.5 equiv.) and the reaction was placed under an atmosphere of hydrogen and left stirring overnight. The mixture was filtered over a pad of Celite and washed with MeOH. The filtrate was concentrated in vacuo to provide methyl 6-(2-fluoro-5-propylphenyl)picolinate as a light grey oil in 97% yield. LC/MS=274.2 (M+H), Rt=0.61 min.

Synthesis of 6-(2-fluoro-5-propylphenyl)picolinic acid

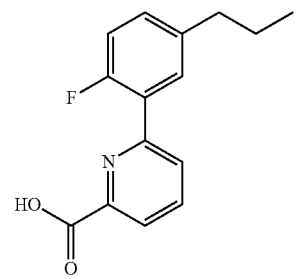 [SMILES: CCCc1ccc(F)c(-c2cccc(C(=O)O)n2)c1]

To a solution of methyl 6-(2-fluoro-5-propylphenyl)picolinate (1.0 equiv.) in THF was added lithium hydroxide (10 equiv.) and the reaction was stirred at room temperature for 1 hour. The THF solvent was removed in vacuo and the remaining basic phase was acidified with concentrated HCl. The aqueous layer was extracted with ethyl acetate (2×), the organic phase was dried with sodium sulfate, filtered and concentrated to give 6-(2-fluoro-5-propylphenyl)picolinic acid in 35% yield. LC/MS=260.2 (M+H), Rt=0.36 min.

Method 8

Synthesis of methyl 6-(2,6-difluoro-3-(trifluoromethyl-sulfonyloxy)phenyl)-5-fluoropicolinate

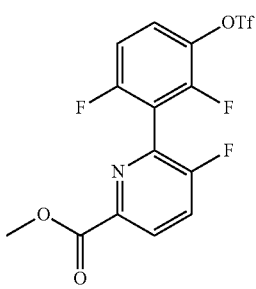 [SMILES: COC(=O)c1ccc(F)c(-c2c(F)ccc(OS(=O)(=O)C(F)(F)F)c2F)n1]

To a solution of methyl 6-(2,6-difluoro-3-hydroxyphenyl)-5-fluoropicolinate (1.0 equiv.) in DCM (0.2 M) was added DIEA (2.0 equiv.) and 1,1,1-trifluoro-N-phenyl-N-(trifluoromethylsulfonyl)methanesulfonamide (1.5 equiv.). The reaction was allowed to stir overnight at room temperature. The solution was quenched with water, the organic phase was dried with sodium sulfate, and concentrated. The crude material was purified via ISCO chromatography eluting with ethyl acetate and hexanes (0-30% ethyl acetate). The pure fractions were concentrated to give methyl 6-(2,6-difluoro-3-(trifluoromethylsulfonyloxy)phenyl)-5-fluoropicolinate as the desired product as a clear oil in 68% yield. LC/MS=416.1 (M+H), Rt=1.08 min.

Synthesis of methyl 6-(2,6-difluoro-3-(trifluoromethylsulfonyloxy)-phenyl)picolinate

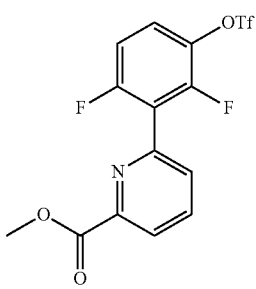 [SMILES: COC(=O)c1cccc(-c2c(F)ccc(OS(=O)(=O)C(F)(F)F)c2F)n1]

Method 8 was followed using methyl 6-(2,6-difluoro-3-(trifluoromethylsulfonyloxy)phenyl)-5-fluoropicolinate (1.0 equiv.) to yield methyl 6-(2,6-difluoro-3-(trifluoromethylsulfonyloxy)phenyl)picolinate as a colorless oil in >99% yield. LC/MS=397.9 (M+H), Rt=1.03 min.

Synthesis of 6-(2,6-difluoro-3-methylphenyl)-5-fluoropicolinic acid

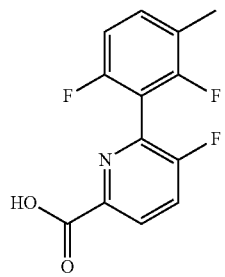 [SMILES: Cc1ccc(F)c(-c2nc(C(=O)O)ccc2F)c1F]

To a solution methyl 6-(2,6-difluoro-3-(trifluoromethylsulfonyloxy)phenyl)-5-fluoropicolinate (1.0 equiv.) in dioxane and water (10:1, 0.15M) was added methyl boronic acid (3.0 equiv.) and potassium carbonate (3.0 equiv.). The reaction was degassed with nitrogen for 10 min, then Pd(PPh$_3$)$_4$ (0.1 equiv.) was added to the solution and heated to 100° C. for 3 hours. LC/MS of the reaction at this point indicated complete conversion to the carboxylic acid product (M+H=268). Cooled to room temperature and added water and ethyl acetate. The two layers were separated, the aqueous phase was acidified with concentrated HCl to pH=1 and extracted with ethyl acetate. The organic phase was dried with sodium sulfate, filtered, and concentrated under vacuo to give 6-(2,6-difluoro-3-methylphenyl)-5-fluoropicolinic acid as a clear oil in 97% yield. LC/MS=268.1 (M+H), Rt=0.82 min.

Synthesis of methyl 6-(2,6-difluoro-3-methylphenyl)picolinate

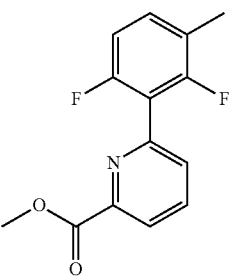 [SMILES: COC(=O)c1cccc(-c2c(F)ccc(C)c2F)n1]

To a solution of methyl 6-(2,6-difluoro-3-(trifluoromethylsulfonyloxy)-phenyl)picolinate (1.0 equiv.) in toluene was added Pd(dppf)Cl$_2$-DCM (0.1 equiv.) followed by dimethyl zinc (3.0 equiv.). The solution turned from orange to bright yellow. The reaction was heated to 80° C. for 2 hours at which time, LC/MS analysis indicated complete conversion to product. The reaction was cooled to room temperature, diluted with ethyl acetate and washed with brine. The organic layer was dried with magnesium sulfate, filtered, and concentrated in vacuo to provide methyl 6-(2,6-difluoro-3-methylphenyl)picolinate as a brown oil in quantitative yield. LC/MS=264.0 (M+H), Rt=0.90 min.

Synthesis of 6-(2,6-difluoro-3-methylphenyl)picolinic acid

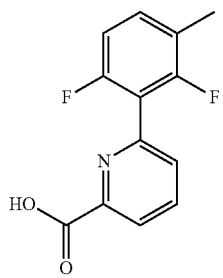 [SMILES: Cc1ccc(F)c(-c2cccc(C(=O)O)n2)c1F]

To a solution of methyl 6-(2,6-difluoro-3-methylphenyl)picolinate (1.0 equiv.) in THF was added sodium hydroxide (10 equiv.) and the reaction was stirred for 2 hours. The solution was diluted with ethyl acetate and washed with 1N NaOH (2×). The combined basic aqueous washes were combined and acidified with concentrated HCl. The acidic aqueous phase was extracted with ethyl acetate (2×), the combined organic layers were dried with magnesium sulfate, filtered, and concentrated in vacuo to provide 6-(2,6-difluoro-3-methylphenyl)picolinic acid as a white solid in 85% yield. LC/MS=250.0 (M+H), Rt=0.76 min.

Synthesis of 6-(3-ethyl-2,6-difluorophenyl)picolinic acid

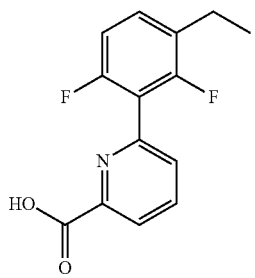 [SMILES: CCc1ccc(F)c(-c2cccc(C(=O)O)n2)c1F]

To a solution of methyl 6-(2,6-difluoro-3-(trifluoromethylsulfonyloxy)-phenyl)picolinate (1.0 equiv.) in toluene (0.15$\underline{M}$) was added Pd(dppf)Cl$_2$-DCM (0.1 equiv.) followed by diethyl zinc (3.0 equiv.). The solution turned from orange to bright yellow. The reaction was heated to 70° C. for 2 hours at which time, LC/MS analysis indicated a mixture of 1:3:1 ratio of hydrolyzed product, desired product and unknown by-product. The reaction was cooled to room temperature, diluted with ethyl acetate and washed with 1N NaOH (2×). The organic layer was dried over magnesium sulfate, filtered, and concentrated in vacuo to provide a brown oil. The oil was redissolved in THF and treated with 1N NaOH for one hour. The reaction was then diluted with ethyl acetate and washed with 1N NaOH (2×). The basic washings were combined, acidified with concentrated HCl and extracted with ethyl acetate (3×). The organic phase was dried with magnesium sulfate, filtered, and concentrated in vacuo to provide 6-(3-ethyl-2,6-difluorophenyl)picolinic acid as a light brown oil in >99% yield. LC/MS=264.1 (M+H), Rt=0.88 min.

Method 9

A homogeneous solution of 1 eq each of amine, carboxylic acid, HOAT and EDC in DMF, at a concentration of 0.5 $\underline{M}$, was left standing for 24 hours at which time water and ethyl acetate were added. The organic phase was dried with sodium sulfate and purified via silica gel column chromatography eluting with ethyl acetate and hexanes to give the desired protected amide product. Alternatively the crude reaction mixture was directly purified by HPLC. Upon lyophilization, the TFA salt of the protected amide product was obtained. Alternatively, the HPLC fractions could be added to EtOAc and solid Na$_2$CO$_3$, separated and washed with NaCl$_{(sat.)}$. Upon drying over MgSO$_4$, filtering and removing the volatiles in vacuo, the protected amide product was obtained as a free base. Alternatively, the crude reaction mixture was used for the deprotection step without further purification.

If an N-Boc protected amine was present, it was removed by treating with excess 4$\underline{M}$ HCl/dioxane for 14 hours or by treating with 25% TFA/CH$_2$Cl$_2$ for 2 hours. Upon removal of the volatiles in vacuo, the material was purified by RP HPLC yielding after lyophilization the amide product as the TFA salt. Alternatively, the HPLC fractions could be added to EtOAc and solid Na$_2$CO$_3$, separated and washed with NaCl$_{(sat.)}$. Upon drying over MgSO$_4$, filtering and removing the volatiles in vacuo the free base was obtained. Upon dissolving in MeCN/H$_2$O, adding 1 eq. of 1 $\underline{N}$ HCl and lyophilizing, the HCl salt of the amide product was obtained.

If an N-Boc1,2 amino alcohol cyclic carbamate was present, prior to Boc deprotection the cyclic carbamate could be cleaved by treating with Cs$_2$CO$_3$ (0.5 eq) in ethanol at a concentration of 0.1 $\underline{M}$ for three hours. After removal of volatiles in vacuo, the Boc amino group was deprotected as described above.

If an N-Boc, OAc group were present, prior to Boc deprotection, the acetate group could be cleaved by treating with K$_2$CO$_3$ (2.0 equiv.) in ethanol at a concentration of 0.1M for 24 hours.

If an N-phthalimide group was present, the amine was deprotected by treating with hydrazine in MeOH at 65° C. for three hours. Upon cooling and filtering off the white precipitate, the filtrate was concentrated and purified by RP HPLC to yield the amino amide product.

If a TBDMS ether was present, it was deprotected prior to Boc removal by treating with 6$\underline{N}$ HCl, THF, methanol (1:2:1) at room temperature for 12 h. After removal of volatiles in vacuo, the Boc amino group was deprotected as described above. Alternatively, the TBDMS ether and Boc group could be both deprotected with 6$\underline{N}$ HCl, THF, methanol (1:2:1) if left at rt for 24 hours, or heated at 60° C. for 3 hours.

If a OMe group was present, it was deprotected by treating with 1M BBr$_3$ in DCM (2.0 equiv.) for 24 hours. Water was added dropwise and the volatiles were removed in vacuo. The material was purified via reverse phase HPLC as described above.

If a OBn group was present, it was deprotected by treatment with 10% Pd/C (0.2 equiv.) under an atmosphere of hydrogen in ethyl acetate and methanol (1:2). Upon completion, the reaction was filtered through Celite, washed with methanol, and the filtrate was concentrated in vacuo.

Synthesis of (+/−)-3-amino-N-(4-(3-amino-4-hydroxycyclohex-1-enyl)pyridin-3-yl)-6-(2,6-difluorophenyl)picolinamide Synthesis of (+/−)-3-amino-N-(4-(3-amino-4-hydroxycyclohexyl)-pyridin-3-yl)-6-(2,6-difluorophenyl)picolinamide

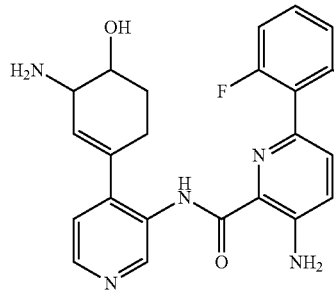

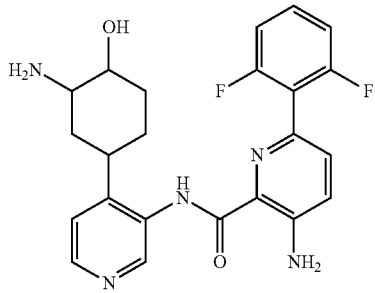

Following Method 9, (+/−)-tert-butyl 3-(3-aminopyridin-4-yl)-6-(tert-butyldimethylsilyloxy)cyclohex-2-enylcarbamate and 3-amino-6-(2,6-difluorophenyl)-picolinic acid were coupled and deprotected to yield (+/−)-3-amino-N-(4-(3-amino-4-hydroxycyclohex-1-enyl)pyridin-3-yl)-6-(2,6-difluorophenyl)picolinamide as the TFA salt. LCMS (m/z): 438.2 (MH⁺), LC $R_t$=2.00 min.

Following Method 9, (+/−)-tert-butyl 5-(3-aminopyridin-4-yl)-2-(tert-butyldimethylsilyloxy)cyclohexylcarbamate and 3-amino-6-(2,6-difluorophenyl)picolinic acid were coupled and deprotected to yield (+/−)-3-amino-N-(4-(3-amino-4-hydroxycyclohexyl)pyridin-3-yl)-6-(2,6-difluorophenyl)picolinamide as the TFA salt in 18% yield. LCMS (m/z): 440.3 (MH⁺), LC $R_t$=2.04 min.

Following the procedures of Method 9, the following compounds were prepared:

TABLE 1

| Example No. | Structure | LC/MS (M + H on UPCL) | LC/MS (Rf on UPCL) | Chemical Name |
|---|---|---|---|---|
| 1 | Chiral | 442.2 | 0.75 | 6-(2,6-difluorophenyl)-5-fluoro-N-(4-((1R,3S,5S)-3-hydroxy-5-methylcyclohexyl)pyridin-3-yl)picolinamide |
| 2 | Chiral | 474.3 | 0.52 | N-(4-((3R,4R,5S)-3-amino-4-hydroxy-5-methylpiperidin-1-yl)pyridin-3-yl)-6-(2,6-difluoro-4-hydroxyphenyl)-5-fluoropicolinamide |

TABLE 1-continued

| Example No. | Structure | LC/MS (M + H on UPCL) | LC/MS (Rf on UPCL) | Chemical Name |
|---|---|---|---|---|
| 3 | Chiral | 473.3 | 0.55 | 3-amino-N-(4-((3R,4R,5S)-3-amino-4-hydroxy-5-methylpiperidin-1-yl)pyridin-3-yl)-6-(2,6-difluorophenyl)-5-fluoropicolinamide |
| 4 | Chiral | 473.3 | 0.52 | N-(4-((1R,3R,4R,5S)-3-amino-4-hydroxy-5-methylcyclohexyl)pyridin-3-yl)-6-(2,6-difluoro-4-hydroxyphenyl)-5-fluoropicolinamide |
| 5 | Chiral | 455.3 | 0.55 | N-(4-((1R,3R,4R,5S)-3-amino-4-hydroxy-5-methylcyclohexyl)pyridin-3-yl)-5-fluoro-6-(2-fluoro-5-hydroxyphenyl)picolinamide |
| 6 | Chiral | 407.2 | 0.52 | N-(4-((1R,3S)-3-aminocyclohexyl)pyridin-3-yl)-6-(2-fluoro-4-hydroxyphenyl)picolinamide |

TABLE 1-continued

| Example No. | Structure | LC/MS (M + H on UPCL) | LC/MS (Rf on UPCL) | Chemical Name |
|---|---|---|---|---|
| 7 | 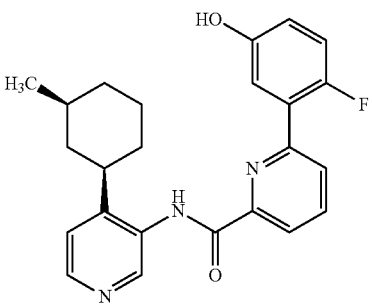 Chiral | 407.2 | 0.53 | N-(4-((1R,3S)-3-aminocyclohexyl)pyridin-3-yl)-6-(2-fluoro-5-hydroxyphenyl)picolinamide |
| 8 | 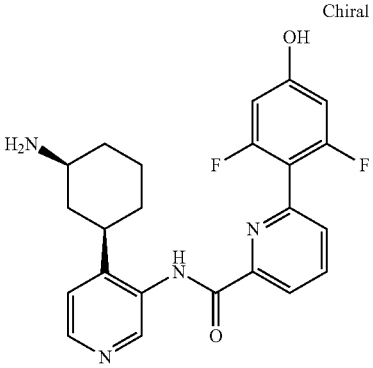 [SMILES: N[C@H]1CCC[C@@H](c2ccncc2NC(=O)c2cccc(-c3c(F)cc(O)cc3F)n2)C1] Chiral | 425.2 | 0.54 | N-(4-((1R,3S)-3-aminocyclohexyl)pyridin-3-yl)-6-(2,6-difluoro-4-hydroxyphenyl)picolinamide |
| 9 | 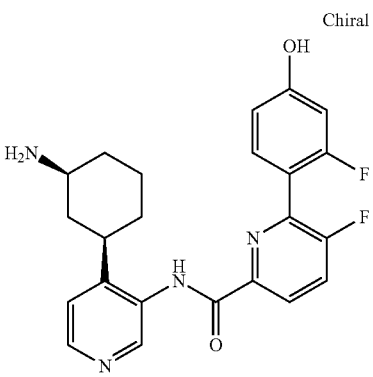 [SMILES: N[C@H]1CCC[C@@H](c2ccncc2NC(=O)c2ccc(F)c(-c3ccc(O)cc3F)n2)C1] Chiral | 425.2 | 0.53 | N-(4-((1R,3S)-3-aminocyclohexyl)pyridin-3-yl)-5-fluoro-6-(2-fluoro-4-hydroxyphenyl)picolinamide |
| 10 | 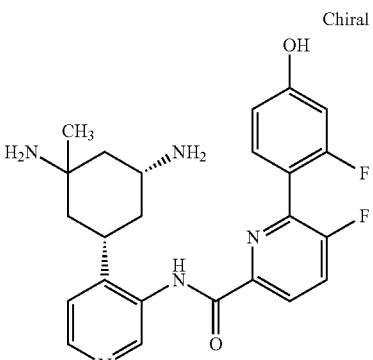 Chiral | 453.3 | 0.58 | N-(4-((1R,5R)-5-amino-3,3-dimethylcyclohexyl)pyridin-3-yl)-5-fluoro-6-(2-fluoro-4-hydroxyphenyl)picolinamide |

TABLE 1-continued

| Example No. | Structure | LC/MS (M + H on UPCL) | LC/MS (Rf on UPCL) | Chemical Name |
|---|---|---|---|---|
| 11 | Chiral | 469.2 | 0.7 | N-(4-((1R,5R)-5-amino-3,3-dimethylcyclohexyl)pyridin-3-yl)-6-(2,6-difluoro-3-methylphenyl)-5-fluoropicolinamide |
| 12 | Chiral | 451.1 | 0.69 | N-(4-((1R,5R)-5-amino-3,3-dimethylcyclohexyl)pyridin-3-yl)-6-(2,6-difluoro-3-methylphenyl)picolinamide |
| 13 | Chiral | 454.2 | 0.58 | N-(4-((3R,4R,5S)-3-amino-4-hydroxy-5-methylpiperidin-1-yl)pyridin-3-yl)-6-(2,6-difluoro-3-methylphenyl)picolinamide |
| 14 | Chiral | 445.2 | 0.62 | N-(4-((1R,3S)-3-aminocyclohexyl)pyridin-3-yl)-5-fluoro-6-(2,3,5-trifluorophenyl)picolinamide |

TABLE 1-continued

| Example No. | Structure | LC/MS (M + H on UPCL) | LC/MS (Rf on UPCL) | Chemical Name |
|---|---|---|---|---|
| 15 | Chiral | 467.5 | 0.63 | N-(4-((1R,3R,4R,5S)-3-amino-4-hydroxy-5-methylcyclohexyl)pyridin-3-yl)-6-(3-ethyl-2,6-difluorophenyl)picolinamide |
| 16 | 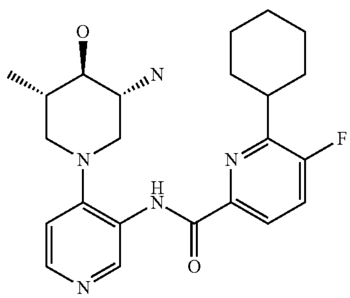 [SMILES: C[C@H]1CN(c2ccncc2NC(=O)c2ccc(F)c(C3CCCCC3)n2)C[C@@H](N)[C@@H]1O] | 428.2 | 0.63 | N-(4-((3R,4R,5S)-3-amino-4-hydroxy-5-methylpiperidin-1-yl)pyridin-3-yl)-6-cyclohexyl-5-fluoropicolinamide |
| 17 | Chiral | 467.3 | 0.64 | N-(4-((1R,3R,4S,5S)-3-amino-4-hydroxy-5-methylcyclohexyl)pyridin-3-yl)-6-(3-ethyl-2,6-difluorophenyl)picolinamide |
| 18 | Chiral | 453.2 | 0.66 | N-(4-((1R,3R,4S)-3-amino-4-hydroxycyclohexyl)pyridin-3-yl)-6-(3-ethyl-2,6-difluorophenyl)picolinamide |

TABLE 1-continued

| Example No. | Structure | LC/MS (M + H on UPCL) | LC/MS (Rf on UPCL) | Chemical Name |
|---|---|---|---|---|
| 19 | Chiral | 437.2 | 0.67 | N-(4-((1R,3S)-3-aminocyclohexyl)pyridin-3-yl)-6-(3-ethyl-2,6-difluorophenyl)picolinamide |
| 20 | Chiral | 441.2 | 0.64 | N-(4-((1R,3S)-3-aminocyclohexyl)pyridin-3-yl)-6-(2,6-difluoro-3-methylphenyl)-5-fluoropicolinamide |
| 21 | Chiral | 451.2 | 0.7 | N-(4-((1R,3S,5S)-3-amino-5-methylcyclohexyl)pyridin-3-yl)-6-(3-ethyl-2,6-difluorophenyl)picolinamide |
| 22 | Chiral | 472.3 | 0.59 | N-(4-((3R,4R,5S)-3-amino-4-hydroxy-5-methylpiperidin-1-yl)pyridin-3-yl)-6-(2,6-difluoro-3-methylphenyl)-5-fluoropicolinamide |

TABLE 1-continued

| Example No. | Structure | | LC/MS (M + H on UPCL) | LC/MS (Rf on UPCL) | Chemical Name |
|---|---|---|---|---|---|
| 23 | 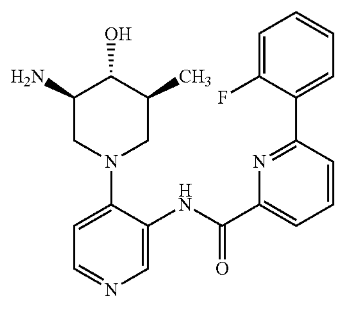 | Chiral | 422.3 | 0.53 | N-(4-((3R,4R,5S)-3-amino-4-hydroxy-5-methylpiperidin-1-yl)pyridin-3-yl)-6-(2-fluorophenyl)picolinamide |
| 24 | 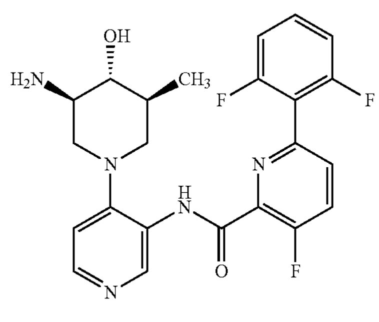 | Chiral | 458.3 | 0.51 | N-(4-((3R,4R,5S)-3-amino-4-hydroxy-5-methylpiperidin-1-yl)pyridin-3-yl)-6-(2,6-difluorophenyl)-3-fluoropicolinamide |
| 25 | 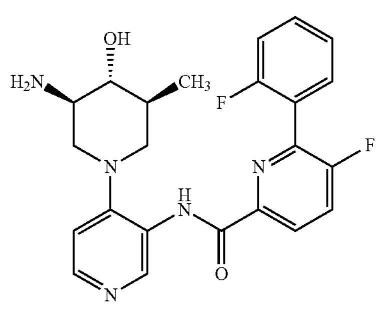 | Chiral | 440.3 | 0.54 | N-(4-((3R,4R,5S)-3-amino-4-hydroxy-5-methylpiperidin-1-yl)pyridin-3-yl)-5-fluoro-6-(2-fluorophenyl)picolinamide |
| 26 | 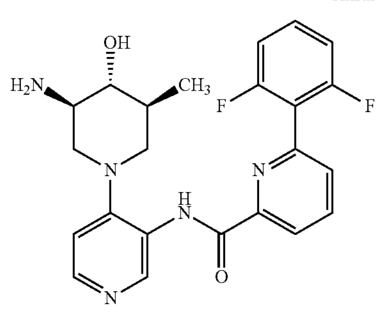 | Chiral | 440.2 | 0.53 | N-(4-((3R,4R,5S)-3-amino-4-hydroxy-5-methylpiperidin-1-yl)pyridin-3-yl)-6-(2,6-difluorophenyl)picolinamide |

TABLE 1-continued

| Example No. | Structure | LC/MS (M + H on UPCL) | LC/MS (Rf on UPCL) | Chemical Name |
|---|---|---|---|---|
| 27 | Chiral | 455.3 | 0.66 | N-(4-((1R,3S,5S)-3-amino-5-methylcyclohexyl)pyridin-3-yl)-6-(2,6-difluoro-3-methylphenyl)-5-fluoropicolinamide |
| 28 | Chiral | 423.2 | 0.61 | N-(4-((1R,3S)-3-aminocyclohexyl)pyridin-3-yl)-6-(2,6-difluoro-3-methylphenyl)picolinamide |
| 29 | Chiral | 437.2 | 0.64 | N-(4-((1R,3S,5S)-3-amino-5-methylcyclohexyl)pyridin-3-yl)-6-(2,6-difluoro-3-methylphenyl)picolinamide |
| 30 | Chiral | 453.2 | 0.59 | N-(4-((1R,3R,4R,5S)-3-amino-4-hydroxy-5-methylcyclohexyl)pyridin-3-yl)-6-(2,6-difluoro-3-methylphenyl)picolinamide |

TABLE 1-continued

| Example No. | Structure | LC/MS (M + H on UPCL) | LC/MS (Rf on UPCL) | Chemical Name |
|---|---|---|---|---|
| 31 | Chiral | 453.2 | 0.6 | N-(4-((1R,3R,4S,5S)-3-amino-4-hydroxy-5-methylcyclohexyl)pyridin-3-yl)-6-(2,6-difluoro-3-methylphenyl)picolinamide |
| 32 | Chiral | 443.2 | 0.55 | N-(4-((1R,3S)-3-aminocyclohexyl)pyridin-3-yl)-6-(2,6-difluoro-4-hydroxyphenyl)-5-fluoropicolinamide |
| 33 | Chiral | 425.2 | 0.53 | N-(4-((1R,3S)-3-aminocyclohexyl)pyridin-3-yl)-5-fluoro-6-(2-fluoro-5-hydroxyphenyl)picolinamide |
| 34 | Chiral | 425.2 | 0.52 | N-(4-((1R,3S)-3-aminocyclohexyl)pyridin-3-yl)-3-fluoro-6-(2-fluoro-5-hydroxyphenyl)picolinamide |

TABLE 1-continued

| Example No. | Structure | LC/MS (M + H on UPCL) | LC/MS (Rf on UPCL) | Chemical Name |
|---|---|---|---|---|
| 35 | Chiral | 421.1 | 0.56 | N-(4-((1R,3S,5S)-3-amino-5-methylcyclohexyl)pyridin-3-yl)-6-(2-fluoro-5-hydroxyphenyl)picolinamide |
| 36 | Chiral | 439.2 | 0.57 | N-(4-((1R,3S,5S)-3-amino-5-methylcyclohexyl)pyridin-3-yl)-6-(2,6-difluoro-4-hydroxyphenyl)picolinamide |
| 37 | Chiral | 421.1 | 0.56 | N-(4-((1R,3S,5S)-3-amino-5-methylcyclohexyl)pyridin-3-yl)-6-(2-fluoro-4-hydroxyphenyl)picolinamide |
| 38 | Chiral | 439.2 | 0.57 | N-(4-((1R,3S,5S)-3-amino-5-methylcyclohexyl)pyridin-3-yl)-5-fluoro-6-(2-fluoro-4-hydroxyphenyl)picolinamide |

TABLE 1-continued

| Example No. | Structure | LC/MS (M + H on UPCL) | LC/MS (Rf on UPCL) | Chemical Name |
| --- | --- | --- | --- | --- |
| 39 | Chiral | 439.2 | 0.55 | N-(4-((1R,3S,5S)-3-amino-5-methylcyclohexyl)pyridin-3-yl)-3-fluoro-6-(2-fluoro-4-hydroxyphenyl)picolinamide |
| 40 | Chiral | 471.2 | 0.62 | N-(4-((1R,3R,4S,5S)-3-amino-4-hydroxy-5-methylcyclohexyl)pyridin-3-yl)-6-(2,6-difluoro-3-methylphenyl)-5-fluoropicolinamide |
| 41 | Chiral | 439.2 | 0.57 | N-(4-((1R,3R,4S)-3-amino-4-hydroxycyclohexyl)pyridin-3-yl)-6-(2,6-difluoro-3-methylphenyl)picolinamide |
| 42 | Chiral | 457.2 | 0.56 | N-(4-((1R,3S,5S)-3-amino-5-methylcyclohexyl)pyridin-3-yl)-6-(2,6-difluoro-4-hydroxyphenyl)-3-fluoropicolinamide |

TABLE 1-continued

| Example No. | Structure | LC/MS (M + H on UPCL) | LC/MS (Rf on UPCL) | Chemical Name |
|---|---|---|---|---|
| 43 | Chiral | 439.2 | 0.56 | N-(4-((1R,3S,5S)-3-amino-5-methylcyclohexyl)pyridin-3-yl)-3-fluoro-6-(2-fluoro-5-hydroxyphenyl)picolinamide |
| 44 | Chiral | 471.2 | 0.62 | N-(4-((1R,3R,4R,5S)-3-amino-4-hydroxy-5-methylcyclohexyl)pyridin-3-yl)-6-(2,6-difluoro-3-methylphenyl)-5-fluoropicolinamide |
| 45 | Chiral | 453.1 | 0.61 | N-(4-((1R,3S,5S)-3-amino-5-methylcyclohexyl)pyridin-3-yl)-5-fluoro-6-(2-fluoro-5-methoxyphenyl)picolinamide |
| 46 | Chiral | 439.1 | 0.56 | N-(4-((1R,3S,5S)-3-amino-5-methylcyclohexyl)pyridin-3-yl)-5-fluoro-6-(2-fluoro-5-hydroxyphenyl)picolinamide |

TABLE 1-continued

| Example No. | Structure | LC/MS (M + H on UPCL) | LC/MS (Rf on UPCL) | Chemical Name |
|---|---|---|---|---|
| 47 | Chiral | 487.1 | | N-(4-((1R,3R,4R,5S)-3-amino-4-hydroxy-5-methylcyclohexyl)pyridin-3-yl)-6-(2,6-difluoro-3-methoxyphenyl)-5-fluoropicolinamide |
| 48 | Chiral | 427.2 | 0.59 | N-(4-((1R,3S)-3-aminocyclohexyl)pyridin-3-yl)-6-(2,3,5-trifluorophenyl)picolinamide |
| 49 | Chiral | 455.2 | 0.63 | N-(4-((1R,5R)-5-amino-3,3-dimethylcyclohexyl)pyridin-3-yl)-6-(2,6-difluorophenyl)-5-fluoropicolinamide |
| 50 | Chiral | 457.2 | 0.58 | N-(4-((1R,3R,4R,5S)-3-amino-4-hydroxy-5-methylcyclohexyl)pyridin-3-yl)-6-(2,6-difluorophenyl)-5-fluoropicolinamide |

TABLE 1-continued

| Example No. | Structure | | LC/MS (M + H on UPCL) | LC/MS (Rf on UPCL) | Chemical Name |
|---|---|---|---|---|---|
| 51 | 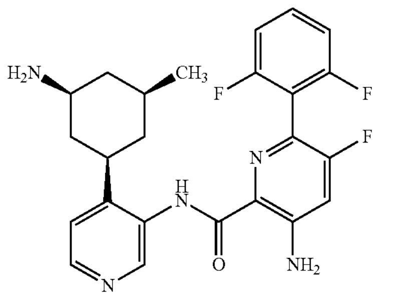 | Chiral | 456.1 | 0.58 | 3-amino-N-(4-((1R,3S,5S)-3-amino-5-methylcyclohexyl)pyridin-3-yl)-6-(2,6-difluorophenyl)-5-fluoropicolinamide |
| 52 | 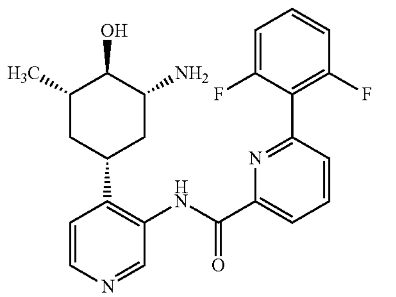 | Chiral | 439.1 | 0.68 | N-(4-((1S,3S,4S,5R)-3-amino-4-hydroxy-5-methylcyclohexyl)pyridin-3-yl)-6-(2,6-difluorophenyl)picolinamide |
| 53 | 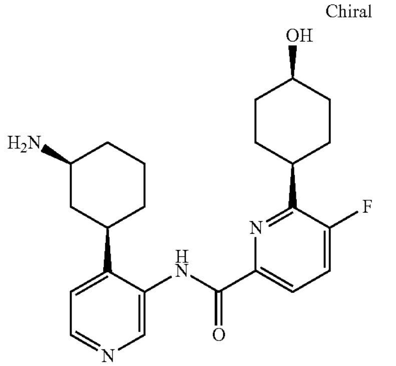 [SMILES: N[C@H]1CCC[C@@H](c2ccncc2NC(=O)c2ccc(F)c([C@H]3CC[C@@H](O)CC3)n2)C1] | Chiral | 413.3 | 0.55 | N-(4-((1R,3S)-3-aminocyclohexyl)pyridin-3-yl)-5-fluoro-6-((1s,4s)-4-hydroxycyclohexyl)picolinamide |
| 54 | 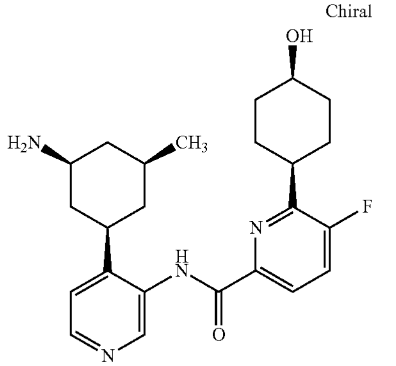 [SMILES: C[C@@H]1C[C@H](N)C[C@H](c2ccncc2NC(=O)c2ccc(F)c([C@H]3CC[C@@H](O)CC3)n2)C1] | Chiral | 427.3 | 0.59 | N-(4-((1R,3S,5S)-3-amino-5-methylcyclohexyl)pyridin-3-yl)-5-fluoro-6-((1s,4s)-4-hydroxycyclohexyl)picolinamide |

TABLE 1-continued

| Example No. | Structure | | LC/MS (M + H on UPCL) | LC/MS (Rf on UPCL) | Chemical Name |
|---|---|---|---|---|---|
| 55 | 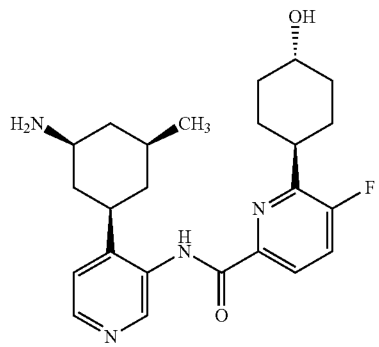 | Chiral | 427.3 | 0.55 | N-(4-((1R,3S,5S)-3-amino-5-methylcyclohexyl)pyridin-3-yl)-5-fluoro-6-((1r,4r)-4-hydroxycyclohexyl)picolinamide |
| 56 | 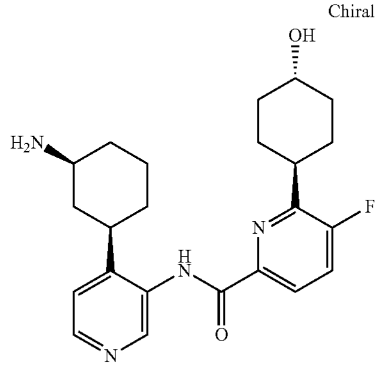 [SMILES: N[C@H]1CCC[C@@H](c2ccncc2NC(=O)c2ccc(F)c([C@H]3CC[C@H](O)CC3)n2)C1] | Chiral | 413.3 | 0.48 | N-(4-((1R,3S)-3-aminocyclohexyl)pyridin-3-yl)-5-fluoro-6-((1r,4r)-4-hydroxycyclohexyl)picolinamide |
| 57 | 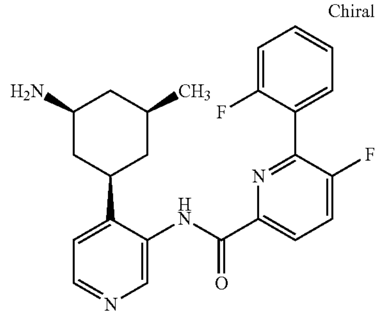 [SMILES: C[C@@H]1C[C@H](N)C[C@H](c2ccncc2NC(=O)c2ccc(F)c(-c3ccccc3F)n2)C1] | Chiral | 423.3 | 0.64 | N-(4-((1R,3S,5S)-3-amino-5-methylcyclohexyl)pyridin-3-yl)-5-fluoro-6-(2-fluorophenyl)picolinamide |
| 58 | 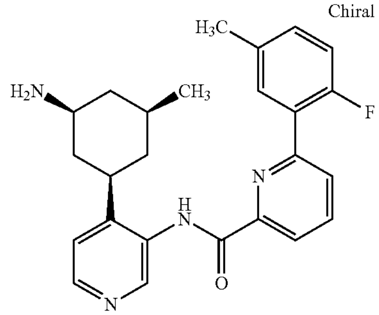 [SMILES: Cc1ccc(F)c(-c2cccc(C(=O)Nc3cnccc3[C@@H]3C[C@H](C)C[C@H](N)C3)n2)c1] | Chiral | 419.3 | 0.67 | N-(4-((1R,3S,5S)-3-amino-5-methylcyclohexyl)pyridin-3-yl)-6-(2-fluoro-5-methylphenyl)picolinamide |

TABLE 1-continued

| Example No. | Structure | LC/MS (M + H on UPCL) | LC/MS (Rf on UPCL) | Chemical Name |
|---|---|---|---|---|
| 59 | 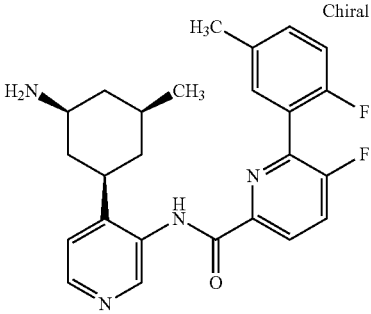 [SMILES: Cc1ccc(F)c(-c2nc(C(=O)Nc3cnccc3[C@@H]3C[C@H](C)C[C@H](N)C3)ccc2F)c1] | 437.3 | 0.67 | N-(4-((1R,3S,5S)-3-amino-5-methylcyclohexyl)pyridin-3-yl)-5-fluoro-6-(2-fluoro-5-methylphenyl)picolinamide |
| 60 | 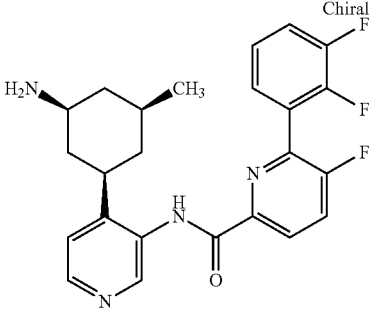 [SMILES: C[C@@H]1C[C@H](N)C[C@H](c2ccncc2NC(=O)c2ccc(F)c(-c3cccc(F)c3F)n2)C1] | 441.2 | 0.70 | N-(4-((1R,3S,5S)-3-amino-5-methylcyclohexyl)pyridin-3-yl)-6-(2,3-difluorophenyl)-5-fluoropicolinamide |
| 61 | 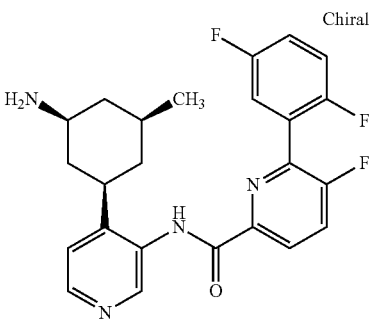 [SMILES: C[C@@H]1C[C@H](N)C[C@H](c2ccncc2NC(=O)c2ccc(F)c(-c3cc(F)ccc3F)n2)C1] | 441.2 | 0.68 | N-(4-((1R,3S,5S)-3-amino-5-methylcyclohexyl)pyridin-3-yl)-6-(2,5-difluorophenyl)-5-fluoropicolinamide |
| 62 | 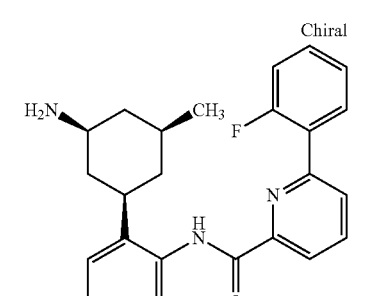 | 405.2 | 0.67 | N-(4-((1R,3S,5S)-3-amino-5-methylcyclohexyl)pyridin-3-yl)-6-(2-fluorophenyl)picolinamide |

TABLE 1-continued

| Example No. | Structure | LC/MS (M + H on UPCL) | LC/MS (Rf on UPCL) | Chemical Name |
|---|---|---|---|---|
| 63 | Chiral | 423.2 | 0.65 | N-(4-((1R,3S,5S)-3-amino-5-methylcyclohexyl)pyridin-3-yl)-6-(2,6-difluorophenyl)picolinamide |
| 64 | Chiral | 483.2 | 0.66 | N-(4-((1R,3R,4S)-3-amino-4-hydroxycyclohexyl)pyridin-3-yl)-5-fluoro-6-(2-fluoro-5-propoxyphenyl)picolinamide |
| 65 | 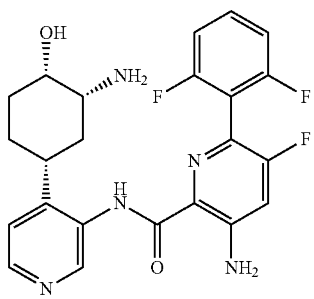 [SMILES: Nc1cc(F)c(-c2c(F)cccc2F)nc1C(=O)Nc1cnccc1[C@@H]1CC[C@H](O)[C@H](N)C1] | 458.1 | 0.55 | 3-amino-N-(4-((1R,3R,4S)-3-amino-4-hydroxycyclohexyl)pyridin-3-yl)-6-(2,6-difluorophenyl)-5-fluoropicolinamide |
| 66 | 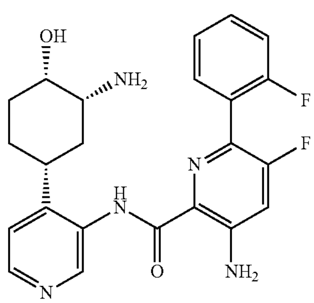 [SMILES: Nc1cc(F)c(-c2ccccc2F)nc1C(=O)Nc1cnccc1[C@@H]1CC[C@H](O)[C@H](N)C1] | 440.1 | 0.55 | 3-amino-N-(4-((1R,3R,4S)-3-amino-4-hydroxycyclohexyl)pyridin-3-yl)-5-fluoro-6-(2-fluorophenyl)picolinamide |
| 67 | 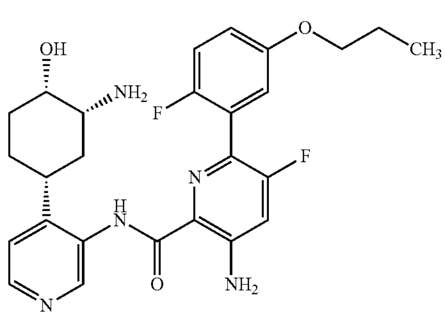 [SMILES: CCCOc1ccc(F)c(-c2nc(C(=O)Nc3cnccc3[C@@H]3CC[C@H](O)[C@H](N)C3)c(N)cc2F)c1] | 498.2 | 0.66 | 3-amino-N-(4-((1R,3R,4S)-3-amino-4-hydroxycyclohexyl)pyridin-3-yl)-5-fluoro-6-(2-fluoro-5-propoxyphenyl)picolinamide |

TABLE 1-continued

| Example No. | Structure | LC/MS (M + H on UPCL) | LC/MS (Rf on UPCL) | Chemical Name |
|---|---|---|---|---|
| 68 | 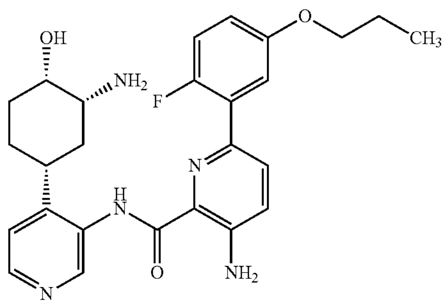 [SMILES: CCCOc1ccc(F)c(-c2ccc(N)c(C(=O)Nc3cnccc3[C@@H]3CC[C@H](O)[C@H](N)C3)n2)c1] | 480.2 | 0.65 | 3-amino-N-(4-((1R,3R,4S)-3-amino-4-hydroxycyclohexyl)pyridin-3-yl)-6-(2-fluoro-5-propoxyphenyl)picolinamide |
| 69 | Chiral | 441.3 | 0.67 | N-(4-((1R,3S,5S)-3-amino-5-methylcyclohexyl)pyridin-3-yl)-6-(2,6-difluorophenyl)-3-fluoropicolinamide |
| 70 | Chiral | 441.3 | 0.70 | N-(4-((1R,3S,5S)-3-amino-5-methylcyclohexyl)pyridin-3-yl)-6-(2,6-difluorophenyl)-5-fluoropicolinamide |
| 71 | Chiral | 441.3 | 0.66 | N-(4-((1S,3R,5R)-3-amino-5-methylcyclohexyl)pyridin-3-yl)-6-(2,6-difluorophenyl)-3-fluoropicolinamide |

TABLE 1-continued

| Example No. | Structure | LC/MS (M + H on UPCL) | LC/MS (Rf on UPCL) | Chemical Name |
| --- | --- | --- | --- | --- |
| 72 | Chiral | 441.3 | 0.70 | N-(4-((1S,3R,5R)-3-amino-5-methylcyclohexyl)pyridin-3-yl)-6-(2,6-difluorophenyl)-5-fluoropicolinamide |
| 73 | Chiral | 453.1 | 0.7 | N-(4-((1R,3R,4S,5S)-3-amino-4-hydroxy-5-methylcyclohexyl)pyridin-3-yl)-5-fluoro-6-(2-fluoro-5-methylphenyl)picolinamide |
| 74 | Chiral | 435.0 | 0.6 | N-(4-((1R,3R,4S,5S)-3-amino-4-hydroxy-5-methylcyclohexyl)pyridin-3-yl)-6-(2-fluoro-5-methylphenyl)picolinamide |
| 75 | Chiral | 439.2 | 0.57 | N-(4-((1R,3R,4S,5S)-3-amino-4-hydroxy-5-methylcyclohexyl)pyridin-3-yl)-5-fluoro-6-(2-fluorophenyl)picolinamide |

TABLE 1-continued

| Example No. | Structure | LC/MS (M + H on UPCL) | LC/MS (Rf on UPCL) | Chemical Name |
|---|---|---|---|---|
| 76 | Chiral | 439.2 | 0.55 | N-(4-((1R,3R,4S,5S)-3-amino-4-hydroxy-5-methylcyclohexyl)pyridin-3-yl)-6-(2,6-difluorophenyl)picolinamide |
| 77 | Chiral | 441.3 | 0.62 | N-(4-((1R,3S,5S)-3-amino-5-methylcyclohexyl)pyridin-3-yl)-6-(2,4-difluorophenyl)-5-fluoropicolinamide |
| 78 | Chiral | 425.2 | 0.52 | N-(4-((1R,3R,4S)-3-amino-4-hydroxycyclohexyl)pyridin-3-yl)-6-(2,6-difluorophenyl)picolinamide |
| 79 | Chiral | 427.2 | 0.58 | N-(4-((1R,3S)-3-aminocyclohexyl)pyridin-3-yl)-6-(2,3-difluorophenyl)-5-fluoropicolinamide |

TABLE 1-continued

| Example No. | Structure | LC/MS (M + H on UPCL) | LC/MS (Rf on UPCL) | Chemical Name |
|---|---|---|---|---|
| 80 | Chiral | 427.2 | 0.54 | N-(4-((1R,3S)-3-aminocyclohexyl)pyridin-3-yl)-6-(2,6-difluorophenyl)-3-fluoropicolinamide |
| 81 | Chiral | 427.2 | 0.57 | N-(4-((1R,3S)-3-aminocyclohexyl)pyridin-3-yl)-6-(2,5-difluorophenyl)-5-fluoropicolinamide |
| 82 | Chiral | 427.2 | 0.58 | N-(4-((1R,3S)-3-aminocyclohexyl)pyridin-3-yl)-6-(2,4-difluorophenyl)-5-fluoropicolinamide |
| 83 | Chiral | 407.1 | 0.51 | N-(4-((1R,3R,4S)-3-amino-4-hydroxycyclohexyl)pyridin-3-yl)-6-(2-fluorophenyl)picolinamide |

TABLE 1-continued

| Example No. | Structure | LC/MS (M + H on UPCL) | LC/MS (Rf on UPCL) | Chemical Name |
|---|---|---|---|---|
| 84 | Chiral | 465.2 | 0.62 | N-(4-((1R,3R,4S)-3-amino-4-hydroxycyclohexyl)pyridin-3-yl)-6-(2-fluoro-5-propoxyphenyl)picolinamide |
| 85 | Chiral | 457.2 | 0.56 | N-(4-((1R,3R,4S,5S)-3-amino-4-hydroxy-5-methylcyclohexyl)pyridin-3-yl)-6-(2,6-difluorophenyl)-5-fluoropicolinamide |
| 86 | Chiral | 457.0 | 0.56 | N-(4-((1R,3R,4S,5S)-3-amino-4-hydroxy-5-methylcyclohexyl)pyridin-3-yl)-6-(2,6-difluorophenyl)-5-fluoropicolinamide |
| 87 | Chiral | 425.1 | 0.52 | N-(4-((1R,3R,4S)-3-amino-4-hydroxycyclohexyl)pyridin-3-yl)-5-fluoro-6-(2-fluorophenyl)picolinamide |

TABLE 1-continued

| Example No. | Structure | LC/MS (M + H on UPCL) | LC/MS (Rf on UPCL) | Chemical Name |
|---|---|---|---|---|
| 88 | Chiral | 443.0 | 0.53 | N-(4-((1S,3S,4R)-3-amino-4-hydroxycyclohexyl)pyridin-3-yl)-6-(2,6-difluorophenyl)-5-fluoropicolinamide |
| 89 | 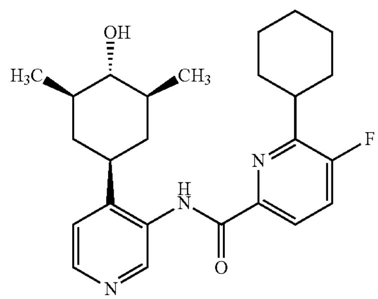 [SMILES: C[C@@H]1C[C@H](c2ccncc2NC(=O)c2ccc(F)c(C3CCCCC3)n2)C[C@H](C)[C@H]1O] | 427.3 | 0.63 | N-(4-(3-amino-4-hydroxy-5-methylcyclohexyl)pyridin-3-yl)-6-cyclohexyl-5-fluoropicolinamide |
| 90 | 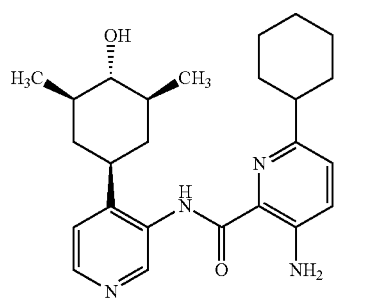 [SMILES: C[C@@H]1C[C@H](c2ccncc2NC(=O)c2nc(C3CCCCC3)ccc2N)C[C@H](C)[C@H]1O] | 424.3 | 0.6 | 3-amino-N-(4-(3-amino-4-hydroxy-5-methylcyclohexyl)pyridin-3-yl)-6-cyclohexylpicolinamide |
| 91 | 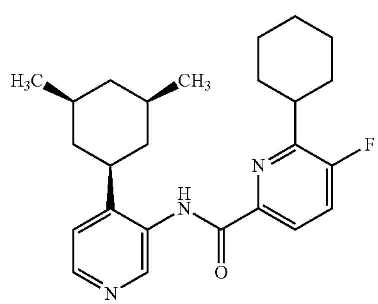 [SMILES: C[C@@H]1C[C@H](C)C[C@H](c2ccncc2NC(=O)c2ccc(F)c(C3CCCCC3)n2)C1] | 411.3 | 0.67 | N-(4-(3-amino-5-methylcyclohexyl)pyridin-3-yl)-6-cyclohexyl-5-fluoropicolinamide |
| 92 | 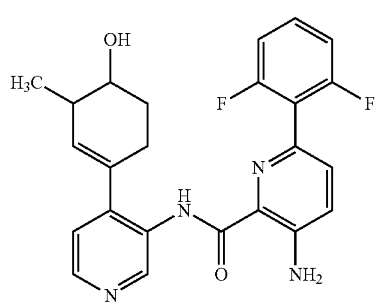 [SMILES: CC1C=C(c2ccncc2NC(=O)c2nc(-c3c(F)cccc3F)ccc2N)CCC1O] | 438.3 | 0.51 | 3-amino-N-(4-(trans)-3-amino-4-hydroxycyclohex-1-enyl)pyridin-3-yl)-6-(2,6-difluorophenyl)picolinamide |

TABLE 1-continued

| Example No. | Structure | LC/MS (M + H on UPCL) | LC/MS (Rf on UPCL) | Chemical Name |
|---|---|---|---|---|
| 93 | 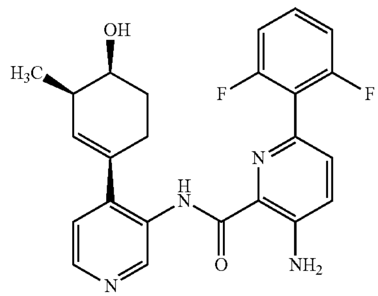 | 438.3 | 0.51 | 3-amino-N-(4-(cis)-3-amino-4-hydroxycyclohex-1-enyl)pyridin-3-yl)-6-(2,6-difluorophenyl)picolinamide |
| 94 | 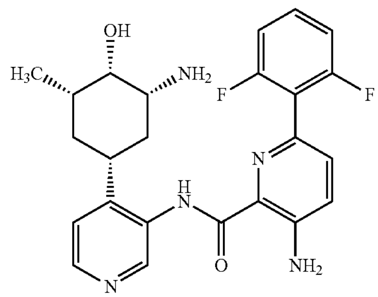 [SMILES: C[C@H]1C[C@@H](c2ccncc2NC(=O)c2nc(-c3c(F)cccc3F)ccc2N)C[C@@H](N)[C@H]1O] | 454.1 | 0.54 | 3-amino-N-(4-(3-amino-4-hydroxy-5-methylcyclohexyl)pyridin-3-yl)-6-(2,6-difluorophenyl)picolinamide |
| 95 | 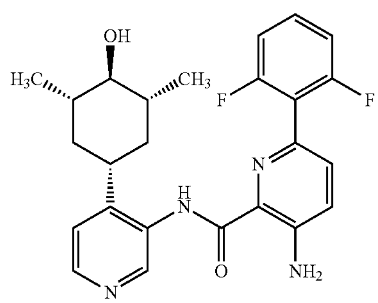 [SMILES: C[C@@H]1C[C@H](c2ccncc2NC(=O)c2nc(-c3c(F)cccc3F)ccc2N)C[C@H](C)[C@H]1O] | 454.3 | 0.54 | 3-amino-N-(4-(3-amino-4-hydroxy-5-methylcyclohexyl)pyridin-3-yl)-6-(2,6-difluorophenyl)picolinamide |
| 96 | 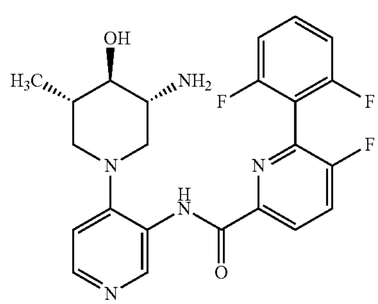 [SMILES: C[C@H]1CN(c2ccncc2NC(=O)c2ccc(F)c(-c3c(F)cccc3F)n2)C[C@@H](N)[C@@H]1O] | 458.1 | 0.54 | N-(4-((3R,4R,5S)-3-amino-4-hydroxy-5-methylpiperidin-1-yl)pyridin-3-yl)-6-(2,6-difluorophenyl)-5-fluoropicolinamide |
| 97 | Chiral | 454.1 | 0.55 | 3-amino-N-(4-(3-amino-4-hydroxy-5-methylcyclohexyl)pyridin-3-yl)-6-(2,6-difluorophenyl)picolinamide |

TABLE 1-continued

| Example No. | Structure | LC/MS (M + H on UPCL) | LC/MS (Rf on UPCL) | Chemical Name |
|---|---|---|---|---|
| 98 | Chiral | 454.1 | 0.54 | 3-amino-N-(4-(3-amino-4-hydroxy-5-methylcyclohexyl)pyridin-3-yl)-6-(2,6-difluorophenyl)picolinamide |
| 99 | Chiral | 427.2 | 0.55 | N-(4-((1R,3S)-3-aminocyclohexyl)pyridin-3-yl)-6-(2,6-difluorophenyl)-5-fluoropicolinamide |
| 100 | Chiral | 442.2 | 0.59 | 3-amino-N-(4-((1R,3S)-3-aminocyclohexyl)pyridin-3-yl)-6-(2,6-difluorophenyl)-5-fluoropicolinamide |
| 101 | 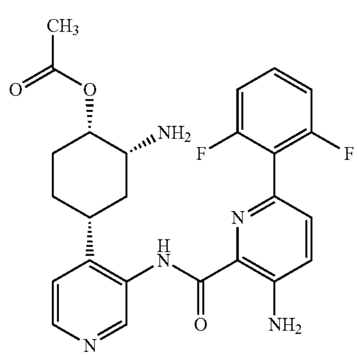 [SMILES: CC(=O)O[C@H]1CC[C@@H](c2ccncc2NC(=O)c2nc(-c3c(F)cccc3F)ccc2N)C[C@H]1N] | 482.2 | 0.56 | 2-amino-4-(3-(3-amino-6-(2,6-difluorophenyl)picolinamido)pyridin-4-yl)cyclohexyl acetate |

TABLE 1-continued

| Example No. | Structure | LC/MS (M + H on UPCL) | LC/MS (Rf on UPCL) | Chemical Name |
|---|---|---|---|---|
| 102 | 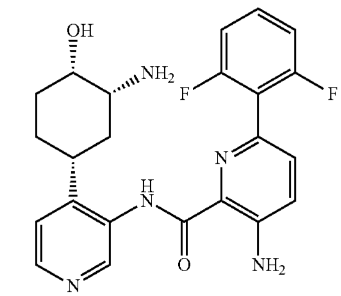 [SMILES: Nc1ccc(-c2c(F)cccc2F)nc1C(=O)Nc1cnccc1[C@@H]1CC[C@H](O)[C@H](N)C1] | 440.3 | 0.52 | 3-amino-N-(4-(3-amino-4-hydroxycyclohexyl)pyridin-3-yl)-6-(2,6-difluorophenyl)picolinamide |
| 103 | Chiral | 455.3 | 0.53 | 3-amino-N-(4-((3R,4S,5R)-3-amino-4-hydroxy-5-methylpiperidin-1-yl)pyridin-3-yl)-6-(2,6-difluorophenyl)picolinamide |
| 104 | 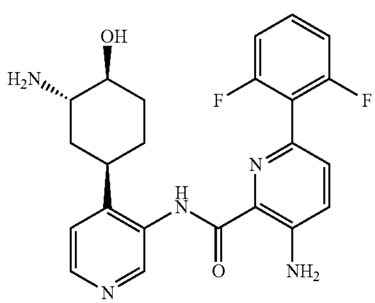 [SMILES: Nc1ccc(-c2c(F)cccc2F)nc1C(=O)Nc1cnccc1[C@@H]1CC[C@H](O)[C@@H](N)C1] | 440.2 | 0.52 | 3-amino-N-(4-((1R,3S,4S)-3-amino-4-hydroxycyclohexyl)pyridin-3-yl)-6-(2,6-difluorophenyl)picolinamide |
| 105 | 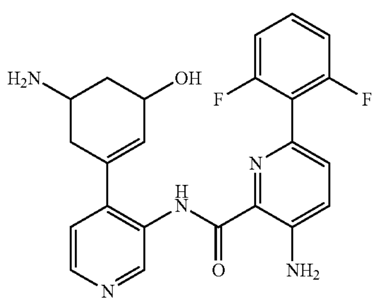 [SMILES: Nc1ccc(-c2c(F)cccc2F)nc1C(=O)Nc1cnccc1C1=CC(O)CC(N)C1] | 438.2 | 2.92 | 3-amino-6-(2,6-difluorophenyl)-N-(4-(3-hydroxy-5-methylcyclohex-1-enyl)pyridin-3-yl)picolinamide |
| 106 | 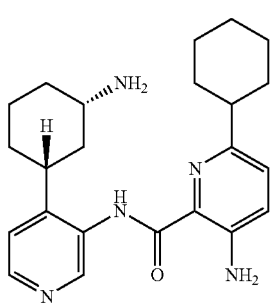 | 394.3 | 0.74 | 3-amino-N-(4-((1R,3S)-3-aminocyclohexyl)pyridin-3-yl)-6-cyclohexylpicolinamide |

TABLE 1-continued

| Example No. | Structure | LC/MS (M + H on UPCL) | LC/MS (Rf on UPCL) | Chemical Name |
|---|---|---|---|---|
| 107 | 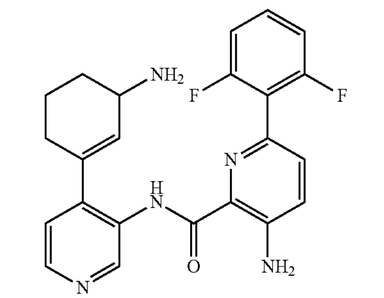 [SMILES: Nc1ccc(-c2c(F)cccc2F)nc1C(=O)Nc1cnccc1C1=CC(N)CCC1] | 421.9 | 0.59 | 3-amino-N-(4-(3-aminocyclohex-1-enyl)pyridin-3-yl)-6-(2,6-difluorophenyl)picolinamide |
| 108 | Chiral | 473.3 | 0.67 | N-(4-((1R,3R,5S)-3-amino-5-(trifluoromethyl)cyclohexyl)pyridin-3-yl)-6-(2-fluoro-5-methylphenyl)picolinamide |
| 109 | Chiral | 507.2 | 0.65 | N-(4-((1R,3R,5S)-3-amino-5-(trifluoromethyl)cyclohexyl)pyridin-3-yl)-6-(2,6-difluoro-4-methoxyphenyl)picolinamide |
| 110 | Chiral | 510.2 | 0.64 | 3-amino-N-(4-((1R,3R,5S)-3-amino-5-(trifluoromethyl)cyclohexyl)pyridin-3-yl)-6-(2,6-difluorophenyl)-5-fluoropicolinamide |

TABLE 1-continued

| Example No. | Structure | LC/MS (M + H on UPCL) | LC/MS (Rf on UPCL) | Chemical Name |
|---|---|---|---|---|
| 111 | Chiral | 465.3 | 0.72 | N-(4-((1R,3R,5S)-3-amino-5-(trifluoromethyl)cyclohexyl)pyridin-3-yl)-6-cyclohexyl-5-fluoropicolinamide |
| 112 | Chiral | 492.2 | 0.62 | 3-amino-N-(4-((1R,3R,5S)-3-amino-5-(trifluoromethyl)cyclohexyl)pyridin-3-yl)-6-(2,6-difluorophenyl)picolinamide |
| 113 | Chiral | 458.2 | 0.55 | N-(4-((3S,4S,5R)-3-amino-4-hydroxy-5-methylpiperidin-1-yl)pyridin-3-yl)-6-(2,6-difluorophenyl)-5-fluoropicolinamide |
| 114 | Chiral | 441.1 | 0.61 | N-(4-((3R,4R,5S)-3,4-dihydroxy-5-methylpiperidin-1-yl)pyridin-3-yl)-5-fluoro-6-(2-fluorophenyl)picolinamide |

TABLE 1-continued

| Example No. | Structure | | LC/MS (M + H on UPCL) | LC/MS (Rf on UPCL) | Chemical Name |
|---|---|---|---|---|---|
| 115 | 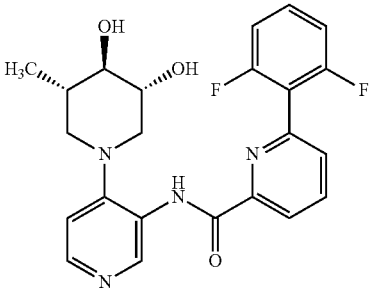 | Chiral | 441.1 | 0.6 | 6-(2,6-difluorophenyl)-N-(4-((3R,4R,5S)-3,4-dihydroxy-5-methylpiperidin-1-yl)pyridin-3-yl)picolinamide |
| 116 | 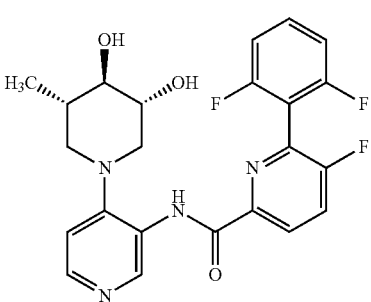 | Chiral | 459.1 | 0.61 | 6-(2,6-difluorophenyl)-N-(4-((3R,4R,5S)-3,4-dihydroxy-5-methylpiperidin-1-yl)pyridin-3-yl)-5-fluoropicolinamide |
| 117 | 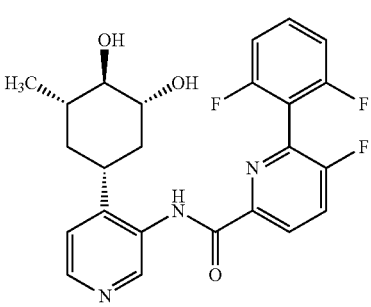 | Chiral | 458.2 | 0.62 | 6-(2,6-Difluorophenyl)-N-(4-((1R,3R,4R,5S)-3,4-dihydroxy-5-methylcyclohexyl)pyridin-3-yl)-5-fluoropicolinamide |
| 118 | 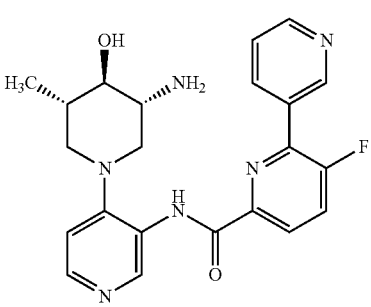 | Chiral | 423.2 | 0.32 | N-(4-((3R,4R,5S)-3-amino-4-hydroxy-5-methylpiperidin-1-yl)pyridin-3-yl)-3-fluoro-2,3'-bipyridine-6-carboxamide |

TABLE 1-continued

| Example No. | Structure | LC/MS (M + H on UPCL) | LC/MS (Rf on UPCL) | Chemical Name |
|---|---|---|---|---|
| 119 | 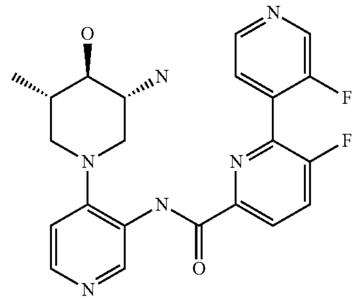 [SMILES: C[C@H]1CN(c2ccncc2NC(=O)c2ccc(F)c(-c3ccncc3F)n2)C[C@@H](N)[C@@H]1O] | 441.2 | 0.46 | N-(4-((3R,4R,5S)-3-amino-4-hydroxy-5-methylpiperidin-1-yl)pyridin-3-yl)-3,3'-difluoro-2,4'-bipyridine-6-carboxamide |
| 120 | 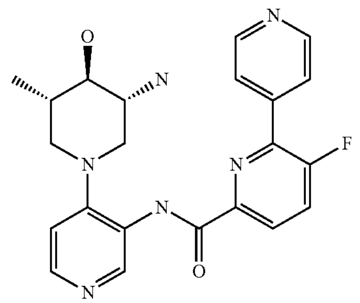 [SMILES: C[C@H]1CN(c2ccncc2NC(=O)c2ccc(F)c(-c3ccncc3)n2)C[C@@H](N)[C@@H]1O] | 423.1 | 0.3 | N-(4-((3R,4R,5S)-3-amino-4-hydroxy-5-methylpiperidin-1-yl)pyridin-3-yl)-3-fluoro-2,4'-bipyridine-6-carboxamide |
| 121 | Chiral | 473.1 | 0.68 | 3-amino-6-(2,6-difluorophenyl)-N-(4-((1R,3R,4R,5S)-3,4-dihydroxy-5-methylcyclohexyl)pyridin-3-yl)-5-fluoropicolinamide |

Synthesis of 6-bromo-N-(4-(3-(tert-butyldimethylsilyloxy)-5-methylcyclohex-1-enyl)pyridin-3-yl)-5-fluoropicolinamide

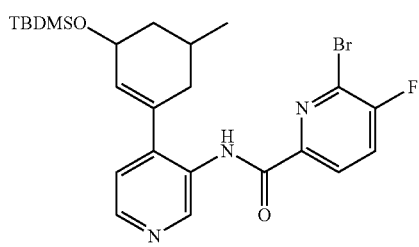 [SMILES: CC1CC(c2ccncc2NC(=O)c2ccc(F)c(Br)n2)=CC(O[Si](C)(C)C(C)(C)C)C1]

Following Method 9,4-(3-(tert-butyldimethylsilyloxy)-5-methylcyclohex-1-enyl)pyridin-3-amine and 6-bromo-5-fluoropicolinic acid were coupled and following addition of EtOAc and washing with H$_2$O, NaCl$_{(sat.)}$ and drying over MgSO$_4$, 6-bromo-N-(4-(3-(tert-butyldimethylsilyloxy)-5-methylcyclohex-1-enyl)pyridin-3-yl)-5-fluoropicolinamide was obtained. LCMS (m/z): 455.3 (MH$^+$); LC R$_t$=2.09 min.

Synthesis of 6-bromo-N-(4-((1R,3S)-3-(1,3-dioxoisoindolin-2-yl)-cyclohexyl)pyridin-3-yl)-5-fluoropicolinamide

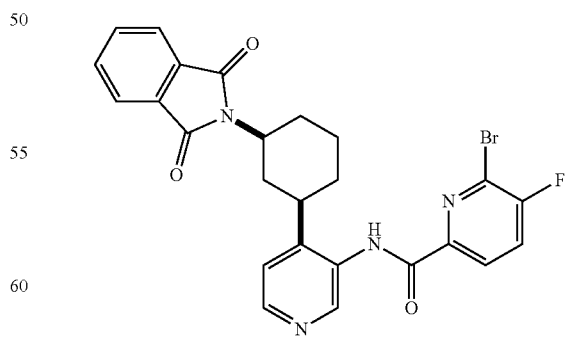

Following Method 9,2-(3-(3-aminopyridin-4-yl)cyclohexyl)isoindoline-1,3-dione and 6-bromo-5-fluoropicolinic acid were coupled and following addition of EtOAc and washing with H$_2$O, NaCl$_{(sat.)}$ and drying over MgSO$_4$, 6-bromo-N-(4-((1R,3S)-3-(1,3-dioxoisoindolin-2-yl)cyclohexyl)pyridin-3-yl)-5-fluoropicolinamide was obtained. LCMS (m/z): 523.2/525.2 (MH⁺); LC R_t=3.31 min.

Synthesis of 3-amino-6-bromo-N-(4-((1R,3S)-3-(1,3-dioxoisoindolin-2-yl)cyclohexyl)pyridin-3-yl)-5-fluoropicolinamide

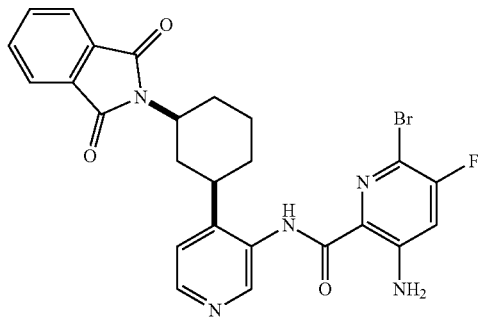 [SMILES: Nc1cc(F)c(Br)nc1C(=O)Nc1cnccc1[C@@H]1CCC[C@H](N2C(=O)c3ccccc3C2=O)C1]

Following Method 9,2-(3-(3-aminopyridin-4-yl)cyclohexyl)-isoindoline-1,3-dione and 3-amino-6-bromo-5-fluoropicolinic acid were coupled and following addition of EtOAc and washing with H₂O, NaCl_(sat.) and drying over MgSO₄, 3-amino-6-bromo-N-(4-((1R,3S)-3-(1,3-dioxoisoindolin-2-yl)cyclohexyl)pyridin-3-yl)-5-fluoropicolinamide was obtained. LCMS (m/z): 538.1/540.1 (MH⁺); LC R_t=3.46 min.

Synthesis of tert-butyl (1S,3R,5S)-3-(3-(6-bromo-5-fluoropicolinamido)-pyridin-4-yl)-5-methylcyclohexylcarbamate

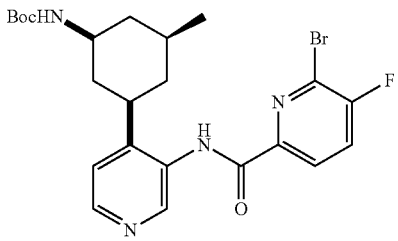

Following Method 9, tert-butyl (1S,3R,5S)-3-(3-aminopyridin-4-yl)-5-methylcyclohexylcarbamate and 6-bromo-5-fluoropicolinic acid were coupled and following addition of EtOAc and washing with H₂O, NaCl_(sat.) and drying over MgSO₄, tert-butyl (1S,3R,5S)-3-(3-(6-bromo-5-fluoropicolinamido)pyridin-4-yl)-5-methylcyclohexylcarbamate was obtained. LCMS (m/z): 507.1/509.1 (MH⁺); R_t=0.90 min.

Synthesis of (1R,2R,4R,6S)-4-(3-(6-bromo-5-fluoropicolinamido)pyridin-4-yl)-2-(tert-butoxycarbonylamino)-6-methylcyclohexyl acetate

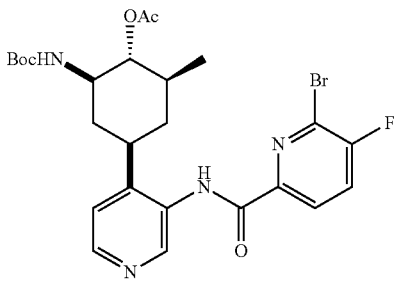

Following Method 9, (1R,2R,4R,6S)-4-(3-aminopyridin-4-yl)-2-(tert-butoxycarbonylamino)-6-methylcyclohexyl acetate and 6-bromo-5-fluoropicolinic acid were coupled and following addition of EtOAc and washing with H₂O, NaCl_(sat.) and drying over MgSO₄, (1R,2R,4R,6S)-4-(3-(6-bromo-5-fluoropicolinamido)pyridin-4-yl)-2-(tert-butoxycarbonylamino)-6-methylcyclohexyl acetate was obtained. LCMS (m/z): 567.2 (MH⁺), R_t=0.82 min.

Synthesis of (+/−)-tert-butyl 5-(3-(6-bromo-5-fluoropicolinamido)pyridin-4-yl)-7-methyl-2-oxohexahydrobenzo[d]oxazole-3(2H)-carboxylate

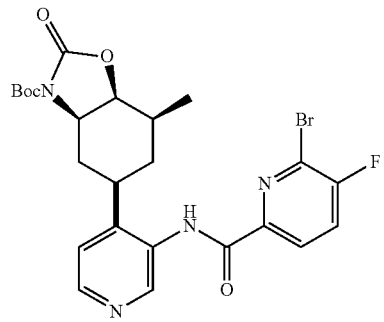

Following Method 9, (+/−)-tert-butyl 5-(3-aminopyridin-4-yl)-7-methyl-2-oxohexahydrobenzo[d]oxazole-3(2H)-carboxylate and 6-bromo-5-fluoropicolinic acid were coupled and following addition of EtOAc and washing with H₂O, NaCl_(sat.) and drying over MgSO₄, (+/−)-tert-butyl 5-(3-(6-bromo-5-fluoropicolinamido)pyridin-4-yl)-7-methyl-2-oxohexahydrobenzo[d]oxazole-3(2H)-carboxylate was obtained. LCMS (m/z): 549.2/551.2 (MH⁺), R_t=0.78 min.

Synthesis of tert-butyl 5-(3-(6-bromo-5-fluoropicolinamido)pyridin-4-yl)-2-oxohexahydrobenzo[d]oxazole-3(2H)-carboxylate

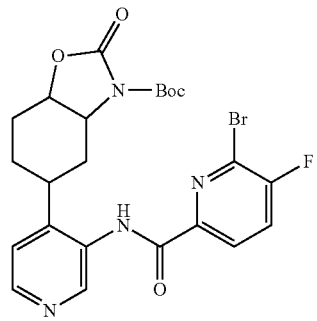 [SMILES: CC(C)(C)OC(=O)N1C(=O)OC2CCC(c3ccncc3NC(=O)c3ccc(F)c(Br)n3)CC21]

Following Method 9, tert-butyl 5-(3-aminopyridin-4-yl)-2-oxohexahydrobenzo[d]oxazole-3(2H)-carboxylate and 6-bromo-5-fluoropicolinic acid were coupled and following addition of EtOAc and washing with H₂O, NaCl_(sat.) and drying over MgSO₄, tert-butyl 5-(3-(6-bromo-5-fluoropicolinamido)pyridin-4-yl)-2-oxohexahydrobenzo[d]oxazole-3(2H)-carboxylate was obtained. LCMS (m/z): 537.1 (MH⁺); LCMS R_t=0.71 min.

Synthesis of 6-bromo-N-(4-((1R,5R)-5-(1,3-dioxoisoindolin-2-yl)-3,3-dimethylcyclohexyl)pyridin-3-yl)-5-fluoropicolinamide

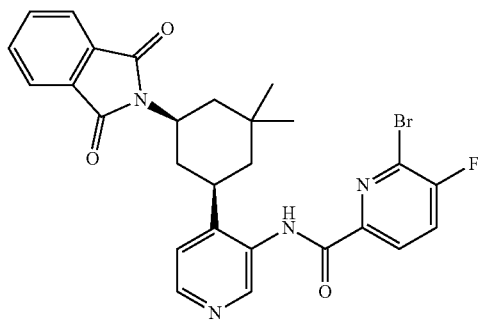 [SMILES: CC1(C)C[C@@H](c2ccncc2NC(=O)c2ccc(F)c(Br)n2)C[C@@H](N2C(=O)c3ccccc3C2=O)C1]

Following Method 9, 2-((1R,5R)-5-(3-aminopyridin-4-yl)-3,3-dimethylcyclohexyl)isoindoline-1,3-dione and 6-bromo-5-fluoropicolinic acid were coupled and following addition of EtOAc and washing with H$_2$O, NaCl$_{(sat.)}$ and drying over MgSO$_4$, 6-bromo-N-(4-((1R,5R)-5-(1,3-dioxoisoindolin-2-yl)-3,3-dimethylcyclohexyl)pyridin-3-yl)-5-fluoropicolinamide was obtained. LCMS (m/z): 551/553 (MH$^+$), R$_t$=0.95 min.

Synthesis of N-(4-((1R,3R,4S,5R)-3,4-bis(tert-butyldimethylsilyloxy)-5-methylcyclohexyl)pyridin-3-yl)-6-bromo-5-fluoropicolinamide

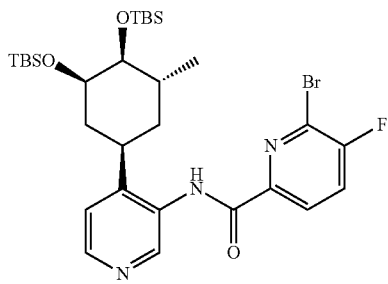 [SMILES: C[C@@H]1C[C@@H](c2ccncc2NC(=O)c2ccc(F)c(Br)n2)C[C@@H](O[Si](C)(C)C(C)(C)C)[C@H]1O[Si](C)(C)C(C)(C)C]

Following Method 9, 4-((1R,3R,4S,5R)-3,4-bis(tert-butyldimethylsilyloxy)-5-methylcyclohexyl)pyridin-3-amine and 6-bromo-5-fluoropicolinic acid were coupled and following addition of EtOAc and washing with H$_2$O, NaCl$_{(sat.)}$ and drying over MgSO$_4$, N-(4-((1R,3R,4S,5R)-3,4-bis(tert-butyldimethylsilyloxy)-5-methylcyclohexyl)pyridin-3-yl)-6-bromo-5-fluoropicolinamide was obtained. LCMS (m/z): 652.5, 652.4 (MH$^+$); LC R$_t$=5.82 min.

Synthesis of N-(4-((1S,3S,4R,5S)-3,4-bis(tert-butyldimethylsilyloxy)-5-methylcyclohexyl)pyridin-3-yl)-6-bromo-5-fluoropicolinamide

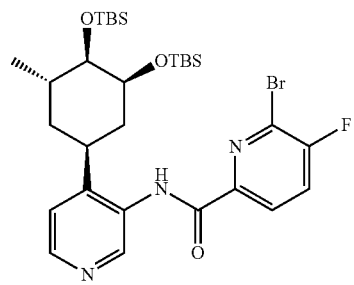 [SMILES: C[C@H]1C[C@H](c2ccncc2NC(=O)c2ccc(F)c(Br)n2)C[C@H](O[Si](C)(C)C(C)(C)C)[C@@H]1O[Si](C)(C)C(C)(C)C]

Following Method 9, 4-((1S,3S,4R,5S)-3,4-bis(tert-butyldimethylsilyloxy)-5-methylcyclohexyl)pyridin-3-amine and 6-bromo-5-fluoropicolinic acid were coupled and following addition of EtOAc and washing with H$_2$O, NaCl$_{(sat.)}$ and drying over MgSO$_4$, N-(4-((1S,3S,4R,5S)-3,4-bis(tert-butyldimethylsilyloxy)-5-methylcyclohexyl)pyridin-3-yl)-6-bromo-5-fluoropicolinamide was obtained. LCMS (m/z): 652.5, 652.4 (MH$^+$); LC R$_t$=5.83 min.

Method 10

Synthesis of 6-(2,6-difluorophenyl)-5-fluoro-N-(4-(3-hydroxy-5-methylcyclohex-1-enyl)pyridin-3-yl)picolinamide

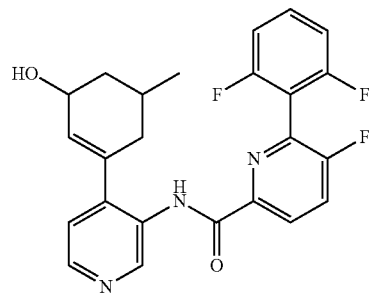 [SMILES: CC1CC(c2ccncc2NC(=O)c2ccc(F)c(-c3c(F)cccc3F)n2)=CC(O)C1]

A solution of 6-bromo-N-(4-(3-(tert-butyldimethylsilyloxy)-5-methylcyclohex-1-enyl)pyridin-3-yl)-5-fluoropicolinamide (1.0 equiv), 2,6-difluorophenyl boronic acid (3.0 equiv.), tetrakistriphenylphosphine (0.2 equiv.) and triethylamine (3.0 equiv.) in 1:1 EtOH/toluene (0.1 M) was heated at 120° C. with microwave irradiation for 1200 seconds. Upon cooling, removal of the volatiles in vacuo, the Suzuki product was directly purified by reverse phase HPLC. The product fraction was lyophilized and the resulting TBDMS ether was deprotected as described in Method 9 yielding, after RP HPLC purification and lyophilization, 6-(2,6-difluorophenyl)-5-fluoro-N-(4-(3-hydroxy-5-methylcyclohex-1-enyl)pyridin-3-yl)picolinamide as the TFA salt. LCMS (m/z): 438.2 (MH$^+$); LC Rt=2.00 min.

Synthesis of N-(4-((1R,3S)-3-aminocyclohexyl)pyridin-3-yl)-6-(2,6-difluorophenyl)-5-fluoropicolinamide

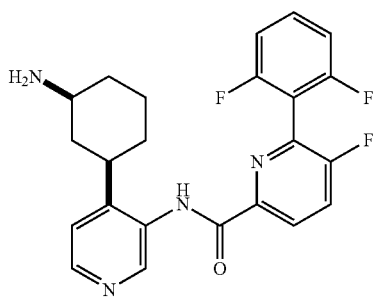

A solution of 6-bromo-N-(4-((1R,3S)-3-(1,3-dioxoisoindolin-2-yl)-cyclohexyl)pyridin-3-yl)-5-fluoropicolinamide (1.0 equiv), 2,6-difluorophenyl boronic acid (3.0 equiv.), tetrakistriphenylphosphine (0.2 equiv.) and triethylamine (3.0 equiv.) in 1:1 EtOH/toluene (0.1 M) was heated at 120° C. with microwave irradiation for 1200 seconds. Upon cooling, removal of the volatiles in vacuo, the Suzuki product was directly purified by reverse phase HPLC. The product fraction was lyophilized and the resulting phthalimide group was deprotected as described in Method 9 yielding, after RP HPLC purification and lyophilization, N-(4-((1R,3S)-3-aminocyclohexyl)pyridin-3-yl)-6-(2,6-difluorophenyl)-5-fluoropicolinamide as the TFA salt. LCMS (m/z): 427.2 (MH+); LC Rt=2.26 min.

Synthesis of 3-amino-N-(4-((1R,3S)-3-aminocyclohexyl)pyridin-3-yl)-6-(2,6-difluorophenyl)-5-fluoropicolinamide

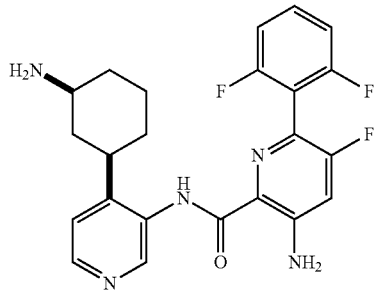

A solution of 3-amino-6-bromo-N-(4-((1R,3S)-3-(1,3-dioxoisoindolin-2-yl)cyclohexyl)pyridin-3-yl)-5-fluoropicolinamide (1.0 equiv), 2,6-difluorophenyl boronic acid (3.0 equiv.), tetrakistriphenylphosphine (0.2 equiv.) and triethylamine (3.0 equiv.) in 1:1 EtOH/toluene (0.1 M) was heated at 120° C. with microwave irradiation for 1200 seconds. Upon cooling, removal of the volatiles in vacuo, the Suzuki product was directly purified by reverse phase HPLC. The product fraction was lyophilized and the resulting phthalimide group was deprotected as described in Method 9 yielding, after RP HPLC purification and lyophilization, 3-amino-N-(4-((1R,3S)-3-aminocyclohexyl)pyridin-3-yl)-6-(2,6-difluorophenyl)-5-fluoropicolinamideas the TFA salt. LCMS (m/z): 442.2 (MH+); LC Rt=2.24 min.

Synthesis of N-(4-(3-amino-4-hydroxycyclohexyl)pyridin-3-yl)-6-(2,6-difluorophenyl)-5-fluoropicolinamide

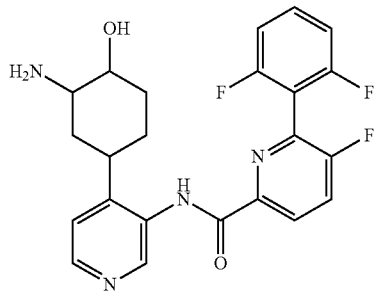 [SMILES: NC1CC(c2ccncc2NC(=O)c2ccc(F)c(-c3c(F)cccc3F)n2)CCC1O]

A solution of tert-butyl 5-(3-(6-bromo-5-fluoropicolinamido)pyridin-4-yl)-2-oxohexahydrobenzo[d]oxazole-3(2H)-carboxylate (1.0 equiv), 2,6-difluorophenyl boronic acid (3.0 equiv.), tetrakistriphenylphosphine (0.2 equiv.) and triethylamine (3.0 equiv.) in 1:1 EtOH/toluene (0.1 M) was heated at 120° C. with microwave irradiation for 1200 seconds. Upon cooling, removal of the volatiles in vacuo, the Suzuki product was directly purified by reverse phase HPLC. The product fraction was lyophilized and the resulting cyclic carbamate and Boc groups were deprotected as described in Method 9 yielding, after RP HPLC purification and lyophilization, N-(4-(3-amino-4-hydroxycyclohexyl)pyridin-3-yl)-6-(2,6-difluorophenyl)-5-fluoropicolinamideas the TFA salt. LCMS (m/z): 443.2 (MH+); LC Rt=2.11 min.

Synthesis of 5-amino-N-(4-((1R,3S)-3-aminocyclohexyl)pyridin-3-yl)-3,3'-difluoro-2,4'-bipyridine-6-carboxamide

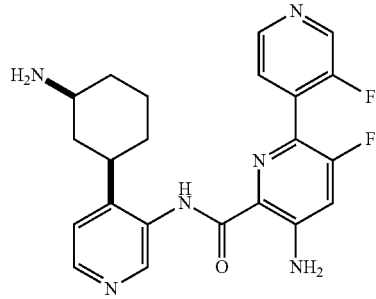

A solution of 3-amino-6-bromo-N-(4-((1R,3S)-3-(1,3-dioxoisoindolin-2-yl)cyclohexyl)pyridin-3-yl)-5-fluoropicolinamide (1.0 equiv), 3-fluoropyridin-4-yl-boronic acid (3.0 equiv.), tetrakistriphenylphosphine (0.2 equiv.) and triethylamine (3.0 equiv.) in 1:1 EtOH/toluene (0.1 M) was heated at 120° C. with microwave irradiation for 1200 seconds. Upon cooling, removal of the volatiles in vacuo, the Suzuki product was directly purified by reverse phase HPLC. The product fraction was lyophilized and the resulting phthalimide group was deprotected as described in Method 9 yielding, after RP HPLC purification and lyophilization, 5-amino-N-(4-((1R,3S)-3-aminocyclohexyl)-pyridin-3-yl)-3,3'-difluoro-2,4'-bipyridine-6-carboxamide as the TFA salt. LCMS (m/z): 425.1 (MH+); LC Rt=2.08 min.

Synthesis of N-(4-((1R,3S,5S)-3-amino-5-methylcyclohexyl)pyridin-3-yl)-6-(2,6-difluoro-3-hydroxyphenyl)-5-fluoropicolinamide

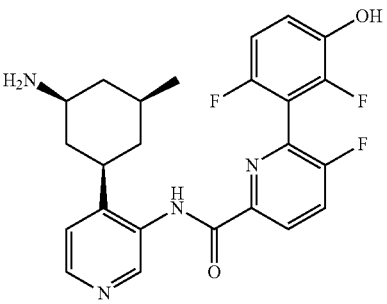 [SMILES: C[C@@H]1C[C@H](N)C[C@H](c2ccncc2NC(=O)c2ccc(F)c(-c3c(F)ccc(O)c3F)n2)C1]

To a solution of tert-butyl (1S,3R,5S)-3-(3-(6-bromo-5-fluoropicolinamido)pyridin-4-yl)-5-methylcyclohexylcarbamate (1.0 equiv.) in a microwave vial was added 2,6-difluoro-3-hydroxyphenylboronic acid (5.0 equiv.), KF (5.5 equiv.) and Pd2(dba)3 (0.2 equiv.) followed by THF and water (10:1, 0.03 M). To this mixture was added P(t-Bu)3 (0.4 equiv.) and the reaction was heated in the microwave at 100° C. for 30 min. The organic phase was then separated, the aqueous layer was washed with ethyl acetate, and the organics were combined and concentrated in vacuo. The crude mixture was purified via prep-HPLC, the product fractions were lyophilized and the resulting BOC group was deprotected as described in Method 9 yielding, after RP HPLC purification and lyophilization, N-(4-((1R,3S,5S)-3-amino-5-methylcyclohexyl)pyridin-3-yl)-6-(2,6-difluoro-3-hydroxyphenyl)-5-fluoropicolinamide as the TFA salt. LCMS (m/z): 457.2 (MH+); LC Rt=2.17 min.

The following compounds were prepared using Method 10:

TABLE 2

| Example No./ NVP ID | Structure | | LC/MS (M + H on UPCL) | LC/MS (Rf on UPCL) | Chemical Name |
|---|---|---|---|---|---|
| 122 | 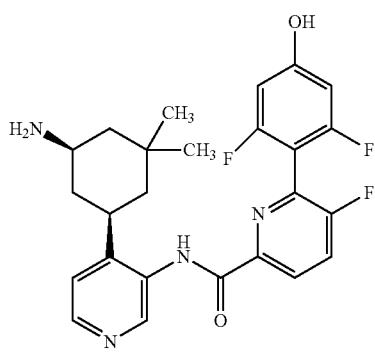 | Chiral | 471.2 | 0.58 | N-(4-((1R,5R)-5-amino-3,3-dimethylcyclohexyl)pyridin-3-yl)-6-(2,6-difluoro-4-hydroxyphenyl)-5-fluoropicolinamide |
| 123 | 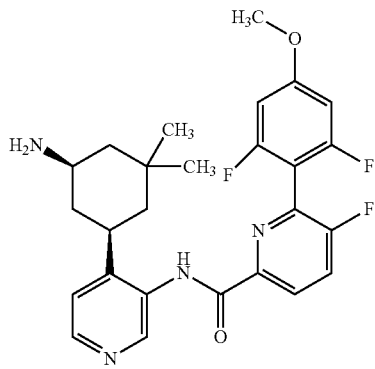 | Chiral | 485.2 | 0.65 | N-(4-((1R,5R)-5-amino-3,3-dimethylcyclohexyl)pyridin-3-yl)-6-(2,6-difluoro-4-methoxyphenyl)-5-fluoropicolinamide |
| 124 | 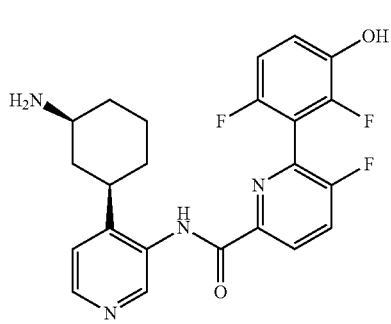 | Chiral | 443.2 | 0.54 | N-(4-((1R,3S)-3-aminocyclohexyl)pyridin-3-yl)-6-(2,6-difluoro-3-hydroxyphenyl)-5-fluoropicolinamide |
| 125 | 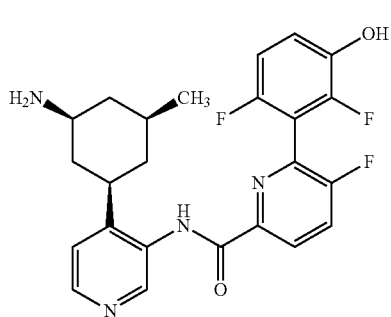 | Chiral | 457.2 | 0.57 | N-(4-((1R,3S,5S)-3-amino-5-methylcyclohexyl)pyridin-3-yl)-6-(2,6-difluoro-3-hydroxyphenyl)-5-fluoropicolinamide |

TABLE 2-continued

| Example No./ NVP ID | Structure | LC/MS (M + H on UPCL) | LC/MS (Rf on UPCL) | Chemical Name |
|---|---|---|---|---|
| 126 | Chiral | 507.1 | 0.65 | N-(4-((1R,3R,4R,5S)-3-amino-4-hydroxy-5-methylcyclohexyl)pyridin-3-yl)-5-fluoro-6-(2-fluoro-5-(trifluoromethyl)phenyl)picolinamide |
| 127 | Chiral | 507.1 | 0.65 | N-(4-((1R,3R,4R,5S)-3-amino-4-hydroxy-5-methylcyclohexyl)pyridin-3-yl)-5-fluoro-6-(2-fluoro-3-(trifluoromethyl)phenyl)picolinamide |
| 128 | 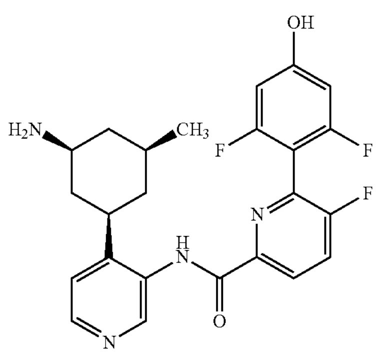 [SMILES: C[C@@H]1C[C@H](N)C[C@H](c2ccncc2NC(=O)c2ccc(F)c(-c3c(F)cc(O)cc3F)n2)C1] | 457.2 | 0.58 | N-(4-((1R,3S,5S)-3-amino-5-methylcyclohexyl)pyridin-3-yl)-6-(2,6-difluoro-4-hydroxyphenyl)-5-fluoropicolinamide |
| 129 | Chiral | 459.2 | 0.62 | N-(4-((1R,3S,5S)-3-amino-5-methylcyclohexyl)pyridin-3-yl)-5-fluoro-6-(2,3,6-trifluorophenyl)picolinamide |

TABLE 2-continued

| Example No./ NVP ID | Structure | LC/MS (M + H on UPCL) | LC/MS (Rf on UPCL) | Chemical Name |
|---|---|---|---|---|
| 130 | 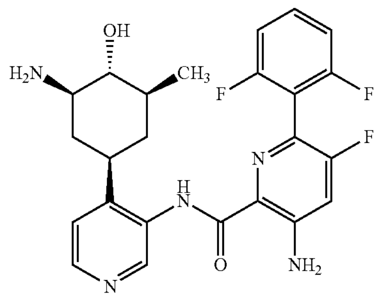 [SMILES: C[C@H]1C[C@@H](c2ccncc2NC(=O)c2nc(-c3c(F)cccc3F)c(F)cc2N)C[C@@H](N)[C@@H]1O] | 472.1 | 0.56 | 3-amino-N-(4-(3-amino-4-hydroxy-5-methylcyclohexyl)pyridin-3-yl)-6-(2,6-difluorophenyl)-5-fluoropicolinamide |
| 131 | 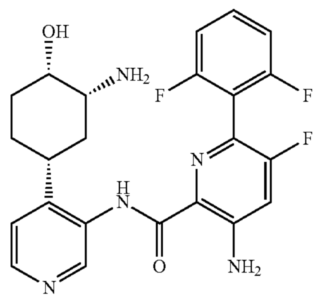 [SMILES: Nc1cc(F)c(-c2c(F)cccc2F)nc1C(=O)Nc1cnccc1[C@@H]1CC[C@H](O)[C@H](N)C1] | 458.0 | 0.57 | 3-amino-N-(4-(3-amino-4-hydroxycyclohexyl)pyridin-3-yl)-6-(2,6-difluorophenyl)-5-fluoropicolinamide |
| 132 | 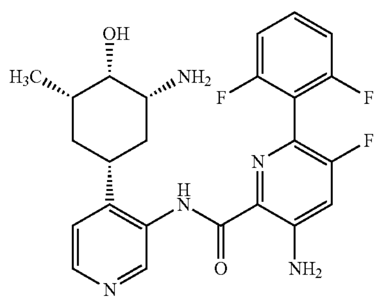 [SMILES: C[C@H]1C[C@@H](c2ccncc2NC(=O)c2nc(-c3c(F)cccc3F)c(F)cc2N)C[C@@H](N)[C@H]1O] | 472.1 | 0.56 | 3-amino-N-(4-(3-amino-4-hydroxy-5-methylcyclohexyl)pyridin-3-yl)-6-(2,6-difluorophenyl)-5-fluoropicolinamide |
| 133 | 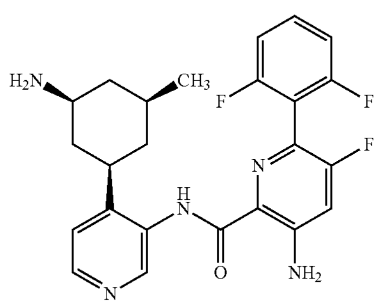 [SMILES: C[C@@H]1C[C@H](N)C[C@H](c2ccncc2NC(=O)c2nc(-c3c(F)cccc3F)c(F)cc2N)C1] | 456.3 | 0.60 | 3-amino-N-(4-(3-amino-5-methylcyclohexyl)pyridin-3-yl)-6-(2,6-difluorophenyl)-5-fluoropicolinamide |
| 134 | 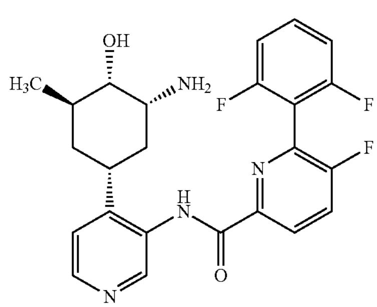 [SMILES: C[C@@H]1C[C@@H](c2ccncc2NC(=O)c2ccc(F)c(-c3c(F)cccc3F)n2)C[C@@H](N)[C@H]1O] | 457.1 | 0.57 | N-(4-(-3-amino-4-hydroxy-5-methylcyclohexyl)pyridin-3-yl)-6-(2,6-difluorophenyl)-5-fluoropicolinamide |

TABLE 2-continued

| Example No./ NVP ID | Structure | | LC/MS (M + H on UPCL) | LC/MS (Rf on UPCL) | Chemical Name |
|---|---|---|---|---|---|
| 135 | 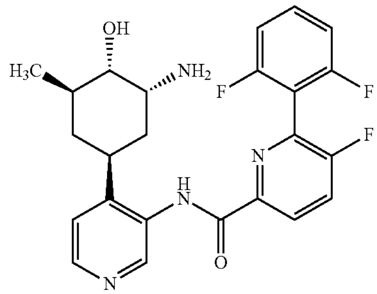 [SMILES: C[C@@H]1C[C@H](c2ccncc2NC(=O)c2ccc(F)c(-c3c(F)cccc3F)n2)C[C@@H](N)[C@H]1O] | | 457.1 | 0.55 | N-(4-(3-amino-4-hydroxy-5-methylcyclohexyl)pyridin-3-yl)-6-(2,6-difluorophenyl)-5-fluoropicolinamide |
| 136 | 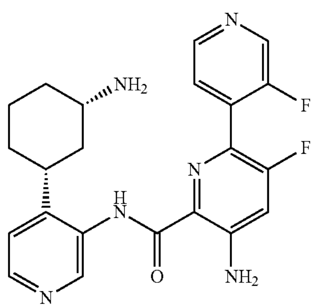 | Chiral | 425.1 | 0.46 | 5-amino-N-(4-((1R,3S)-3-aminocyclohexyl)pyridin-3-yl)-3,3'-difluoro-2,4'-bipyridine-6-carboxamide |
| 137 | 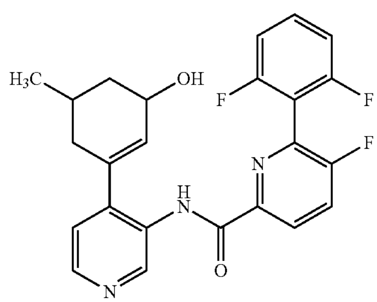 [SMILES: CC1CC(c2ccncc2NC(=O)c2ccc(F)c(-c3c(F)cccc3F)n2)=CC(O)C1] | | 440.2 | 0.75 | 6-(2,6-difluorophenyl)-5-fluoro-N-(4-(3-hydroxy-5-methylcyclohex-1-enyl)pyridin-3-yl)picolinamide |
| 138 | 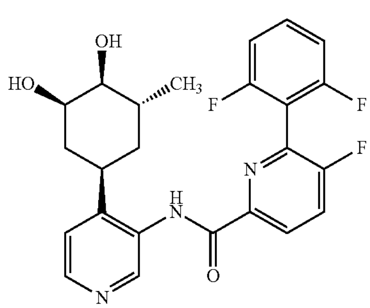 | Chiral | 458.2 | 0.64 | 6-(2,6-difluorophenyl)-N-(4-((1R,3R,4S,5R)-3,4-dihydroxy-5-methylcyclohexyl)pyridin-3-yl)-5-fluoropicolinamide |

Example 139

Synthesis of N-(4-((1R,3R,4S,5S)-3-amino-4-fluoro-5-methylcyclohexyl)-pyridin-3-yl)-6-(2,6-difluorophenyl)-5-fluoropicolinamide

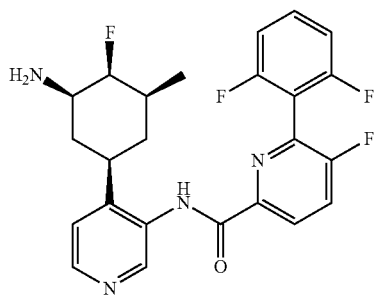 [SMILES: C[C@H]1C[C@@H](c2ccncc2NC(=O)c2ccc(F)c(-c3c(F)cccc3F)n2)C[C@@H](N)[C@H]1F]

To a solution of tert-butyl (1R,2R,3S,5R)-5-(3-(6-(2,6-difluorophenyl)-5-fluoropicolinamido)pyridin-4-yl)-2-hydroxy-3-methylcyclohexylcarbamate (1.0 equiv.) in DCM (0.04 M) at 0° C. was added DAST (1.0 equiv.). The reaction was stirred for 1.5 h at 0° C., then TFA (10 equiv.) was added to the reaction. After 2 h, the reaction was concentrated in vacuo and the residue was purified via prep-HPLC to afford N-(4-((1R,3R,4S,5S)-3-amino-4-fluoro-5-methylcyclohexyl)pyridin-3-yl)-6-(2,6-difluorophenyl)-5-fluoropicolinamide as the TFA salt. LCMS (m/z): 459.3 (MH$^+$); LC Rt=2.39 min.

In addition to LC/MS and LC characterization, representative compounds were analyzed by $^1$H-NMR. The following are typical spectra of the compounds of the invention.

| Example # | $^1$H-NMR data |
|---|---|
| 50 | HCl salt, 1H-NMR (400 MHz, DMSO-d6): d 10.54 (bs, 1H), 8.80 (bs, 1H), 8.55 (d, 1H), 8.34 (dd, 1H), 8.20 (t, 1H), 8.00 (bs, 2H), 7.69 (m, 1H), 7.56 (d, 1H), 7.34 (t, 2H), 3.10-3.0 (m, 2H), 2.83 (m, 1H), 2.03 (d, 1H), 1.76-1.59 (m, 2H), 1.40 (m, 1H), 1.31-1.21 (m, 1H), 0.92 (d, 3H). |
| 52 | HCl salt, 1H-NMR (DMSO-d6): d 10.4 (s, 1H), 8.71 (s, 1H), 8.37 (d, 1H), 8.14-8.20 (m, 2H), 7.94 (bs, 2H), 7.86-7.88 (m, 2H), 7.54-7.58 (m, 1H), 7.30 (d, 1H), 7.22-7.26 (m, 2H), 2.09-3.02 (m, 2H), 2.78 (m, 1H), 1.96-1.99 (m, 1H), 1.68-1.71 (m, 1H), 1.60 (q, 1H), 1.37 (m, 1H), 1.15-1.24 (m, 1H), 0.88 (d, 3H) |
| 70 | HCl salt, 1H NMR (400 MHz, DMSO-d6): d 10.59 (s, 1H), 8.92 (s, 1H), 8.62 (d, 1H), 8.37 (dd, 1H), 8.23 (t, 1H), 8.19 (bs, 2H), 7.68-7.71 (m, 2H), 7.36-7.40 (m, 2H), 3.01-3.10 (m, 2H), 2.01-2.05 (m, 1H), 1.94-1.97 (m, 1H), 1.72-1.76 (m, 1H), 1.46-1.53 (m, 2H), 1.01-1.13 (m, 2H), 0.89 (d, 3H) |
| 85 | HCl salt, 1H NMR (DMSO-d6): d 10.37 (s, 1H), 8.61 (s, 1H), 8.41 (d, 1H), 8.29 (dd, 1H), 8.13 (t, 1H), 7.8 (bs, 2H), 7.69-7.61 (m, 1H), 7.34-7.28 (m, 3H), 3.061 (m, 1H), 2.86 (m, 1H), 1.76-1.63 (m, 2H), 1.53-1.47 (m, 1H), 1.4-1.34 (m, 2H), 0.82 (d, 3H). |
| 88 | HCl salt, 1H NMR (DMSO-d6): d 10.42 (s, 1H), 8.62 (s, 1H), 8.46 (m, 1H), 8.32 (m, 1H), 8.18 (t, 1H), 7.76 (m, 2H), 7.67 (m, 1H), 7.35 (m, 3H), 5.33 (brs, 1H), 3.108 (m, 2H), 2.88 (m, 2H), 1.65 (m, 2H), 1.48 (m, 3H). |
| 96 | HCl salt, 1H NMR (400 MHz, CD3OD): d 9.09 (s, 1 H), 8.46 (dd, 1 H), 8.39 (dd, 1 H), 8.05 (t, 1 H), 7.57-7.67 (m, 1 H), 7.53 (d, 1 H), 7.16-7.25 (m, 2 H), 4.03-4.12 (m, 1 H), 3.85-3.94 (m, 1 H), 3.20 (s, 3 H), 2.70-2.80 (m, 1 H), 1.67-1.79 (m, 1 H), 0.83 (d, 3 H). |
| 99 | free-base, 1H NMR (CDCl3): d 9.93 (s, 1H), 9.38 (s, 1H), 8.40-8.45 (m, 1H), 8.40 (d, 1H), 7.74-7.80 (m, 1H), 7.47-7.55 (m, 1H), 7.19 (d, 1H), 7.06-7.13 (m, 2H), 2.68-2.83 (m, 2H), 1.97-2.05 (m, 1H), 1.65-1.95 (m, 5H), 1.22-1.40 (m, 3H), 1.04-1.15 (m, 1H). |
| 100 | HCl salt, 1H NMR (DMSO-d6): d 10.13 (s, 1H), 8.82 (s, 1H), 8.41 (d, 1H), 7.94 (bs, 2H), 7.52-7.62 (m, 1H), 7.36 (d, 1H), 7.36 (bs, 2H), 7.20-7.31 (m, 3H), 2.78-2.88 (m, 2H), 1.70-2.02 (m, 4H), 1.16-1.54 (m, 4H). |
| 102 | HCl salt, 1H NMR (400 MHz, DMSO-d6): d 10.59 (s, 1H), 9.30 (s, 1H), 8.54 (d, 1H) 8.08 (br s, 3H), 7.75 (d, 1H), 7.65 (d, 1H), 7.60-7.56 (m, 1H), 7.49 (d, 1H), 7.33 (t, 2H), 4.04 (br s, 1H), 3.16 (br s, 2H) 3.05 (br t, 1H), 1.98-1.20 (m, 7H) |
| 116 | HCl salt, 1H-NMR (400, d6-DMSO): d 10.47 (s, 1H), 8.56 (s, 1H), 8.33 (dd, 1H), 8.26 (dd, 1H), 8.20 (t, 1H), 7.62-7.72 (m, 1H), 7.30-7.35 (m, 3H), 3.82-3.92 (m, 2H), 3.18-3.22 (m, 1H), 2.84-2.91 (m, 1H), 2.69 (t, J = 13.2, 1H), 1.38-1.46 (m, 1H), 0.69 (d, 3H). |
| 128 | HCl salt, 1H-NMR (400, d6-DMSO): d 11.00 (s, 1H), 10.46 (s, 1H), 8.55 (d, 1H), 8.29 (dd, 1H), 8.15 (t, 1H), 8.05 (bs, 2H), 7.54 (d, 1H), 6.72 (d, 2H), 3.04-3.10 (m, 1H), 2.92-3.04 (m, 1H), 2.01 (d, 1H), 1.95 (d, 1H), 1.74 (d, 1H), 1.42-1.52 (m, 2H), 0.97-1.08 (m, 2 H), 0.88 (d, 3H). |

Example 140

Pim1 ATP Depletion Assay

The activity of PIM1 is measured using a luciferase-luciferin based ATP detection reagent to quantify ATP depletion resulting from kinase-catalyzed phosphoryl transfer to a peptide substrate. Compounds to be tested are dissolved in 100% DMSO and directly distributed into white 384-well plates at 0.5 µl per well. To start the reaction, 10 µl of 5 nM Pim1 kinase and 80 µM BAD peptide (RSRHSSYPAGT-OH) in assay buffer (50 mM HEPES pH 7.5, 5 mM $MgCl_2$, 1 mM DTT, 0.05% BSA) is added into each well. After 15 minutes, 10 µl of 40 µM ATP in assay buffer is added. Final assay concentrations are 2.5 nM PIM1, 20 µM ATP, 40 µM BAD peptide and 2.5% DMSO. The reaction is performed until approximately 50% of the ATP is depleted, then stopped with the addition of 20 µl KinaseGlo Plus (Promega Corporation) solution. The stopped reaction is incubated for 10 minutes and the remaining ATP detected via luminescence on the Victor2 (Perkin Elmer). Compounds of the foregoing examples were tested by the Pim1 ATP depletion assay and found to exhibit an $IC_{50}$ values as shown in Table 3, below. $IC_{50}$, the half maximal inhibitory concentration, represents the concentration of a test compound that is required for 50% inhibition of its target in vitro.

Example 141

Pim2 ATP depletion assay

The activity of PIM2 is measured using a luciferase-luciferin based ATP detection reagent to quantify ATP depletion resulting from kinase-catalyzed phosphoryl transfer to a peptide substrate. Compounds to be tested are dissolved in 100% DMSO and directly distributed into white 384-well plates at 0.5 µl per well. To start the reaction, 10 µl of 10 nM Pim2 kinase and 20 µM BAD peptide (RSRHSSYPAGT-OH) in assay buffer (50 mM HEPES pH 7.5, 5 mM $MgCl_2$, 1 mM DTT, 0.05% BSA) is added into each well. After 15 minutes, 10 µl of 8 µM ATP in assay buffer is added. Final assay concentrations are 5 nM PIM2, 4 µM ATP, 10 µM BAD peptide and 2.5% DMSO. The reaction is performed until approximately 50% of the ATP is depleted, then stopped with the addition of 20 µl KinaseGlo Plus (Promega Corporation) solution. The stopped reaction is incubated for 10 minutes and the remaining ATP detected via luminescence on the Victor2 (Perkin Elmer). Compounds of the foregoing examples were tested by the Pim2 ATP depletion assay and found to exhibit an $IC_{50}$ values as shown in Table 3, below.

Example 142

Pim3 ATP Depletion Assay

The activity of PIM3 is measured using a luciferase-luciferin based ATP detection reagent to quantify ATP depletion resulting from kinase-catalyzed phosphoryl transfer to a peptide substrate. Compounds to be tested are dissolved in 100% DMSO and directly distributed into white 384-well plates at 0.5 µl per well. To start the reaction, 10 µl of 10 nM Pim3 kinase and 200 µM BAD peptide (RSRHSSYPAGT-OH) in assay buffer (50 mM HEPES pH 7.5, 5 mM $MgCl_2$, 1 mM DTT, 0.05% BSA) is added into each well. After 15 minutes, 10 µl of 80 µM ATP in assay buffer is added. Final assay concentrations are 5 nM PIM1, 40 µM ATP, 100 µM BAD peptide and 2.5% DMSO. The reaction is performed until approximately 50% of the ATP is depleted, then stopped by the addition of 20 µl KinaseGlo Plus (Promega Corporation) solution. The stopped reaction is incubated for 10 minutes and the remaining ATP detected via luminescence on the Victor2 (Perkin Elmer). Compounds of the foregoing examples were tested by the Pim3 ATP depletion assay and found to exhibit an $IC_{50}$ values as shown in Table 3, below.

Example 143

Cell Proliferation Assay

KMS11 (human myeloma cell line), were cultured in IMDM supplemented with 10% FBS, sodium pyruvate and antibiotics. Cells were plated in the same medium at a density of 2000 cells per well into 96 well tissue culture plates, with outside wells vacant, on the day of assay. MM1.s (human myeloma cell line), were cultured in RPMI1640 supplemented with 10% FBS, sodium pyruvate and antibiotics. Cells were plated in the same medium at a density of 5000 cells per well into 96 well tissue culture plates, with outside wells vacant, on the day of assay.

Test compounds supplied in DMSO were diluted into DMSO at 500 times the desired final concentrations before dilution into culture media to 2 times final concentrations. Equal volumes of 2× compounds were added to the cells in 96 well plates and incubated at 37° C. for 3 days.

After 3 days plates were equilibrated to room temperature and equal volume of CellTiter-Glow Reagent (Promega) was added to the culture wells. The plates were agitated briefly and luminescent signal was measured with luminometer. The percent inhibition of the signal seen in cells treated with DMSO alone vs. cells treated with control compound was calculated and used to determine $EC_{50}$ values (i.e., the concentration of a test compound that is required to obtain 50% of the maximum effect in the cells) for tested compounds, as shown in Table 3.

Using the procedures of Examples 140 (Pim1 ATP depletion assay), 141 (Pim2 ATP depletion assay), and 142 (Pim3 ATP depletion assay), the $IC_{50}$ concentration of compounds of the previous examples were determined as shown in the following table 3.

Using the procedures of Example 143 (cell proliferation assay), the $EC_{50}$ concentration of compounds of the examples in were determined in KMS11 cells as shown in Table 3.

TABLE 3

| Example No./NVP ID | Structure | | Pim1 IC50 μM | Pim2 IC50 μM | Pim3 IC50 μM | KMS11-luc EC50 μM |
|---|---|---|---|---|---|---|
| 1 | [Structure: cyclohexane with HO and CH3 substituents, connected to pyridine-NH-C(O)-pyridine with 2,6-difluorophenyl and F] | Chiral | 0.001 | 0.018 | 0.006 | 7.6 |
| 2 | [Structure: piperidine with H3C, OH, NH2 substituents, N-linked to pyridine-NH-C(O)-pyridine with 2,6-difluoro-4-hydroxyphenyl and F] | Chiral | 0.001 | 0.001 | 0.001 | 0.07 |
| 3 | [Structure: piperidine with H3C, OH, NH2 substituents, N-linked to pyridine-NH-C(O)-pyridine with 2,6-difluorophenyl, F and NH2] | Chiral | 0.001 | 0.001 | 0.001 | 0.01 |
| 4 | [Structure: cyclohexane with H3C, OH, NH2 substituents, connected to pyridine-NH-C(O)-pyridine with 2,6-difluoro-4-hydroxyphenyl and F] | Chiral | 0.001 | 0.003 | 0.002 | 1.3 |

TABLE 3-continued

| Example No./ NVP ID | Structure | | Pim1 IC50 μM | Pim2 IC50 μM | Pim3 IC50 μM | KMS11-luc EC50 μM |
|---|---|---|---|---|---|---|
| 5 | 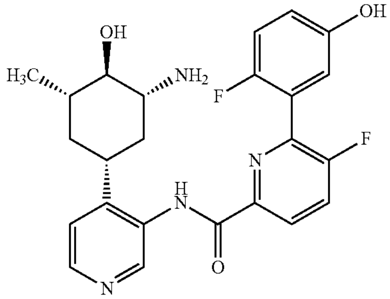 | Chiral | 0.003 | 0.020 | 0.009 | 4.8 |
| 6 | 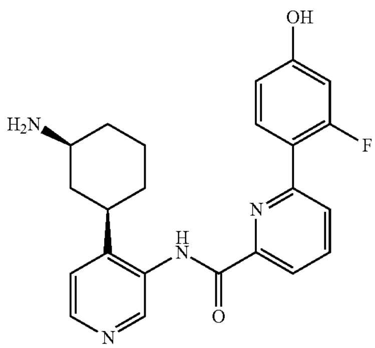 | Chiral | 0.002 | 0.012 | 0.003 | 4.1 |
| 7 | 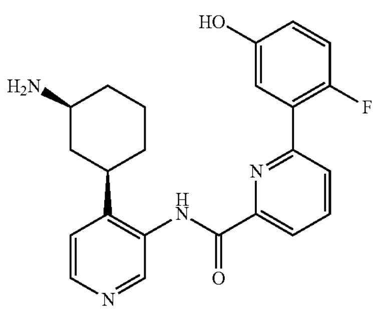 | Chiral | 0.001 | 0.008 | 0.002 | 0.33 |
| 8 | 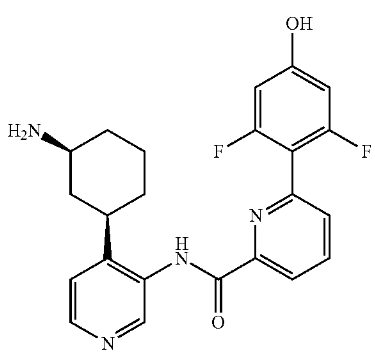 | Chiral | 0.001 | 0.004 | 0.002 | 0.51 |

TABLE 3-continued

| Example No./ NVP ID | Structure | | Pim1 IC50 μM | Pim2 IC50 μM | Pim3 IC50 μM | KMS11-luc EC50 μM |
|---|---|---|---|---|---|---|
| 9 | [Structure] | Chiral | 0.001 | 0.008 | 0.002 | 1.6 |
| 10 | [Structure] | Chiral | 0.001 | 0.012 | 0.006 | 2.9 |
| 11 | [Structure] | Chiral | 0.001 | 0.005 | 0.004 | 2.6 |
| 12 | [Structure] | Chiral | 0.001 | 0.010 | 0.004 | 2.4 |

TABLE 3-continued
| Example No./ NVP ID | Structure | | Pim1 IC50 μM | Pim2 IC50 μM | Pim3 IC50 μM | KMS11-luc EC50 μM |
|---|---|---|---|---|---|---|
| 13 | 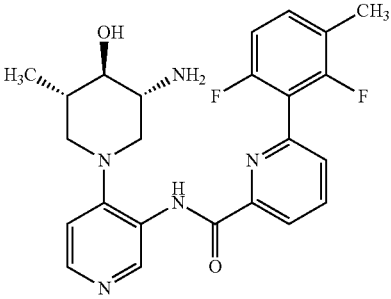 | Chiral | 0.001 | 0.004 | 0.003 | 0.67 |
| 14 | 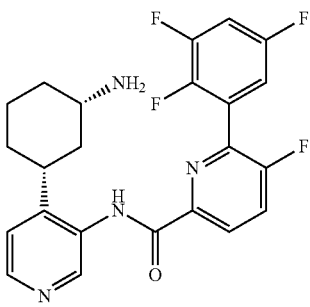 | Chiral | 0.006 | 0.040 | 0.012 | 8.5 |
| 15 | 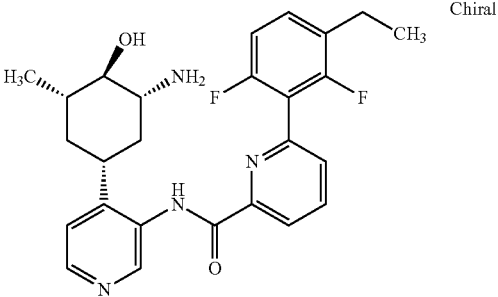 [SMILES: CCc1ccc(F)c(-c2cccc(C(=O)Nc3cnccc3[C@H]3C[C@@H](N)[C@H](O)[C@@H](C)C3)n2)c1F] | Chiral | 0.003 | 0.027 | 0.006 | 5.5 |
| 16 | 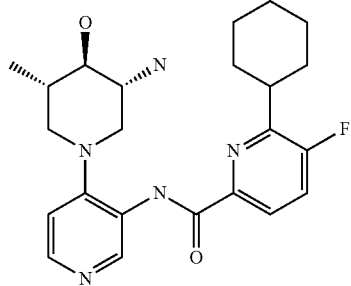 [SMILES: C[C@H]1CN(c2ccncc2NC(=O)c2ccc(F)c(C3CCCCC3)n2)C[C@@H](N)[C@@H]1O] | | 0.001 | 0.003 | 0.003 | 1.7 |

TABLE 3-continued

| Example No./ NVP ID | Structure | | Pim1 IC50 μM | Pim2 IC50 μM | Pim3 IC50 μM | KMS11-luc EC50 μM |
|---|---|---|---|---|---|---|
| 17 | 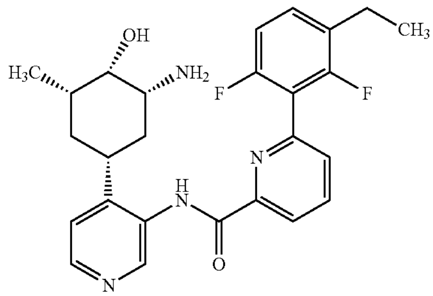 | Chiral | 0.001 | 0.013 | 0.005 | 3.5 |
| 18 | 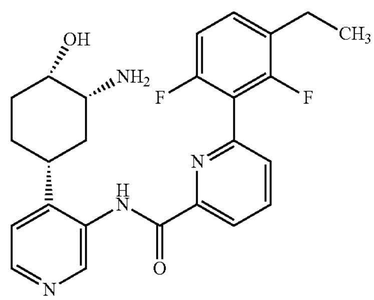 | Chiral | 0.003 | 0.062 | 0.007 | 6.3 |
| 19 | 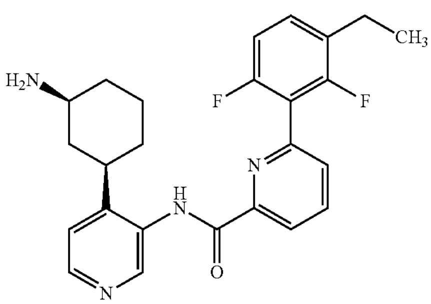 | Chiral | 0.003 | 0.054 | 0.007 | 4.5 |
| 20 | 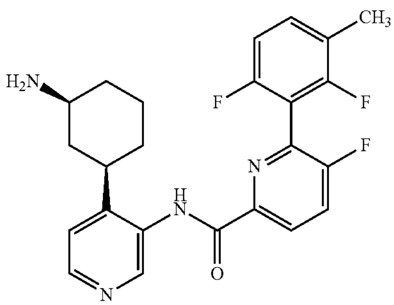 | Chiral | 0.001 | 0.007 | 0.003 | 1.5 |

TABLE 3-continued

| Example No./ NVP ID | Structure | | Pim1 IC50 μM | Pim2 IC50 μM | Pim3 IC50 μM | KMS11-luc EC50 μM |
|---|---|---|---|---|---|---|
| 21 | 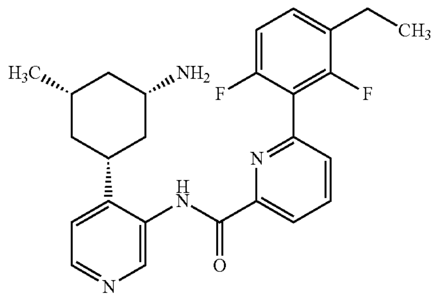 | Chiral | 0.002 | 0.013 | 0.006 | 3.3 |
| 22 | 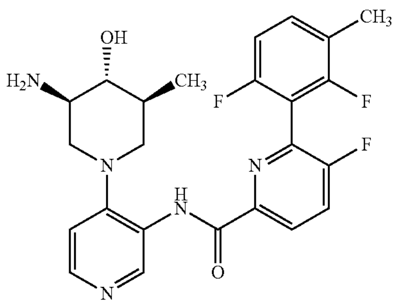 | Chiral | 0.001 | 0.002 | 0.003 | 0.21 |
| 23 | 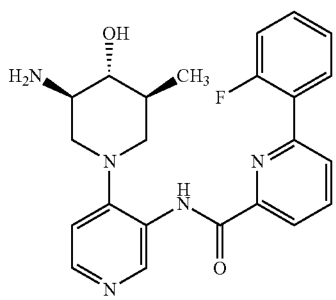 | Chiral | 0.002 | 0.005 | 0.003 | 1.9 |
| 24 | 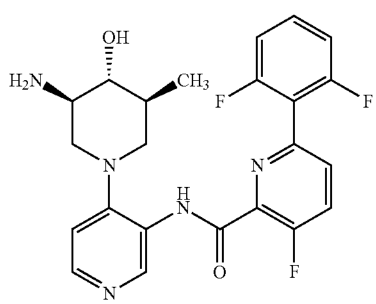 | Chiral | 0.001 | 0.002 | 0.001 | 0.62 |
| 25 | 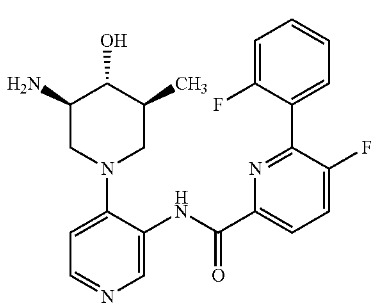 | Chiral | 0.001 | 0.002 | 0.002 | 0.37 |

TABLE 3-continued
| Example No./ NVP ID | Structure | | Pim1 IC50 μM | Pim2 IC50 μM | Pim3 IC50 μM | KMS11-luc EC50 μM |
|---|---|---|---|---|---|---|
| 26 | 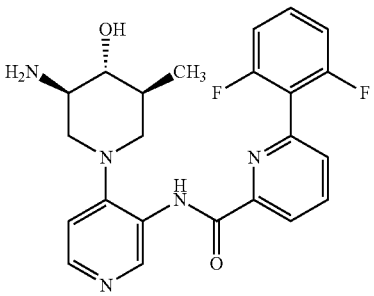 | Chiral | 0.001 | 0.002 | 0.002 | 0.29 |
| 27 | 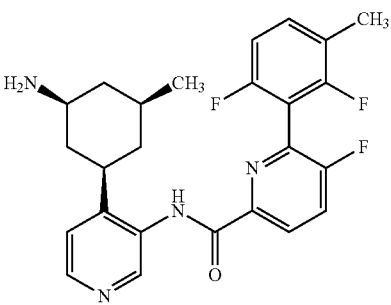 | Chiral | 0.001 | 0.003 | 0.002 | 0.95 |
| 28 | 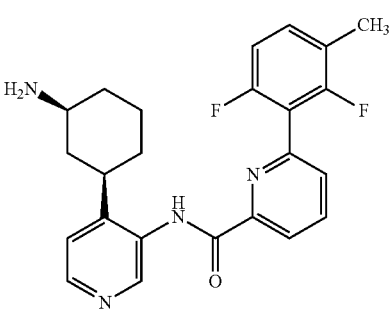 | Chiral | 0.001 | 0.011 | 0.002 | 2.2 |
| 29 | 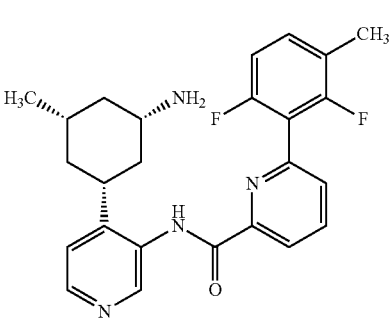 | Chiral | 0.001 | 0.004 | 0.003 | 1.4 |

TABLE 3-continued

| Example No./ NVP ID | Structure | | Pim1 IC50 μM | Pim2 IC50 μM | Pim3 IC50 μM | KMS11-luc EC50 μM |
|---|---|---|---|---|---|---|
| 30 | 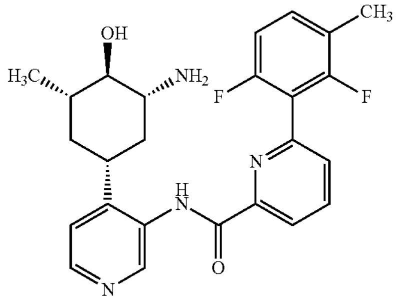 | Chiral | 0.002 | 0.012 | 0.004 | 2.1 |
| 31 | 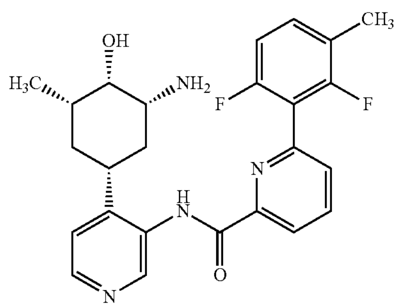 | Chiral | 0.002 | 0.007 | 0.004 | 1.1 |
| 32 | 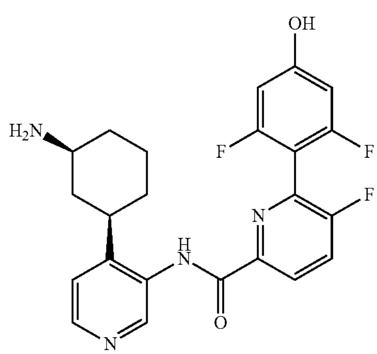 | Chiral | 0.001 | 0.004 | 0.003 | 0.39 |
| 33 | 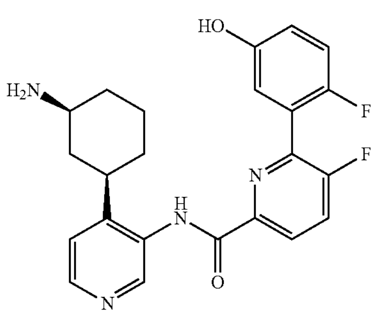 | Chiral | 0.001 | 0.009 | 0.003 | 1.4 |

TABLE 3-continued

| Example No./ NVP ID | Structure | | Pim1 IC50 μM | Pim2 IC50 μM | Pim3 IC50 μM | KMS11-luc EC50 μM |
|---|---|---|---|---|---|---|
| 34 | 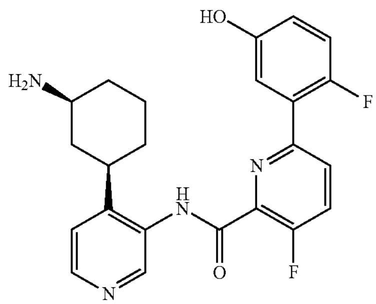 | Chiral | 0.004 | 0.067 | 0.006 | 6.0 |
| 35 | 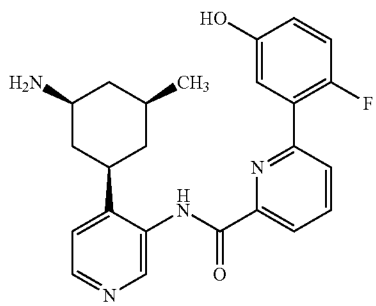 | Chiral | 0.001 | 0.006 | 0.003 | 0.67 |
| 36 | 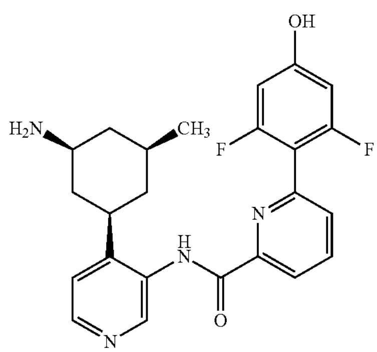 | Chiral | 0.001 | 0.003 | 0.003 | 0.24 |
| 37 | 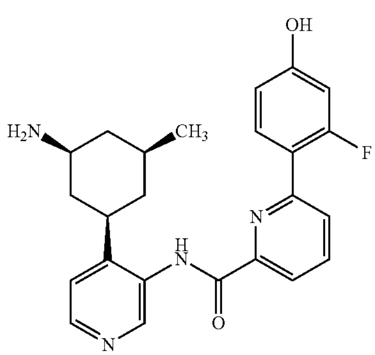 | Chiral | 0.002 | 0.007 | 0.005 | 1.5 |

TABLE 3-continued
| Example No./ NVP ID | Structure | | Pim1 IC50 μM | Pim2 IC50 μM | Pim3 IC50 μM | KMS11-luc EC50 μM |
|---|---|---|---|---|---|---|
| 38 | 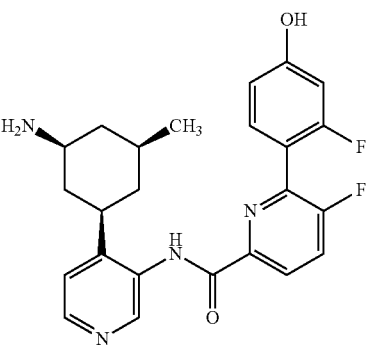 | Chiral | 0.001 | 0.004 | 0.003 | 0.73 |
| 39 | 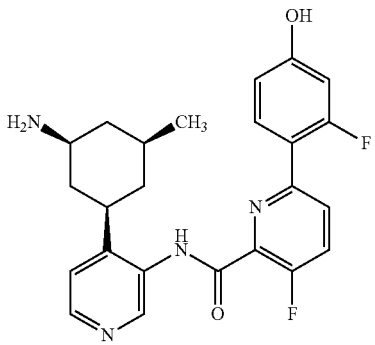 | Chiral | 0.007 | 0.028 | 0.012 | 6.6 |
| 40 | 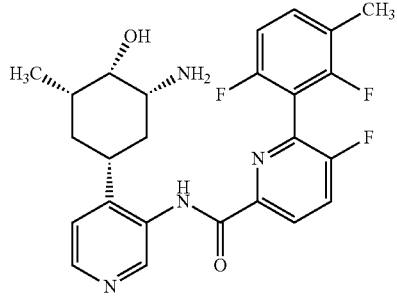 | Chiral | 0.001 | 0.003 | 0.002 | 0.99 |
| 41 | 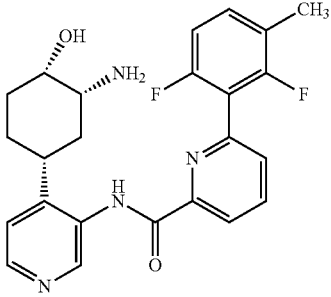 | Chiral | 0.002 | 0.027 | 0.005 | 2.0 |

TABLE 3-continued

| Example No./ NVP ID | Structure | | Pim1 IC50 μM | Pim2 IC50 μM | Pim3 IC50 μM | KMS11-luc EC50 μM |
|---|---|---|---|---|---|---|
| 42 | (structure) | Chiral | 0.001 | 0.002 | 0.002 | 3.0 |
| 43 | (structure) | Chiral | 0.001 | 0.006 | 0.002 | 2.2 |
| 44 | (structure) | Chiral | 0.001 | 0.002 | 0.002 | 1.9 |
| 45 | (structure) | Chiral | 0.001 | 0.002 | 0.002 | 1.3 |

TABLE 3-continued

| Example No./ NVP ID | Structure | | Pim1 IC50 μM | Pim2 IC50 μM | Pim3 IC50 μM | KMS11-luc EC50 μM |
|---|---|---|---|---|---|---|
| 46 | 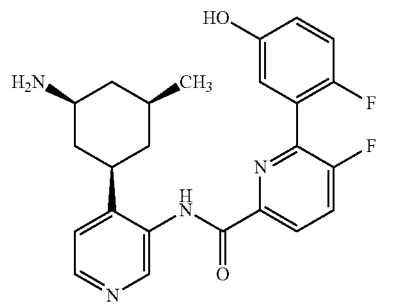 | Chiral | 0.001 | 0.002 | 0.002 | 0.76 |
| 47 | 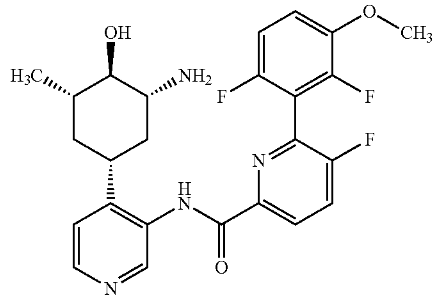 | Chiral | 0.001 | 0.004 | 0.003 | 1.3 |
| 48 | 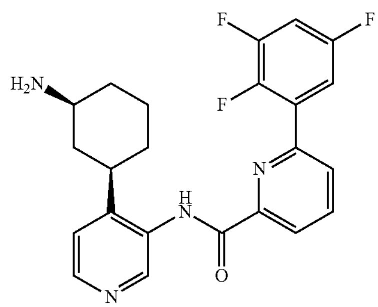 | Chiral | 0.007 | 0.076 | 0.009 | |
| 49 | 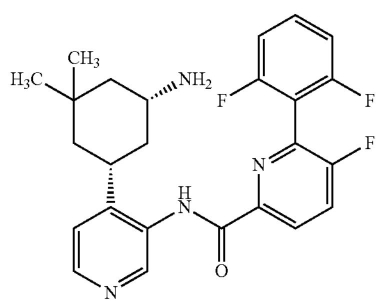 | Chiral | 0.001 | 0.003 | 0.002 | 1.8 |
| 50 | 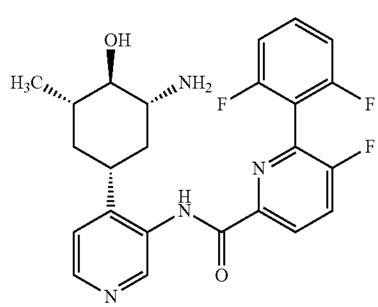 | Chiral | 0.001 | 0.003 | 0.002 | 1.2 |

TABLE 3-continued

| Example No./ NVP ID | Structure | | Pim1 IC50 μM | Pim2 IC50 μM | Pim3 IC50 μM | KMS11-luc EC50 μM |
|---|---|---|---|---|---|---|
| 51 | 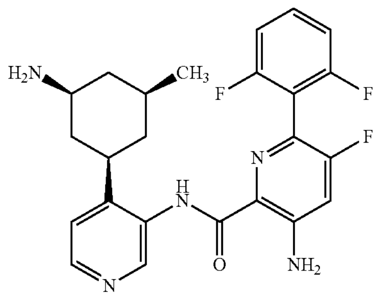 | Chiral | 0.001 | 0.002 | 0.001 | 0.31 |
| 52 | 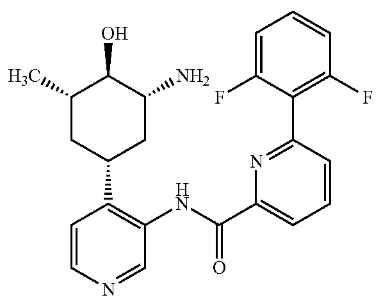 | Chiral | 0.001 | 0.003 | 0.002 | 0.83 |
| 53 | 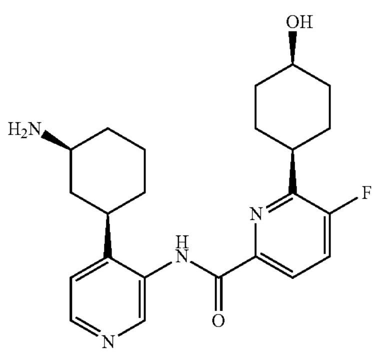 | Chiral | 0.010 | 0.149 | 0.065 | >10 |
| 54 | 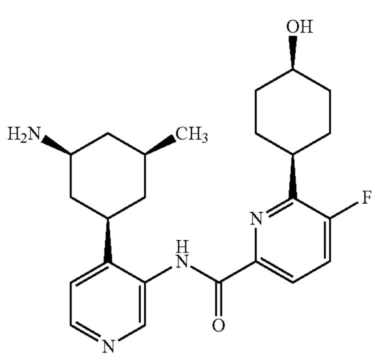 | Chiral | 0.003 | 0.026 | 0.024 | 3.8 |

TABLE 3-continued

| Example No./ NVP ID | Structure | | Pim1 IC50 μM | Pim2 IC50 μM | Pim3 IC50 μM | KMS11-luc EC50 μM |
|---|---|---|---|---|---|---|
| 55 | 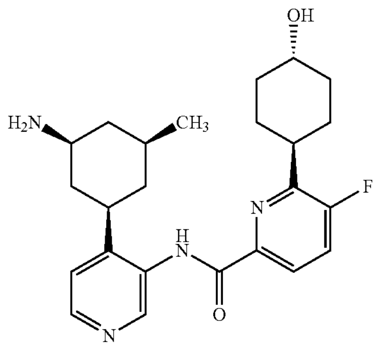 | Chiral | 0.003 | 0.011 | 0.030 | 4.9 |
| 56 | 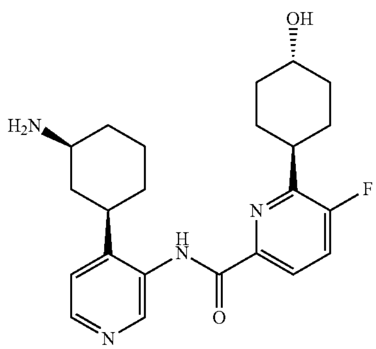 | Chiral | 0.011 | 0.081 | 0.102 | >10 |
| 57 | 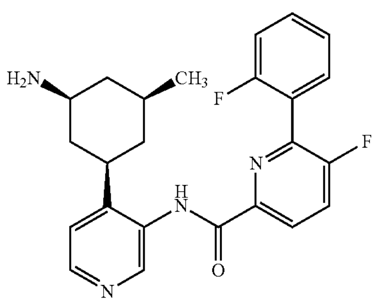 | Chiral | 0.001 | 0.004 | 0.002 | 1.4 |
| 58 | 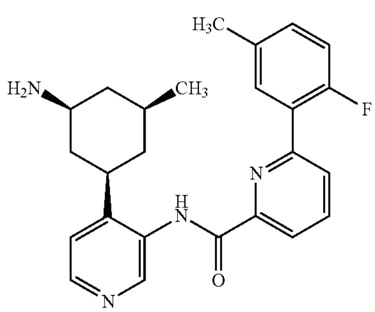 | Chiral | 0.001 | 0.008 | 0.003 | 1.8 |

TABLE 3-continued

| Example No./ NVP ID | Structure | | Pim1 IC50 μM | Pim2 IC50 μM | Pim3 IC50 μM | KMS11-luc EC50 μM |
|---|---|---|---|---|---|---|
| 59 | (structure) | Chiral | 0.001 | 0.003 | 0.002 | 1.1 |
| 60 | (structure) | Chiral | 0.001 | 0.005 | 0.003 | 1.3 |
| 61 | (structure) | Chiral | 0.001 | 0.006 | 0.004 | 1.2 |
| 62 | (structure) | Chiral | 0.001 | 0.007 | 0.003 | 2.4 |
| 63 | (structure) | Chiral | 0.001 | 0.003 | 0.002 | 0.53 |

TABLE 3-continued

| Example No./ NVP ID | Structure | | Pim1 IC50 μM | Pim2 IC50 μM | Pim3 IC50 μM | KMS11-luc EC50 μM |
|---|---|---|---|---|---|---|
| 64 | 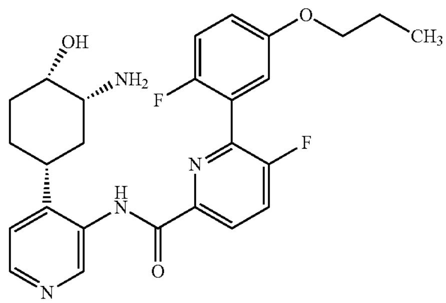 | Chiral | 0.002 | 0.076 | 0.005 | 5.6 |
| 65 | 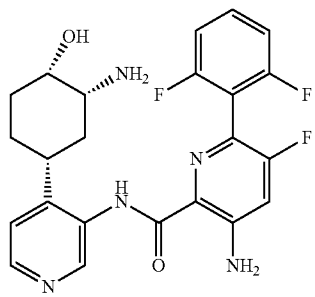 [SMILES: Nc1cc(F)c(-c2c(F)cccc2F)nc1C(=O)Nc1cnccc1[C@@H]1CC[C@H](O)[C@H](N)C1] | | 0.001 | 0.004 | 0.003 | 0.16 |
| 66 | 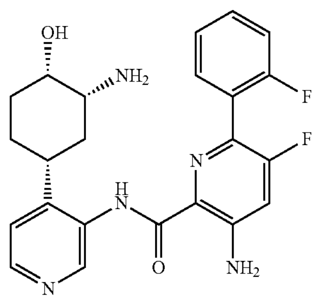 [SMILES: Nc1cc(F)c(-c2ccccc2F)nc1C(=O)Nc1cnccc1[C@@H]1CC[C@H](O)[C@H](N)C1] | | 0.001 | 0.004 | 0.002 | 0.52 |
| 67 | 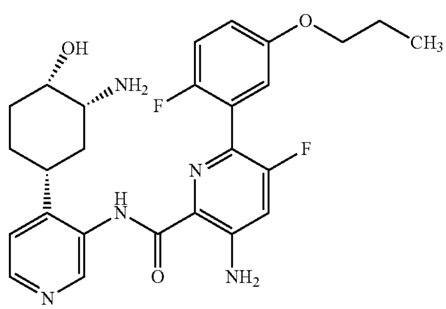 [SMILES: CCCOc1ccc(F)c(-c2nc(C(=O)Nc3cnccc3[C@@H]3CC[C@H](O)[C@H](N)C3)c(N)cc2F)c1] | | 0.001 | 0.007 | 0.003 | 1.2 |
| 68 | 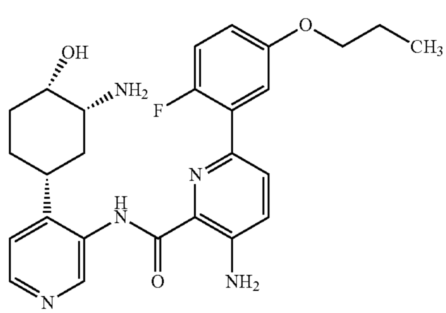 [SMILES: CCCOc1ccc(F)c(-c2ccc(N)c(C(=O)Nc3cnccc3[C@@H]3CC[C@H](O)[C@H](N)C3)n2)c1] | | 0.001 | 0.008 | 0.004 | 1.4 |

TABLE 3-continued

| Example No./ NVP ID | Structure | Pim1 IC50 μM | Pim2 IC50 μM | Pim3 IC50 μM | KMS11-luc EC50 μM |
|---|---|---|---|---|---|
| 69 | Chiral | 0.003 | 0.007 | 0.006 | 1.0 |
| 70 | Chiral | 0.001 | 0.002 | 0.002 | 0.48 |
| 71 | Chiral | 0.662 | 1.947 | 1.05 | |
| 72 | Chiral | 0.095 | 0.522 | 0.369 | |

TABLE 3-continued

| Example No./ NVP ID | Structure | | Pim1 IC50 μM | Pim2 IC50 μM | Pim3 IC50 μM | KMS11-luc EC50 μM |
|---|---|---|---|---|---|---|
| 73 | 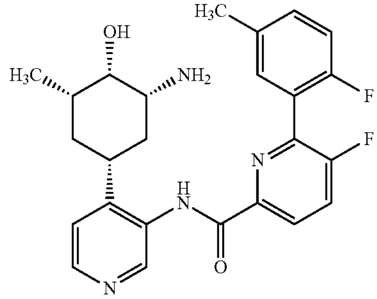 | Chiral | 0.001 | 0.008 | 0.004 | 1.4 |
| 74 | 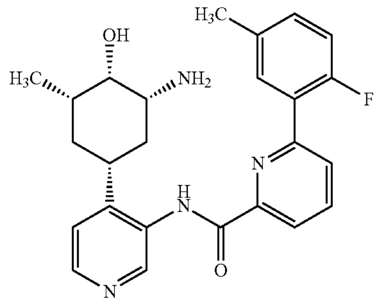 | Chiral | 0.001 | 0.017 | 0.004 | 2.9 |
| 75 | 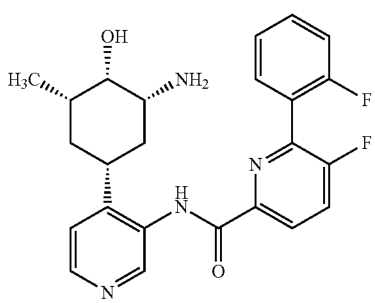 | Chiral | 0.001 | 0.008 | 0.003 | 2.1 |
| 76 | 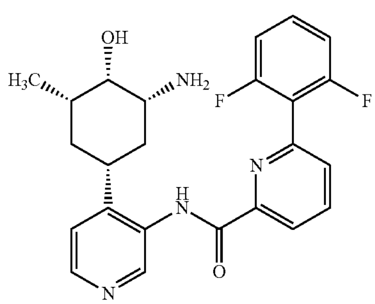 | Chiral | 0.001 | 0.003 | 0.002 | 0.83 |

TABLE 3-continued

| Example No./ NVP ID | Structure | | Pim1 IC50 μM | Pim2 IC50 μM | Pim3 IC50 μM | KMS11-luc EC50 μM |
|---|---|---|---|---|---|---|
| 77 | 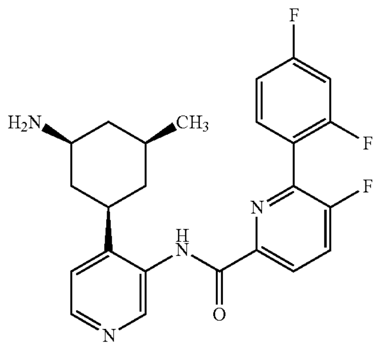 | Chiral | 0.001 | 0.013 | 0.003 | 3.9 |
| 78 | 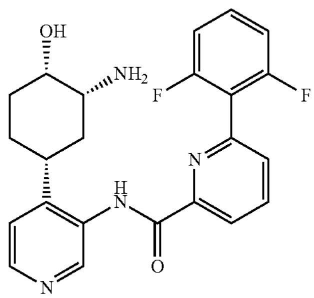 | Chiral | 0.002 | 0.015 | 0.003 | 3.6 |
| 79 | 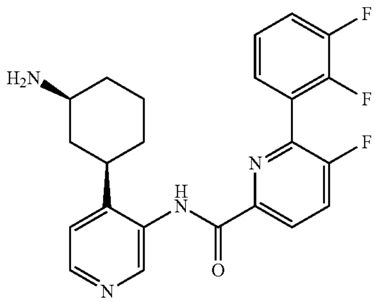 | Chiral | 0.002 | 0.020 | 0.003 | 4.6 |
| 80 | 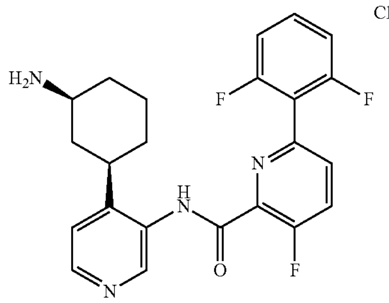 | Chiral | 0.006 | 0.044 | 0.007 | 7.9 |

TABLE 3-continued

| Example No./ NVP ID | Structure | Pim1 IC50 μM | Pim2 IC50 μM | Pim3 IC50 μM | KMS11-luc EC50 μM |
|---|---|---|---|---|---|
| 81 | Chiral | 0.002 | 0.025 | 0.005 | 5.940 |
| 82 | Chiral | 0.003 | 0.080 | 0.009 | >10 |
| 83 | Chiral | 0.004 | 0.048 | 0.005 | >10 |
| 84 | Chiral | 0.004 | 0.163 | 0.007 | 6.9 |

TABLE 3-continued
| Example No./ NVP ID | Structure | | Pim1 IC50 μM | Pim2 IC50 μM | Pim3 IC50 μM | KMS11-luc EC50 μM |
|---|---|---|---|---|---|---|
| 85 | 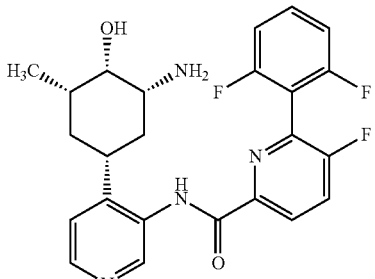 | Chiral | 0.001 | 0.003 | 0.002 | 0.41 |
| 86 | 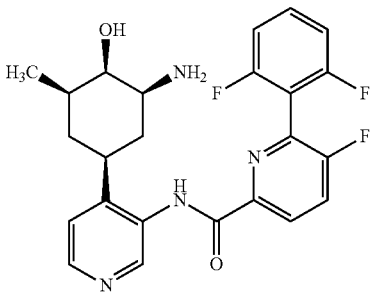 | Chiral | 0.031 | 0.124 | 0.106 | 6.1 |
| 87 | 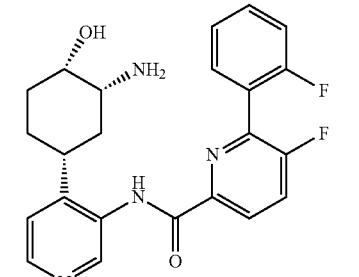 | Chiral | 0.002 | 0.035 | 0.005 | 7.7 |
| 88 | 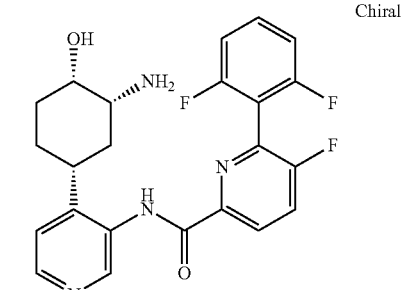 | Chiral | 0.001 | 0.011 | 0.005 | 0.79 |

TABLE 3-continued

| Example No./ NVP ID | Structure | Pim1 IC50 μM | Pim2 IC50 μM | Pim3 IC50 μM | KMS11-luc EC50 μM |
|---|---|---|---|---|---|
| 89 | 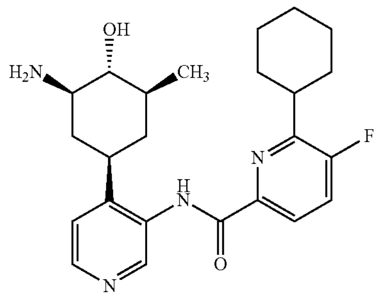 | 0.008 | 0.021 | 0.029 | |
| 90 | 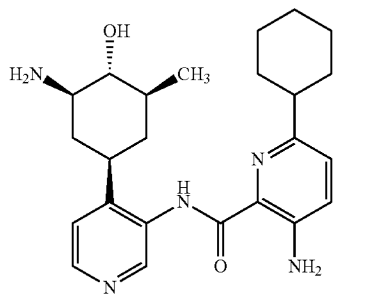 | 0.003 | 0.010 | 0.012 | |
| 91 | 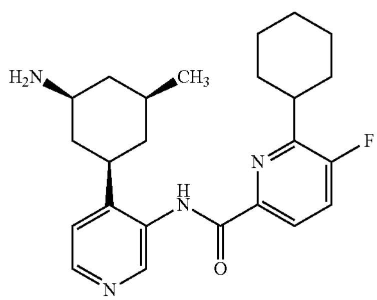 | 0.003 | 0.012 | 0.021 | 2.9 |
| 92 | 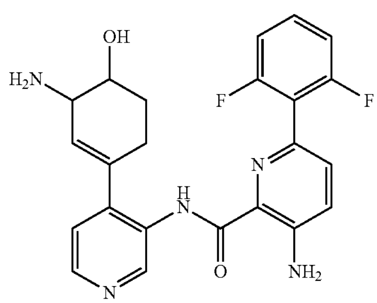 | 0.002 | 0.009 | 0.005 | |
| 93 | 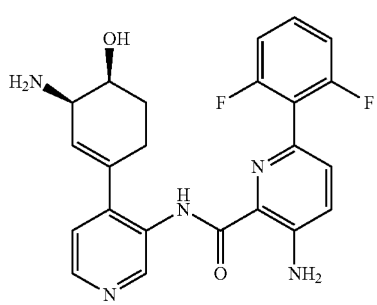 [SMILES: Nc1ccc(-c2c(F)cccc2F)nc1C(=O)Nc1cnccc1C1=C[C@@H](N)[C@@H](O)CC1] | 0.001 | 0.008 | 0.005 | |

TABLE 3-continued

| Example No./ NVP ID | Structure | Pim1 IC50 μM | Pim2 IC50 μM | Pim3 IC50 μM | KMS11-luc EC50 μM |
|---|---|---|---|---|---|
| 94 | 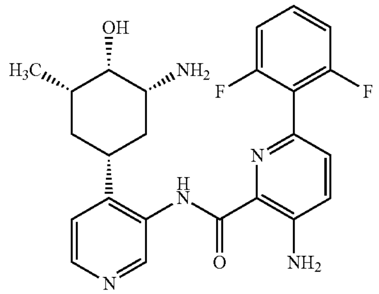 [SMILES: C[C@H]1C[C@@H](c2ccncc2NC(=O)c2nc(-c3c(F)cccc3F)ccc2N)C[C@@H](N)[C@H]1O] | 0.001 | 0.003 | 0.005 | 0.239 |
| 95 | 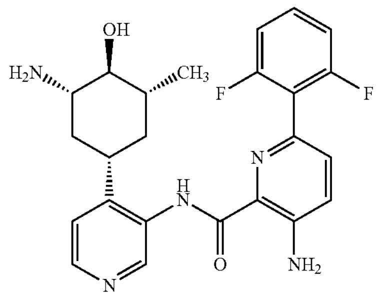 | 0.001 | 0.005 | 0.006 | 0.537 |
| 96 | 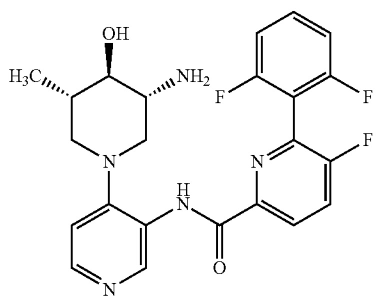 [SMILES: C[C@H]1CN(c2ccncc2NC(=O)c2ccc(F)c(-c3c(F)cccc3F)n2)C[C@@H](N)[C@@H]1O] | 0.001 | 0.001 | 0.001 | 0.03 |
| 97 | Chiral | 0.002 | 0.010 | 0.007 | 3.3 |
| 98 | Chiral | 0.002 | 0.005 | 0.005 | 0.81 |

TABLE 3-continued

| Example No./ NVP ID | Structure | | Pim1 IC50 μM | Pim2 IC50 μM | Pim3 IC50 μM | KMS11-luc EC50 μM |
|---|---|---|---|---|---|---|
| 99 | 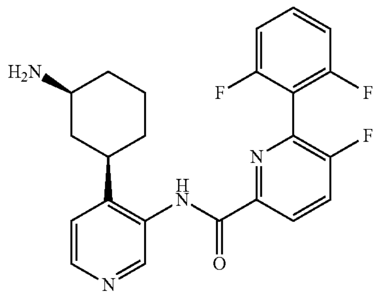 | Chiral | 0.001 | 0.005 | 0.003 | 0.93 |
| 100 | 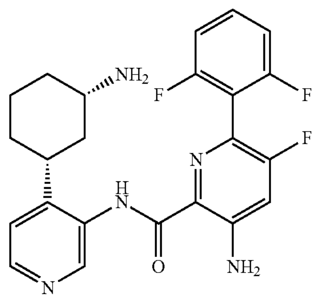 | Chiral | 0.001 | 0.001 | 0.001 | 0.28 |
| 101 | 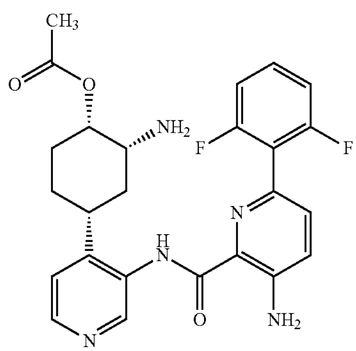 [SMILES: CC(=O)O[C@H]1CC[C@@H](c2ccncc2NC(=O)c2nc(-c3c(F)cccc3F)ccc2N)C[C@H]1N] | | 0.002 | 0.007 | 0.005 | |
| 102 | 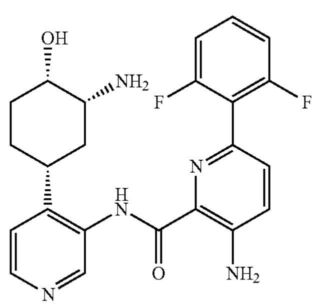 [SMILES: Nc1ccc(-c2c(F)cccc2F)nc1C(=O)Nc1cnccc1[C@@H]1CC[C@H](O)[C@H](N)C1] | | 0.001 | 0.004 | 0.004 | 0.87 |

TABLE 3-continued

| Example No./ NVP ID | Structure | Pim1 IC50 μM | Pim2 IC50 μM | Pim3 IC50 μM | KMS11-luc EC50 μM |
|---|---|---|---|---|---|
| 103 | Chiral | 0.002 | 0.008 | 0.004 | |
| 104 | 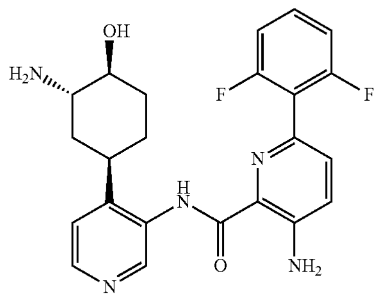 [SMILES: Nc1ccc(-c2c(F)cccc2F)nc1C(=O)Nc1cnccc1[C@@H]1CC[C@H](O)[C@@H](N)C1] | 0.003 | 0.013 | 0.005 | |
| 105 | 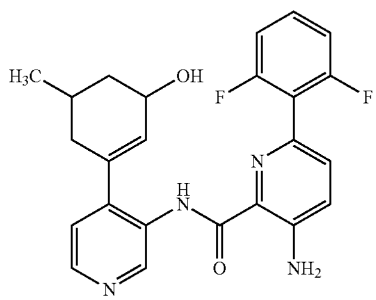 | 0.001 | 0.006 | 0.004 | |
| 106 | Chiral | 0.005 | 0.022 | 0.014 | |
| 107 | 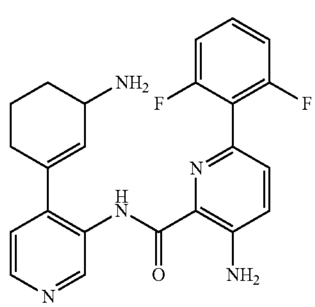 [SMILES: Nc1ccc(-c2c(F)cccc2F)nc1C(=O)Nc1cnccc1C1=CC(N)CCC1] | 0.002 | 0.007 | 0.006 | 0.93 |

TABLE 3-continued

| Example No./ NVP ID | Structure | | Pim1 IC50 μM | Pim2 IC50 μM | Pim3 IC50 μM | KMS11-luc EC50 μM |
|---|---|---|---|---|---|---|
| 108 | 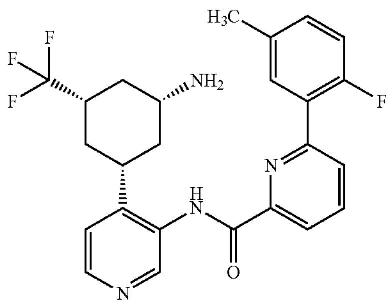 | Chiral | 0.001 | 0.007 | 0.003 | |
| 109 | 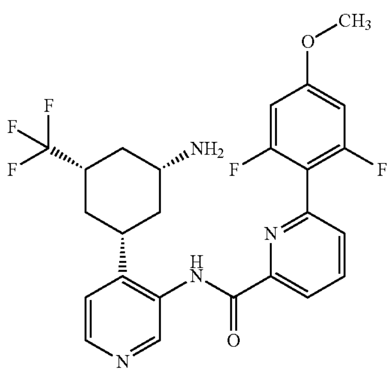 | Chiral | 0.001 | 0.002 | 0.002 | |
| 110 | 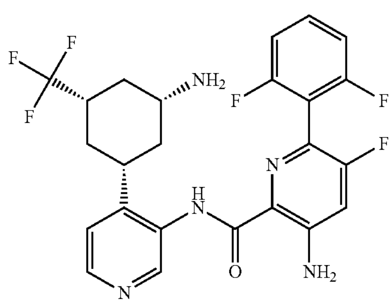 | Chiral | 0.001 | 0.001 | 0.001 | |
| 111 | 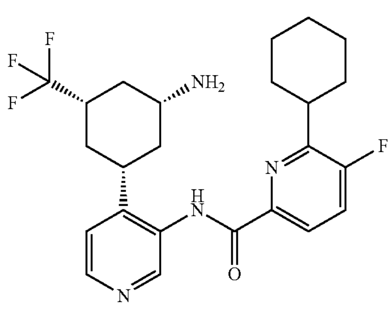 | Chiral | 0.002 | 0.005 | 0.011 | |

TABLE 3-continued

| Example No./ NVP ID | Structure | | Pim1 IC50 μM | Pim2 IC50 μM | Pim3 IC50 μM | KMS11-luc EC50 μM |
|---|---|---|---|---|---|---|
| 112 | 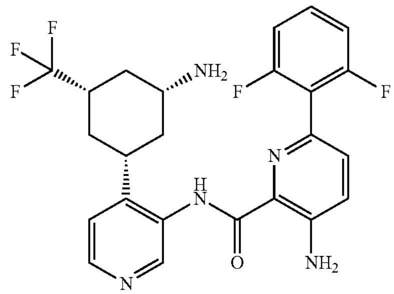 | Chiral | 0.001 | 0.001 | 0.001 | |
| 113 | 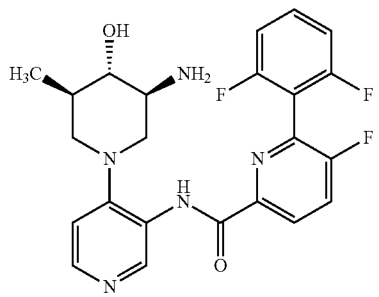 | Chiral | 0.004 | 0.089 | 0.028 | |
| 114 | 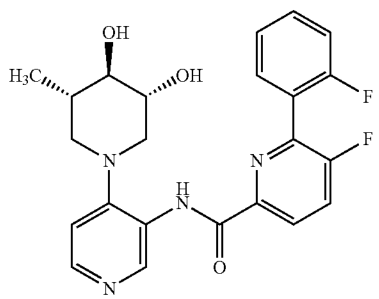 | Chiral | 0.001 | 0.003 | 0.001 | 0.64 |
| 115 | 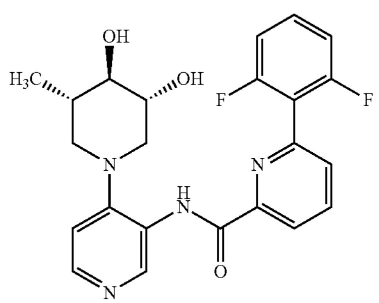 | Chiral | 0.001 | 0.002 | 0.001 | 0.59 |
| 116 | 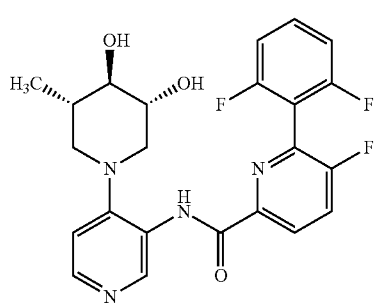 | Chiral | 0.001 | 0.001 | 0.001 | 0.29 |

TABLE 3-continued
| Example No./ NVP ID | Structure | | Pim1 IC50 μM | Pim2 IC50 μM | Pim3 IC50 μM | KMS11-luc EC50 μM |
|---|---|---|---|---|---|---|
| 117 | 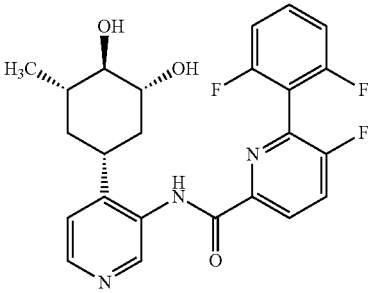 | Chiral | 0.001 | 0.006 | 0.002 | 2.5 |
| 118 | 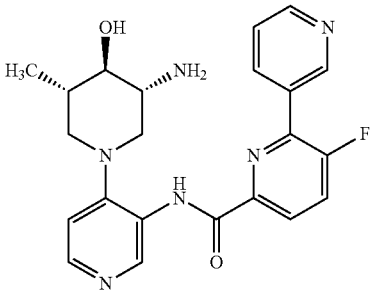 | Chiral | 0.004 | 0.029 | 0.009 | 4.6 |
| 119 | 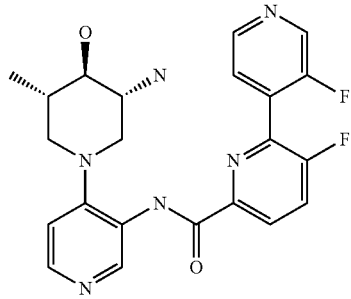 | | 0.001 | 0.004 | 0.002 | 1.2 |
| 120 | 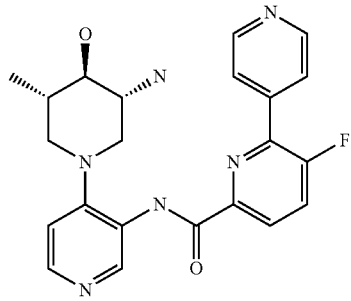 [SMILES: C[C@H]1CN(c2ccncc2NC(=O)c2ccc(F)c(-c3ccncc3)n2)C[C@@H](N)[C@@H]1O] | | 0.003 | 0.018 | 0.007 | 8.5 |
| 121 | 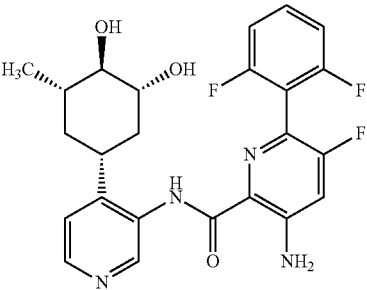 | Chiral | 0.001 | 0.001 | 0.002 | |

TABLE 3-continued

| Example No./ NVP ID | Structure | | Pim1 IC50 μM | Pim2 IC50 μM | Pim3 IC50 μM | KMS11-luc EC50 μM |
|---|---|---|---|---|---|---|
| 122 | 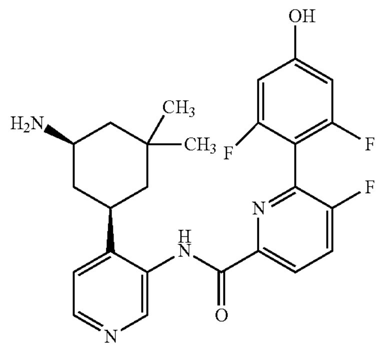 | Chiral | 0.001 | 0.002 | 0.002 | 0.23 |
| 123 | 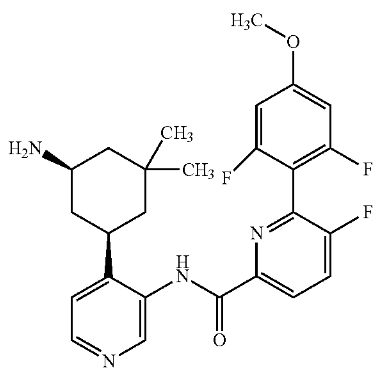 | Chiral | 0.001 | 0.004 | 0.002 | 0.49 |
| 124 | 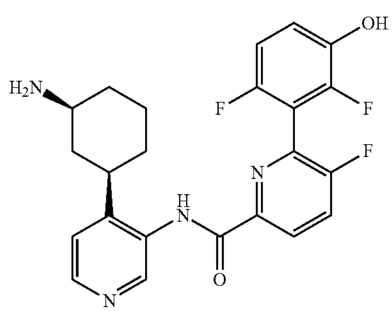 | Chiral | 0.001 | 0.002 | 0.001 | 0.78 |
| 125 | 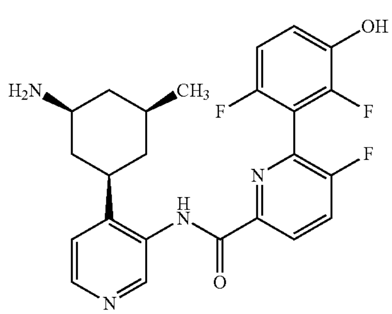 | Chiral | 0.001 | 0.001 | 0.001 | 0.41 |

TABLE 3-continued

| Example No./ NVP ID | Structure | Pim1 IC50 μM | Pim2 IC50 μM | Pim3 IC50 μM | KMS11-luc EC50 μM |
|---|---|---|---|---|---|
| 126 | Chiral | 0.002 | 0.068 | 0.017 | |
| 127 | Chiral | 0.011 | 0.131 | 0.027 | |
| 128 | 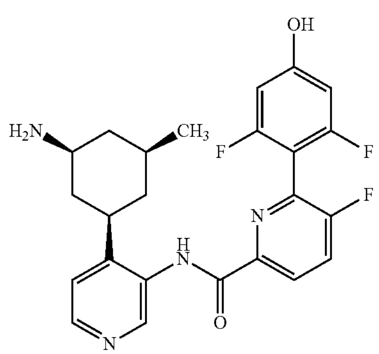 [SMILES: C[C@@H]1C[C@H](N)C[C@H](c2ccncc2NC(=O)c2ccc(F)c(-c3c(F)cc(O)cc3F)n2)C1] | 0.001 | 0.001 | 0.001 | 0.26 |
| 129 | Chiral | 0.001 | 0.003 | 0.002 | 1.2 |

TABLE 3-continued

| Example No./ NVP ID | Structure | Pim1 IC50 μM | Pim2 IC50 μM | Pim3 IC50 μM | KMS11-luc EC50 μM |
|---|---|---|---|---|---|
| 130 | 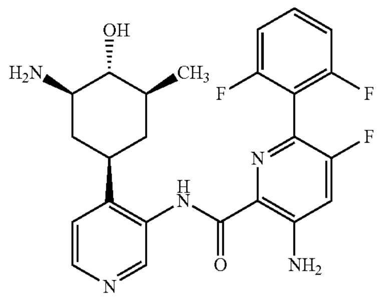 [SMILES: C[C@H]1C[C@@H](c2ccncc2NC(=O)c2nc(-c3c(F)cccc3F)c(F)cc2N)C[C@@H](N)[C@@H]1O] | 0.002 | 0.007 | 0.008 | 1.0 |
| 131 | 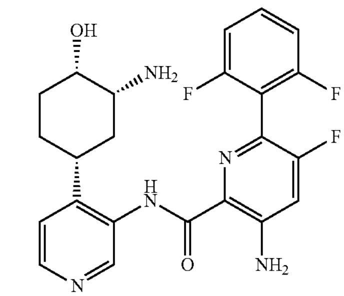 [SMILES: Nc1cc(F)c(-c2c(F)cccc2F)nc1C(=O)Nc1cnccc1[C@@H]1CC[C@H](O)[C@H](N)C1] | 0.002 | 0.007 | 0.006 | 0.43 |
| 132 | 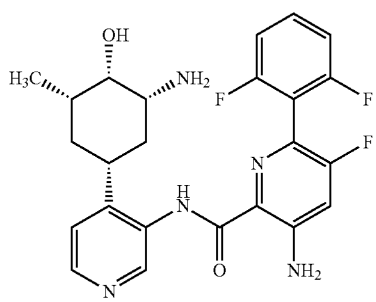 [SMILES: C[C@H]1C[C@@H](c2ccncc2NC(=O)c2nc(-c3c(F)cccc3F)c(F)cc2N)C[C@@H](N)[C@H]1O] | 0.001 | 0.005 | 0.006 | 0.38 |
| 133 | 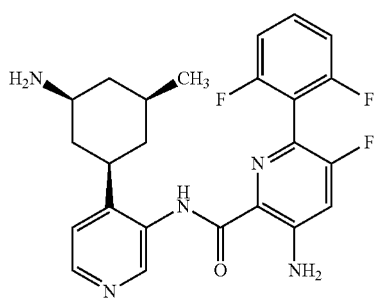 [SMILES: C[C@@H]1C[C@H](N)C[C@H](c2ccncc2NC(=O)c2nc(-c3c(F)cccc3F)c(F)cc2N)C1] | 0.001 | 0.004 | 0.007 | 0.24 |
| 134 | 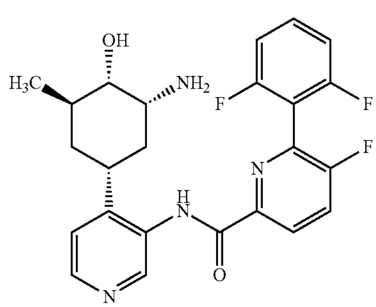 [SMILES: C[C@@H]1C[C@@H](c2ccncc2NC(=O)c2ccc(F)c(-c3c(F)cccc3F)n2)C[C@@H](N)[C@H]1O] | 0.002 | 0.016 | 0.008 | 1.9 |

TABLE 3-continued

| Example No./ NVP ID | Structure | Pim1 IC50 μM | Pim2 IC50 μM | Pim3 IC50 μM | KMS11-luc EC50 μM |
|---|---|---|---|---|---|
| 135 | 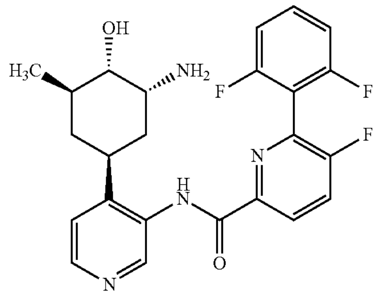 [SMILES: C[C@@H]1C[C@H](c2ccncc2NC(=O)c2ccc(F)c(-c3c(F)cccc3F)n2)C[C@@H](N)[C@H]1O] | 0.023 | 0.088 | 0.036 | |
| 136 | Chiral | 0.002 | 0.024 | 0.009 | 6.4 |
| 137 | 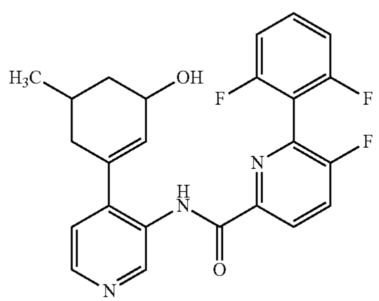 [SMILES: CC1CC(c2ccncc2NC(=O)c2ccc(F)c(-c3c(F)cccc3F)n2)=CC(O)C1] | 0.001 | 0.020 | 0.007 | |
| 138 | Chiral | 0.002 | 0.045 | 0.006 | |

TABLE 3-continued

| Example No./NVP ID | Structure | Pim1 IC50 μM | Pim2 IC50 μM | Pim3 IC50 μM | KMS11-luc EC50 μM |
|---|---|---|---|---|---|
| 139 | Chiral | 0.001 | 0.005 | 0.004 | 1.9 |

Example 144

Biological Method Pharmacology Target Modulation and Efficacy Study in Multiple Myeloma Xenograft Model KMS11-luc multiple myeloma cancer cells, obtained from Suzanne Trudel (University Health Network, Toronto, Canada), express stable luciferase achieved by retroviral transfection and were maintained in DMEM supplemented with 10% heat-inactivated fetal bovine serum with 1% glutamine (Invitrogen, Inc.). Female SCID/bg mice (8-12 weeks old, 20-25 g, Charles River) were used for all in vivo pharmacology studies. The mice were housed and maintained in accordance with state and federal guidelines for the humane treatment and care of laboratory animals, and received food and water ad libitum. Cancer cells were harvested from mid-log phase cultures, viable cell count was established with an automated cell counter (Vi-CELL, Beckman-Coulter), and cells were resuspended in equal parts HBSS and Matrigel (Invitrogen, Inc.). Ten millions cells were subcutaneously injected into the right flank of each mouse. Compound treatment was initiated when tumor size reached 250-350 mm³ for PK/PD studies, and 150-250 mm³ for efficacy studies, with tumor volumes determined using StudyDirector software (StudyLog Systems, Inc.). All compound treatment was administered orally.

For in vivo target modulation in PK/PD time-course studies, tumor-bearing mice were administered a single oral dose of vehicle or compound at different concentrations. At 1, 8 and 24 hours after dosing, tumor tissues and blood samples were taken from individual mice. Resected tumor tissues were snap frozen and pulverized using a liquid nitrogen-cooled cryomortar and pestle. Blood samples were taken by cardiac puncture, and plasma was separated utilizing centrifugation tubes containing lithium heparin and plasma separator (BD Microtainer). Frozen tumor samples were lysed in cold buffer (Meso Scale Discovery) supplemented with EDTA free protease inhibitor (Roche), phosphatase inhibitors 1 and 2, and 1M NaF (Sigma) according to manufacturer's instructions. Following homogenization with a dounce apparatus or by MagNA Lyser (Roche), clear supernatant was obtained following centrifugation at 300×g for 30 minutes at 4° C. and protein concentration was determined by BCA (BioRad). Target modulation was determined using the Meso Scale phospho-Bad$^{Ser112}$/total Bad duplex kit, according to manufacturer's instructions. Briefly, an equal amount of protein was loaded into each well of a Meso Scale phospho-Serine$^{112}$/total Bad duplex 96-well plate (Meso Scale Discovery) and samples were incubated for 30 minutes at room temperature or overnight at 4° C., shaking. Plates were washed with 1×MSD wash buffer, and Sulfo-Tag detection antibody was added to the wells and incubated for 1 hour at room temperature, shaking. The plates were washed again and captured analyte detected following the addition of Read Buffer T to the wells. Plates were read on a SECTOR Imager 6000 Instrument (Meso Scale Discovery). Ratios of the signal from pBad to total Bad were used to correct for variability between samples. Data shown in the following table express the percent inhibition of pBad$^{Ser112}$ phosphorylation relative to total Bad phosphorylation by representative compounds of the invention, normalized to vehicle control group. The extent of modulation is expressed as a percent, relative to vehicle control (n.d., not determined).

| Compound of Example No. | 1 hr | 8 hr | 24 hr |
|---|---|---|---|
| 99 (50 mg/kg) | 40 | 55 | 0 |
| 99 (100 mg/kg) | 62 | 66 | 24 |
| 70 (25 mg/kg) | 34 | 50 | n.d. |
| 70 (50 mg/kg) | 28 | 62 | 0 |
| 70 (100 mg/kg) | 5 | 67 | 68 |
| 96 (25 mg/kg) | 0 | 24 | n.d. |
| 96 (50 mg/kg) | 44 | 69 | 16 |
| 96 (100 mg/kg) | 58 | 71 | 53 |

For efficacy studies, tumor-bearing mice were randomized into groups with equivalent tumor volume variation ranging from 150-250 mm³ utilizing the StudyDirector software (StudyLog Systems, Inc.). Following randomization, mice were dosed orally daily or twice daily at multiple compound concentrations in 200 μl incipient. Tumor growth and animal body weight was measured at least twice weekly, and daily clinical observations were used to monitor potential toxicities related to the treatment. Animals were removed from study if tumor volume exceeded 2500 mm³, or if body weight loss exceeded 20% of initial measurements.

Efficacy of the compound of Example 99 was evaluated in the KMS11-luc xenograft model, with mice receiving oral administration of the compound of Example 99 twice daily at 50 and 100 mg/kg, and once daily at 100 mg/kg for 14 days. Dosing was initiated when tumor sizes reached approximately 250 mm³. As shown in FIG. 1, the compound of Example 99 exhibited dose-dependant effects in vivo, with tumor growth inhibition observed with 50 mg/kg twice daily (92%) and 100 mg/kg twice daily (4% regression). Once daily administration of 100 mg/kg was less efficacious (65%) than when dosed twice daily. These results correlate with the extent and magnitude of pBad$^{Ser112}$ modulation, and suggest that extensive and prolonged target modulation is required for maximum efficacy.

Figure 2:
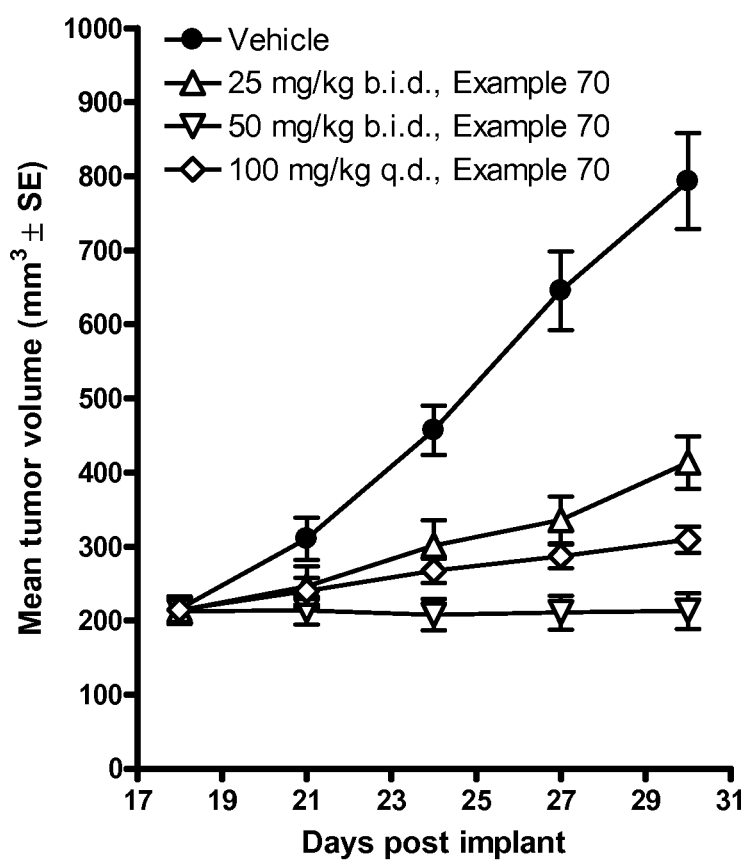
FIG. 2 is a graph showing the efficacy of the compound of Example 70 from an evaluation in the KMS11-luc xenograft model, as described in Example 144.

Efficacy of the compound of Example 70 was evaluated in the KMS11-luc xenograft model, with mice receiving oral administration of the compound of Example 80 twice daily at 25 and 50 mg/kg, and once daily at 100 mg/kg for 14 days. Dosing was initiated when tumor sizes reached approximately 225 mm$^3$. As shown in FIG. 2, the compound of Example 70 exhibited dose-dependant effects in vivo, with tumor growth inhibition observed for 25 mg/kg (65%) and 50 mg/kg (100%). Significant tumor growth inhibition was also observed for 100 mg/kg once daily (84%).

Figure 3:
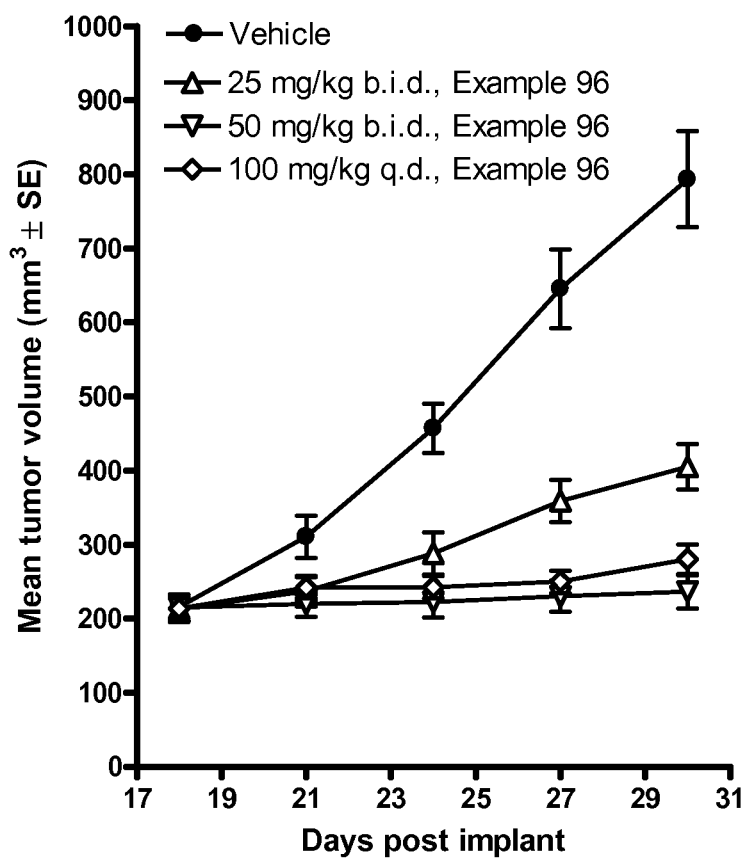
FIG. 3 is a graph showing the efficacy of the compound of Example 96 from an evaluation in the KMS11-luc xenograft model, as described in Example 144.

Efficacy of the compound of Example 96 was evaluated in the KMS11-luc xenograft model, with mice receiving oral administration of the compound of Example 96 twice daily at 25 and 50 mg/kg, and once daily at 100 mg/kg for 14 days. Dosing was initiated when tumor sizes reached approximately 225 mm$^3$. As shown in FIG. 3, compound the compound of Example 96 exhibited dose-dependant effects in vivo, with tumor growth inhibition observed for 25 mg/kg (67%), and 50 mg/kg (96%). Significant tumor growth inhibition was also observed for 100 mg/kg once daily (88%).

While the preferred embodiment of the invention has been illustrated and described, it will be appreciated that various changes can be made therein without departing from the spirit and scope of the invention.

The invention claimed is:

1. A method for treating multiple myeloma, wherein the method comprises the step of: administering to a patient in need of such treatment an effective amount of N-(4-((1R,3S,5S)-3-amino-5-methylcyclohexyl)pyridin-3-yl)-6-(2,6-difluorophenyl)-5-fluoropicolinamide of Formula or a pharmaceutically acceptable salt thereof,

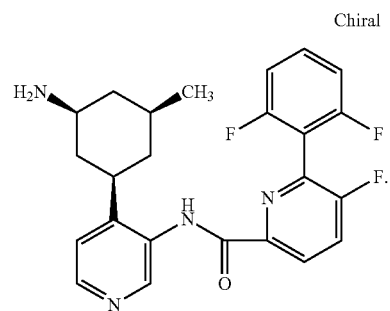 [SMILES: C[C@@H]1C[C@H](N)C[C@H](c2ccncc2NC(=O)c2ccc(F)c(-c3c(F)cccc3F)n2)C1]

2. The method of claim 1, wherein N-(4-((1R,3S,5S)-3-amino-5-methylcyclohexyl)pyridin-3-yl)-6-(2,6-difluorophenyl)-5-fluoropicolinamide is combined with at least one pharmaceutically acceptable carrier.

* * * * *